US012447019B2

(12) United States Patent
Phan

(10) Patent No.: US 12,447,019 B2
(45) Date of Patent: Oct. 21, 2025

(54) HEART VALVE SEALING DEVICES AND DELIVERY DEVICES THEREFOR

(71) Applicant: Edwards Lifesciences Corporation, Irvine, CA (US)

(72) Inventor: Jian Lin Phan, Fountain Valley, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1062 days.

(21) Appl. No.: 17/408,303

(22) Filed: Aug. 20, 2021

(65) Prior Publication Data

US 2022/0039943 A1 Feb. 10, 2022

Related U.S. Application Data

(63) Continuation of application No. PCT/US2020/019495, filed on Feb. 24, 2020.

(60) Provisional application No. 62/809,856, filed on Feb. 25, 2019.

(51) Int. Cl.
*A61F 2/24* (2006.01)

(52) U.S. Cl.
CPC ............ *A61F 2/246* (2013.01); *A61F 2/2454* (2013.01); *A61F 2/2466* (2013.01); *A61F 2220/0008* (2013.01); *A61F 2220/0075* (2013.01); *A61F 2230/0093* (2013.01)

(58) Field of Classification Search
CPC ...... A61F 2/246; A61F 2/2454; A61F 2/2466; A61F 2220/0008; A61F 2220/0075; A61F 2230/0093; A61F 2/07; A61F 17/083
See application file for complete search history.

(56) References Cited

U.S. PATENT DOCUMENTS

| | | | |
|---|---|---|---|
| 3,874,388 | A | 4/1975 | King et al. |
| 4,340,091 | A | 7/1982 | Skelton et al. |
| 4,506,669 | A | 3/1985 | Blake, III |
| 4,590,937 | A | 5/1986 | Deniega |
| 4,693,248 | A | 9/1987 | Failla |
| 4,803,983 | A | 2/1989 | Siegel |
| 5,125,895 | A | 6/1992 | Buchbinder et al. |

(Continued)

FOREIGN PATENT DOCUMENTS

| | | | |
|---|---|---|---|
| CN | 1142351 | A | 2/1997 |
| CN | 1886257 | A | 12/2006 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Jerrah Edwards
*Assistant Examiner* — Jose H. Trevino, III
(74) *Attorney, Agent, or Firm* — Anya Adams

(57) ABSTRACT

An implantable prosthetic device has a coaption element, a pair of paddles, and at least one cover. The coaption element is configured to be positioned within the native heart valve orifice to help fill a space where the native valve is regurgitant and form a more effective seal. The cover can at least partially cover the coaption element and/or the pair of paddles. The cover is at least partially closed by alternating in and out stitches that are substantially unexposed when the cover is secured on the device.

16 Claims, 118 Drawing Sheets

(56) References Cited

U.S. PATENT DOCUMENTS

| | | | |
|---|---|---|---|
| 5,171,252 | A | 12/1992 | Friedland |
| 5,195,962 | A | 3/1993 | Martin et al. |
| 5,292,326 | A | 3/1994 | Green et al. |
| 5,327,905 | A | 7/1994 | Avitall |
| 5,363,861 | A | 11/1994 | Edwards et al. |
| 5,370,685 | A | 12/1994 | Stevens |
| 5,389,077 | A | 2/1995 | Melinyshyn et al. |
| 5,411,552 | A | 5/1995 | Andersen et al. |
| 5,450,860 | A | 9/1995 | O'Connor |
| 5,456,674 | A | 10/1995 | Bos et al. |
| 5,474,057 | A | 12/1995 | Makower et al. |
| 5,478,353 | A | 12/1995 | Yoon |
| 5,487,746 | A | 1/1996 | Yu et al. |
| 5,565,004 | A | 10/1996 | Christoudias |
| 5,607,462 | A | 3/1997 | Imran |
| 5,609,598 | A | 3/1997 | Laufer et al. |
| 5,611,794 | A | 3/1997 | Sauer et al. |
| 5,626,607 | A | 5/1997 | Malecki et al. |
| 5,695,504 | A | 12/1997 | Gifford, III et al. |
| 5,716,417 | A | 2/1998 | Girard et al. |
| 5,727,569 | A | 3/1998 | Benetti et al. |
| 5,741,297 | A | 4/1998 | Simon |
| 5,782,746 | A | 7/1998 | Wright |
| 5,797,960 | A | 8/1998 | Stevens et al. |
| 5,836,311 | A | 11/1998 | Borst et al. |
| 5,843,076 | A | 12/1998 | Webster, Jr. et al. |
| 5,843,178 | A | 12/1998 | Vanney et al. |
| 5,855,590 | A | 1/1999 | Malecki et al. |
| 5,885,271 | A | 3/1999 | Hamilton et al. |
| 5,888,247 | A | 3/1999 | Benetti |
| 5,891,017 | A | 4/1999 | Swindle et al. |
| 5,891,112 | A | 4/1999 | Samson |
| 5,894,843 | A | 4/1999 | Benetti et al. |
| 5,921,979 | A | 7/1999 | Kovac et al. |
| 5,944,738 | A | 8/1999 | Amplatz et al. |
| 5,948,019 | A | 9/1999 | Shu et al. |
| 5,957,835 | A | 9/1999 | Anderson et al. |
| 5,972,020 | A | 10/1999 | Carpentier et al. |
| 5,980,534 | A | 11/1999 | Gimpelson |
| 6,004,329 | A | 12/1999 | Myers et al. |
| 6,010,531 | A | 1/2000 | Donlon et al. |
| 6,017,358 | A | 1/2000 | Yoon et al. |
| 6,086,600 | A | 7/2000 | Kortenbach |
| 6,120,496 | A | 9/2000 | Whayne et al. |
| 6,132,370 | A | 10/2000 | Furnish et al. |
| 6,162,239 | A | 12/2000 | Manhes |
| 6,165,183 | A | 12/2000 | Kuehn et al. |
| 6,182,664 | B1 | 2/2001 | Cosgrove |
| 6,193,732 | B1 | 2/2001 | Frantzen et al. |
| 6,193,734 | B1 | 2/2001 | Bolduc et al. |
| 6,200,315 | B1 | 3/2001 | Galser et al. |
| 6,228,032 | B1 | 5/2001 | Eaton et al. |
| 6,241,743 | B1 | 6/2001 | Levin et al. |
| 6,269,819 | B1 | 8/2001 | Oz et al. |
| 6,269,829 | B1 | 8/2001 | Chen et al. |
| 6,312,447 | B1 | 11/2001 | Grimes |
| 6,461,366 | B1 | 10/2002 | Seguin |
| 6,468,285 | B1 | 10/2002 | Hsu et al. |
| 6,508,806 | B1 | 1/2003 | Hoste |
| 6,508,825 | B1 | 1/2003 | Selmon et al. |
| 6,530,933 | B1 | 3/2003 | Yeung et al. |
| 6,537,290 | B2 | 3/2003 | Adams et al. |
| 6,544,215 | B1 | 4/2003 | Bencini et al. |
| 6,626,930 | B1 | 9/2003 | Allen et al. |
| 6,629,534 | B1 | 10/2003 | St. Goar et al. |
| 6,719,767 | B1 | 4/2004 | Kimblad |
| 6,764,510 | B2 | 7/2004 | Vidlund et al. |
| 6,770,083 | B2 | 8/2004 | Seguin |
| 6,837,867 | B2 | 1/2005 | Kortelling |
| 6,855,137 | B2 | 2/2005 | Bon |
| 6,913,614 | B2 | 7/2005 | Marino et al. |
| 6,939,337 | B2 | 9/2005 | Parker et al. |
| 6,945,956 | B2 | 9/2005 | Waldhauser et al. |
| 7,048,754 | B2 | 5/2006 | Martin et al. |
| 7,101,395 | B2 | 9/2006 | Tremulis et al. |

| | | | |
|---|---|---|---|
| 7,125,421 | B2 | 10/2006 | Tremulis et al. |
| 7,288,097 | B2 | 10/2007 | Seguin |
| 7,371,210 | B2 | 5/2008 | Brock et al. |
| 7,464,712 | B2 | 12/2008 | Oz et al. |
| 7,509,959 | B2 | 3/2009 | Oz et al. |
| 7,569,062 | B1 | 8/2009 | Kuehn et al. |
| 7,618,449 | B2 | 11/2009 | Tremulis et al. |
| 7,682,369 | B2 | 3/2010 | Seguin |
| 7,731,706 | B2 | 6/2010 | Potter |
| 7,744,609 | B2 | 6/2010 | Allen et al. |
| 7,748,389 | B2 | 7/2010 | Salahieh et al. |
| 7,753,932 | B2 | 7/2010 | Gingrich et al. |
| 7,758,596 | B2 | 7/2010 | Oz et al. |
| 7,780,723 | B2 | 8/2010 | Taylor |
| 7,803,185 | B2 | 9/2010 | Gabbay |
| 7,824,443 | B2 | 11/2010 | Salahieh et al. |
| 7,981,123 | B2 | 7/2011 | Seguin |
| 7,988,724 | B2 | 8/2011 | Salahieh et al. |
| 8,052,750 | B2 | 11/2011 | Tuval et al. |
| 8,070,805 | B2 | 12/2011 | Vidlund et al. |
| 8,096,985 | B2 | 1/2012 | Legaspi et al. |
| 8,104,149 | B1 | 1/2012 | McGarity |
| 8,133,239 | B2 | 3/2012 | Oz et al. |
| 8,147,542 | B2 | 4/2012 | Maisano et al. |
| 8,172,856 | B2 | 5/2012 | Eigler et al. |
| 8,206,437 | B2 | 6/2012 | Bonhoeffer et al. |
| 8,216,301 | B2 | 7/2012 | Bonhoeffer et al. |
| 8,303,653 | B2 | 11/2012 | Bonhoeffer et al. |
| 8,313,525 | B2 | 11/2012 | Tuval et al. |
| 8,348,995 | B2 | 1/2013 | Tuval et al. |
| 8,348,996 | B2 | 1/2013 | Tuval et al. |
| 8,414,643 | B2 | 4/2013 | Tuval et al. |
| 8,425,404 | B2 | 4/2013 | Wilson et al. |
| 8,449,599 | B2 | 5/2013 | Chau et al. |
| 8,449,606 | B2 | 5/2013 | Eliasen et al. |
| 8,460,368 | B2 | 6/2013 | Taylor et al. |
| 8,470,028 | B2 | 6/2013 | Thornton et al. |
| 8,480,730 | B2 | 7/2013 | Maurer et al. |
| 8,540,767 | B2 | 9/2013 | Zhang |
| 8,579,965 | B2 | 11/2013 | Bonhoeffer et al. |
| 8,585,756 | B2 | 11/2013 | Bonhoeffer et al. |
| 8,652,202 | B2 | 2/2014 | Alon et al. |
| 8,668,733 | B2 | 3/2014 | Haug et al. |
| 8,721,665 | B2 | 5/2014 | Oz et al. |
| 8,740,918 | B2 | 6/2014 | Seguin |
| 8,771,347 | B2 | 7/2014 | DeBoer et al. |
| 8,778,017 | B2 | 7/2014 | Eliasen et al. |
| 8,834,564 | B2 | 9/2014 | Tuval et al. |
| 8,840,663 | B2 | 9/2014 | Salahieh et al. |
| 8,876,894 | B2 | 11/2014 | Tuval et al. |
| 8,876,895 | B2 | 11/2014 | Tuval et al. |
| 8,945,177 | B2 | 2/2015 | Dell et al. |
| 9,034,032 | B2 | 5/2015 | McLean et al. |
| 9,198,757 | B2 | 12/2015 | Schroeder et al. |
| 9,220,507 | B1 | 12/2015 | Patel et al. |
| 9,259,317 | B2 | 2/2016 | Wilson et al. |
| 9,282,972 | B1 | 3/2016 | Patel et al. |
| 9,301,834 | B2 | 4/2016 | Tuval et al. |
| 9,308,360 | B2 | 4/2016 | Bishop et al. |
| 9,387,071 | B2 | 7/2016 | Tuval et al. |
| 9,427,327 | B2 | 8/2016 | Parrish |
| 9,439,763 | B2 | 9/2016 | Geist et al. |
| 9,510,837 | B2 | 12/2016 | Seguin |
| 9,510,946 | B2 | 12/2016 | Chau et al. |
| 9,572,660 | B2 | 2/2017 | Braido et al. |
| 9,642,704 | B2 | 5/2017 | Tuval et al. |
| 9,700,445 | B2 | 7/2017 | Martin et al. |
| 9,775,963 | B2 | 10/2017 | Miller |
| D809,139 | S | 1/2018 | Marsot et al. |
| 9,889,002 | B2 | 2/2018 | Bonhoeffer et al. |
| 9,949,824 | B2 | 4/2018 | Bonhoeffer et al. |
| 10,076,327 | B2 | 9/2018 | Ellis et al. |
| 10,076,415 | B1 | 9/2018 | Metchik et al. |
| 10,099,050 | B2 | 10/2018 | Chen et al. |
| 10,105,221 | B2 | 10/2018 | Siegel |
| 10,105,222 | B1 | 10/2018 | Metchik et al. |
| 10,111,751 | B1 | 10/2018 | Metchik et al. |
| 10,123,873 | B1 | 11/2018 | Metchik et al. |
| 10,130,475 | B1 | 11/2018 | Metchik et al. |

(56) References Cited

U.S. PATENT DOCUMENTS 10,136,993 B1 11/2018 Metchik et al.
10,159,570 B1 12/2018 Metchik et al.
10,226,309 B2 3/2019 Ho et al.
10,231,837 B1 3/2019 Metchik et al.
10,238,493 B1 3/2019 Metchik et al.
10,238,494 B2 3/2019 McNiven et al.
10,238,495 B2 3/2019 Marsot et al.
10,299,924 B2 5/2019 Kizuka
10,376,673 B2 8/2019 Van Hoven et al.
10,575,841 B1 3/2020 Paulos
2001/0005787 A1 6/2001 Oz et al.
2002/0013571 A1 1/2002 Goldfarb et al.
2002/0107531 A1 8/2002 Schreck et al.
2002/0173811 A1 11/2002 Tu et al.
2002/0183787 A1 12/2002 Wahr et al.
2002/0183834 A1 12/2002 Klaco
2003/0144573 A1 7/2003 Heilman et al.
2003/0187467 A1 10/2003 Schreck
2003/0208231 A1 11/2003 Williamson et al.
2004/0003819 A1 1/2004 St. Goar et al.
2004/0030382 A1 2/2004 St. Goar et al.
2004/0034365 A1 2/2004 Lentz et al.
2004/0044350 A1 3/2004 Martin et al.
2004/0044365 A1 3/2004 Bachman
2004/0049207 A1 3/2004 Goldfarb et al.
2004/0122448 A1 6/2004 Levine
2004/0127981 A1 7/2004 Rahdert et al.
2004/0127982 A1 7/2004 Machold et al.
2004/0147943 A1 7/2004 Kobayashi
2004/0181135 A1 9/2004 Drysen
2004/0181206 A1 9/2004 Chiu et al.
2004/0181238 A1 9/2004 Zarbatany et al.
2004/0186563 A1* 9/2004 Lobbi .................. A61F 2/2418
623/2.11
2004/0210307 A1 10/2004 Khairkhahan
2004/0220593 A1 11/2004 Greenhalgh
2005/0010287 A1 1/2005 Macoviak et al.
2005/0049618 A1 3/2005 Masuda et al.
2005/0070926 A1 3/2005 Ortiz
2005/0137690 A1 6/2005 Salahieh et al.
2005/0143767 A1 6/2005 Kimura et al.
2005/0165429 A1 7/2005 Douglas et al.
2005/0216039 A1 9/2005 Lederman
2005/0251177 A1 11/2005 Saadat et al.
2005/0251183 A1 11/2005 Buckman et al.
2005/0288786 A1 12/2005 Chanduszko
2006/0020275 A1 1/2006 Goldfarb et al.
2006/0089671 A1 4/2006 Goldfarb et al.
2006/0100649 A1 5/2006 Hart
2006/0122647 A1 6/2006 Callaghan et al.
2006/0142694 A1 6/2006 Bednarek et al.
2006/0173251 A1 8/2006 Govari et al.
2006/0178700 A1 8/2006 Quinn
2006/0224169 A1 10/2006 Weisenburgh et al.
2007/0010800 A1 1/2007 Weitzner et al.
2007/0010877 A1 1/2007 Salahieh et al.
2007/0016286 A1 1/2007 Herrmann et al.
2007/0021779 A1 1/2007 Garvin et al.
2007/0032807 A1 2/2007 Ortiz et al.
2007/0093857 A1 4/2007 Rogers et al.
2007/0093890 A1 4/2007 Eliasen et al.
2007/0156197 A1 7/2007 Root et al.
2007/0191154 A1 8/2007 Genereux et al.
2007/0197858 A1 8/2007 Goldfarb et al.
2007/0198038 A1 8/2007 Cohen et al.
2007/0265700 A1 11/2007 Eliasen et al.
2007/0282414 A1 12/2007 Soltis et al.
2007/0293943 A1 12/2007 Quinn
2007/0299387 A1 12/2007 Williams et al.
2007/0299424 A1 12/2007 Cumming et al.
2008/0039743 A1 2/2008 Fox et al.
2008/0039953 A1 2/2008 Davis et al.
2008/0065149 A1 3/2008 Thielen et al.
2008/0077144 A1 3/2008 Crofford
2008/0091169 A1 4/2008 Heideman et al.
2008/0140089 A1 6/2008 Kogiso et al.
2008/0147093 A1 6/2008 Roskopf et al.
2008/0147112 A1 6/2008 Sheets et al.
2008/0149685 A1 6/2008 Smith et al.
2008/0167713 A1 7/2008 Bolling
2008/0177300 A1 7/2008 Mas et al.
2008/0208332 A1 8/2008 Lamphere et al.
2008/0221672 A1 9/2008 Lamphere et al.
2008/0255427 A1 10/2008 Satake et al.
2008/0281411 A1 11/2008 Berreklouw
2008/0287862 A1 11/2008 Weitzner et al.
2008/0294247 A1 11/2008 Yang et al.
2008/0312506 A1 12/2008 Spivey et al.
2008/0319455 A1 12/2008 Harris et al.
2009/0005863 A1 1/2009 Goetz et al.
2009/0024110 A1 1/2009 Heideman et al.
2009/0131880 A1 5/2009 Speziali et al.
2009/0156995 A1 6/2009 Martin et al.
2009/0163934 A1 6/2009 Raschdorf, Jr. et al.
2009/0166913 A1 7/2009 Guo et al.
2009/0177266 A1 7/2009 Powell et al.
2009/0234280 A1 9/2009 Tah et al.
2009/0275902 A1 11/2009 Heeps et al.
2009/0287304 A1 11/2009 Dahlgren et al.
2010/0022823 A1 1/2010 Goldfarb et al.
2010/0057192 A1 3/2010 Celermajer
2010/0069834 A1 3/2010 Schultz
2010/0094317 A1 4/2010 Goldfarb et al.
2010/0106141 A1 4/2010 Osypka et al.
2010/0121434 A1 5/2010 Paul et al.
2010/0249497 A1 9/2010 Peine et al.
2010/0298929 A1 11/2010 Thornton et al.
2010/0324595 A1 12/2010 Linder et al.
2011/0082538 A1 4/2011 Dahlgren et al.
2011/0137410 A1 6/2011 Hacohen
2011/0245855 A1 10/2011 Matsuoka et al.
2011/0257723 A1 10/2011 McNamara
2011/0295281 A1 12/2011 Mizumoto et al.
2012/0022630 A1 1/2012 Wubbeling
2012/0022633 A1 1/2012 Olson et al.
2012/0089125 A1 4/2012 Scheibe et al.
2012/0109160 A1 5/2012 Martinez et al.
2012/0116419 A1 5/2012 Sigmon, Jr.
2012/0209318 A1 8/2012 Qadeer
2012/0277853 A1 11/2012 Rothstein
2013/0035759 A1 2/2013 Gross et al.
2013/0041314 A1 2/2013 Dillon
2013/0066341 A1 3/2013 Ketai et al.
2013/0066342 A1 3/2013 Dell et al.
2013/0072945 A1 3/2013 Terada
2013/0073034 A1 3/2013 Wilson et al.
2013/0110254 A1 5/2013 Osborne
2013/0190798 A1 7/2013 Kapadia
2013/0190861 A1 7/2013 Chau et al.
2013/0268069 A1 10/2013 Zakai et al.
2013/0282059 A1 10/2013 Ketai et al.
2013/0304197 A1 11/2013 Buchbinder et al.
2013/0325110 A1 12/2013 Khalil et al.
2014/0031928 A1 1/2014 Murphy et al.
2014/0046433 A1 2/2014 Kovalsky
2014/0046434 A1 2/2014 Rolando et al.
2014/0052237 A1 2/2014 Lane et al.
2014/0058411 A1 2/2014 Soutorine et al.
2014/0067048 A1 3/2014 Chau et al.
2014/0067052 A1 3/2014 Chau et al.
2014/0094903 A1 4/2014 Miller et al.
2014/0135685 A1 5/2014 Kabe et al.
2014/0194975 A1 7/2014 Quill et al.
2014/0200662 A1 7/2014 Eftel et al.
2014/0207231 A1 7/2014 Hacohen et al.
2014/0222136 A1 8/2014 Geist et al.
2014/0236198 A1 8/2014 Goldfarb et al.
2014/0243968 A1 8/2014 Padala
2014/0251042 A1 9/2014 Asselin et al.
2014/0277404 A1 9/2014 Wilson et al.
2014/0277411 A1 9/2014 Bortlein et al.
2014/0277427 A1 9/2014 Ratz et al.
2014/0316428 A1 10/2014 Golan
2014/0324164 A1 10/2014 Gross et al.

(56) References Cited

U.S. PATENT DOCUMENTS

2014/0330368 A1 11/2014 Gloss et al.
2014/0336751 A1 11/2014 Kramer
2014/0371843 A1 12/2014 Wilson et al.
2015/0005863 A1* 1/2015 Para ...................... A61F 2/2418 623/1.2
2015/0039084 A1 2/2015 Levi et al.
2015/0057704 A1 2/2015 Takahashi
2015/0094802 A1 4/2015 Buchbinder et al.
2015/0100116 A1 4/2015 Mohl et al.
2015/0105808 A1 4/2015 Gordon et al.
2015/0148896 A1 5/2015 Karapetian et al.
2015/0157268 A1 6/2015 Winshtein et al.
2015/0196390 A1 7/2015 Ma et al.
2015/0223793 A1 8/2015 Goldfarb et al.
2015/0230919 A1 8/2015 Chau et al.
2015/0238313 A1 8/2015 Spence et al.
2015/0257757 A1 9/2015 Powers et al.
2015/0257877 A1 9/2015 Hernandez
2015/0257883 A1 9/2015 Basude et al.
2015/0313592 A1 11/2015 Coillard-Lavirotte et al.
2015/0351904 A1 12/2015 Cooper et al.
2015/0366666 A1 12/2015 Khairkhahan et al.
2016/0008129 A1 1/2016 Siegel
2016/0008131 A1 1/2016 Christianson et al.
2016/0022970 A1 1/2016 Forcucci et al.
2016/0051796 A1 2/2016 Kanemasa et al.
2016/0074164 A1 3/2016 Naor
2016/0074165 A1 3/2016 Spence et al.
2016/0106539 A1 4/2016 Buchbinder et al.
2016/0113762 A1 4/2016 Clague et al.
2016/0113764 A1 4/2016 Sheahan et al.
2016/0113766 A1 4/2016 Ganesan et al.
2016/0155987 A1 6/2016 Yoo et al.
2016/0174979 A1 6/2016 Wei
2016/0174981 A1 6/2016 Fago et al.
2016/0242906 A1 8/2016 Morriss et al.
2016/0287387 A1 10/2016 Wei
2016/0302811 A1 10/2016 Rodriguez-Navarro et al.
2016/0317290 A1 11/2016 Chau et al.
2016/0331523 A1* 11/2016 Chau ..................... A61F 2/2454
2016/0354082 A1 12/2016 Oz et al.
2017/0020521 A1 1/2017 Krone et al.
2017/0035561 A1 2/2017 Rowe et al.
2017/0035566 A1 2/2017 Krone et al.
2017/0042456 A1 2/2017 Budiman
2017/0042678 A1 2/2017 Ganesan et al.
2017/0049455 A1 2/2017 Seguin
2017/0100119 A1 4/2017 Baird et al.
2017/0100236 A1 4/2017 Robertson et al.
2017/0224955 A1 8/2017 Douglas et al.
2017/0239048 A1 8/2017 Goldfarb et al.
2017/0252154 A1 9/2017 Tubishevitz et al.
2017/0266413 A1 9/2017 Khuu et al.
2017/0281330 A1 10/2017 Liljegren et al.
2017/0348102 A1 12/2017 Cousins et al.
2018/0008311 A1 1/2018 Shiroff et al.
2018/0021044 A1 1/2018 Miller et al.
2018/0021129 A1 1/2018 Peterson et al.
2018/0021134 A1 1/2018 McNiven et al.
2018/0071487 A1 3/2018 Khuu et al.
2018/0078271 A1 3/2018 Thrasher, III
2018/0078361 A1 3/2018 Naor et al.
2018/0092661 A1 4/2018 Prabhu
2018/0126124 A1 5/2018 Winston et al.
2018/0133008 A1 5/2018 Kizuka et al.
2018/0146964 A1 5/2018 Garcia et al.
2018/0146966 A1 5/2018 Hernandez et al.
2018/0153552 A1 6/2018 King et al.
2018/0161159 A1 6/2018 Lee et al.
2018/0168803 A1 6/2018 Pesce et al.
2018/0185154 A1 7/2018 Cao
2018/0221147 A1 8/2018 Ganesan et al.
2018/0235657 A1 8/2018 Abunassar
2018/0243086 A1 8/2018 Barbarino et al.
2018/0258665 A1 9/2018 Reddy et al.
2018/0263767 A1 9/2018 Chau et al.
2018/0296326 A1 10/2018 Dixon et al.
2018/0296327 A1 10/2018 Dixon et al.
2018/0296328 A1 10/2018 Dixon et al.
2018/0296329 A1 10/2018 Dixon et al.
2018/0296330 A1 10/2018 Dixon et al.
2018/0296331 A1 10/2018 Dixon et al.
2018/0296332 A1 10/2018 Dixon et al.
2018/0296333 A1 10/2018 Dixon et al.
2018/0296334 A1 10/2018 Dixon et al.
2018/0325661 A1 11/2018 Delgado et al.
2018/0325671 A1 11/2018 Abunassar et al.
2018/0333259 A1 11/2018 Dibie
2018/0344457 A1 12/2018 Gross et al.
2018/0353181 A1 12/2018 Wei
2019/0000613 A1 1/2019 Delgado et al.
2019/0000623 A1 1/2019 Pan et al.
2019/0008642 A1 1/2019 Delgado et al.
2019/0008643 A1 1/2019 Delgado et al.
2019/0015199 A1 1/2019 Delgado et al.
2019/0015200 A1 1/2019 Delgado et al.
2019/0015207 A1 1/2019 Delgado et al.
2019/0015208 A1 1/2019 Delgado et al.
2019/0021851 A1 1/2019 Delgado et al.
2019/0021852 A1 1/2019 Delgado et al.
2019/0029498 A1 1/2019 Mankowski et al.
2019/0029810 A1 1/2019 Delgado et al.
2019/0029813 A1 1/2019 Delgado et al.
2019/0030285 A1 1/2019 Prabhu et al.
2019/0053810 A1 2/2019 Griffin
2019/0060058 A1 2/2019 Delgado et al.
2019/0060059 A1 2/2019 Delgado et al.
2019/0060072 A1 2/2019 Zeng
2019/0060073 A1 2/2019 Delgado et al.
2019/0060074 A1 2/2019 Delgado et al.
2019/0060075 A1 2/2019 Delgado et al.
2019/0069991 A1 3/2019 Metchik et al.
2019/0069992 A1 3/2019 Delgado et al.
2019/0069993 A1 3/2019 Delgado et al.
2019/0105156 A1 4/2019 He et al.
2019/0111239 A1 4/2019 Bolduc et al.
2019/0117113 A1 4/2019 Curran
2019/0142589 A1 5/2019 Basude
2019/0159782 A1 5/2019 Kamaraj et al.
2019/0167197 A1 6/2019 Abunassar et al.
2019/0183644 A1 6/2019 Hacohen
2019/0192296 A1 6/2019 Schwartz et al.
2019/0209323 A1 7/2019 Metchik et al.
2019/0261995 A1 8/2019 Goldfarb et al.
2019/0261996 A1 8/2019 Goldfarb et al.
2019/0261997 A1 8/2019 Goldfarb et al.
2019/0314155 A1 10/2019 Franklin et al.
2019/0321166 A1 10/2019 Freschauf et al.
2020/0113683 A1 4/2020 Dale et al.
2020/0138569 A1 5/2020 Basude et al.
2020/0205979 A1 7/2020 O'Carroll et al.
2020/0237512 A1 7/2020 McCann et al.
2020/0337842 A1 10/2020 Metchik et al.
2020/0352717 A1 11/2020 Kheradvar et al.
2020/0360054 A1 11/2020 Walsh et al.
2020/0360132 A1 11/2020 Spence
2020/0368016 A1 11/2020 Pesce et al.
2021/0022850 A1 1/2021 Basude et al.
2021/0059680 A1 3/2021 Lin et al.
2021/0169650 A1 6/2021 Dai et al.
2021/0186698 A1 6/2021 Abunassar et al.
2021/0251757 A1 8/2021 Siegel et al.
2021/0259835 A1 8/2021 Tyler, II et al.
2021/0267781 A1 9/2021 Metchik et al.
2021/0307900 A1 10/2021 Hacohen
2021/0330456 A1 10/2021 Hacohen et al.
2021/0338418 A1 11/2021 Feld
2021/0361238 A1 11/2021 Bak-Boychuk et al.
2021/0361416 A1 11/2021 Stearns
2021/0361422 A1 11/2021 Gross et al.
2021/0361428 A1 11/2021 Dixon
2021/0378818 A1 12/2021 Manash et al.
2021/0401434 A1 12/2021 Tien et al.
2022/0039943 A1 2/2022 Phan

(56) References Cited

U.S. PATENT DOCUMENTS

| | | | |
|---|---|---|---|
| 2022/0039954 | A1 | 2/2022 | Nia et al. |
| 2022/0071767 | A1 | 3/2022 | Dixon et al. |
| 2022/0133327 | A1 | 5/2022 | Zhang et al. |
| 2022/0142780 | A1 | 5/2022 | Zhang et al. |
| 2022/0142781 | A1 | 5/2022 | Zhang et al. |
| 2022/0226108 | A1 | 7/2022 | Freschauf et al. |
| 2022/0233312 | A1 | 7/2022 | Delgado et al. |
| 2022/0257196 | A1 | 8/2022 | Massmann |
| 2022/0287841 | A1 | 9/2022 | Freschauf et al. |
| 2022/0296248 | A1 | 9/2022 | Abunassar et al. |
| 2022/0313433 | A1 | 10/2022 | Ma et al. |
| 2023/0014540 | A1 | 1/2023 | Metchik et al. |
| 2023/0149170 | A1 | 5/2023 | Giese et al. |
| 2023/0218291 | A1 | 7/2023 | Zarbatany et al. |
| 2023/0270549 | A1 | 8/2023 | Guidotti et al. |
| 2024/0148505 | A1 | 5/2024 | Datta et al. |

FOREIGN PATENT DOCUMENTS

| | | | |
|---|---|---|---|
| CN | 105142574 | A | 12/2015 |
| CN | 106175845 | A | 12/2016 |
| CN | 106491245 | A | 3/2017 |
| CN | 107789017 | A | 3/2018 |
| CN | 109953779 | A | 7/2019 |
| CN | 110338857 | A | 10/2019 |
| CN | 110495972 | A | 11/2019 |
| CN | 110537946 | A | 12/2019 |
| CN | 110664515 | A | 1/2020 |
| CN | 209996540 | U | 1/2020 |
| CN | 211243911 | U | 8/2020 |
| CN | 211723546 | U | 10/2020 |
| CN | 111870398 | A | 11/2020 |
| CN | 111904660 | A | 11/2020 |
| CN | 112120831 | A | 12/2020 |
| CN | 112168427 | A | 1/2021 |
| CN | 112190367 | A | 1/2021 |
| CN | 212346813 | U | 1/2021 |
| CN | 212415988 | U | 1/2021 |
| CN | 212490263 | U | 2/2021 |
| CN | 113476182 | A | 10/2021 |
| CN | 113855328 | A | 12/2021 |
| CN | 215019733 | U | 12/2021 |
| EP | 0098100 | A2 | 1/1984 |
| FR | 2146050 | A5 | 2/1973 |
| FR | 9711600 | | 3/1997 |
| WO | 2014064694 | A2 | 5/2014 |
| WO | 2017015632 | A1 | 1/2017 |
| WO | 2018013856 | A1 | 1/2018 |
| WO | 2018050200 | A1 | 3/2018 |
| WO | 2018050203 | A1 | 3/2018 |
| WO | 2018195015 | A1 | 10/2018 |
| WO | 2018195201 | A1 | 10/2018 |
| WO | 2018195215 | A2 | 10/2018 |
| WO | 2018222799 | A1 | 12/2018 |
| WO | WO-2019036359 | A1 | 2/2019 |
| WO | 2019139904 | A1 | 7/2019 |
| WO | 2020106705 | A1 | 5/2020 |
| WO | 2020106827 | A1 | 5/2020 |
| WO | 2020112622 | A1 | 6/2020 |
| WO | 2020167677 | A1 | 8/2020 |
| WO | 2020168081 | A1 | 8/2020 |
| WO | 2020172224 | A1 | 8/2020 |
| WO | 2020176410 | A1 | 9/2020 |
| WO | 2021196580 | A1 | 10/2021 |
| WO | 2021227412 | A1 | 11/2021 |
| WO | 2022006087 | A2 | 1/2022 |
| WO | 2022036209 | A1 | 2/2022 |
| WO | 2022051241 | A1 | 3/2022 |
| WO | 2022052506 | A1 | 3/2022 |
| WO | 2022068188 | A1 | 4/2022 |
| WO | 2022101817 | A2 | 5/2022 |
| WO | 2022140175 | A1 | 6/2022 |
| WO | 2022153131 | A1 | 7/2022 |
| WO | 2022155298 | A2 | 7/2022 |
| WO | 2022157592 | A1 | 7/2022 |
| WO | 2022212172 | A1 | 10/2022 |
| WO | 2023003755 | A1 | 1/2023 |
| WO | 2023004098 | A1 | 1/2023 |
| WO | 2023278663 | A2 | 1/2023 |
| WO | 2023288003 | A1 | 1/2023 |

OTHER PUBLICATIONS

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.
Almagor et al., "Balloon Expandable Stent Implantation in Stenotic Right Heart Valved Conduits", Journal of the American College of Cardiology, vol. 16, No. 5, pp. 1310-1314, Nov. 15, 1990.
Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.
Andersen, H.R. "History of Percutaneous Aortic Valve Prosthesis," Herz, vol. 34., No. 5, pp. 343-346, Aug. 2009, Urban & Vogel, Germany.
Batista RJ et al., "Partial left ventriculectomy to treat end-stage heart disease", Ann Thorac Surg., vol. 64, Issue—3, pp. 634-638, Sep. 1997.
Beall AC Jr. et al., "Clinical experience with a dacron velour-covered teflon-disc mitral-valve prosthesis", Ann Thorac Surg., vol. 5, Issue 5, pp. 402-410, May 1968.
Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977, Elsevier, United States.
Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.
Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.
Fucci et al., "Improved results with mitral valve repair using new surgical techniques", Eur J Cardiothorac Surg. 1995;Issue 9, vol. 11, pp. 621-626.
Inoune et al., "Clinical application of transvenous mitral commissurotomy by a new balloon catheter," The Journal of Thoracic and Cardiovascular Surgery, vol. 87, No. 3, pp. 394-402, Mar. 1984, Elsevier, United States.
Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .
Lawrence, Jr., et al., "Percutaneous Endovascular Graft: Experimental Evaluation", Cardiovascular Radiology 163, pp. 357-360, May 1987.
Maisano F et al., 'The edge-to-edge technique: a simplified method to correct mitral insufficiency', Eur J Cardiothorac Surg., vol. 13, Issue—3, pp. 240-245, Mar. 1998.
Pavonik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.
Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.
Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.
Reul RM et al., "Mitral valve reconstruction for mitral insufficiency", Prog Cardiovasc Dis., vol. 39, Issue—6, May-Jun. 1997.

(56) References Cited

OTHER PUBLICATIONS

Rösch et al., "The Birth, Early Years and Future of Interventional Radiology," Journal of Vascular and Interventional Radiology, vol. 14, No. 7, pp. 841-853, Jul. 1, 2003, Elsevier, United States.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.
Serruys et al., "Stenting of coronary arteries. Are we the sorcerer's apprentice?", European Heart Journal, vol. 10, No. 9 pp. 774-782. Sep. 1, 1989, The European Society of Cardiology, Oxford University Press, United Kingdom.
Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.
Uchida et al., "Modifications of Gianturco Expandable Wire Stents", Technical Note, American Roentgen Ray Society, pp. 1185-1187, May 1988.
Umaña JP et al., Bow-tie'mitral valve repair: an adjuvant technique for ischemic mitral regurgitation', Ann Thorac Surg., vol. 66, Issue—6, pp. 1640-1646, Nov. 1998.
Urban, Philip MD, "Coronary Artery Stenting", pp. 5-47, © 1991, ISBN: 2-88049-054-5, Editions Medecine et Hygiene, Geneva, Switzerland.
Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.
Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.
Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.
Pavcnik D., et al., "Development and Initial Experimental Evaluation of a Prosthetic Aortic Valve for Transcatheter Placement," Cardiovascular Radiology, Apr. 1, 1992, vol. 183(1), pp. 151-154.

* cited by examiner

HEART VALVE SEALING DEVICES AND DELIVERY DEVICES THEREFOR

RELATED APPLICATION

The present application is a continuation application of International Application No. PCT/US2020/019495, filed on Feb. 24, 2020, which claims the benefit of U.S. Provisional Patent Application Ser. No. 62/809,856, filed on Feb. 25, 2019, titled "Heart Valve Sealing Devices and Delivery Devices Therefor," which are incorporated herein by reference in their entireties for all purposes.

BACKGROUND OF THE INVENTION

The native heart valves (i.e., the aortic, pulmonary, tricuspid, and mitral valves) serve critical functions in assuring the forward flow of an adequate supply of blood through the cardiovascular system. These heart valves can be damaged, and thus rendered less effective, for example, by congenital malformations, inflammatory processes, infectious conditions, disease, etc. Such damage to the valves can result in serious cardiovascular compromise or death. Damaged valves can be surgically repaired or replaced during open heart surgery. However, open heart surgeries are highly invasive, and complications may occur. Transvascular techniques can be used to introduce and implant prosthetic devices in a manner that is much less invasive than open heart surgery. As one example, a transvascular technique useable for accessing the native mitral and aortic valves is the trans-septal technique. The trans-septal technique comprises advancing a catheter into the right atrium (e.g., inserting a catheter into the right femoral vein, up the inferior vena cava and into the right atrium). The septum is then punctured, and the catheter passed into the left atrium. A similar transvascular technique can be used to implant a prosthetic device within the tricuspid valve that begins similarly to the trans-septal technique but stops short of puncturing the septum and instead turns the delivery catheter toward the tricuspid valve in the right atrium.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting sides of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the sides of the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Valvular regurgitation involves the valve improperly allowing some blood to flow in the wrong direction through the valve. For example, mitral regurgitation occurs when the native mitral valve fails to close properly and blood flows into the left atrium from the left ventricle during the systolic phase of heart contraction. Mitral regurgitation is one of the most common forms of valvular heart disease. Mitral regurgitation can have many different causes, such as leaflet prolapse, dysfunctional papillary muscles, stretching of the mitral valve annulus resulting from dilation of the left ventricle, more than one of these, etc. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation. Central jet regurgitation occurs when the edges of the leaflets do not meet in the middle and thus the valve does not close, and regurgitation is present.

SUMMARY

This summary is meant to provide some examples and is not intended to be limiting of the scope of the invention in any way. For example, any feature included in an example of this summary is not required by the claims, unless the claims explicitly recite the features. Also, the features, components, steps, concepts, etc. described in examples in this summary and elsewhere in this disclosure can be combined in a variety of ways. Various features and steps as described elsewhere in this disclosure may be included in the examples summarized here.

An example implantable prosthetic device has one or more anchors attachable/securable to leaflets of a native valve. The example implantable prosthetic device can optionally include a coaption element and/or a cover. In some embodiments, an implantable prosthetic device has a coaption element, an anchor or anchor portion including one or more paddles, and at least one cover. The coaption element can be configured to be positioned within the native heart valve orifice to help fill a space where the native valve is regurgitant and form a more effective seal. The cover can at least partially cover the coaption element, the anchor or anchor portion, and/or the paddle(s). The cover can be closed by alternating in and out stitches which are substantially not exposed when the cover is secured on the device.

In some embodiments, a valve repair device for repairing a native valve of a patient includes a pair of paddles and a cover. The valve repair device can optionally include a coaption element. The pair of paddles can be connected to the coaption element and/or another portion of the device. The paddles are movable between an open position and a closed position. The cover can be configured to at least partially surround the paddles and/or the coaption element. At least a portion of the cover is closed around the paddles and/or coaption element by alternating in and out stitches.

In some embodiments, a valve repair device for repairing a native valve of a patient includes an anchor portion and a cover. The anchor portion can comprise a pair of paddles.

The device can also include a coaption portion. In one embodiment, the pair of paddles are connected to a coaption element of the coaption portion. The paddles are movable between an open position and a closed position. The cover at least partially surrounds one or both of the paddles. At least a portion of the cover is closed around one or both of the paddles by alternating in and out stitches.

In some embodiments, a valve repair device for repairing a native valve of a patient includes a coaption element, a pair of paddles, and a cover. The pair of paddles are connected to the coaption element. The paddles are movable between an open position and a closed position. The cover at least partially surrounds the coaption element and at least partially surrounds the at least one of the pair of paddles. At least a portion of the cover is closed around the coaption element by alternating in and out stitches. At least a portion of the cover is closed around the at least one paddle by alternating in and out stitches.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures can be drawn to scale for some embodiments, the figures are not necessarily drawn to scale for all embodiments. Embodiments and other features and advantages of the present disclosure will be described and explained with additional specificity and detail through the use of the accompanying drawings in which.

DETAILED DESCRIPTION

The following description refers to the accompanying drawings, which illustrate specific embodiments of the present disclosure. Other embodiments having different structures and operation do not depart from the scope of the present disclosure.

Example embodiments of the present disclosure are directed to devices and methods for repairing a defective heart valve. It should be noted that various embodiments of native valve reparation devices and systems for delivery are disclosed herein, and any combination of these options can be made unless specifically excluded. In other words, individual components of the disclosed devices and systems can be combined unless mutually exclusive or otherwise physically impossible.

As described herein, when one or more components are described as being connected, joined, affixed, coupled, attached, or otherwise interconnected, such interconnection may be direct as between the components or may be indirect such as through the use of one or more intermediary components. Also as described herein, reference to a "member," "component," or "portion" shall not be limited to a single structural member, component, or element but can include an assembly of components, members, or elements. Also as described herein, the terms "substantially" and "about" are defined as at least close to (and includes) a given value or state (preferably within 10% of, more preferably within 1% of, and most preferably within 0.1% of).

Figure 1:
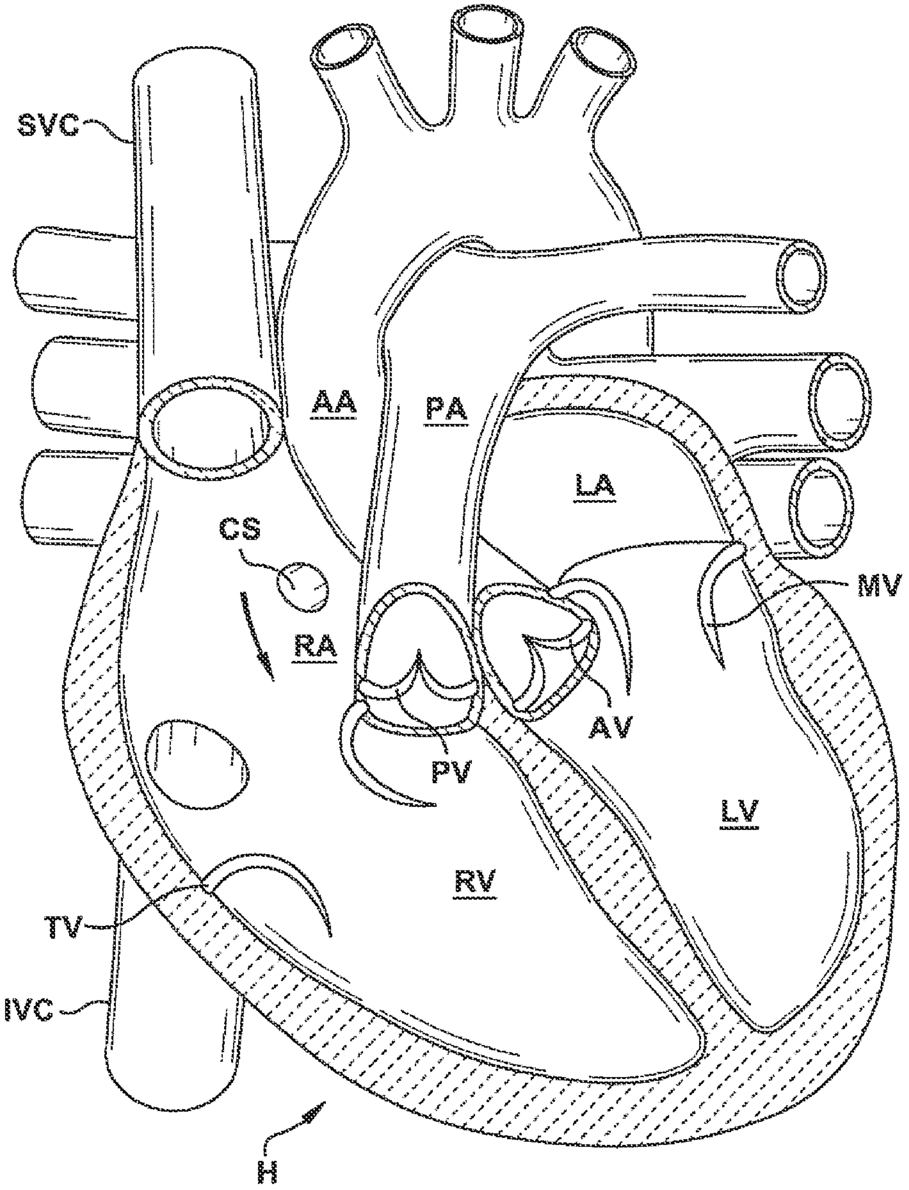
FIG. 1 illustrates a cutaway view of the human heart in a diastolic phase.
Figure 2:
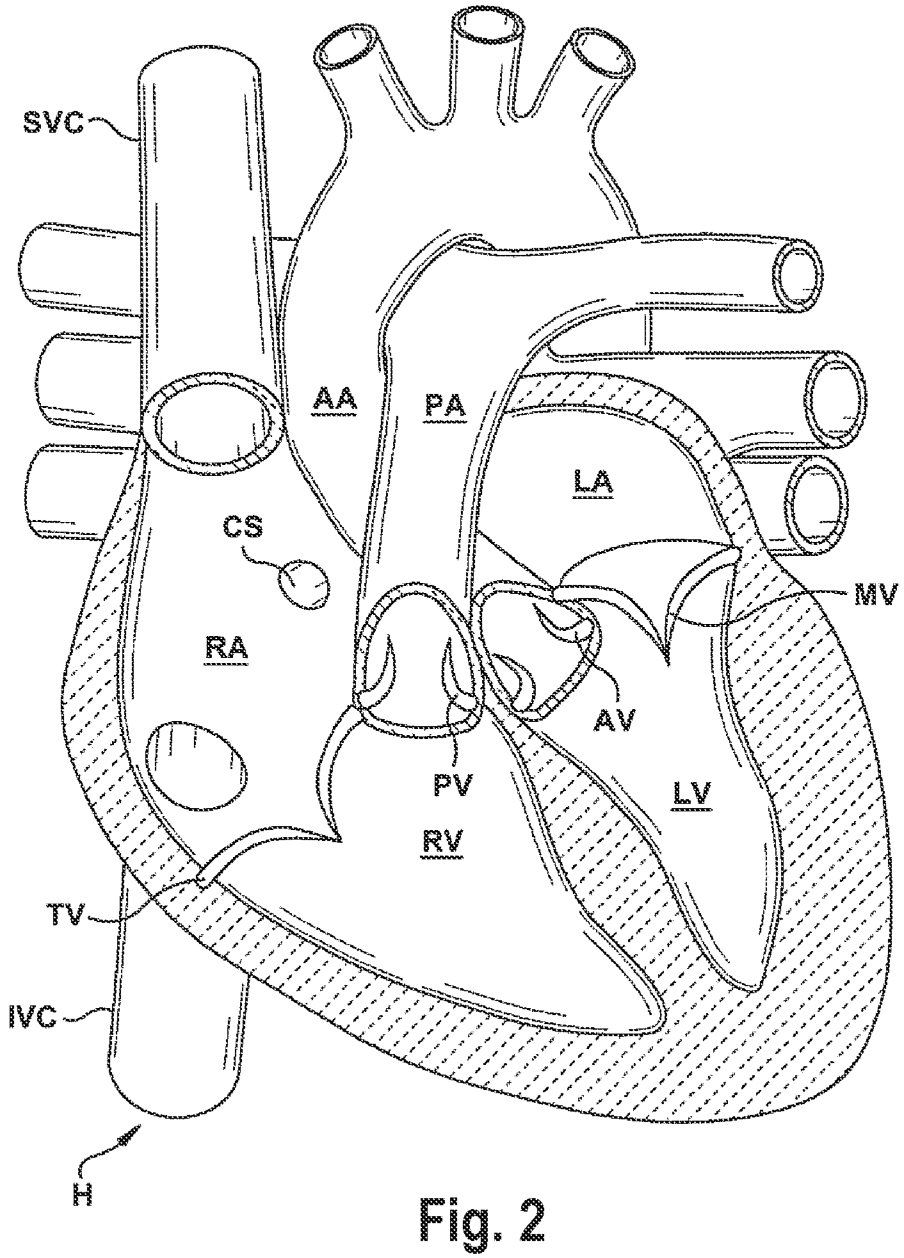
FIG. 2 illustrates a cutaway view of the human heart in a systolic phase.

FIGS. 1 and 2 are cutaway views of the human heart H in diastolic and systolic phases, respectively. The right ventricle RV and left ventricle LV are separated from the right atrium RA and left atrium LA, respectively, by the tricuspid valve TV and mitral valve MV; i.e., the atrioventricular valves. Additionally, the aortic valve AV separates the left ventricle LV from the ascending aorta AA, and the pulmonary valve PV separates the right ventricle from the pulmonary artery PA. Each of these valves has flexible leaflets (e.g., leaflets 20, 22 shown in FIGS. 4 and 5) extending inward across the respective orifices that come together or "coapt" in the flow stream to form the one-way, fluid-occluding surfaces. The native valve repair systems of the present application are described primarily with respect to the mitral valve MV. Therefore, anatomical structures of the left atrium LA and left ventricle LV will be explained in greater detail. It should be understood that the devices described herein may also be used in repairing other native valves, e.g., the devices can be used in repairing the tricuspid valve TV, the aortic valve AV, and the pulmonary valve PV.

The left atrium LA receives oxygenated blood from the lungs. During the diastolic phase, or diastole, seen in FIG. 1, the blood that was previously collected in the left atrium LA (during the systolic phase) moves through the mitral valve MV and into the left ventricle LV by expansion of the left ventricle LV. In the systolic phase, or systole, seen in FIG. 2, the left ventricle LV contracts to force the blood through the aortic valve AV and ascending aorta AA into the body. During systole, the leaflets of the mitral valve MV close to prevent the blood from regurgitating from the left ventricle LV and back into the left atrium LA, and blood is collected in the left atrium from the pulmonary vein. In one example embodiment, the devices described by the present application are used to repair the function of a defective mitral valve MV. That is, the devices are configured to help close the leaflets of the mitral valve to prevent blood from regurgitating from the left ventricle LV and back into the left atrium LA. Many of the devices described in the present application are designed to easily grasp and secure the native leaflets around a coaption element or spacer that acts as a filler in the regurgitant orifice to prevent or inhibit back flow or regurgitation during systole.

Figure 3:
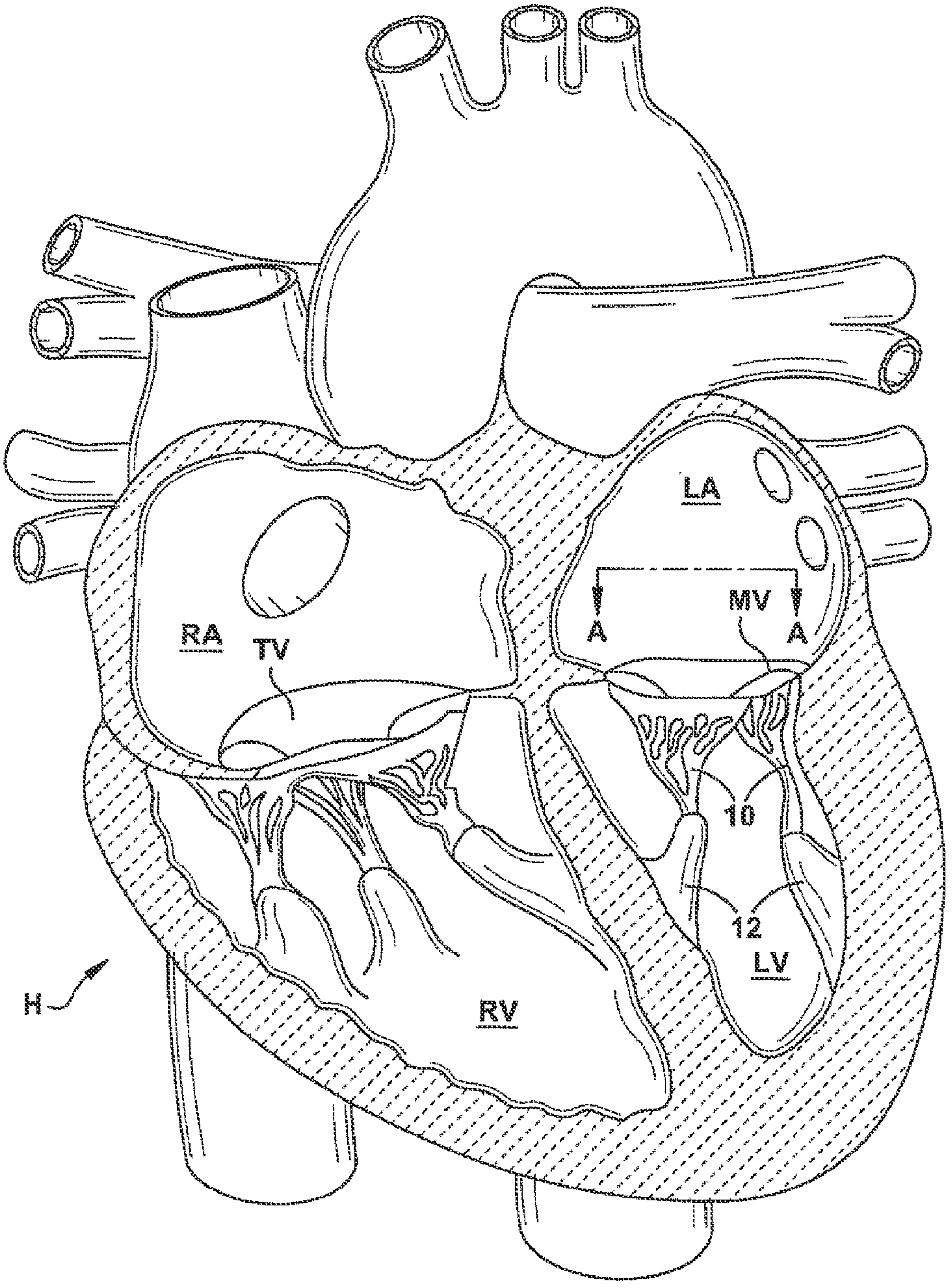
FIG. 3 illustrates a cutaway view of the human heart in a diastolic phase, in which the chordae tendineae are shown attaching the leaflets of the mitral and tricuspid valves to ventricle walls.

Referring now to FIGS. 1-7, the mitral valve MV includes two leaflets, the anterior leaflet 20 and the posterior leaflet 22. The mitral valve MV also includes an annulus 24, which is a variably dense fibrous ring of tissues that encircles the leaflets 20, 22. Referring to FIG. 3, the mitral valve MV is anchored to the wall of the left ventricle LV by chordae tendineae 10. The chordae tendineae 10 are cord-like tendons that connect the papillary muscles 12 (i.e., the muscles located at the base of the chordae tendineae and within the walls of the left ventricle) to the leaflets 20, 22 of the mitral valve MV. The papillary muscles 12 serve to limit the movements of the mitral valve MV and prevent the mitral valve from being reverted. The mitral valve MV opens and closes in response to pressure changes in the left atrium LA and the left ventricle LV. The papillary muscles do not open or close the mitral valve MV. Rather, the papillary muscles brace the mitral valve MV against the high pressure needed to circulate blood throughout the body. Together the papillary muscles and the chordae tendineae are known as the subvalvular apparatus, which functions to keep the mitral valve MV from prolapsing into the left atrium LA when the mitral valve closes.

Various disease processes can impair proper function of one or more of the native valves of the heart H. These disease processes include degenerative processes (e.g., Barlow's Disease, fibroelastic deficiency), inflammatory processes (e.g., Rheumatic Heart Disease), and infectious processes (e.g., endocarditis). In addition, damage to the left ventricle LV or the right ventricle RV from prior heart attacks (i.e., myocardial infarction secondary to coronary artery disease) or other heart diseases (e.g., cardiomyopathy) can distort a native valve's geometry, which can cause the native valve to dysfunction. However, the vast majority of patients undergoing valve surgery, such as surgery to the mitral valve MV, suffer from a degenerative disease that causes a malfunction in a leaflet (e.g., leaflets 20, 22) of a native valve (e.g., the mitral valve MV), which results in prolapse and regurgitation.

Generally, a native valve may malfunction in two different ways: (1) valve stenosis; and (2) valve regurgitation. Valve stenosis occurs when a native valve does not open completely and thereby causes an obstruction of blood flow. Typically, valve stenosis results from buildup of calcified material on the leaflets of a valve, which causes the leaflets to thicken and impairs the ability of the valve to fully open to permit forward blood flow.

The second type of valve malfunction, valve regurgitation, occurs when the leaflets of the valve do not close completely thereby causing blood to leak back into the prior chamber (e.g., causing blood to leak from the left ventricle to the left atrium). There are three main mechanisms by which a native valve becomes regurgitant—or incompetent—which include Carpentier's type I, type II, and type III malfunctions. A Carpentier type I malfunction involves the dilation of the annulus such that normally functioning leaflets are distracted from each other and fail to form a tight seal (i.e., the leaflets do not coapt properly). Included in a type I mechanism malfunction are perforations of the leaflets, as are present in endocarditis. A Carpentier's type II malfunction involves prolapse of one or more leaflets of a native valve above a plane of coaption. A Carpentier's type III malfunction involves restriction of the motion of one or more leaflets of a native valve such that the leaflets are abnormally constrained below the plane of the annulus. Leaflet restriction can be caused by rheumatic disease (Ma) or dilation of a ventricle (IIIb).

Figure 4:
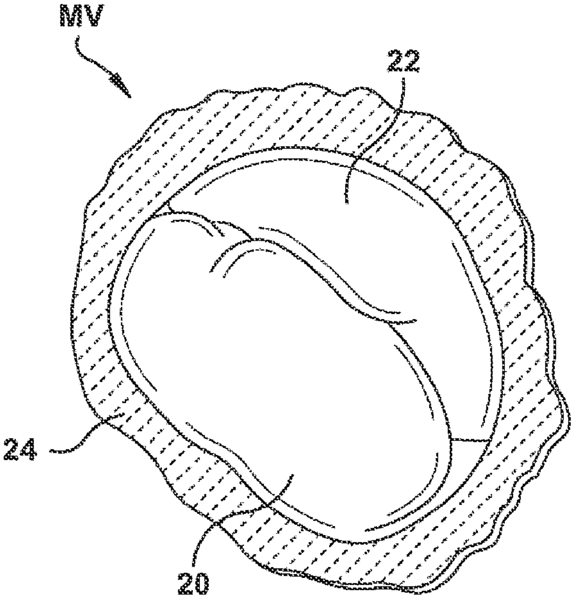
FIG. 4 illustrates a healthy mitral valve with the leaflets closed as viewed from an atrial side of the mitral valve.
Figure 5:
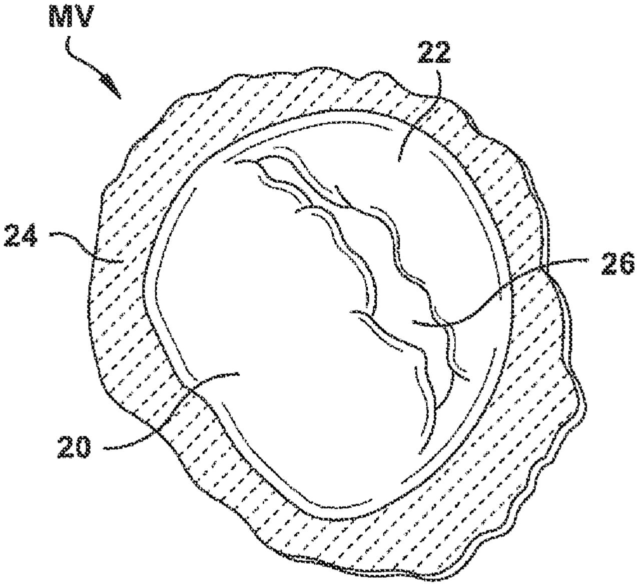
FIG. 5 illustrates a dysfunctional mitral valve with a visible gap between the leaflets as viewed from an atrial side of the mitral valve.

Referring to FIG. 4, when a healthy mitral valve MV is in a closed position, the anterior leaflet 20 and the posterior leaflet 22 coapt, which prevents blood from leaking from the left ventricle LV to the left atrium LA. Referring to FIG. 5, regurgitation occurs when the anterior leaflet 20 and/or the posterior leaflet 22 of the mitral valve MV is displaced into the left atrium LA during systole. This failure to coapt causes a gap 26 between the anterior leaflet 20 and the posterior leaflet 22, which allows blood to flow back into the left atrium LA from the left ventricle LV during systole. As set forth above, there are several different ways that a leaflet (e.g. leaflets 20, 22 of mitral valve MV) may malfunction, which can thereby lead to regurgitation.

Figure 6:
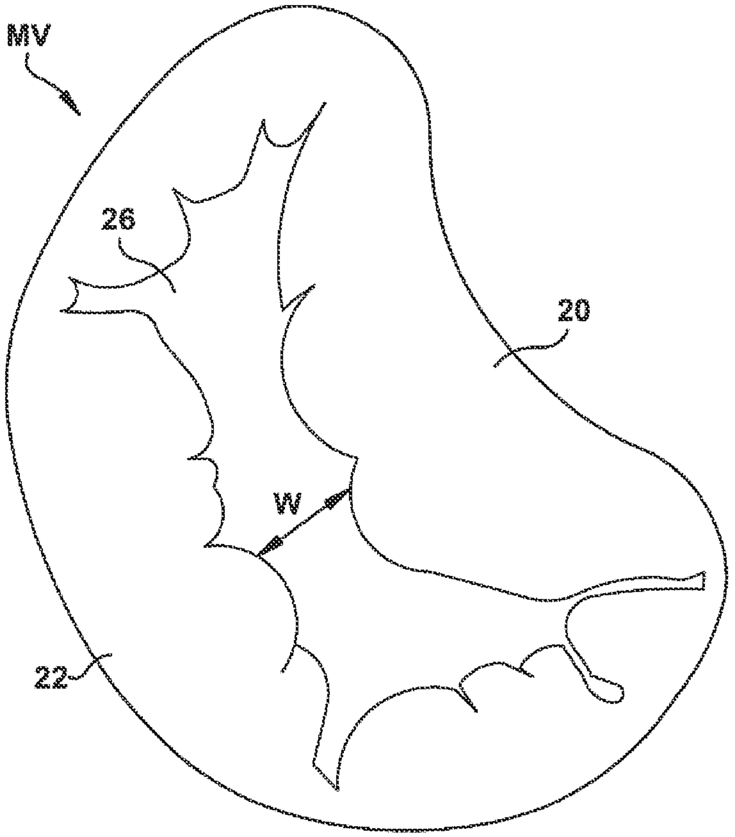
FIG. 6 illustrates a mitral valve having a wide gap between the posterior leaflet and the anterior leaflet.

Referring to FIG. 6, in certain situations, the mitral valve MV of a patient can have a wide gap 26 between the anterior leaflet 20 and the posterior leaflet 22 when the mitral valve is in a closed position (i.e., during the systolic phase). For example, the gap 26 can have a width W between about 2.5 mm and about 17.5 mm, such as between about 5 mm and about 15 mm, such as between about 7.5 mm and about 12.5 mm, such as about 10 mm. In some situations, the gap 26 can have a width W greater than 15 mm. In any of the above-mentioned situations, a valve repair device is desired that is capable of engaging the anterior leaflet 20 and the posterior leaflet 22 to close the gap 26 and prevent regurgitation of blood through the mitral valve MV.

Although stenosis or regurgitation can affect any valve, stenosis is predominantly found to affect either the aortic valve AV or the pulmonary valve PV, and regurgitation is predominantly found to affect either the mitral valve MV or the tricuspid valve TV. Both valve stenosis and valve regurgitation increase the workload of the heart H and may lead to very serious conditions if left un-treated; such as endocarditis, congestive heart failure, permanent heart damage, cardiac arrest, and ultimately death. Because the left side of the heart (i.e., the left atrium LA, the left ventricle LV, the mitral valve MV, and the aortic valve AV) is primarily responsible for circulating the flow of blood throughout the body, malfunction of the mitral valve MV or the aortic valve AV is particularly problematic and often life threatening. Accordingly, because of the substantially higher pressures on the left side of the heart, dysfunction of the mitral valve MV or the aortic valve AV is often more problematic.

Malfunctioning native heart valves may either be repaired or replaced. Repair typically involves the preservation and correction of the patient's native valve. Replacement typically involves replacing the patient's native valve with a biological or mechanical substitute. Typically, the aortic valve AV and pulmonary valve PV are more prone to stenosis. Because stenotic damage sustained by the leaflets is irreversible, the most conventional treatments for a stenotic aortic valve or stenotic pulmonary valve are removal and replacement of the valve with a surgically implanted heart valve, or displacement of the valve with a transcatheter heart valve. The mitral valve MV and the tricuspid valve TV are more prone to deformation of leaflets, which, as described above, prevents the mitral valve or tricuspid valve from closing properly and allows for regurgitation or back flow of blood from the ventricle into the atrium (e.g., a deformed mitral valve MV may allow for regurgitation or back flow from the left ventricle LV to the left atrium LA). The regurgitation or back flow of blood from the ventricle to the atrium results in valvular insufficiency. Deformations in the structure or shape of the mitral valve MV or the tricuspid valve TV are often repairable. In addition, regurgitation can occur due to the chordae tendineae 10 becoming dysfunctional (e.g., the chordae tendineae may stretch or rupture), which allows the anterior leaflet 20 and the posterior leaflet 22 to be reverted such that blood is regurgitated into the left atrium LA. The problems occurring due to dysfunctional chordae tendineae 10 can be repaired by repairing the chordae tendineae or the structure of the mitral valve (e.g., by securing the leaflets 20, 22 at the affected portion of the mitral valve).

The devices and procedures disclosed herein often make reference to repairing a mitral valve for illustration. However, it should be understood that the devices and concepts provided herein can be used to repair any native valve, as well as any component of a native valve. For example, referring now to FIG. 7, any of the devices and concepts provided herein can be used to repair the tricuspid valve TV. For example, any of the devices and concepts provided herein can be used between any two of the anterior leaflet 30, septal leaflet 32, and posterior leaflet 34 to prevent or inhibit regurgitation of blood from the right ventricle into the right atrium. In addition, any of the devices and concepts provided herein can be used on all three of the leaflets 30, 32, 34 together to prevent or inhibit regurgitation of blood from the right ventricle to the right atrium. That is, the valve repair devices provided herein can be centrally located between the three leaflets 30, 32, 34.

An example implantable prosthetic device has a coaption element (e.g., spacer, coaptation element, etc.) and at least one anchor. The coaption element is configured to be positioned within the native heart valve orifice to help fill the space between the leaflets and form a more effective seal, thereby reducing or preventing regurgitation described above. The coaption element can have a structure that is impervious or resistant to blood and that allows the native leaflets to close around the coaption element during ventricular systole to block blood from flowing from the left or right ventricle back into the left or right atrium, respectively. The prosthetic device can be configured to seal against two or three native valve leaflets; that is, the device may be used in the native mitral (bicuspid) and tricuspid valves. The coaption element is sometimes referred to herein as a spacer because the coaption element can fill a space between improperly functioning native mitral or tricuspid leaflets that do not close completely.

The coaption element (e.g., spacer, coaptation element, etc.) can have various shapes. In some embodiments, the coaption element can have an elongated cylindrical shape having a round cross-sectional shape. In some embodiments, the coaption element can have an oval cross-sectional shape, a crescent cross-sectional shape, a rectangular cross-sectional shape, or various other non-cylindrical shapes. The coaption element can have an atrial portion positioned in or adjacent to the left atrium, a ventricular or lower portion positioned in or adjacent to the left ventricle, and a side surface that extends between the native leaflets. In embodiments configured for use in the tricuspid valve, the atrial or upper portion is positioned in or adjacent to the right atrium, and the ventricular or lower portion is positioned in or adjacent to the right ventricle, and the side surface that extends between the native tricuspid leaflets.

The anchor can be configured to secure the device to one or both of the native leaflets such that the coaption element is positioned between the two native leaflets. In embodiments configured for use in the tricuspid valve, the anchor is configured to secure the device to one, two, or three of the tricuspid leaflets such that the coaption element is positioned between the three native leaflets. In some embodiments, the anchor can attach to the coaption element at a location adjacent the ventricular portion of the coaption element. In some embodiments, the anchor can attach to an actuation element, such as a shaft or actuation wire, to which the coaption element is also attached. In some embodiments, the anchor and the coaption element can be positioned independently with respect to each other by separately moving each of the anchor and the coaption element along the longitudinal axis of the actuation element (e.g., actuation shaft, actuation rod, actuation wire, etc.). In some embodiments, the anchor and the coaption element can be positioned simultaneously by moving the anchor and the coaption element together along the longitudinal axis of the actuation element, e.g., shaft or actuation wire. The anchor can be configured to be positioned behind a native leaflet when implanted such that the leaflet is grasped by the anchor.

The prosthetic device can be configured to be implanted via a delivery sheath. The coaption element and the anchor can be compressible to a radially compressed state and can be self-expandable to a radially expanded state when compressive pressure is released. The device can be configured for the anchor to be expanded radially away from the still-compressed coaption element initially in order to create a gap between the coaption element and the anchor. A native leaflet can then be positioned in the gap. The coaption element can be expanded radially, closing the gap between the coaption element and the anchor and capturing the leaflet between the coaption element and the anchor. In some embodiments, the anchor and coaption element are optionally configured to self-expand. The implantation methods for various embodiments can be different and are more fully discussed below with respect to each embodiment. Additional information regarding these and other delivery methods can be found in U.S. Pat. No. 8,449,599 and U.S. Patent Application Publication Nos. 2014/0222136, 2014/0067052, and 2016/0331523, each of which is incorporated herein by reference in its entirety for all purposes. These methods can be performed on a living animal or on a simulation, such as on a cadaver, cadaver heart, simulator (e.g. with the body parts, heart, tissue, etc. being simulated), etc. mutatis mutandis.

The disclosed prosthetic devices can be configured such that the anchor is connected to a leaflet, taking advantage of the tension from native chordae tendineae to resist high systolic pressure urging the device toward the left atrium. During diastole, the devices can rely on the compressive and retention forces exerted on the leaflet that is grasped by the anchor.

Referring now to FIGS. 8-14, a schematically illustrated implantable prosthetic device 100 (e.g., a prosthetic spacer device, etc.) is shown in various stages of deployment. The device 100 can include any other features for an implantable prosthetic device discussed in the present application, and the device 100 can be positioned to engage valve tissue 20, 22 as part of any suitable valve repair system (e.g., any valve repair system disclosed in the present application).

The device 100 is deployed from a delivery sheath or means for delivery 102 and includes a coapting portion or coaptation portion 104 and an anchor portion 106. In some embodiments, the coaptation portion 104 of the device 100 includes a coaption element or means for coapting 110 that is adapted to be implanted between the leaflets of a native valve (e.g., a native mitral valve, tricuspid valve, etc.) and is slidably attached to an actuation element 112 (e.g., actuation wire, actuation shaft, actuation tube, etc.). The anchor portion 106 is actuatable between open and closed conditions and can take a wide variety of forms, such as, for example, paddles, gripping elements, or the like. Actuation of the actuation element or means for actuating 112 opens and closes the anchor portion 106 of the device 100 to grasp the native valve leaflets during implantation. The actuation element or means for actuation 112 (as well as other actuation elements and means for actuation herein) can take a wide variety of different forms (e.g., as a wire, rod, shaft, tube, screw, suture, line, combination of these, etc.). As one example, the actuation element can be threaded such that rotation of the actuation element moves the anchor portion 106 relative to the coaption portion 104. Or, the actuation element can be unthreaded, such that pushing or pulling the actuation element 112 moves the anchor portion 106 relative to the coaption portion 104.

The anchor portion 106 and/or anchors of the device 100 include outer paddles 120 and inner paddles 122 that are, in some embodiments, connected between a cap 114 and the coaption element or means for coapting 110 by portions 124, 126, 128. The connection portions 124, 126, 128 can be jointed and/or flexible to move between all of the positions described below. The interconnection of the outer paddles 120, the inner paddles 122, the coaption element or means for coapting 110, and the cap 114 by the portions 124, 126, and 128 can constrain the device to the positions and movements illustrated herein.

In some implementations, the actuation element or means for actuating 112 (e.g., actuation wire, actuation shaft, etc.) extends through the delivery sheath and the coaption element or means for coapting 110 to the cap 114 at the distal connection of the anchor portion 106. Extending and retracting the actuation element or means for actuating 112 increases and decreases the spacing between the coaption element or means for coapting 110 and the cap 114, respectively. A collar or other attachment element removably attaches the coaption element or means for coapting 110 to the delivery sheath or means for delivery 102 so that the actuation element or means for actuating 112 slides through the collar or other attachment element and through the coaption element or means for coapting 110 during actuation to open and close the paddles 120, 122 of the anchor portion 106.

Figure 11:
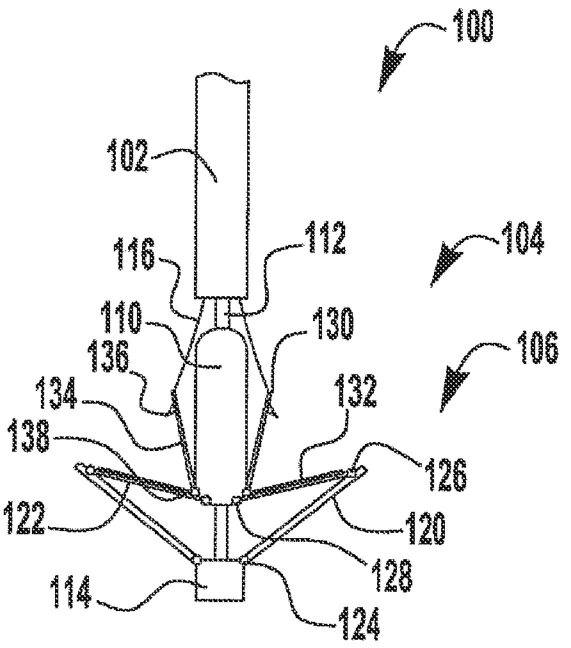

Referring now to FIG. 11, the anchor portion 106 and/or anchors include attachment portions or gripping members. The illustrated gripping members comprise clasps 130 that include a base or fixed arm 132, a moveable arm 134, optional barbs or other means for securing 136, and a joint portion 138. The fixed arms 132 are attached to the inner paddles 122. In some embodiments, the fixed arms 132 are attached to the inner paddles 122 with the joint portion 138 disposed proximate the coapting or coaption element 110 or means for coapting 110. The clasps or barbed clasps have flat surfaces and do not fit in a recess of the inner paddle. Rather, the flat portions of the clasps are disposed against the surface of the inner paddle 122. The joint portion 138 provides a spring force between the fixed and moveable arms 132, 134 of the clasp 130. The joint portion 138 can be any suitable joint, such as a flexible joint, a spring joint, a pivot joint, or the like. In some embodiments, the joint portion 138 is a flexible piece of material integrally formed with the fixed and moveable arms 132, 134. The fixed arms 132 are attached to the inner paddles 122 and remain stationary relative to the inner paddles 122 when the moveable arms 134 are opened to open the clasps 130 and expose the barbs, friction-enhancing elements, or means for securing 136. In some implementations, the clasps 130 are opened by applying tension to actuation lines 116 attached to the moveable arms 134, thereby causing the moveable arms 134 to articulate, flex, or pivot on the joint portions 138. Other actuation mechanisms are also possible.

During implantation, the paddles 120, 122 can be opened and closed, for example, to grasp the native leaflets (e.g., native mitral valve leaflets, etc.) between the paddles 120, 122 and/or between the paddles 120, 122 and a coaption element or means for coapting 110. The clasps 130 can be used to grasp and/or further secure the native leaflets by engaging the leaflets with barbs, friction-enhancing elements, or means for securing 136 and pinching the leaflets between the moveable and fixed arms 134, 132. The barbs, friction-enhancing elements, or other means for securing 136 of the clasps or barbed clasps 130 increase friction with the leaflets or may partially or completely puncture the leaflets. The actuation lines 116 can be actuated separately so that each clasp 130 can be opened and closed separately. Separate operation allows one leaflet to be grasped at a time, or for the repositioning of a clasp 130 on a leaflet that was insufficiently grasped, without altering a successful grasp on the other leaflet. The clasps 130 can be opened and closed relative to the position of the inner paddle 122 (as long as the inner paddle is in an open position), thereby allowing leaflets to be grasped in a variety of positions as the particular situation requires.

The clasps 130 can be opened separately by pulling on an attached actuation line 116 that extends through the delivery sheath or means for delivery 102 to the clasp 130. The actuation line 116 can take a wide variety of forms, such as, for example, a line, a suture, a wire, a rod, a catheter, or the like. The clasps 130 can be spring loaded so that in the closed position the clasps 130 continue to provide a pinching force on the grasped native leaflet. This pinching force remains constant regardless of the position of the inner paddles 122. Barbs or means for securing 136 of the barbed clasps 130 can pierce the native leaflets to further secure the native leaflets.

Figure 8:
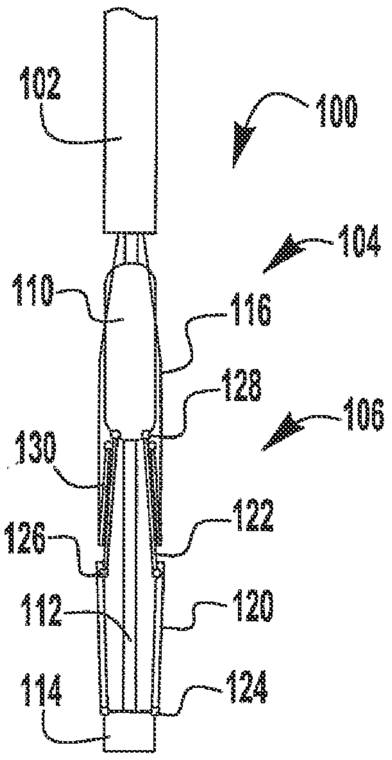
FIGS. 8-14 show an example embodiment of an implantable prosthetic device, in various stages of deployment.

Referring now to FIG. 8, the device 100 is shown in an elongated or fully open condition for deployment from the delivery sheath. The device 100 is loaded in the delivery sheath in the fully open position, because the fully open position takes up the least space and allows the smallest catheter to be used (or the largest device 100 to be used for a given catheter size). In the elongated condition the cap 114 is spaced apart from the coaption element or means for coapting 110 such that the paddles 120, 122 are fully extended. In some embodiments, an angle formed between the interior of the outer and inner paddles 120, 122 is approximately 180 degrees. The clasps 130 are kept in a closed condition during deployment through the delivery sheath or means for delivery 102 so that the barbs or means for securing 136 (FIG. 11) do not catch or damage the sheath or tissue in the patient's heart.

Figure 9:
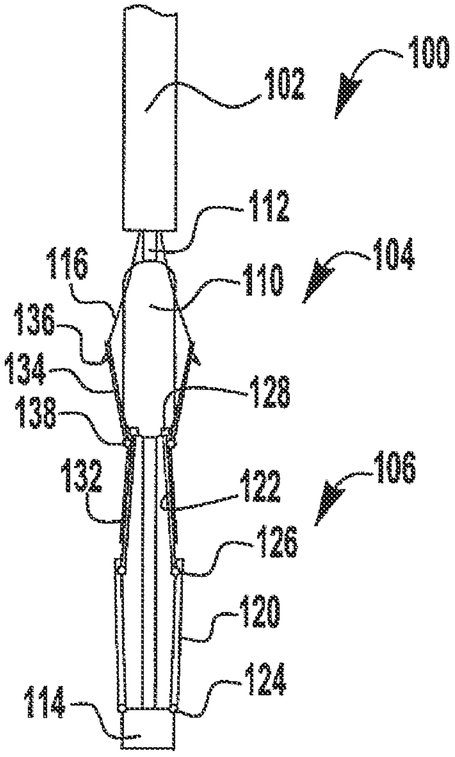

Referring now to FIG. 9, the device 100 is shown in an elongated detangling condition, similar to FIG. 8, but with the clasps 130 in a fully open position, ranging from about 140 degrees to about 200 degrees, from about 170 degrees to about 190 degrees, or about 180 degrees between fixed and moveable portions of the clasps 130. Fully opening the paddles 120, 122 and the clasps 130 has been found to improve ease of detanglement or detachment from anatomy of the patient, such as the chordae tendineae, during implantation of the device 100.

Figure 10:
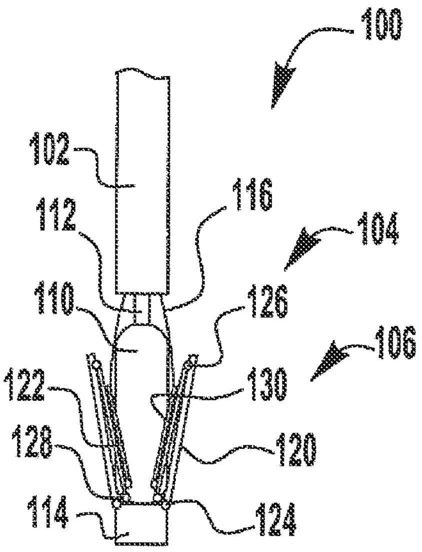

Referring now to FIG. 10, the device 100 is shown in a shortened or fully closed condition. The compact size of the device 100 in the shortened condition allows for easier maneuvering and placement within the heart. To move the device 100 from the elongated condition to the shortened condition, the actuation element or means for actuating 112 is retracted to pull the cap 114 towards the coaption element or means for coapting 110. The connection portion(s) 126 (e.g., joint(s), flexible connection(s), etc.) between the outer paddle 120 and inner paddle 122 are constrained in movement such that compression forces acting on the outer paddle 120 from the cap 114 being retracted towards the coaption element or means for coapting 110 cause the paddles or gripping elements 120, 122 to move radially outward. During movement from the open to closed position, the outer paddles 120 maintain an acute angle with the actuation element or means for actuating 112. The outer paddles 120 can optionally be biased toward a closed position. The inner paddles 122 during the same motion move through a considerably larger angle as they are oriented away from the coaption element or means for coapting 110 in the open condition and collapse along the sides of the coaption element or means for coapting 110 in the closed condition. In some embodiments, the inner paddles 122 are thinner and/or narrower than the outer paddles 120, and the connection portions 126, 128 (e.g., joints, flexible connections, etc.) connected to the inner paddles 122 can be thinner and/or more flexible. For example, this increased flexibility can allow more movement than the connection portion 124 connecting the outer paddle 120 to the cap 114. In some embodiments, the outer paddles 120 are narrower than the inner paddles 122. The connection portions 126, 128 connected to the inner paddles 122 can be more flexible, for example, to allow more movement than the connection portion 124 connecting the outer paddle 120 to the cap 114. In some embodiments, the inner paddles 122 can be the same or substantially the same width as the outer paddles (See for example, FIG. 48A).

Figure 12:
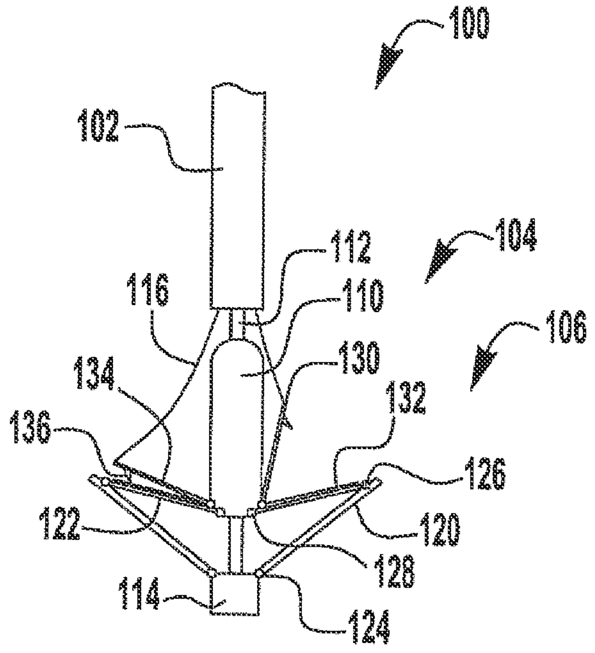
Figure 13:
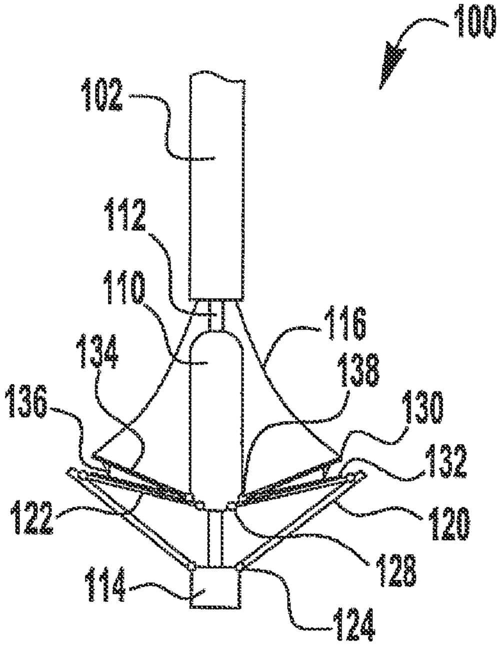

Referring now to FIGS. 11-13, the device 100 is shown in a partially open, grasp-ready condition. To transition from the fully closed to the partially open condition, the actuation element or means for actuating 112 (e.g., actuation wire, actuation shaft, etc.) is extended to push the cap 114 away from the coaption element or means for coapting 110, thereby pulling on the outer paddles 120, which in turn pull on the inner paddles 122, causing the anchors or anchor portion 106 to partially unfold. The actuation lines 116 are also retracted to open the clasps 130 so that the leaflets can be grasped. In the example illustrated by FIG. 11, the pair of inner and outer paddles 122, 120 are moved in unison, rather than independently, by a single actuation element or means for actuating 112. Also, the positions of the clasps 130 are dependent on the positions of the paddles 122, 120. For example, referring to FIG. 10 closing the paddles 122, 120 also closes the clasps.

Figure 11A:
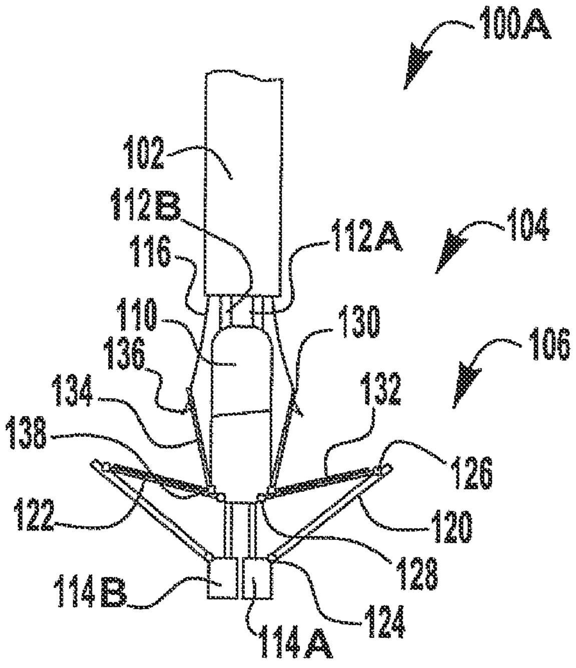
FIG. 11A shows an example embodiment of an implantable prosthetic device that is similar to the device illustrated by FIG. 11, but where the paddles are independently controllable.

FIG. 11A illustrates an example embodiment where the paddles 120, 122 are independently controllable. The device 100A illustrated by FIG. 11A is similar to the device illustrated by FIG. 11, except the device 100A includes an actuation element that is configured as two independent actuation elements or actuation wires 112A, 112B, which are coupled to two independent caps 114A, 114B. To transition a first inner paddle and a first outer paddle from the fully closed to the partially open condition, the actuation element or means for actuating 112A is extended to push the cap 114A away from the coaption element or means for coapting 110, thereby pulling on the outer paddle 120, which in turn pulls on the inner paddle 122, causing the first anchor portion 106 to partially unfold. To transition a second inner paddle and a second outer paddle from the fully closed to the partially open condition, the actuation element or means for actuating 112B is extended to push the cap 114 away from the coaption element or means for coapting 110, thereby pulling on the outer paddle 120, which in turn pulls on the inner paddle 122, causing the second anchor portion 106 to partially unfold. The independent paddle control illustrated by FIG. 11A can be implemented on any of the devices disclosed by the present application.

Referring now to FIG. 12, one of the actuation lines 116 is extended to allow one of the clasps 130 to close. Referring now to FIG. 13, the other actuation line 116 is extended to allow the other clasp 130 to close. Either or both of the actuation lines 116 can be repeatedly actuated to repeatedly open and close the clasps 130.

Figure 14:
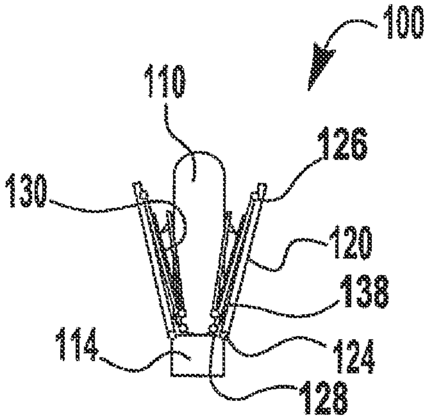

Referring now to FIG. 14, the device 100 is shown in a fully closed and deployed condition. The delivery sheath or means for delivery 102 and actuation element or means for actuating 112 is/are retracted and the paddles 120, 122 and clasps 130 remain in a fully closed position. Once deployed, the device 100 can be maintained in the fully closed position with a mechanical latch or can be biased to remain closed through the use of spring materials, such as steel, other metals, plastics, composites, etc. or shape-memory alloys such as Nitinol. For example, the connection portions 124, 126, 128, the joint portion(s) 138, and/or the inner and outer paddles 122, 120 and/or an additional biasing component (see component 524 in FIG. 28) can be formed of metals such as steel or shape-memory alloy, such as Nitinol—produced in a wire, sheet, tubing, or laser sintered powder—and are biased to hold the outer paddles 120 closed around the coaption element or means for coapting 110 and the clasps 130 pinched around native leaflets. Similarly, the fixed and moveable arms 132, 134 of the clasps 130 are biased to pinch the leaflets. In certain embodiments, the attachment or connection portions 124, 126, 128, joint portion(s) 138, and/or the inner and outer paddles 122, 120 and/or an additional biasing component (see component 524 in FIG. 28) can be formed of any other suitably elastic material, such as a metal or polymer material, to maintain the device in the closed condition after implantation.

Referring now to FIGS. 98-103, the implantable device 100 is shown provided with a cover 140. The cover 140 can be a cloth material such as polyethylene cloth of a fine mesh. The cloth cover can provide a blood seal on the surface of the spacer, and/or promote rapid tissue ingrowth. The cover 140 includes first and second cover portions 142, 144 that each cover different portions of the device 100. In some embodiments, a portion of one of the first and second cover portions 142, 144 overlaps a portion of the other of the first and second cover portion 142, 144. The first and second cover portions 142, 144 can be arranged in various ways, and in some embodiments, can include an overlapping portion 146 that overlaps one of the first and second cover portions 142, 144.

Figure 98:
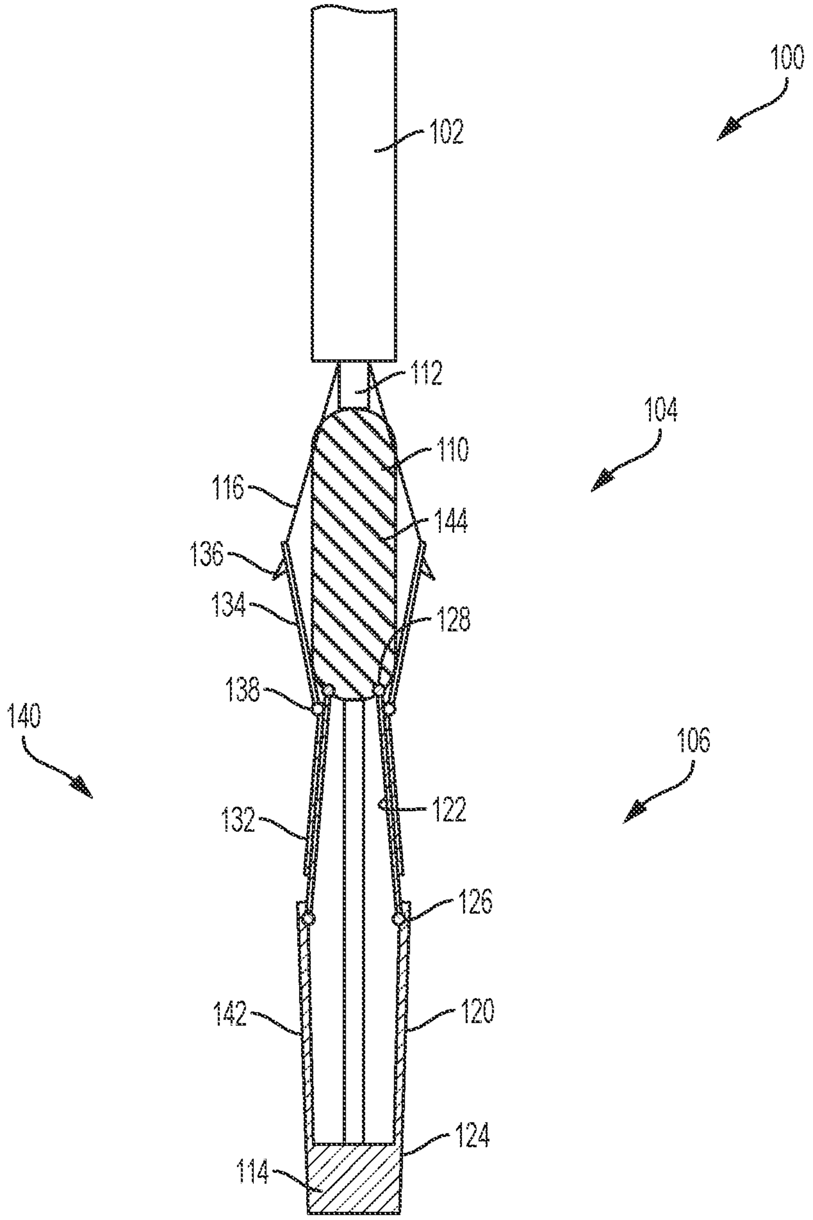
FIG. 98 shows an example embodiment of an implantable prosthetic device with a two-piece cover.

Referring now to FIGS. 98-101, various arrangements of the first and second cover portions 142, 144 are shown without overlapping portions 146. Referring now to FIG. 98, the first cover portion 142 (represented by thin line cross-hatching), which can be made from a single piece of material, extends from the cap 114 to cover the cap 114, outer paddles 120, inner paddles 122, and the fixed arms 132 of the clasps 130. The second cover 144 (represented by thick line cross-hatching), which can be a single piece of material, covers the coaption element or means for coapting 110.

Figure 99:
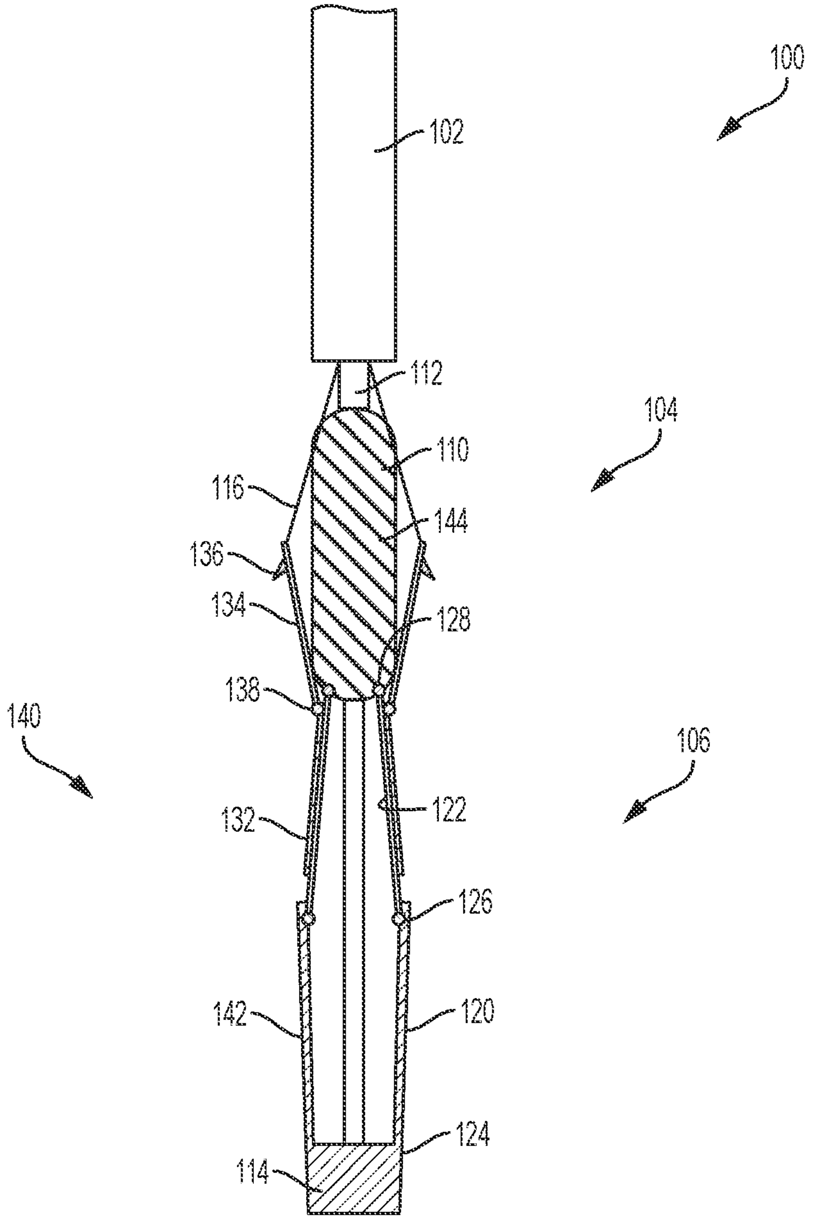
FIG. 99 shows an example embodiment of an implantable prosthetic device with a two-piece cover.

Referring now to FIG. 99, the first cover portion 142, which can be made from a single piece of material, extends from the cap 114 to cover the cap 114, outer paddles 120, inner paddles 122, the fixed arms 132 and moveable arms 134 of the clasps 130. As with the cover 140 of FIG. 98, the second cover 144 covers the coaption element or means for coapting 110.

Figure 100:
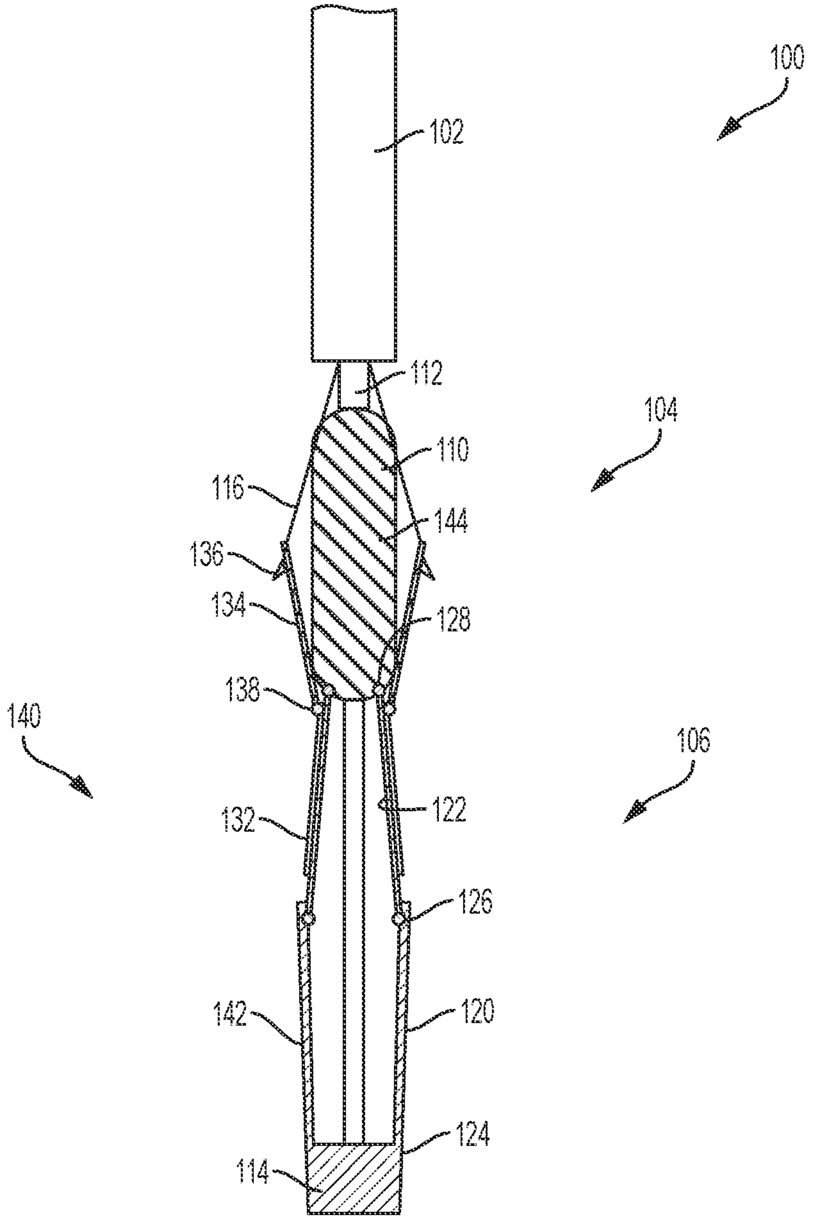
FIG. 100 shows an example embodiment of an implantable prosthetic device with a two-piece cover.

Referring now to FIG. 100, the first cover portion 142, which can be made from a single piece of material, extends from the cap 114 to cover the cap 114, outer paddles 120, inner paddles 122, and the fixed arms 132 of the clasps 130. The second cover 144, which can be made from a single piece of material, covers the coaption element or means for coapting 110 and extends from the coaption element or means for coapting 110 to cover the moveable arms 134 of the clasps 130.

Figure 101:
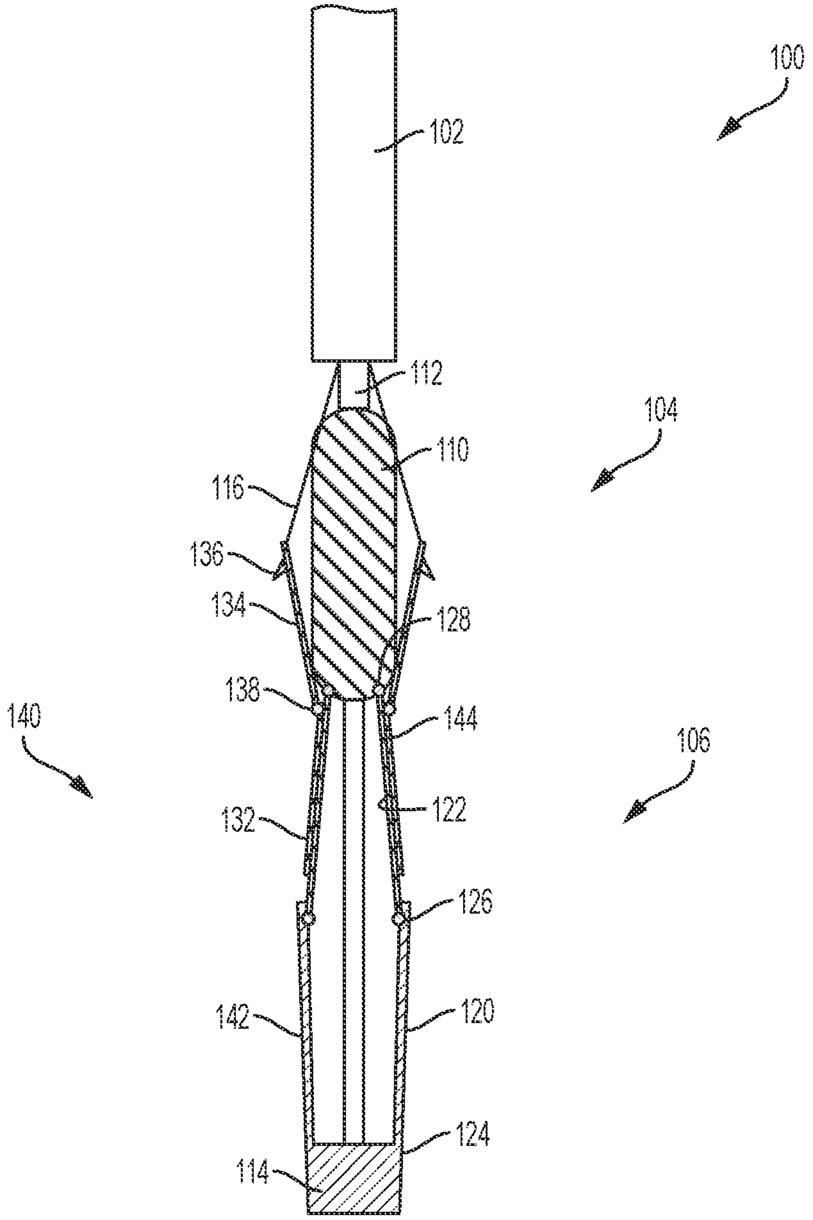
FIG. 101 shows an example embodiment of an implantable prosthetic device with a two-piece cover.

Referring now to FIG. 101, the first cover portion 142, which can be made from a single piece of material, extends from the cap 114 to cover the cap 114 and outer paddles 120. The second cover 144, which can be made from a single piece of material, covers the coaption element or means for coapting 110 and extends from the coaption element or means for coapting 110 to cover the inner paddles 122, and the fixed arms 132 and moveable arms 134 of the clasps 130.

Figure 102:
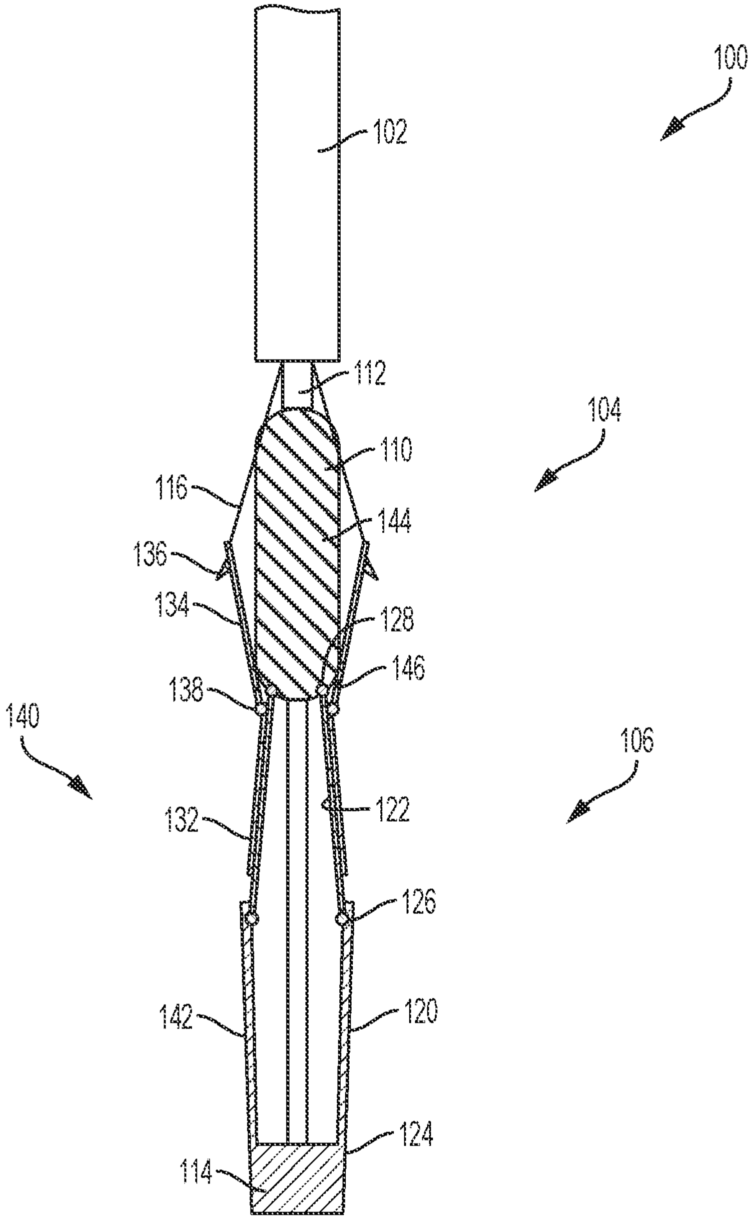
FIG. 102 shows an example embodiment of an implantable prosthetic device with a two-piece cover.
Figure 103:
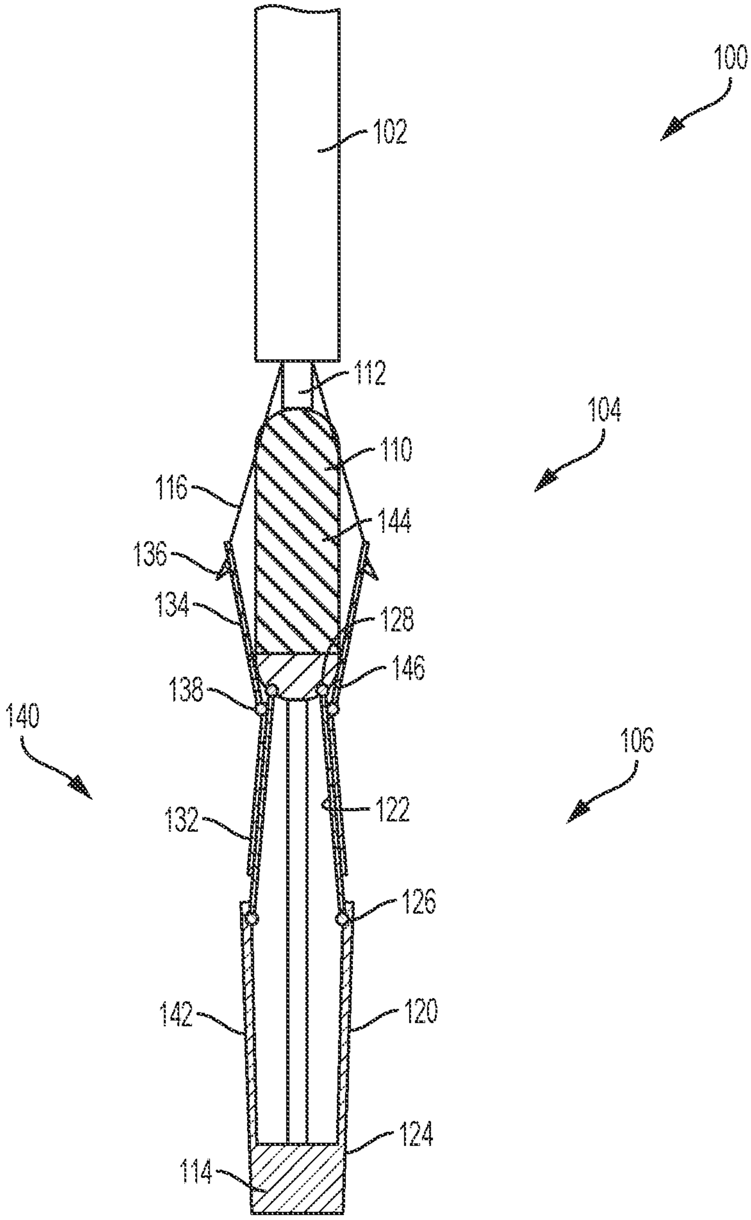
FIG. 103 shows an example embodiment of an implantable prosthetic device with a two-piece cover.

Referring now to FIGS. 102-103, arrangements of the first and second cover portions 142, 144 are shown that include an overlapping portion 146. Referring now to FIG. 102, the first cover portion 142, which can be made from a single piece of material, extends from the cap 114 to cover the cap 114, outer paddles 120, inner paddles 122, and the fixed arms 132 and moveable arms 134 of the clasps 130. The second cover 144, which can be made from a single piece of material, covers the coaption element or means for coapting 110 and includes overlapping portions 146 that extend from the coaption element or means for coapting 110 to overlap a portion of the moveable arms 134 that are covered by the first cover 142.

Referring now to FIG. 103, the first cover portion 142, which can be made from a single piece of material, extends from the cap 114 to cover the cap 114, outer paddles 120, inner paddles 122, and the fixed arms 132 of the clasps 130. The second cover 144, which can be made from a single piece of material, covers the coaption element or means for coapting 110 and moveable arms 134 of the clasps 130. The first cover 142 also includes overlapping portions 146 that extend from the fixed arms 132 and inner paddles 122 to overlap a portion of the moveable arms 134 and coaption element or means for coapting 110 that are covered by the second cover 144.

Referring now to FIGS. 15-20, the implantable device 100 of FIGS. 8-14 is shown being delivered and implanted within the native mitral valve MV of the heart H. The methods and steps shown and/or discussed can be performed on a living animal or on a simulation, such as on a cadaver, cadaver heart, simulator (e.g. with the body parts, heart, tissue, etc. being simulated), etc.

Figure 15:
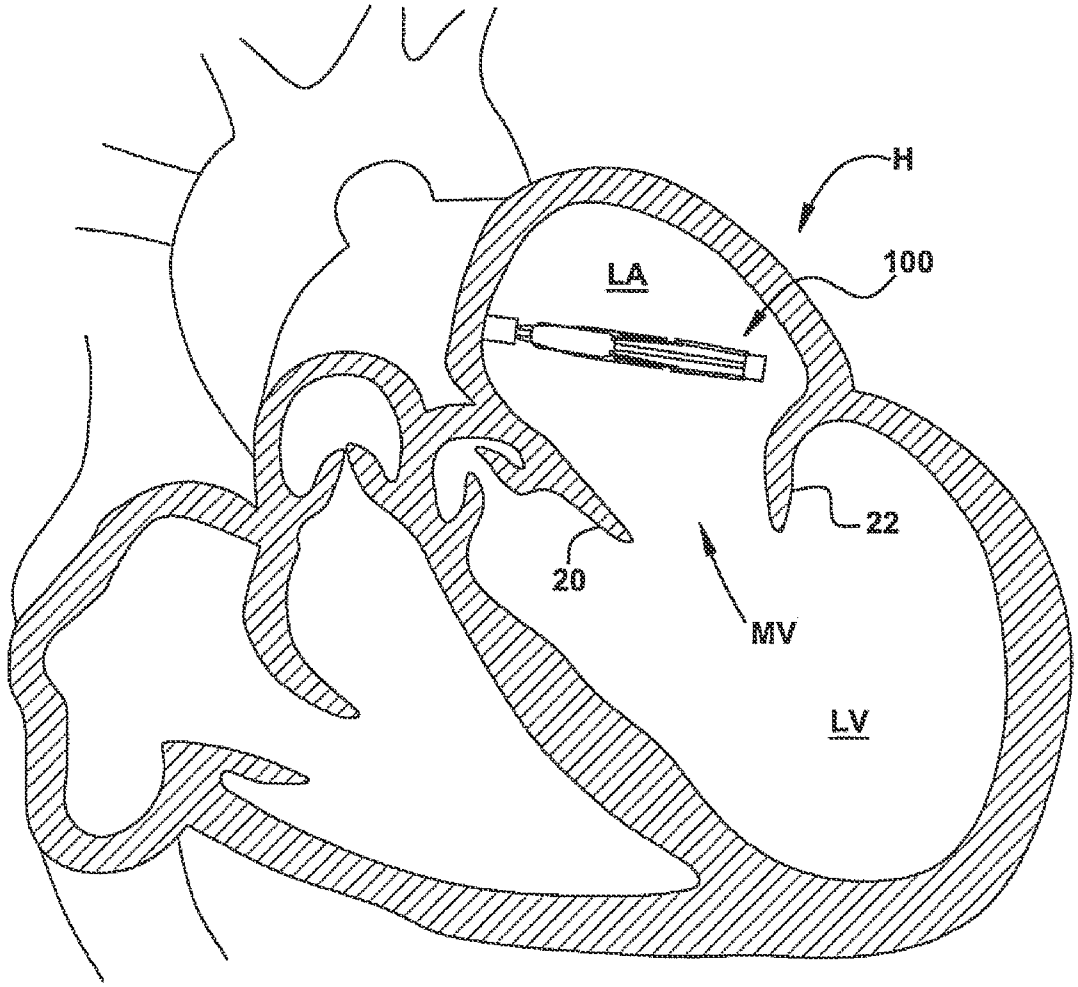
FIGS. 15-20 show the implantable prosthetic device of FIGS. 8-14 being delivered and implanted within the native valve.
Figure 16:
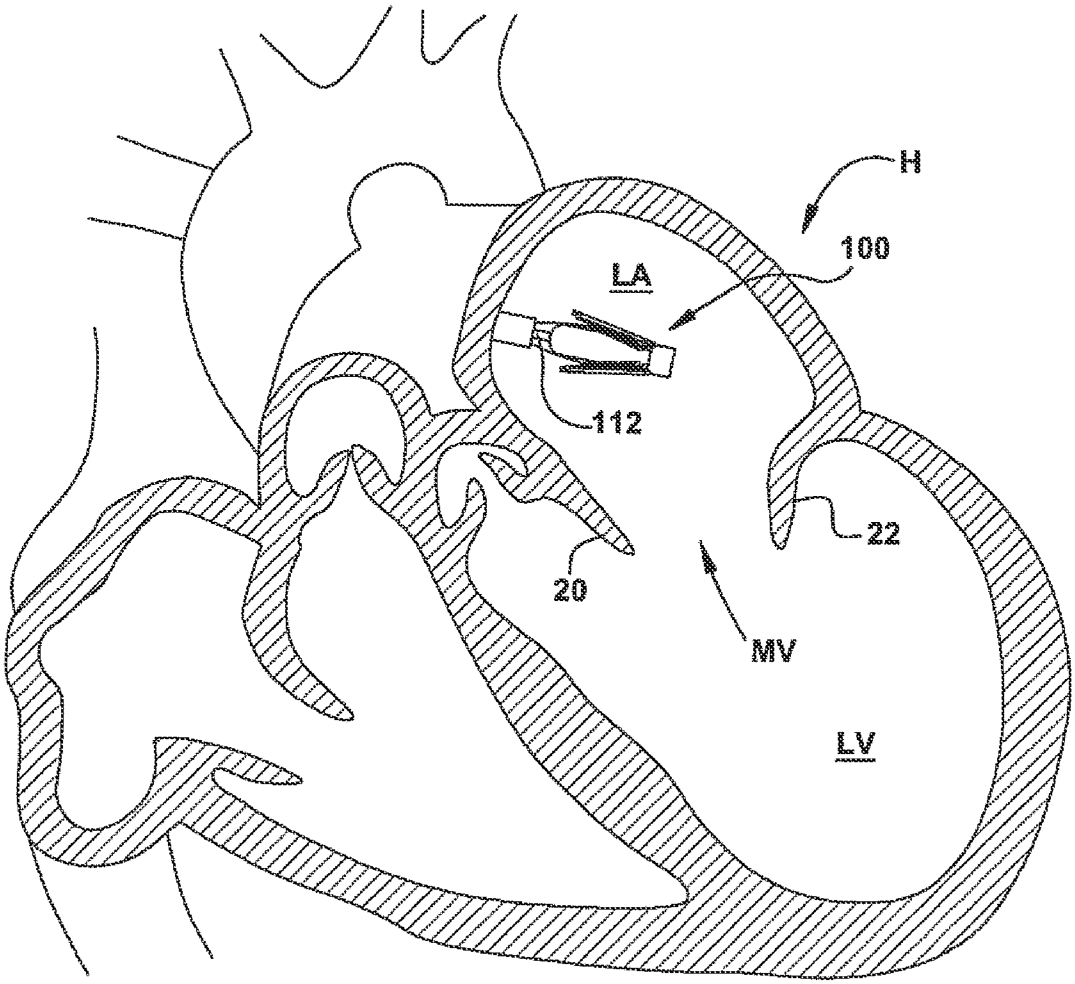
Figure 17:
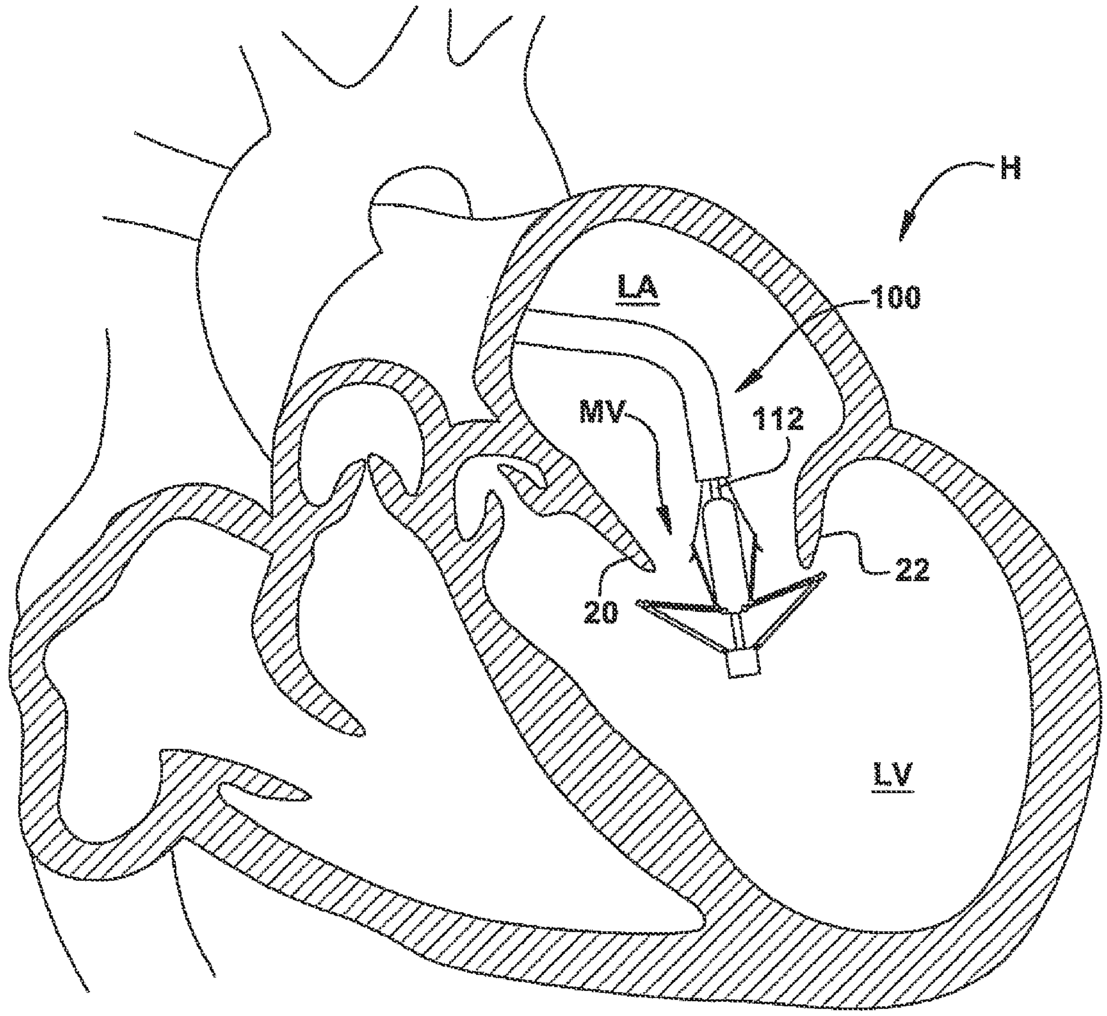
Figure 18:
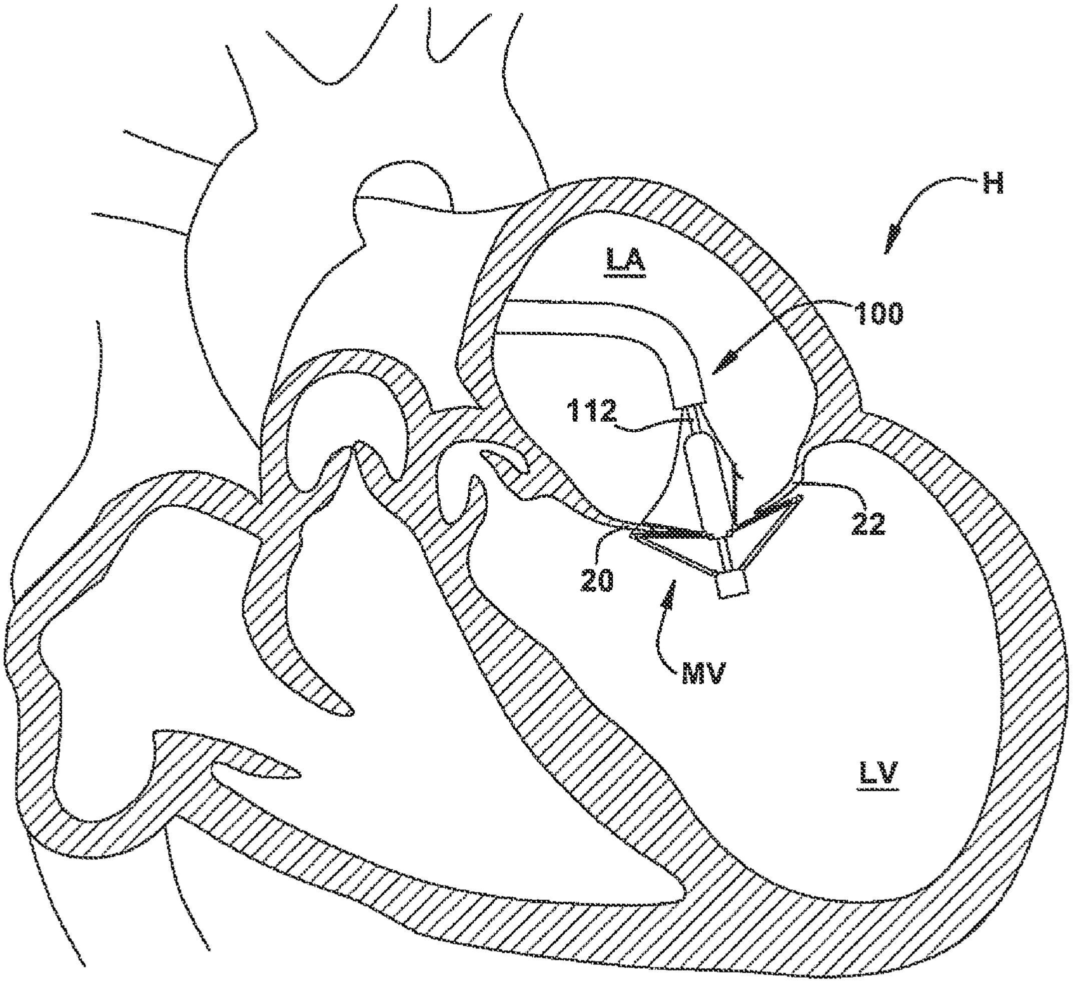
Figure 19:
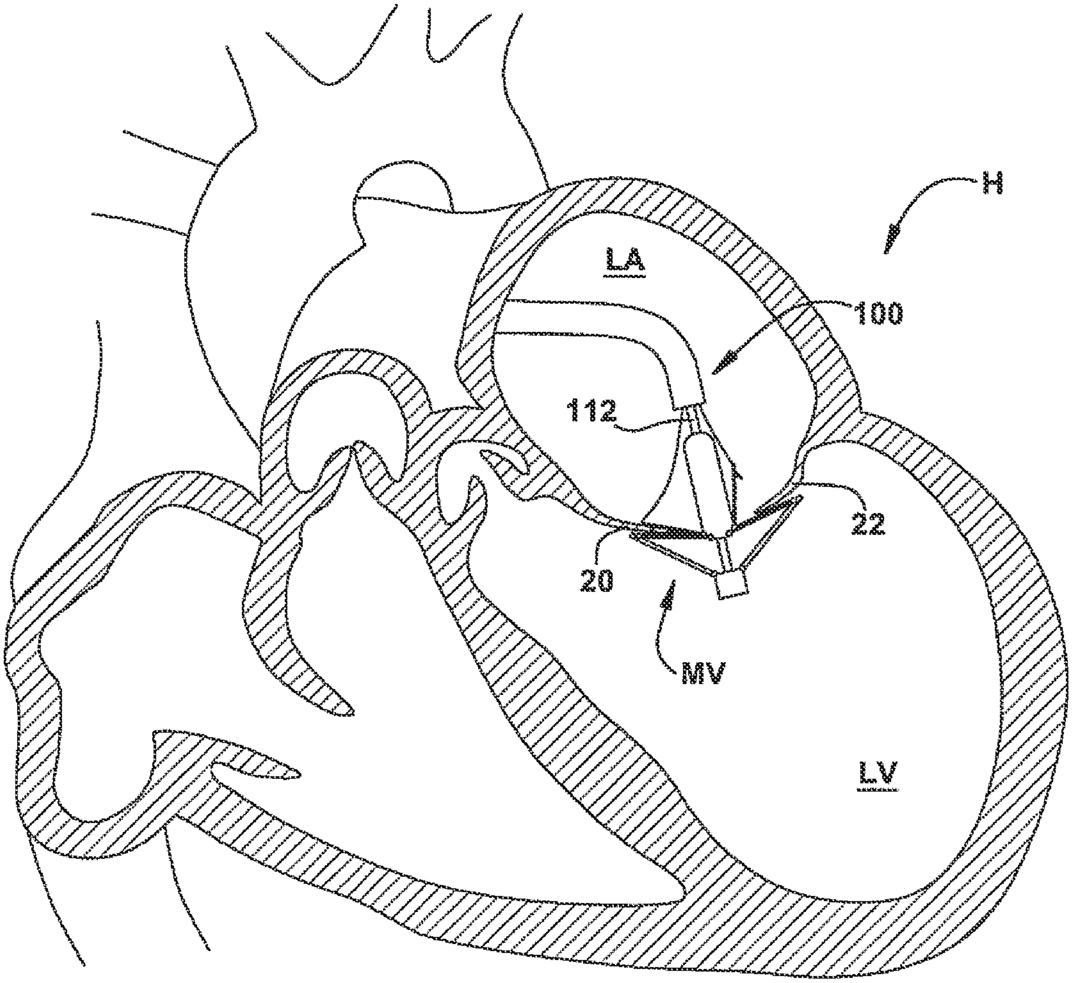
Figure 20:
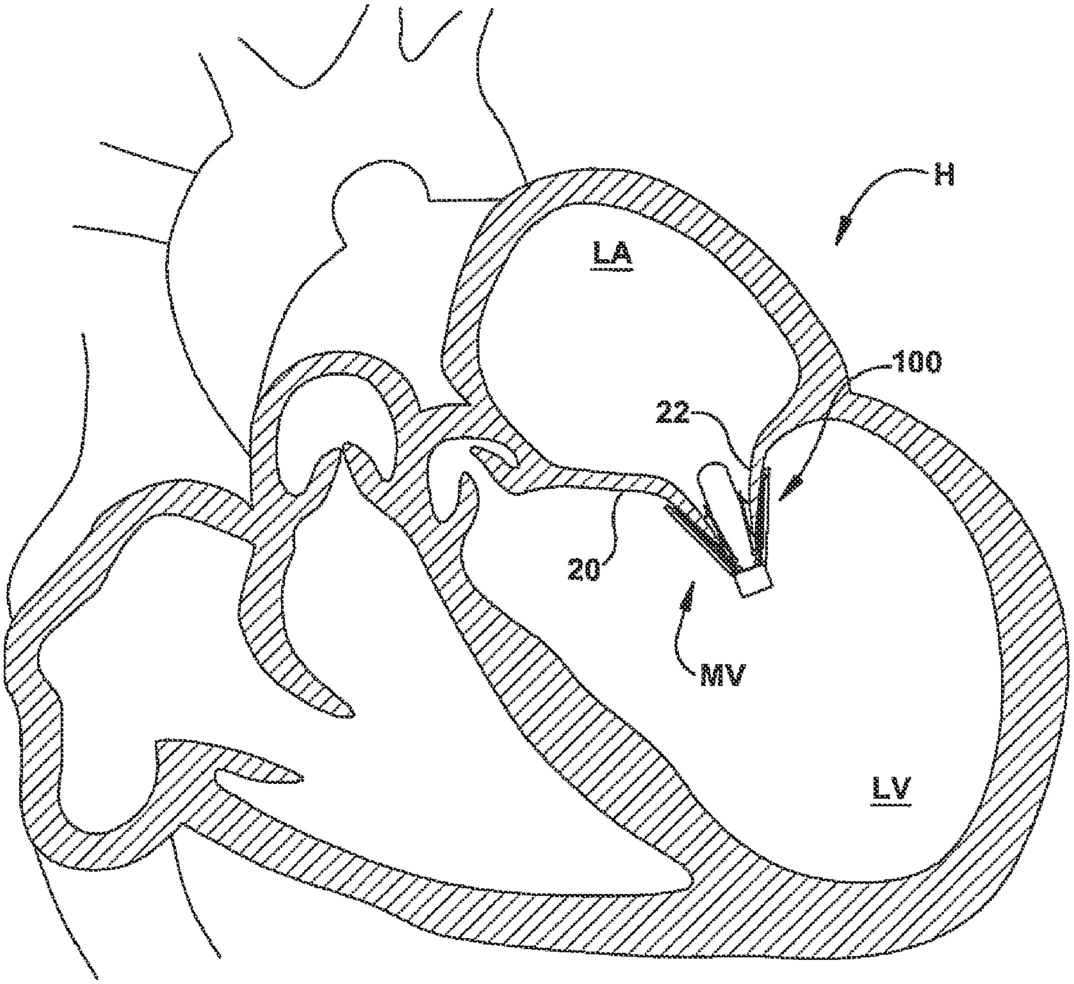

Referring now to FIG. 15, the delivery sheath is inserted into the left atrium LA through the septum and the device 100 is deployed from the delivery sheath in the fully open condition. The actuation element or means for actuating 112 is then retracted to move the device 100 into the fully closed condition shown in FIG. 16. As can be seen in FIG. 17, the device 100 is moved into position within the mitral valve MV into the ventricle LV and partially opened so that the leaflets 20,22 can be grasped. Referring now to FIG. 18, an actuation line 116 is extended to close one of the clasps 130, capturing a leaflet 20. FIG. 19 shows the other actuation line 116 being then extended to close the other clasp 130, capturing the remaining leaflet 22. As can be seen in FIG. 20, the delivery sheath or means for delivery 102 and actuation element or means for actuating 112 and actuation lines 116 are then retracted and the device 100 is fully closed and deployed in the native mitral valve MV.

Figure 21:
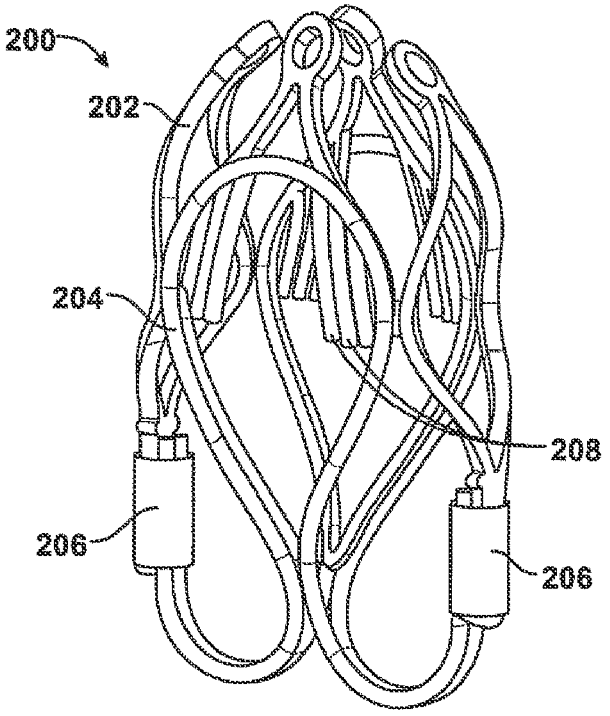
FIG. 21 shows an example embodiment of an implantable prosthetic device or frame of an implantable prosthetic device.

Referring now to FIG. 21, an example implantable prosthetic device 200 or frame thereof is shown. In some embodiments, the device 200 includes an annular spacer member 202, a fabric cover (not shown), and anchors 204 extending from the spacer member 202. The ends of each anchor 204 can be coupled to respective struts of the spacer member 202 by respective sleeves 206 that can be crimped or welded around the connection portions of the anchors 204 and the struts of the spacer member 202. In an example embodiment, a latching mechanism can bind the spacer member 202 to the anchor 204 within the sleeve 206. For example, the sleeve can be machined to have an interior shape that matches or is slightly smaller than the exterior shape of the ends of the spacer member 202 and the anchor 204, so that the sleeve can be friction fit on the connection portions. One or more barbs or projections 208 can be mounted on the frame of the spacer member 202. The free ends of the barbs or projections 208 can comprise various shapes including rounded, pointed, barbed, or the like. The projections 208 can exert a retaining force against native leaflets by virtue of the anchors 204, which are shaped to force the native leaflets inwardly into the spacer member 202.

Figure 22:
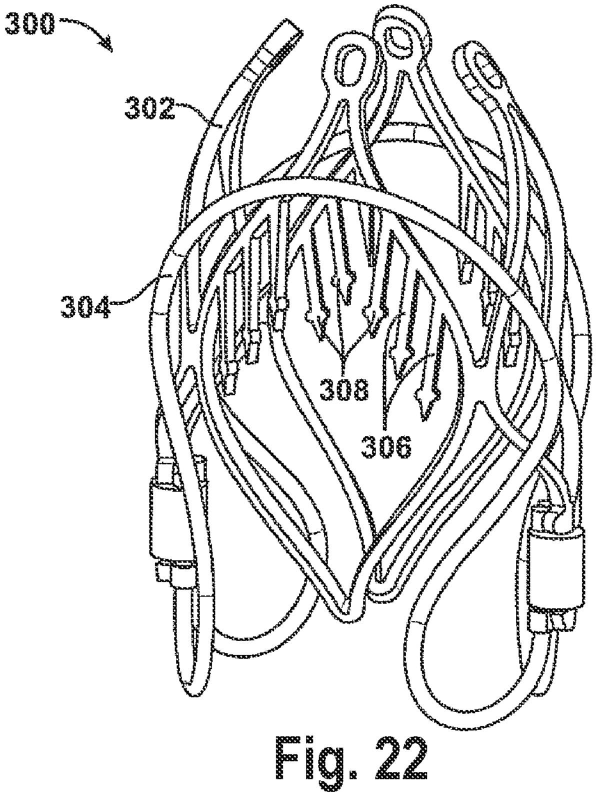
FIG. 22 shows an example embodiment of an implantable prosthetic device or frame of an implantable prosthetic device.

Referring now to FIG. 22, an example implantable prosthetic device 300 or frame thereof is shown. In some embodiments, the prosthetic spacer device 300 includes an annular spacer member 302, a fabric cover (not shown), and anchors 304 extending from the spacer member 302 and can be configured similar to the prosthetic spacer device 200. One or more barbs or projections 306 can be mounted on the frame of the spacer member 302. The ends of the projections 306 can comprise stoppers 308. The stoppers 308 of the projections can be configured in a wide variety of different ways. For example, the stoppers 308 can be configured to limit the extent of the projections 306 that can engage and/or penetrate the native leaflets and/or the stoppers can be configured to prevent removal of the projections 306 from the tissue after the projections 306 have penetrated the tissue.

The anchors 304 of the prosthetic spacer device 300 can be configured similar to the anchors 204 of the prosthetic spacer device 200 except that the curve of each anchor 304 comprises a larger radius than the anchors 204. As such, the anchors 304 cover a relatively larger portion of the spacer member 302 than the anchors 204. This can, for example, distribute the clamping force of the anchors 304 against the native leaflets over a relatively larger surface of the native leaflets in order to further protect the native leaflet tissue.

Additional details regarding the prosthetic spacer devices can be found, for example, in U.S. Patent Application Publication No. 2016/0331523 and U.S. Provisional Application No. 62/161,688, which applications are incorporated by reference herein. The devices 200, 300 can include any other features for an implantable prosthetic device discussed in the present application, and the device 200, 300 can be positioned to engage valve tissue 20, 22 as part of any suitable valve repair system (e.g., any valve repair system disclosed in the present application).

Referring now to FIGS. 23-27, an example embodiment of an implantable prosthetic spacer device 400 and components thereof are shown. The device 400 can include any other features for an implantable prosthetic device discussed in the present application, and the device 400 can be positioned to engage valve tissue 20, 22 as part of any suitable valve repair system (e.g., any valve repair system disclosed in the present application).

Figure 23:
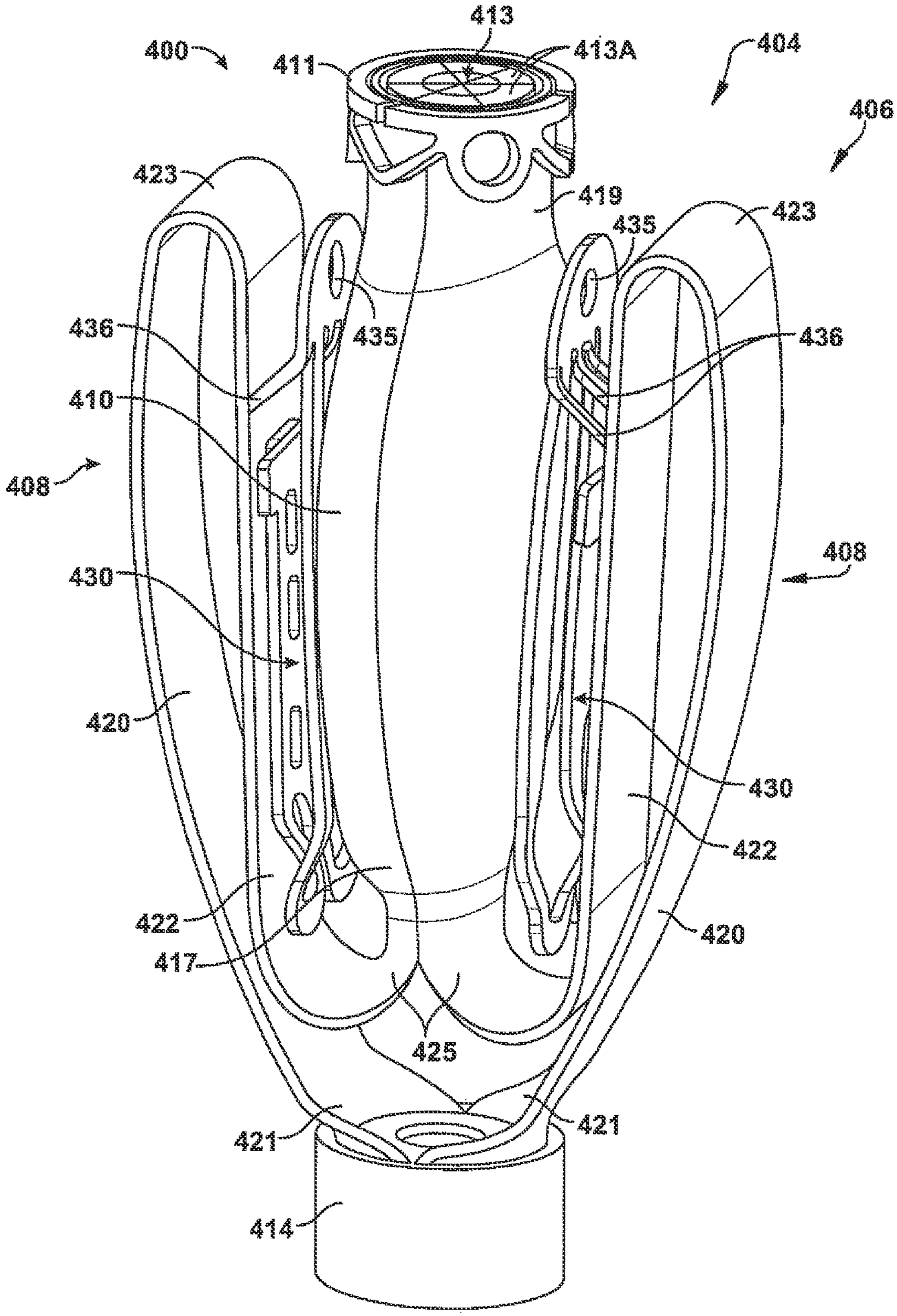
FIGS. 23-25 show example embodiments of an implantable prosthetic device or component of an implantable prosthetic device.

Referring now to FIG. 23, the implantable medical device 400 (e.g., implantable prosthetic device, prosthetic spacer, or coaption device, etc.) can include a coaption portion 404 and an anchor portion 406, the anchor portion 406 including a plurality of anchors 408. The coaption portion 404 includes a coaption or spacer member 410. The anchor portion 406 includes a plurality of paddles 420 (e.g., two in the illustrated embodiment), and a plurality of clasps 430 (e.g., two in the illustrated embodiment). A first or proximal collar 411, and a second collar or cap 414 are used to move the coaption portion 404 and the anchor portion 406 relative to one another.

Figure 25:
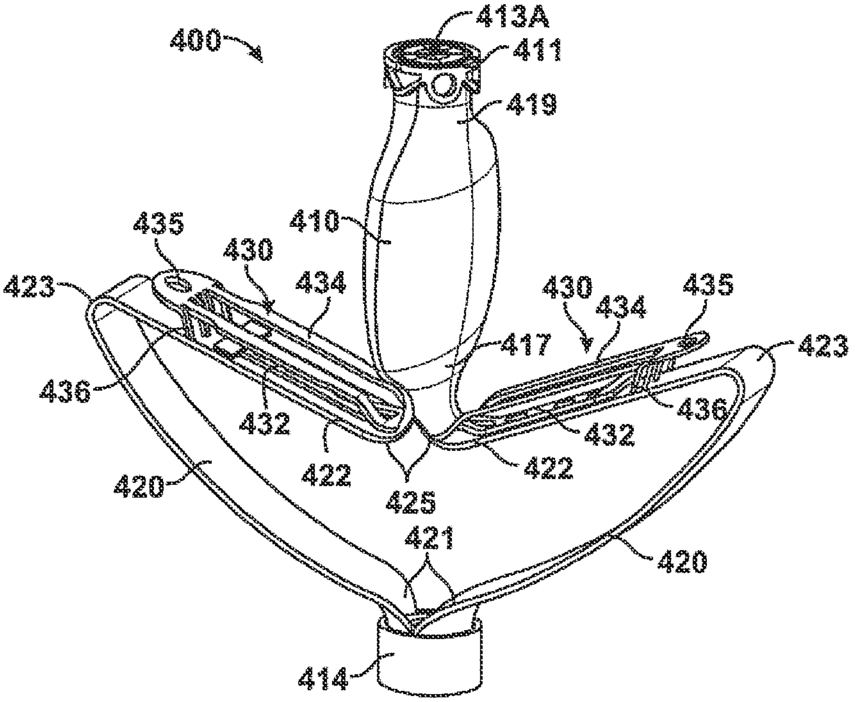

As shown in FIG. 25, first connection portions 425 of the anchors 408 can be coupled to and extend from a first portion 417 of the coaption or spacer member 410, and second connection portions 421 of the anchors 408 can be coupled to the second collar 414. The proximal collar 411 can be coupled to a second portion 419 of the coaption member 410.

The coaption member 410 and the anchors 408 can be coupled together in various ways. For example, as shown in the illustrated embodiment, the coaption member 410 and the anchors 408 can be coupled together by integrally forming the coaption member 410 and the anchors 408 as a single, unitary component. This can be accomplished, for example, by forming the coaption member 410 and the anchors 408 from a braided or woven material, such as braided or woven nitinol wire. In some embodiments, the coaption member 410 and the anchors 408 can be coupled together by welding, fasteners, adhesive, joint connections, sutures, friction fittings, swaging, and/or other means for coupling.

Figure 24:
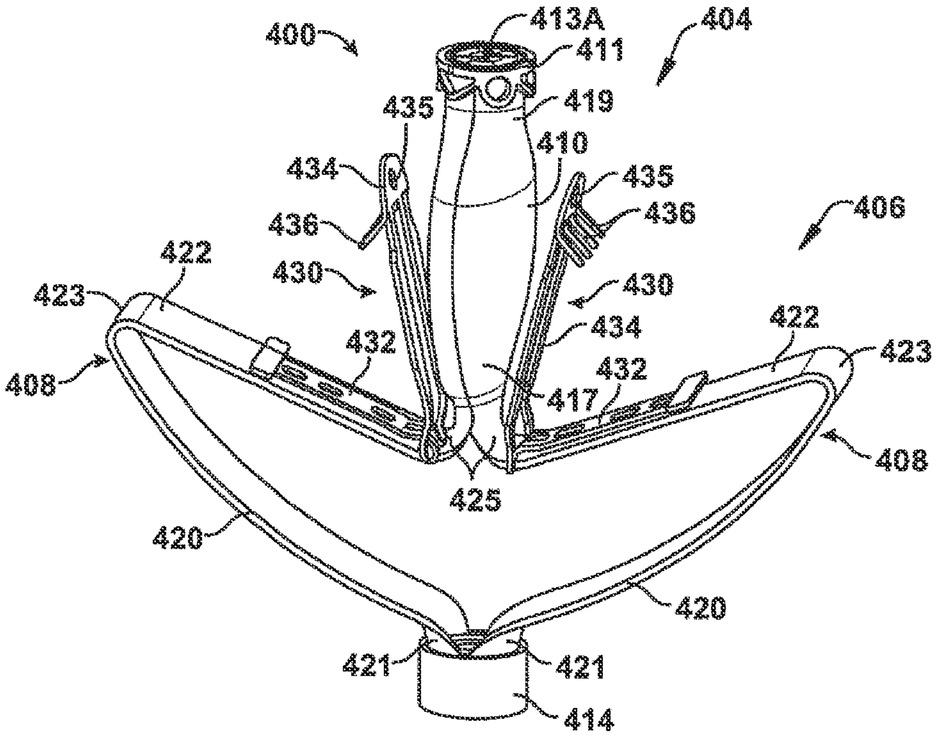

Referring now to FIG. 24, the anchors 408 can comprise first portions or outer paddles 420 and second portions or inner paddles 422 separated by joint portions 423. In this manner, the anchors 408 are configured similar to legs in that the inner paddles 422 are like upper portions of the legs, the outer paddles 420 are like lower portions of the legs, and the joint portions 423 are like knee portions of the legs. In some embodiments, the inner paddle portion 422, the outer paddle portion 420, and the joint portion 423 are formed from a continuous strip of a fabric, such as a metal fabric. In some embodiments, the strip of fabric can be a composite strip of fabric.

The anchors 408 can be configured to move between various configurations by axially moving the cap 414 relative to the proximal collar 411 and thus moving the anchors 408 (e.g., moving the anchors 408 relative to a coaption member 410 and/or another portion of the device) along a longitudinal axis extending between the first or distal and second or proximal portions 417,419 of the coaption member 410. For example, the anchors 408 can be positioned in a straight configuration by moving the cap 414 away from the coaption member 410 and/or another portion of the device. In the straight configuration, the paddle portions are aligned or straight in the direction of the longitudinal axis of the device and the joint portions 423 of the anchors 408 are adjacent the longitudinal axis of the device and/or a coaption member 410 of the device. From the straight configuration, the anchors 408 can be moved to a fully folded configuration (e.g., FIG. 23) by moving the anchors 408 toward the coaption member 410 and/or another portion of the device. Initially as the cap 414 moves toward the coaption member 410 and/or another portion of the device, the anchors 408 bend at the joint portions 423,425,421 and the joint portions 423 move radially outwardly relative to the longitudinal axis of the device and/or a coaption member 410 of the device and axially toward the first portion 417 of the device and/or coaption member 410, as shown in FIGS. 24-25. As the cap 414 continues to move toward the coaption member 410 and/or another portion of the device, the joint portions 423 move radially inwardly relative to the longitudinal axis of the device and/or coaption member 410 and axially toward the proximal portion 419 of the device and/or coaption member 410, as shown in FIG. 23.

In some embodiments, an angle between the inner paddles 422 of the anchors 408 and the coaption member 410 and/or a midline of the device can be approximately 180 degrees when the anchors 408 are in a straight configuration, and the angle between the inner paddles 422 of the anchors 408 and the coaption member 410 and/or a midline of the device can be approximately 0 degrees when the anchors 408 are in the fully folded configuration (See FIG. 23). The anchors 408 can be positioned in various partially folded configurations such that the angle between the inner paddles 422 of the anchors 408 and the coaption member 410 and/or a midline of the device can be approximately 10-170 degrees or approximately 45-135 degrees. The midline can be a longitudinal axis of the device.

Configuring the prosthetic spacer device 400 such that the anchors 408 can extend to a straight or approximately straight configuration (e.g. approximately 120-180 degrees relative to the coaption member 410 and/or a midline of the device) can provide several advantages. For example, this can reduce the radial crimp profile of the prosthetic spacer device 400. It can also make it easier to grasp the native leaflets by providing a larger opening in which to grasp the native leaflets. Additionally, the relatively narrow, straight configuration can prevent or reduce the likelihood that the prosthetic spacer device 400 will become entangled in native anatomy (e.g., chordae tendineae) when positioning and/or retrieving the prosthetic spacer device 400 into the delivery apparatus.

Referring again to FIG. 24, the clasps 430 can comprise attachment or fixed portions 432 and arm or moveable portions 434. The attachment or fixed portions 432 can be coupled to the inner paddles 422 of the anchors 408 in various ways such as with sutures, adhesive, fasteners, welding, stitching, swaging, friction fit and/or other means for coupling or fastening.

In some embodiments, the moveable portions 434 can articulate, flex, or pivot relative to the fixed portions 432 between an open configuration (e.g., FIG. 24) and a closed configuration (FIGS. 23 and 25). In some embodiments, the clasps 430 can be biased to the closed configuration. In some embodiments, in the open configuration, the fixed portions 432 and the moveable portions 434 flex or pivot away from each other such that native leaflets can be positioned between the fixed portions 432 and the moveable portions 434. In some embodiments, in the closed configuration, the fixed portions 432 and the moveable portions 434 flex or pivot toward each other, thereby clamping the native leaflets between the fixed portions 432 and the moveable portions 434.

Figure 26:
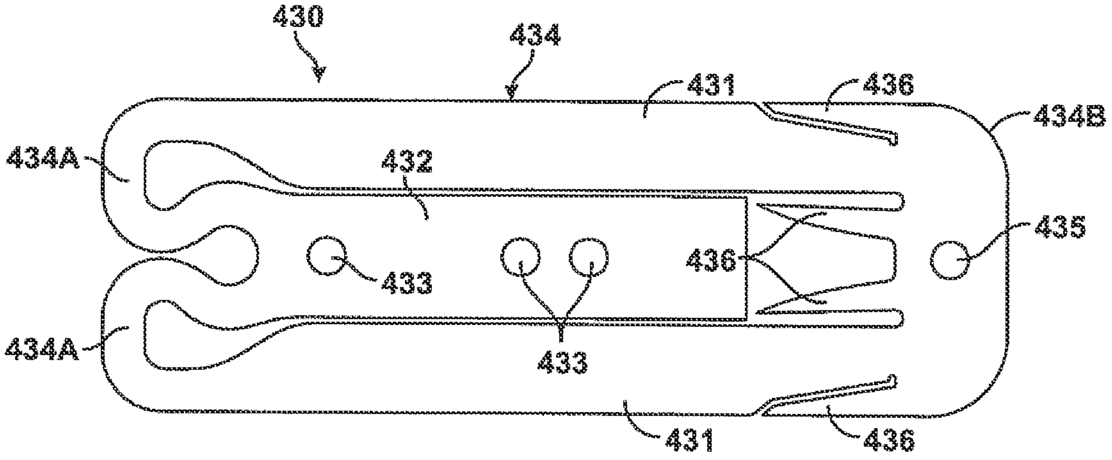
FIGS. 26 and 27 show an example embodiment of a clasp for use in an implantable prosthetic device.
Figure 27:
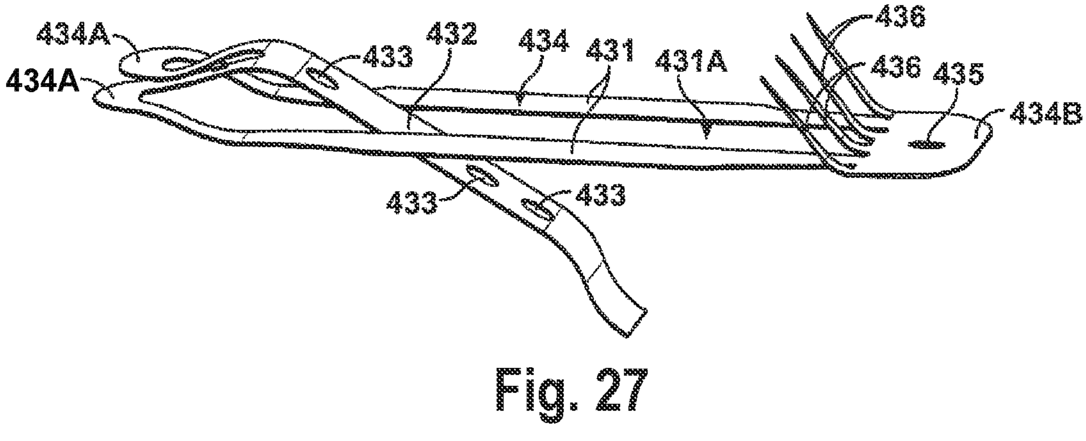

Referring to FIGS. 26-27, clasps 430 are shown in top and perspective views. The fixed portions 432 (only one shown in FIGS. 26-27) can comprise one or more openings 433 (e.g., three in the illustrated embodiment). At least some of the openings 433 can be used to couple the fixed portions 432 to the anchors 408. For example, sutures and/or fasteners can extend through the openings 433 to couple the fixed portions 432 to the anchors 408 or other attachments, such as welding, adhesives, etc. can be used.

The moveable portions 434 can comprise one or more side beams 431. When two side beams are included as illustrated, the side beams can be spaced apart to form slots 431A. The slots 431A can be configured to receive the fixed portions 432. The moveable portions 434 can also include spring portions 434A that are coupled to the fixed portions 432 and barb support portions 434B disposed opposite the spring portions 434A.

The barb support portions 434B can comprise gripper or attachment elements such as barbs 436 and/or other means for frictionally engaging native leaflet tissue. The gripper elements can be configured to engage and/or penetrate the native leaflet tissue to help retain the native leaflets between the fixed portions 432 and moveable portions 434 of the clasps 430.

The barb support portions 434B can also comprise eyelets 435, which can be used to couple the barb support portions 434B to an actuation mechanism configured to flex or pivot the moveable portions 434 relative to the fixed portions 432. Additional details regarding coupling the clasps 430 to the actuation mechanism are provided below.

In some embodiments, the clasps 430 can be formed from a shape memory material such as nitinol, stainless steel, and/or shape memory polymers. In certain embodiments, the clasps 430 can be formed by laser-cutting a piece of flat sheet material (e.g., nitinol) or a tube in the configuration shown in FIG. 26 or a similar or different configuration and then shape-setting the clasp 430 in the configuration shown in FIG. 27.

Shape-setting the clasps 430 in this manner can provide several advantages. For example, the clasps 430 can optionally be compressed from the shape-set configuration (e.g., FIG. 27) to the flat configuration (e.g., FIG. 26), or another configuration which reduces the radial crimp profile of the clasps 430. For example, the barbs can optionally be compressed to a flat configuration. Reducing the radial crimp profile can improve trackability and retrievability of the prosthetic spacer device 400 relative to a catheter shaft of a delivery apparatus because barbs 436 are pointing radially inwardly toward the anchors 408 when the prosthetic spacer device 400 is advanced through or retrieved into the catheter shaft (see, e.g., FIG. 33). This can prevent or reduce the likelihood that the clasps 430 may snag or skive the catheter shaft.

In addition, shape-setting the clasps 430 in the configuration shown in FIG. 27 can increase the clamping force of the clasps 430 when the clasps 430 are in the closed configuration. This is because the moveable portions 434 are shape-set relative to the fixed portions 432 to a first position (e.g., FIG. 27) which is beyond the position the moveable portions 434 can achieve when the clasps 430 are attached to the anchors 408 (e.g., FIG. 25) because the anchors 408 prevent the moveable portions 434 from further movement toward the shape-set configuration. This results in moveable portions 434 having a preload (i.e., the clamping force is greater than zero) when the clasps 430 are attached to the anchors 408 and in the closed configuration. Thus, shape-setting the clasps 430 in the FIG. 27 configuration can increase the clamping force of the clasps 430 compared to clasps that are shape-set in the closed configuration.

The magnitude of the preload of the clasps 430 can be altered by adjusting the angle in which the moveable portions 434 are shape-set relative to the fixed portions 432. For example, increasing the relative angle between the moveable portions 434 and the fixed portions 432 increases the preload, and decreasing the relative angle between the moveable portions 434 and the fixed portions 432 decreases the preload. It can also be adjusted in other ways, such as based on the configuration of the joint, hinge, materials, etc.

In some embodiments, the proximal collar 411 and/or the coaption member 410 can comprise a hemostatic seal 413 configured to reduce or prevent blood from flowing through the proximal collar 411 and/or the coaption member 410. For example, in some embodiments, the hemostatic seal 413 can comprise a plurality of flexible flaps 413A, as shown in FIG. 23. In some embodiments, the flaps 413A can be configured to pivot from a sealed configuration to an open configuration to allow a shaft of a delivery apparatus to extend through the second collar 414. In one example embodiment, the flaps 413A form a seal around the shaft of the delivery apparatus. When the shaft of the delivery apparatus is removed, the flaps 413A can be configured to return to the sealed configuration from the open configuration.

Figure 23A:
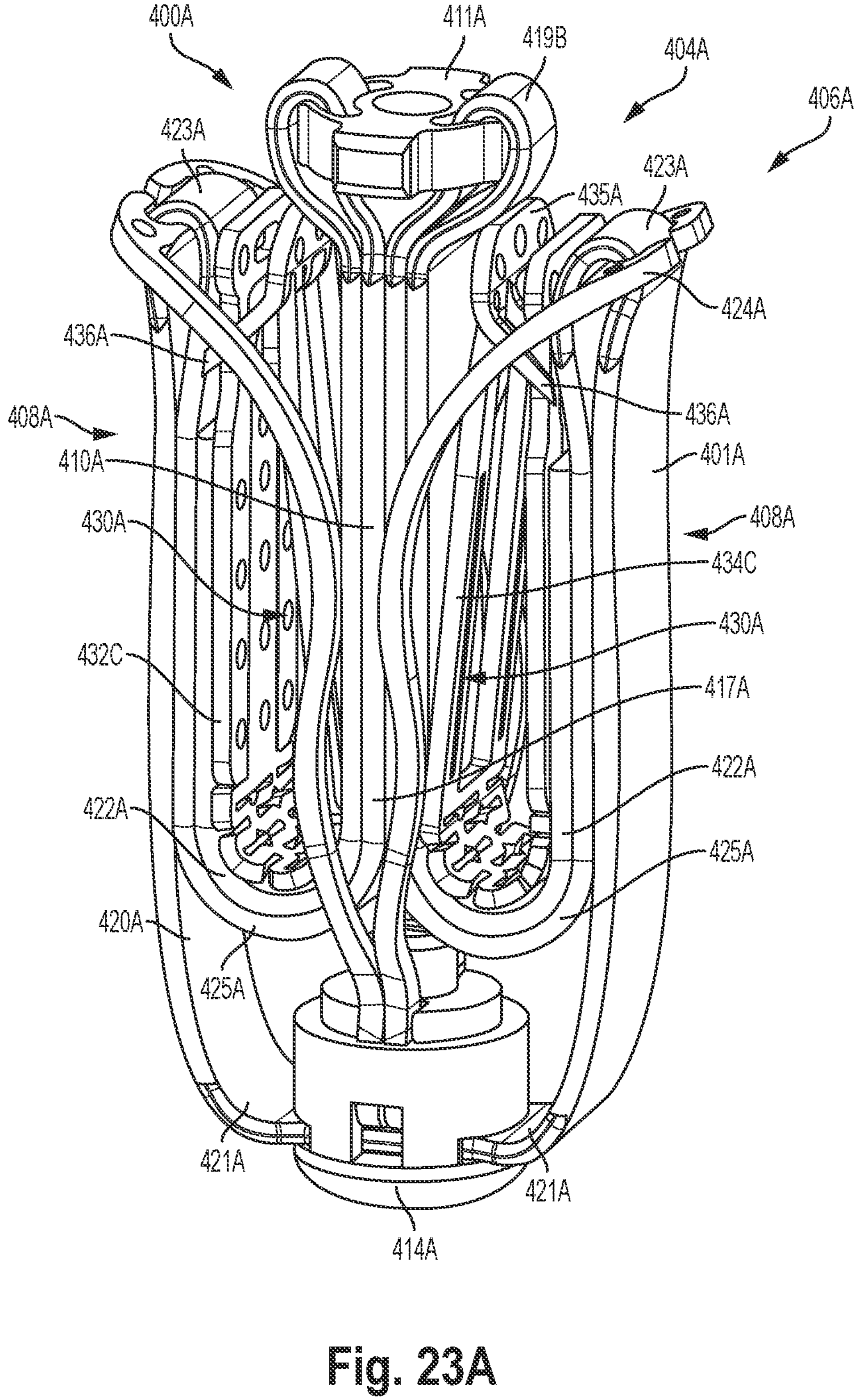
FIG. 23A shows an example embodiment of an implantable prosthetic device.

Referring now to FIG. 23A, an embodiment of an implantable prosthetic spacer device 400A is shown. The device 400A can include any other features for an implantable prosthetic device discussed in the present application, and the device 400A can be positioned to engage valve tissue 20, 22 as part of any suitable valve repair system (e.g., any valve repair system disclosed in the present application).

The implantable medical device 400A (e.g., implantable prosthetic device, prosthetic spacer, or coaption device, etc.) can include a coaption portion 404A and an anchor portion 406A, the anchor portion 406A including a plurality of anchors 408A. The coaption portion 404A includes a coaption member or spacer 410A. The anchor portion 406A includes a plurality of paddles 420A (e.g., two in the illustrated embodiment), and a plurality of clasps 430A (e.g., two in the illustrated embodiment). A first or proximal collar 411A, and a second collar or cap 414A are used to move the coaption portion 404A and the anchor portion 406A relative to one another.

The coaption member 410A extends from a proximal portion 419A assembled to the collar 411A to a distal portion 417A that connects to the anchors 408A. The coaption member 410A and the anchors 408A can be coupled together in various ways. For example, as shown in the illustrated embodiment, the coaption member 410A and the anchors 408A can be coupled together by integrally forming the coaption member 410A and the anchors 408A as a single, unitary component. This can be accomplished, for example, by forming the coaption member 410A and the anchors 408A from a continuous strip 401A of a braided or woven material, such as braided or woven nitinol wire.

The anchors 408A are attached to the coaption member 410A by hinge portions 425A and to the cap 414A by hinge portions 421A. The anchors 408A can comprise first portions or outer paddles 420A and second portions or inner paddles 422A separated by joint portions 423A. The joint portions 423A are attached to paddle frames 424A that are hingeably attached to the cap 414A. In this manner, the anchors 408A are configured similar to legs in that the inner paddles 422A are like upper portions of the legs, the outer paddles 420A are like lower portions of the legs, and the joint portions 423A are like knee portions of the legs. In the illustrated example, the inner paddle portion 422A, the outer paddle portion 420A, and the joint portion 423A are formed from the continuous strip of fabric 401A, such as a metal fabric.

The anchors 408A can be configured to move between various configurations by axially moving the cap 414A relative to the proximal collar 411A and thus moving the anchors 408A (e.g., moving the anchors 408A relative to a coaption member 410A and/or another portion of the device) along a longitudinal axis extending between the cap 414A and the proximal collar 411A. For example, the anchors 408 can be positioned in a straight configuration by moving the cap 414A away from the coaption member 410A and/or another portion of the device. In the straight configuration, the paddle portions 420A, 422A are aligned or straight in the direction of the longitudinal axis of the device and the joint portions 423A of the anchors 408A are adjacent the longitudinal axis of the device and/or coaption member 410A of the device. From the straight configuration, the anchors 408 can be moved to a fully folded configuration (e.g., FIG. 23A) by moving the toward the coaption member 410A and/or another portion of the device. Initially, as the cap 414A moves toward the coaption member 410A and/or another portion of the device, the anchors 408A bend at joint portions 421A, 423A, 425A, and the joint portions 423A move radially outwardly relative to the longitudinal axis of the device 400A and axially toward the distal portion 417A of the device and/or coaption member 410A. As the cap 414A continues to move toward the coaption member 410A and/or another portion of the device, the joint portions 423A move radially inwardly relative to the longitudinal axis of the device 400A and axially toward the proximal portion 419B of the device and/or coaption member 410A, as shown in FIG. 23A.

In some embodiments, an angle between the inner paddles 422A of the anchors 408A and the coaption member 410A and/or a midline of the device can be approximately 180 degrees when the anchors 408A are in the straight configuration, and the angle between the inner paddles 422A of the anchors 408A and the coaption member 410A and/or a midline of the device can be approximately 0 degrees when the anchors 408A are in the fully folded configuration (see FIG. 23A). The anchors 408A can be positioned in various partially folded configurations such that the angle between the inner paddles 422A of the anchors 408A and the coaption member 410A and/or a midline of the device can be approximately 10-170 degrees or approximately 45-135 degrees. The midline can be a longitudinal axis of the device.

Configuring the prosthetic spacer device 400A such that the anchors 408A can extend to a straight or approximately straight configuration (e.g. approximately 120-180 degrees relative to the coaption member 410A and/or a midline of the device) can provide several advantages. For example, this can reduce the radial crimp profile of the prosthetic spacer device 400A. It can also make it easier to grasp the native leaflets by providing a larger opening in which to grasp the native leaflets. Additionally, the relatively narrow, straight configuration can prevent or reduce the likelihood that the prosthetic spacer device 400A will become entangled in native anatomy (e.g., chordae tendineae) when positioning and/or retrieving the prosthetic spacer device 400A into the delivery apparatus.

The clasps 430A can comprise attachment or fixed portions 432C and arm or moveable portions 434C. The attachment or fixed portions 432C can be coupled to the inner paddles 422A of the anchors 408A in various ways such as with sutures, adhesive, fasteners, welding, stitching, swaging, friction fit, and/or other means for coupling. The clasps 430A are similar to the clasps 430.

In some embodiments, the moveable portions 434C can articulate, flex, or pivot relative to the fixed portions 432C between an open configuration and a closed configuration. In some embodiments, the clasps 430A can be biased to the closed configuration. In the open configuration, the fixed portions 432C and the moveable portions 434C articulate, pivot, or flex away from each other such that native leaflets can be positioned between the fixed portions 432C and the moveable portions 434C. In the closed configuration, the fixed portions 432C and the moveable portions 434C articulate, pivot, or flex toward each other, thereby clamping the native leaflets between the fixed portions 432C and the moveable portions 434C.

The strip 401A is attached to the collar 411A, cap 414A, paddle frames 424A, clasps 430A to form both the coaption portion 404A and the anchor portion 406A of the device 400A. In the illustrated embodiment, the coaption member 410A, hinge portions 421A, 423A, 425A, outer paddles 420A, and inner paddles 422A are formed from the continuous strip 401A. The continuous strip 401A can be a single layer of material or can include two or more layers. In certain embodiments, portions of the device 400A have a single layer of the strip of material 401A and other portions are formed from multiple overlapping or overlying layers of the strip of material 401A. For example, FIG. 23A shows the coaption member 410A and inner paddles 422A formed from multiple overlapping layers of the strip of material 401A. The single continuous strip of material 401A can start and end in various locations of the device 400A. The ends of the strip of material 401A can be in the same location or different locations of the device 400A. For example, in the illustrated embodiment of FIG. 23A, the strip of material begins and ends in the location of the inner paddles 422A.

Figure 30:
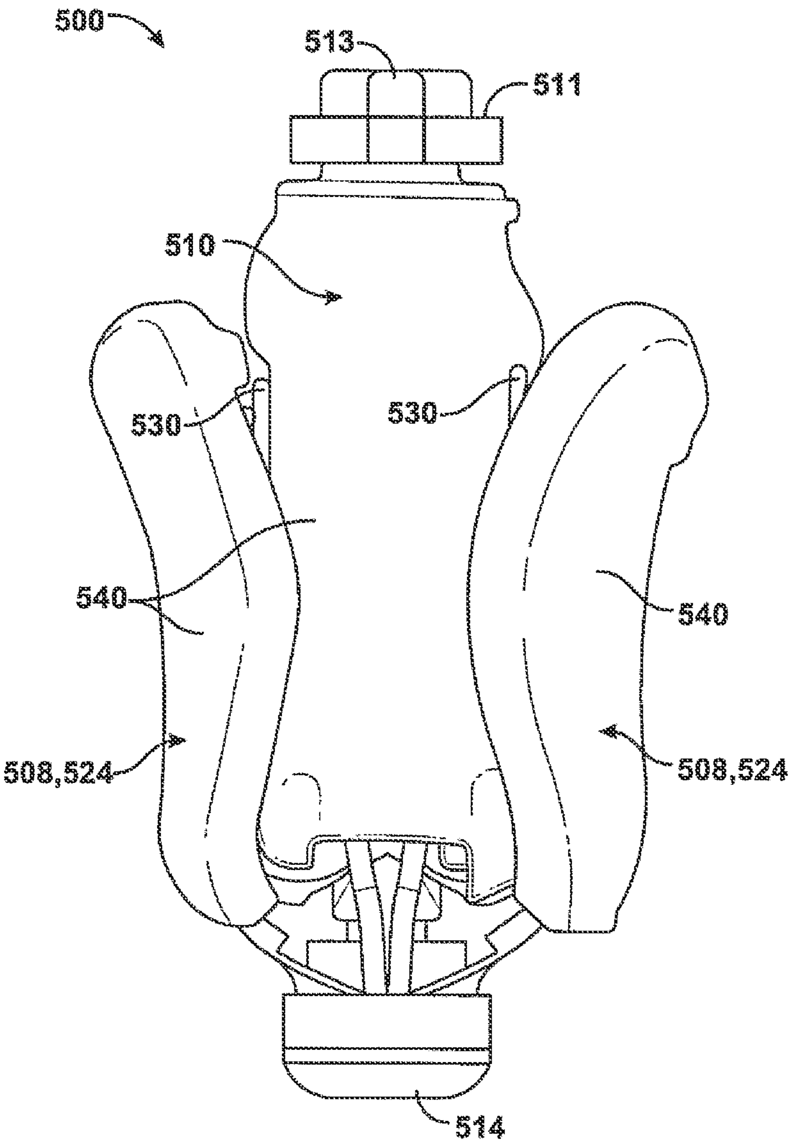
Figure 30A:
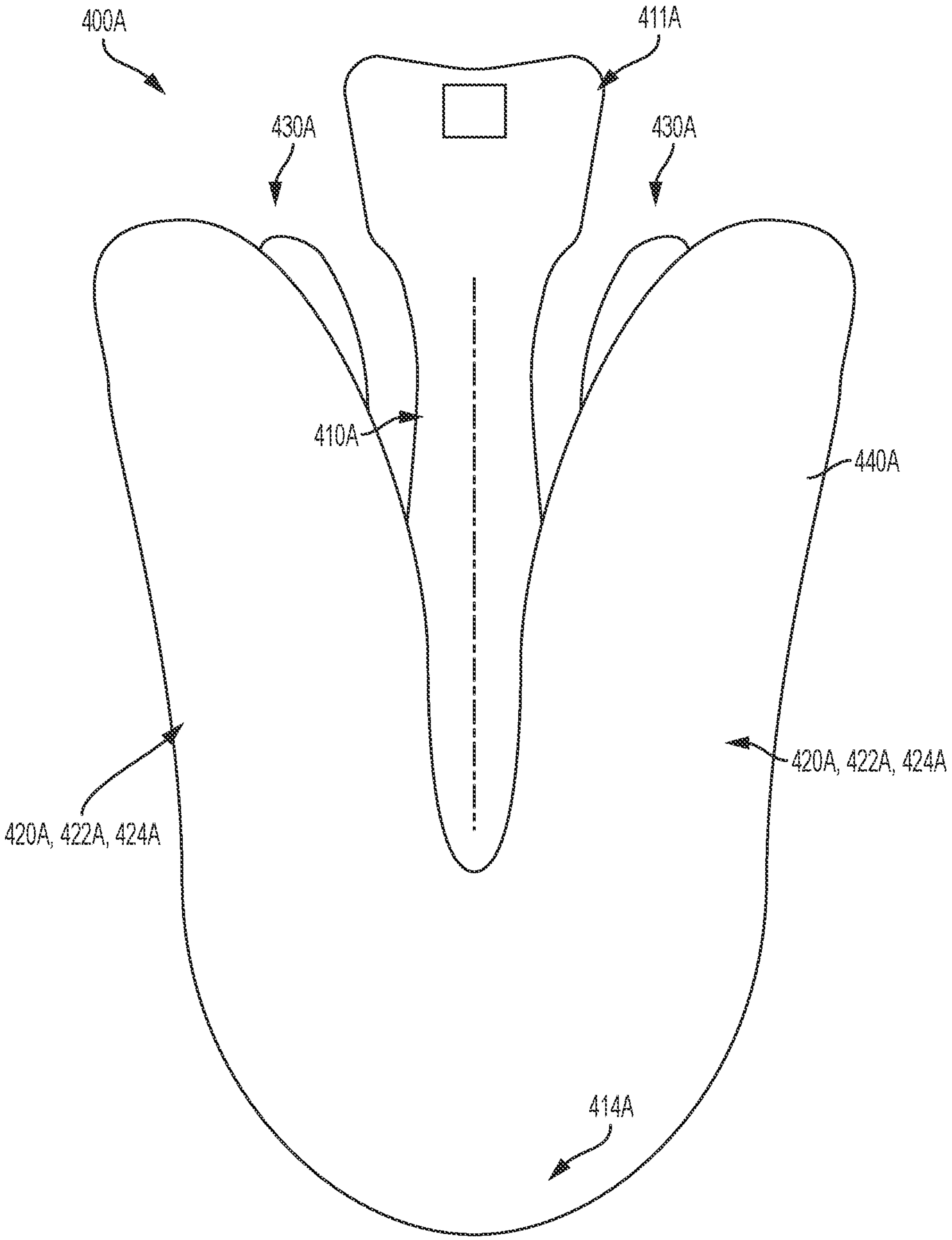
FIG. 30A shows an example embodiment of an implantable prosthetic device.

Referring now to FIG. 30A, the example implantable prosthetic device 400A is shown covered with a cover 440A. The cover 440A is disposed on the coaption member 410A, the collar 411A, the cap 414A, the paddles 420A, 422A, the paddle frames 424A, and the clasps 430A. The cover 440A can be configured to prevent or reduce blood-flow through the prosthetic spacer device 400A and/or to promote native tissue ingrowth. In some embodiments, the cover 440A can be a cloth or fabric such as PET, velour, or other suitable fabric. In some embodiments, in lieu of or in addition to a fabric, the cover 440A can include a coating (e.g., polymeric material, silicone, etc.) that is applied to the prosthetic spacer device 400A.

Figure 28:
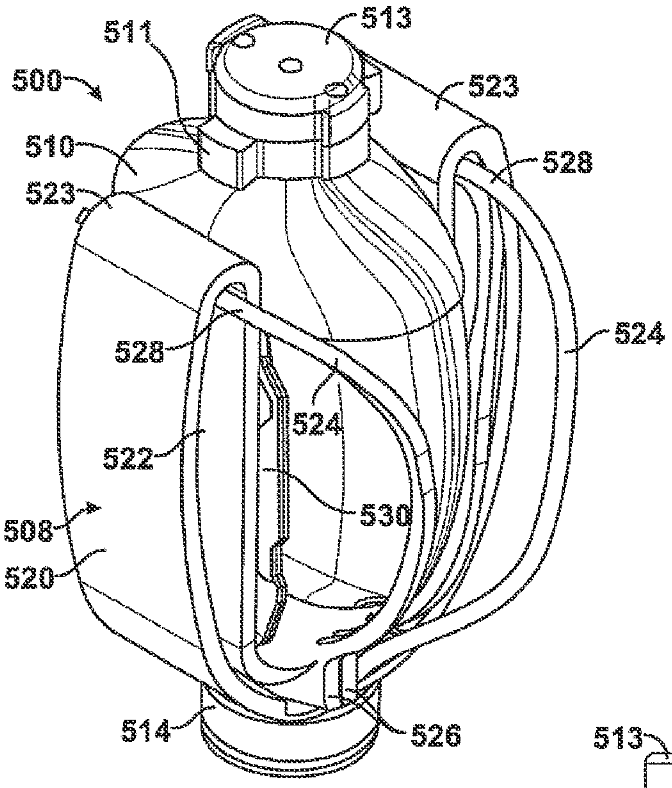
FIGS. 28-32 show an example embodiment of an implantable prosthetic device.
Figure 29:
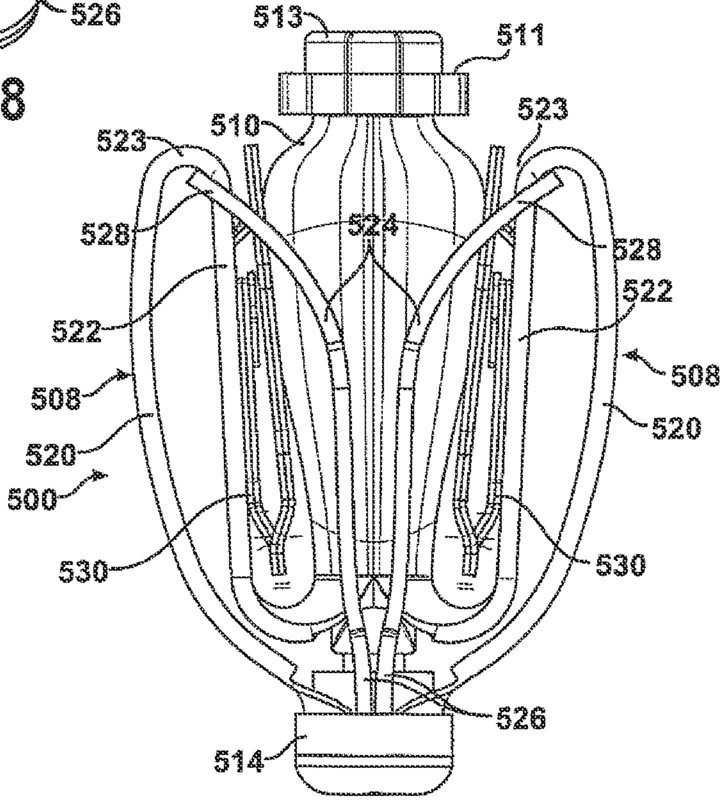

Referring now to FIGS. 28-30, an example embodiment of an implantable prosthetic device 500 (e.g., a prosthetic spacer device, etc.) is shown. The implantable device 500 is one of the many different configurations that the device 100 that is schematically illustrated in FIGS. 8-20 can take. The device 500 can include any other features for an implantable prosthetic device discussed in the present application, and the device 500 can be positioned to engage valve tissue 20, 22 as part of any suitable valve repair system (e.g., any valve repair system disclosed in the present application).

The implantable medical device 500 (e.g., prosthetic spacer device, etc.) can comprise a plurality of anchors 508 that include outer paddles 520, inner paddles 522, clasps 530, a first or proximal collar 511, and a second collar or cap 514. These components of the prosthetic spacer device 500 can be configured the same or substantially similar to one or more of the corresponding components of the implantable medical device 400. Implantable medical device 500 can optionally include a coaption element or spacer member 510.

The implantable medical device 500 can also include a plurality of paddle extension members or paddle frames 524. The paddle frames 524 can be configured with a round three-dimensional shape with first connection portions 526 coupled to and extending from the cap 514 and second connection portions 528 disposed opposite the first connection portions 526. In some embodiments, the paddle frames 524 are configured to extend circumferentially farther around a coaption member 510 than the outer paddles 520. For example, in some embodiments, each of the paddle frames 524 extend around approximately half of the circumference of the coaption member 510 (as shown in FIG. 29), and the outer paddles 520 extend around less than half of the circumference of the coaption member 510 (as shown in FIG. 28). The paddle frames 524 can also be configured to extend laterally (i.e., perpendicular to a longitudinal axis of the device and/or a coaption member 510 of the device), e.g., beyond an outer diameter of the coaption member 510. In the illustrated example, the inner paddle portions 522 and the outer paddle portions 520 can be formed from a continuous strip of fabric that are connected to the paddle frames 524. For example, the inner paddle portions and the outer paddle portions can be connected to the connection portion of the paddle frame at the flexible connection between the inner paddle portion and the outer paddle portion.

The paddle frames 524 can further be configured such that connection portions 528 of the paddle frames 524 are connected to or axially adjacent a joint portion 523. The connection portions of the paddle frames 524 can be positioned between outer and inner paddles 520, 522, on the outside of the paddle portion 520, on the inside of the inner paddle portion, or on top of the joint portion 523 when the implantable medical device 500 is in a folded configuration (e.g., FIGS. 28-30). The connections between the paddle frames 524, the single strip that forms the outer and inner paddles 520, 522, the cap 514, and/or the coaption element can constrain each of these parts to the movements and positions described herein. In particular the joint portion 523 is constrained by its connection between the outer and inner paddles 520, 522 and by its connection to the paddle frame. Similarly, the paddle frame 524 is constrained by its attachment to the joint portion 523 (and thus the inner and outer paddles) and to the cap.

Configuring the paddle frames 524 in this manner provides increased surface area compared to the outer paddles 520 alone. This can, for example, make it easier to grasp and secure the native leaflets. The increased surface area can also distribute the clamping force of the paddles 520 and paddle frames 524 against the native leaflets over a relatively larger surface of the native leaflets in order to further protect the native leaflet tissue.

The increased surface area of the paddle frames 524 can also allow the native leaflets to be clamped to the prosthetic device 500, such that the native leaflets coapt entirely around the coaption member 510. This can, for example, improve sealing of the native leaflet and thus prevent or further reduce mitral regurgitation.

Referring to FIG. 30, the implantable medical device 500 can also include a cover 540. In some embodiments, the cover 540 can be disposed on the coaption member 510, the paddles 520, 522, and/or the paddle frames 524. The cover 540 can be configured to prevent or reduce blood-flow through the prosthetic device 500 and/or to promote native tissue ingrowth. In some embodiments, the cover 540 can be a cloth or fabric such as PET, velour, or other suitable fabric. In some embodiments, in lieu of or in addition to a fabric, the cover 540 can include a coating (e.g., polymer, silicone, etc.) that is applied to the prosthetic device 500.

Figure 31:
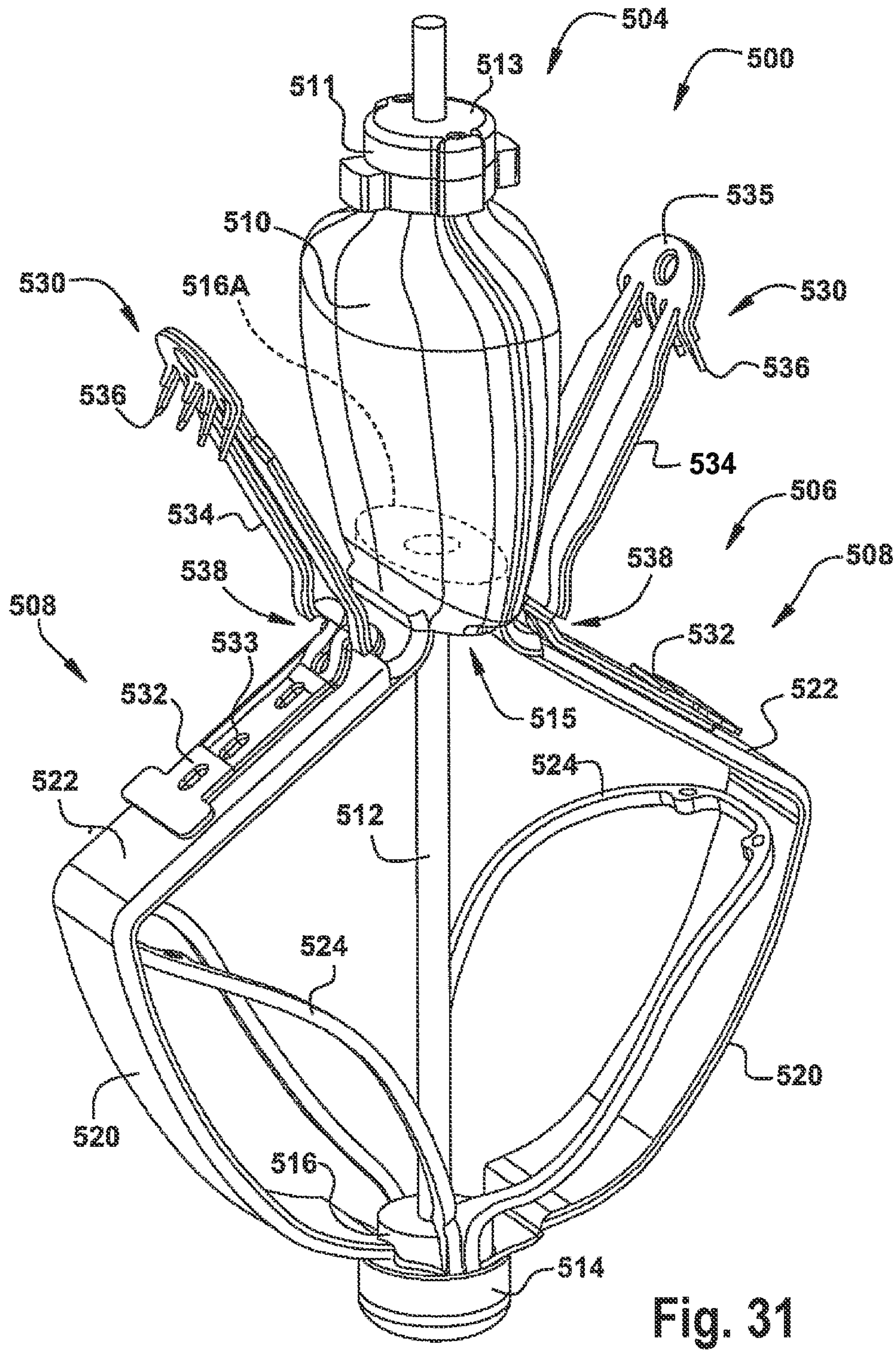
Figure 32:
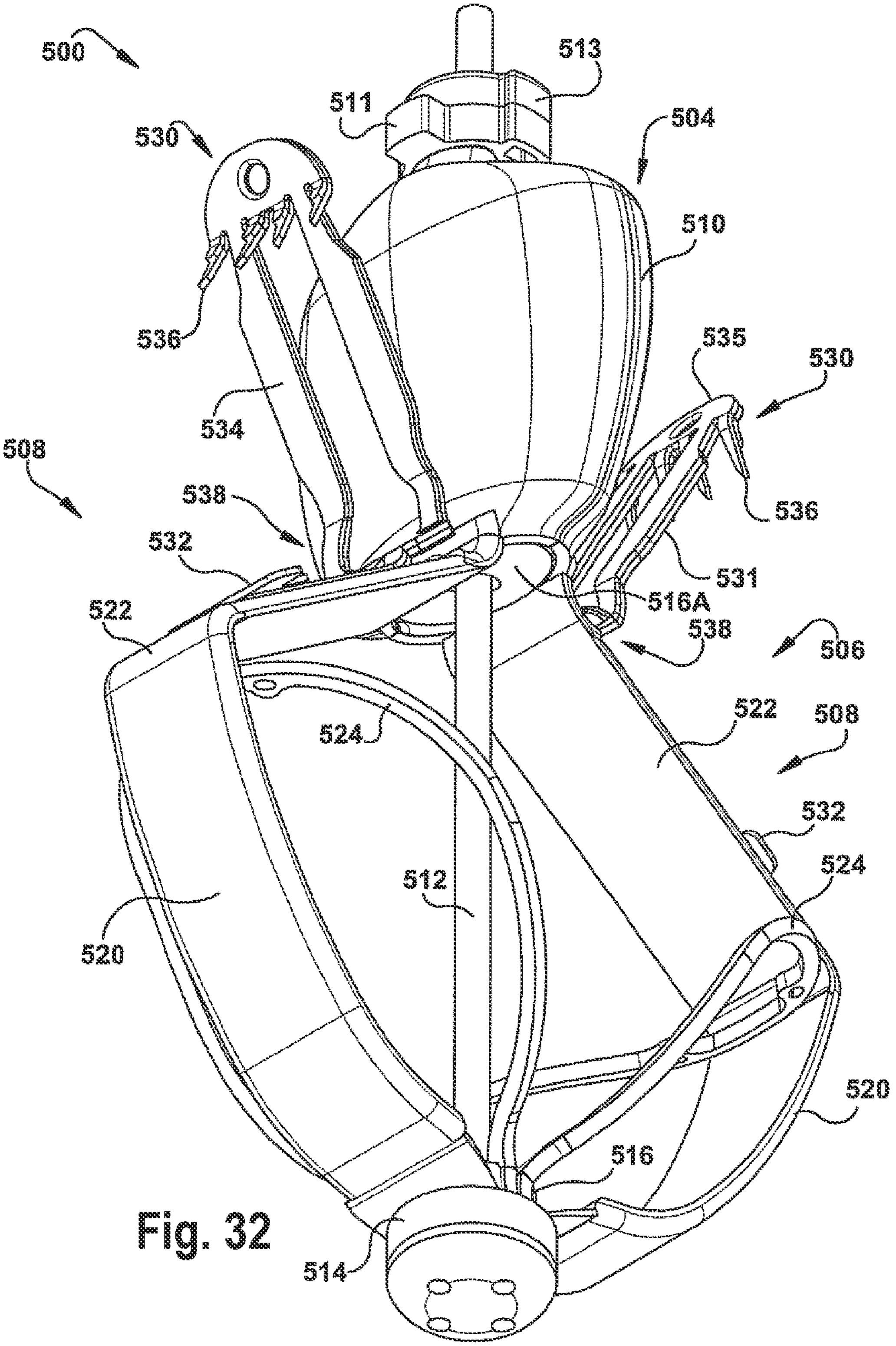

FIGS. 31-32 illustrate the implantable prosthetic device 500 of FIGS. 28 and 29 with anchors 508 of an anchor portion 506 and clasps 530 in open positions. The device 500 is deployed from a delivery sheath (not shown). The device 500 can include a coaption portion 504 and/or an anchor portion 506. The device 500 is loaded in the delivery sheath in the fully extended or bailout position, because the fully extended or bailout position takes up the least space and allows the smallest catheter to be used (See FIG. 35). Or, the fully extended position allows the largest device 500 to be used for a given catheter size.

In some embodiments, the coaption portion 504 of the device can include a coaption element 510 for implantation between the native leaflets of a native valve (e.g., mitral valve, tricuspid valve, etc.). An insert 516A is disposed inside the coaption element 510. The insert 516A and the coaption element 510 are slidably attached to an actuation element or means for actuation 512 (e.g., actuation wire, rod, shaft, tube, screw, suture, line, combination of these, etc.). The anchors 508 of the device 500 include outer paddles 520 and inner paddles 522 that are flexibly connected to the cap 514 and the coaption element 510. Actuation of the actuation element or means for actuation 512 opens and closes the anchors 508 of the device 500 to grasp the native valve leaflets during implantation.

The actuation element 512 extends through the delivery sheath (not shown) and one, some, or all of the proximal collar 511, a coaption element 510, and/or the insert 516A, and extends to the cap 514. In some embodiments, extending and retracting the actuation element 512 increases and decreases the spacing between the coaption element 510 and the cap 514, respectively. This changing of the spacing between the cap 514 and the coaption element 510 (or optionally another element of the device) causes the anchor portion 506 of the device to move between different positions.

The proximal collar 511 optionally includes a collar seal 513 that forms a seal around the actuation element or means for actuation 512 during implantation of the device 500, and that seals shut when the actuation element 512 is removed to close or substantially close the proximal end of the device 500 to blood flow through the interior of the coaption element 510 after implantation. In some embodiments, a coupler or means for coupling 2214 removably engages and attaches the proximal collar 511 and the coaption element 510 to the delivery sheath. In some embodiments, coupler or means for coupling 2214 is held closed around the proximal collar 511 by the actuation element 512, such that removal of the actuation element 512 allows fingers of the coupler or means for coupling 2214 to open, releasing the proximal collar 511.

Figure 32A:
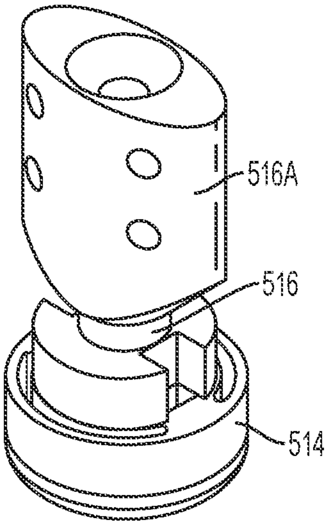
FIGS. 32A and 32B are perspective views of a cap and a coaption element insert of the implantable prosthetic device of FIGS. 28-32 in sealed and spaced apart positions, respectively.
Figure 32B:
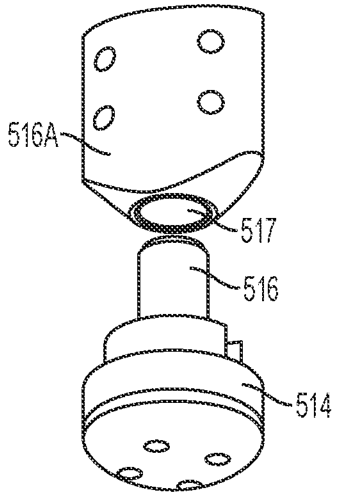

In some embodiments, the proximal collar 511 and the insert 516A in the coaption element 510 slide along the actuation element 512 during actuation to open and close the paddles 520, 522 of the anchors 508. Referring to FIGS. 32A and 32B, in some embodiments the cap 514 optionally includes a sealing projection 516 that sealingly fits within a sealing opening 517 of the insert 516A. In an example embodiment, the cap 514 includes a sealing opening and the insert 516A includes a sealing projection. The insert 516A can sealingly fit inside a distal opening 515 of the coaption element 510, the coaption element 510 having a hollow interior. Referring to FIG. 32A, the sealing projection 516 of the cap 514 sealingly engages the opening 517 in the insert 516A to maintain the distal end of the coaption element 510 closed or substantially closed to blood flow when the device 500 is implanted and/or in the closed position.

In an example embodiment, instead of the sealing engagement between the cap 514 and the insert 516A, the insert 516A can optionally include a seal, like the collar seal 513 of the proximal collar, that forms a seal around the actuation element or means for actuation 512 during implantation of the device 500, and that seals shut when the actuation element 512 is removed. Such a seal can close or substantially close the distal end of the coaption element 510 to blood flow after implantation.

In some embodiments, the coaption element 510 and/or paddles 520, 522 are formed from a flexible material that can be a metal fabric, such as a mesh, woven, braided, or formed in any other suitable way or a laser cut or otherwise cut flexible material. The material can be cloth, shape-memory alloy wire—such as Nitinol—to provide shape-setting capability, or any other flexible material suitable for implantation in the human body. Paddle frames 524 provide additional pinching force between the inner paddles 522 and the coaption element 510 and assist in wrapping the leaflets around the sides of the coaption element 510 for a better seal between the coaption element 510 and the leaflets. In some embodiments, the covering 540 illustrated by FIG. 30 extends around the paddle frames 524.

The clasps 530 include a base or fixed arm 532, a moveable arm 534, friction-enhancing elements or barbs 536, and a joint portion 538. The fixed arms 532 are attached to the inner paddles 522, with the joint portion 538 disposed proximate the coaption element 510. The clasps or barbed clasps have flat surfaces and do not fit in a recess of the paddle. Rather, the flat portion of the clasps are disposed against the surface of the inner paddle 522. For example, the fixed arms 532 are attached to the inner paddles 522 through holes or slots 533 with sutures (not shown). The fixed arms 532 can be attached to the inner paddles 522 or another portion of the device with any suitable means, such as screws or other fasteners, crimped sleeves, mechanical latches or snaps, welding, adhesive, or the like. The fixed arms 532 remain stationary or substantially stationary relative to the inner paddles 522 when the moveable arms 534 are opened to open the clasps 530 and expose the barbs 536. The clasps 530 are opened by applying tension to actuation lines (not shown) attached to holes 535 in the moveable arms 534, thereby causing the moveable arms 534 to pivot or flex on the joint portions 538.

During implantation, the anchors 508 are opened and closed to grasp the native valve leaflets between the paddles 520, 522/or between the paddles 520, 522 and the coaption element 510. The clasps 530 further secure the native leaflets by engaging the leaflets with friction-enhancing elements or barbs 536 and pinching the leaflets between the moveable and fixed arms 534, 532. The friction-enhancing elements or barbs 536 of the clasps 530 increase friction with the leaflets or may partially or completely puncture the leaflets. The actuation lines can be actuated separately so that each clasp 530 can be opened and closed separately. Separate operation allows one leaflet to be grasped at a time, or for the repositioning of a clasp 530 on a leaflet that was insufficiently grasped, without altering a successful grasp on the other leaflet. The clasps 530 can open and close when the inner paddle 522 is not closed, thereby allowing leaflets to be grasped in a variety of positions as the particular situation requires.

Figure 33:
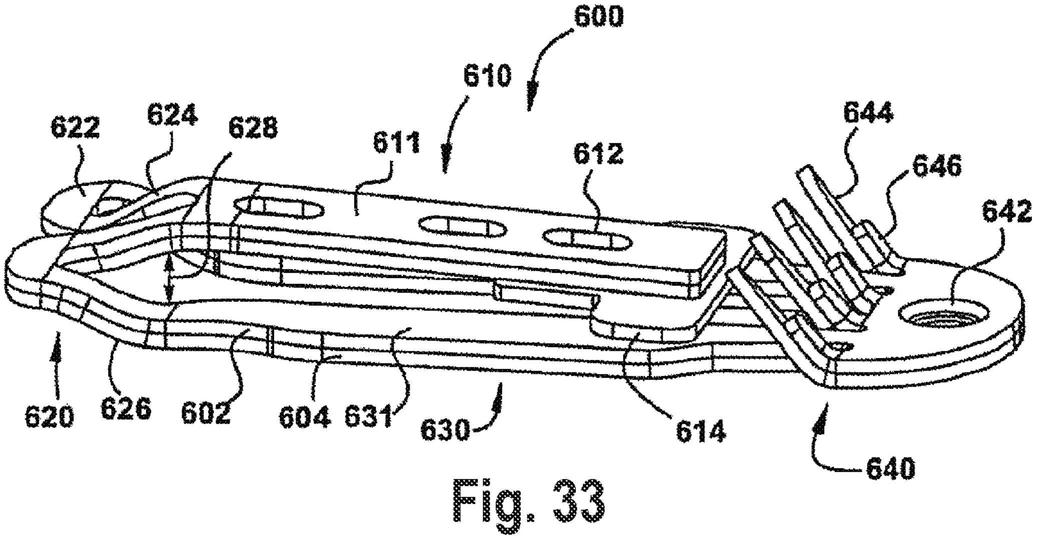
FIG. 33 shows a clasp for use in an implantable prosthetic device.

Referring now to FIG. 33, an example clasp or barbed clasp 600 for use in implantable prosthetic devices, such as the devices described above, is shown. However, a wide variety of different clasps can be used. Examples of clasps that can be used include but are not limited to any of the clasps or barbed clasps disclosed in the present application and any of the applications that are incorporated herein by reference and/or that the present application claims priority to. In the illustrated example, the barbed clasp 600 is formed from a top layer 602 and a bottom layer 604. The two-layer design of the clasp 600 allow thinner sheets of material to be used, thereby improving the flexibility of the clasp 600 over a clasp formed from a single thicker sheet, while maintaining the strength of the clasp 600 needed to successfully retain a native valve leaflet.

The clasp 600 includes a fixed arm 610, a jointed portion 620, and a movable arm 630 having a barbed portion 640. The top and bottom layers 602, 604 have a similar shape and in certain embodiments are attached to each other at the barbed portion 640. However, the top and bottom layers 602, 604 can be attached to one another at other or additional locations. The jointed portion 620 is spring-loaded so that the fixed and moveable arms 610, 630 are biased toward each other when the clasp 600 is in a closed condition. When assembled to an implantable prosthetic device, the fixed arm 610 is attached to a portion of the prosthetic device. The clasp 600 is opened by pulling on an actuation line attached to the moveable arm 630 until the spring force of the joint portion 620 is overcome.

The fixed arm 610 is formed from a tongue 611 of material extending from the jointed portion 620 between two side beams 631 of the moveable arm 630. The tongue 611 is biased between the side beams 631 by the joint portion 620 such that force must be applied to move the tongue 611 from a neutral position located beyond the side beams 631 to a preloaded position parallel or substantially parallel with the side beams 631. The tongue 611 is held in the preloaded position by an optional T-shaped crossbar 614 that is attached to the tongue 611 and extends outward to engage the side beams 631. In an example embodiment, the crossbar is omitted and the tongue 611 is attached to the inner paddle 522, and the inner paddle 522 maintains the clasp in the preloaded position. In the two-layer clasp application, the top and bottom layers 602, 604 or just the top layer can be attached to the inner paddle. In some embodiments, the angle between the fixed and moveable arms 610, 630 when the tongue is in the neutral position is about 30 to about 100 degrees, 30 to about 90 degrees, or about 30 to about 60 degrees, or about 40 to about 50 degrees, or about 45 degrees.

The tongue 611 includes holes 612 for receiving sutures (not shown) that attach the fixed arm 610 to an implantable device. The fixed arm 610 can be attached to an implantable device, such as with screws or other fasteners, crimped sleeves, mechanical latches or snaps, welding, adhesive, or the like. In certain embodiments, the holes 612 are elongated slots or oval-shaped holes to accommodate sliding of the layers 602, 604 without damaging the sutures attaching the clasp 600 to an implantable device.

The joint portion 620 is formed by two beam loops 622 that extend from the tongue 611 of the fixed arm 610 to the side beams 631 of the moveable arm 630. In certain embodiments, the beam loops 622 are narrower than the tongue 611 and side beam 631 to provide additional flexibility. The beam loops 622 each include a center portion 624 extending from the tongue 611 and an outer portion 626 extending to the side beams 631. The beam loops 622 are bent into a somewhat spiral or helical shape by bending the center and outer portions 624, 626 in opposite directions, thereby forming an offset or step distance 628 between the tongue 611 and side beams 631. The step distance 628 provides space between the arms 610, 630 to accommodate the native leaflet of the native valve after it is grasped. In some embodiments, the step distance 628 is about 0.5 millimeter to about 1 millimeter, or about 0.75 millimeters.

When viewed in a top plan view, the beam loops have an "omega-like" shape. This shape of the beam loops 622 allows the fixed and moveable arms 610, 630 to move considerably relative to each other without plastically deforming the clasp material. For example, in certain embodiments, the tongue 611 can be flexed or pivoted from a neutral position that is approximately 45 degrees beyond the moveable arm 630 to a fully open position that ranges from about 140 degrees to about 200 degrees, from about 170 degrees to about 190 degrees, or about 180 degrees from the moveable arm 630 without plastically deforming the clasp material. In certain embodiments, the clasp material plastically deforms during opening without reducing or without substantially reducing the pinch force exerted between the fixed and moveable arms in the closed position.

Preloading the tongue 611 enables the clasp 600 to maintain a pinching or clipping force on the native leaflet when closed. The preloading of the tongue 611 provides a significant advantage over prior art clips that provide little or no pinching force when closed. Additionally, closing the clasp 600 with spring force is a significant improvement over clips that use a one-time locking closure mechanism, as the clasp 600 can be repeatedly opened and closed for repositioning on the leaflet while still maintaining sufficient pinching force when closed. In addition, the spring-loaded clasps also allow for easier removal of the device over time as compared to a device that locks in a closed position (after tissue ingrowth). In one example embodiment, both the clasps and the paddles are spring biased to their closed positions (as opposed to being locked in the closed position), which can allow for easier removal of the device after tissue ingrowth.

The barbed portion 640 of the moveable arm 630 includes an eyelet 642, barbs 644, and barb supports 646. Positioning the barbed portion of the clasp 600 toward an end of the moveable arm 630 increases the space between the barbs 644 and the fixed arm 610 when the clasp 600 is opened, thereby improving the ability of the clasp 600 to successfully grasp a leaflet during implantation. This distance also allows the barbs 644 to more reliably disengage from the leaflet for repositioning. In certain embodiments, the barbs of the clasps can be staggered longitudinally to further distribute pinch forces and local leaflet stress.

The barbs 644 are laterally spaced apart at the same distance from the joint portion 620, providing a superior distribution of pinching forces on the leaflet tissue while also making the clasp more robust to leaflet grasp than barbs arranged in a longitudinal row. In some embodiments, the barbs 644 can be staggered to further distribute pinch forces and local leaflet stress.

The barbs 644 are formed from the bottom layer 604 and the barb supports 646 are formed from the top layer. In certain embodiments, the barbs are formed from the top layer 602 and the barb supports are formed from the bottom layer 604. Forming the barbs 644 only in one of the two layers 602, 604 allows the barbs to be thinner and therefore effectively sharper than a barb formed from the same material that is twice as thick. The barb supports 646 extend along a lower portion of the barbs 644 to stiffen the barbs 644, further improving penetration and retention of the leaflet tissue. In certain embodiments, the ends of the barbs 644 are further sharpened using any suitable sharpening means.

The barbs 644 are angled away from the moveable arm 630 such that they easily penetrate tissue of the native leaflets with minimal pinching or clipping force. The barbs 644 extend from the moveable arm at an angle of about 45 degrees to about 75 degrees, or about 45 degrees to about 60 degrees, or about 48 to about 56 degrees, or about 52 degrees. The angle of the barbs 644 provides further benefits, in that force pulling the implant off the native leaflet will encourage the barbs 644 to further engage the tissue, thereby ensuring better retention. Retention of the leaflet in the clasp 600 can be further improved by the position of the T-shaped cross bar 614 near the barbs 644 when the clasp 600 is closed. In this arrangement, the tissue pierced by the barbs 644 is pinched against the moveable arm 630 at the cross bar 614 location, thereby forming the tissue into an S-shaped torturous path as it passes over the barbs 644. Thus, forces pulling the leaflet away from the clasp 600 will encourage the tissue to further engage the barbs 644 before the leaflets can escape. For example, leaflet tension during diastole can encourage the barbs to pull toward the end portion of the leaflet. The S-shaped path can utilize the leaflet tension during diastole to more tightly engage the leaflets with the barbs.

Each layer 602, 604 of the clasp 600 is laser cut from a sheet of shape-memory alloy, such as Nitinol. The top layer 602 is aligned and attached to the bottom layer 604. In certain embodiments, the layers 602, 604 are attached at the barbed portion 640 of the moveable arm 630. For example, the layers 602, 604 can be attached only at the barbed portion 640, to allow the remainder of the layers to slide relative to one another. Portions of the combined layers 602, 604, such as a fixed arm 610, barbs 644 and barb supports 646, and beam loops 622 are bent into a desired position. The layers 602, 604 can be bent and shape-set together or can be bent and shape-set separately and then joined together. The clasp 600 is then subjected to a shape-setting process so that internal forces of the material will tend to return to the set shape after being subjected to deformation by external forces. After shape-setting, the tongue 611 is moved to its preloaded position so that the crossbar 614 can be attached. In one example embodiment, the clasp 600 can optionally be completely flattened for delivery through a delivery sheath and allowed to expand once deployed within the heart. The clasp 600 is opened and closed by applying and releasing tension on an actuation line, suture, wire, rod, catheter, or the like (not shown) attached to the moveable arm 630. In some embodiments, the actuation line or suture is inserted through an eyelet 642 near the barbed portion 640 of the moveable arm 630 and wraps around the moveable arm 630 before returning to the delivery sheath. In certain embodiments, an intermediate loop or intermediate suture loop is made through the eyelet and the line/suture is inserted through the intermediate loop. In one embodiment, the intermediate loop can be composed of fabric or another material attached to the movable arm, instead of a suture loop.

An intermediate loop of material or suture material reduces friction experienced by the actuation line/suture relative to the friction between the actuation line/suture and the clasp material. When the line/suture is looped through the eyelet 642 or intermediate loop, both ends of the actuation line/suture extend back into and through a delivery sheath (e.g., FIG. 8). The line/suture can be removed by pulling one end of the line/suture proximally until the other end of the line/suture pulls through the eyelet or intermediate loop and back into the delivery sheath.

Figure 34:
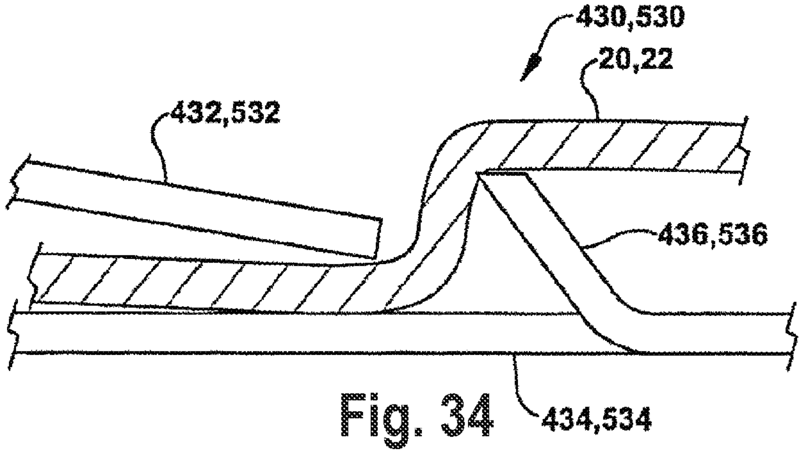
FIG. 34 shows a portion of native valve tissue grasped by a clasp.

Referring now to FIG. 34, a close-up view of one of the leaflets 20, 22 grasped by a clasp such as clasps 430, 530 is shown. The leaflet 20, 22 is grasped between the moveable and fixed arms 434, 532 of the clasp 430, 530. As shown in FIG. 34, the tissue of the leaflet 20, 22 is not pierced by the friction-enhancing elements or barbs 436, 536, though in some embodiments the barbs 436, 536 may partially or fully pierce through the leaflet 20, 22. The angle and height of the barbs 436, 536 relative to the moveable arm 434, 534 helps to secure the leaflet 20, 22 within the clasp 430, 530. In particular, a force pulling the implant off of the native leaflet will encourage the barbs 436, 536 to further engage the tissue, thereby ensuring better retention. Retention of the leaflet 20, 22 in the clasp 430, 530 is further improved by the position of fixed arm 432, 532 near the barbs 436, 536 when the clasp 430, 530 is closed. In this arrangement, the tissue is formed by the fixed arms 432, 532 and the moveable arms 434, 534 and the barbs 436, 536 into an S-shaped torturous path. Thus, forces pulling the leaflet away from the clasp 430, 530 will encourage the tissue to further engage the barbs 436, 536 before the leaflets can escape. For example, as mentioned above, leaflet tension during diastole can encourage the barbs to pull toward the end portion of the leaflet. The S-shaped path can utilize the leaflet tension during diastole to more tightly engage the leaflets with the barbs.

Referring now to FIGS. 35-46, the implantable device 500 is shown being delivered and implanted within the native valve of the heart H. The methods and steps shown and/or discussed can be performed on a living animal or on a simulation, such as on a cadaver, cadaver heart, simulator (e.g. with the body parts, heart, tissue, etc. being simulated), etc.

As described above, the device 500 has a covering 540 (see FIG. 30) over the coaption element 510, clasps 530, inner paddles 522 and/or the outer paddles 520. The device 500 is deployed from a delivery sheath 502. The device 500 can include a coaption portion 504 and/or an anchor portion 506 including a plurality of anchors 508 (i.e., two in the illustrated embodiment). In some embodiments, the coaption portion 504 of the device includes a coaption element 510 (e.g., spacer, plug, etc.) for implantation between the leaflets 20, 22 of the native mitral valve MV that is slidably attached to an actuation element or means for actuation 512. Actuation of the actuation element or means for actuation 512 opens and closes the anchors 508 of the device 500 to grasp the mitral valve leaflets 20, 22 during implantation.

In some embodiments, the anchors 508 of the device 500 include outer paddles 520 and inner paddles 522 that are flexibly connected to the cap 514 and the coaption element 510. The actuation element 512 extends through a capture mechanism 503 (see FIG. 41), delivery sheath 502, and the coaption element 510 to the cap 514 connected to the anchor portion 506. Extending and retracting the actuation element 512 increases and decreases the spacing between the coaption element 510 and the cap 514, respectively. In the example illustrated by FIGS. 35-46, the pair of inner and outer paddles 522, 520 are moved in unison, rather than independently, by a single actuation element 512. Also, the positions of the clasps 530 are dependent on the positions of the paddles 522, 520. For example, referring to FIG. 45 closing the paddles 522, 520 also closes the clasps. In one example embodiment, the device 500 can be made to have the paddles 520, 522 be independently controllable in the same manner as the FIG. 11A embodiment.

Fingers of the capture mechanism 503 removably attach the collar 511 to the delivery sheath 502. The collar 511 and the coaption element 510 slide along the actuation element 512 during actuation to open and close the anchors 508 of the anchor portion 506. In some embodiments, the capture mechanism 503 is held closed around the collar 511 by the actuation element 512, such that removal of the actuation element 512 allows the fingers of the capture mechanism 503 to open, releasing the collar 511, and thus the coaption element 510.

In some embodiments, the coaption element 510 and/or paddles 520, 522 are formed from a flexible material that can be a metal fabric, such as a mesh, woven, braided, or formed in any other suitable way or a laser cut or otherwise cut flexible material. The flexible material can be cloth, shape-memory alloy wire—such as Nitinol—to provide shape-setting capability, or any other flexible material suitable for implantation in the human body. Other configurations are also possible.

The clasps 530 include a base or fixed arm 532, a moveable arm 534, barbs 536 (see FIG. 41), and a joint portion 538. The fixed arms 532 are attached to the inner paddles 522. In some embodiments, the joint portions 538 are disposed proximate a coaption element 510. Sutures (not shown) attach the fixed arms 532 to the inner paddles 522. The fixed arms 532 can be attached to the inner paddles 522 and/or another portion of the device with any suitable means, such as screws or other fasteners, crimped sleeves, mechanical latches or snaps, welding, adhesive, or the like. The fixed arms 532 remain stationary or substantially stationary when the moveable arms 534 are opened to open the barbed clasps 530 and expose the barbs 536. The clasps 530 are opened by applying tension to clasp control members or actuation lines 537 attached to the moveable arms 534, thereby causing the moveable arms 534 to pivot or flex on the joint portions 538.

During implantation, the anchors 508 are opened and closed to grasp the native valve leaflets between the paddles 520, 522 and/or between the paddles 520, 522 and the coaption element 510. The outer paddles 520 have a wide curved shape that fits around the curved shape of the coaption element 510 to more securely grip the leaflets 20, 22. The curved shape and rounded edges of the outer paddle 520 also prohibits tearing of the leaflet tissue. The clasps or barbed clasps 530 further secure the native leaflets by engaging the leaflets with friction-enhancing elements or barbs 536 and pinching the leaflets between the moveable and fixed arms 534, 532. The friction-enhancing elements or barbs 536 of the clasps 530 increase friction with the leaflets or may partially or completely puncture the leaflets. The actuation lines can be actuated separately so that each clasp 530 can be opened and closed separately. Separate operation allows one leaflet to be grasped at a time, or for the repositioning of a clasp 530 on a leaflet that was insufficiently grasped, without altering a successful grasp on the other leaflet. The clasps 530 can be fully opened and closed when the inner paddle 522 is not closed, thereby allowing leaflets to be grasped in a variety of positions as the particular situation requires.

Figure 35:
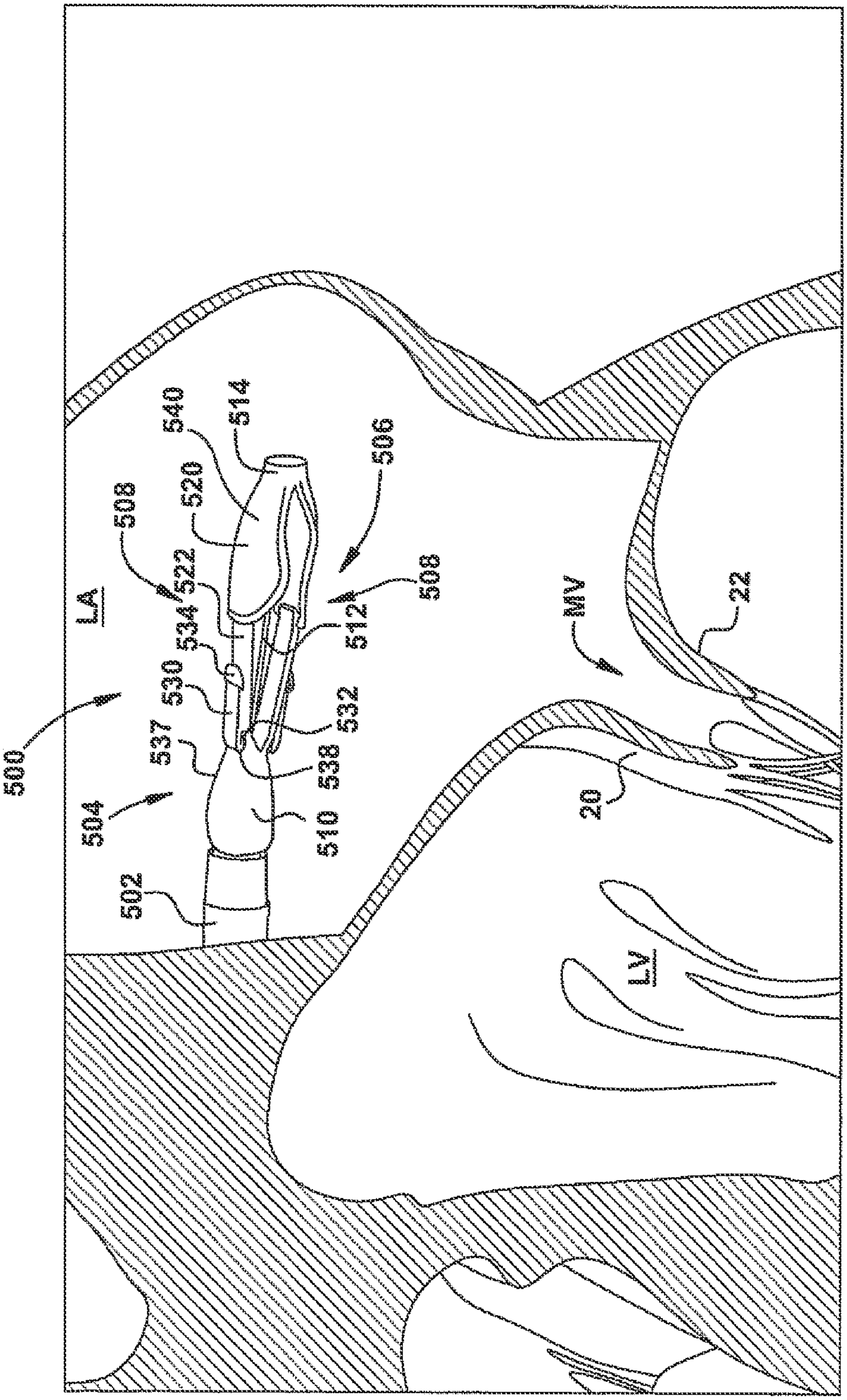
FIGS. 35-46 show an example embodiment of an implantable prosthetic device being delivered and implanted within the native valve.
Figure 36:
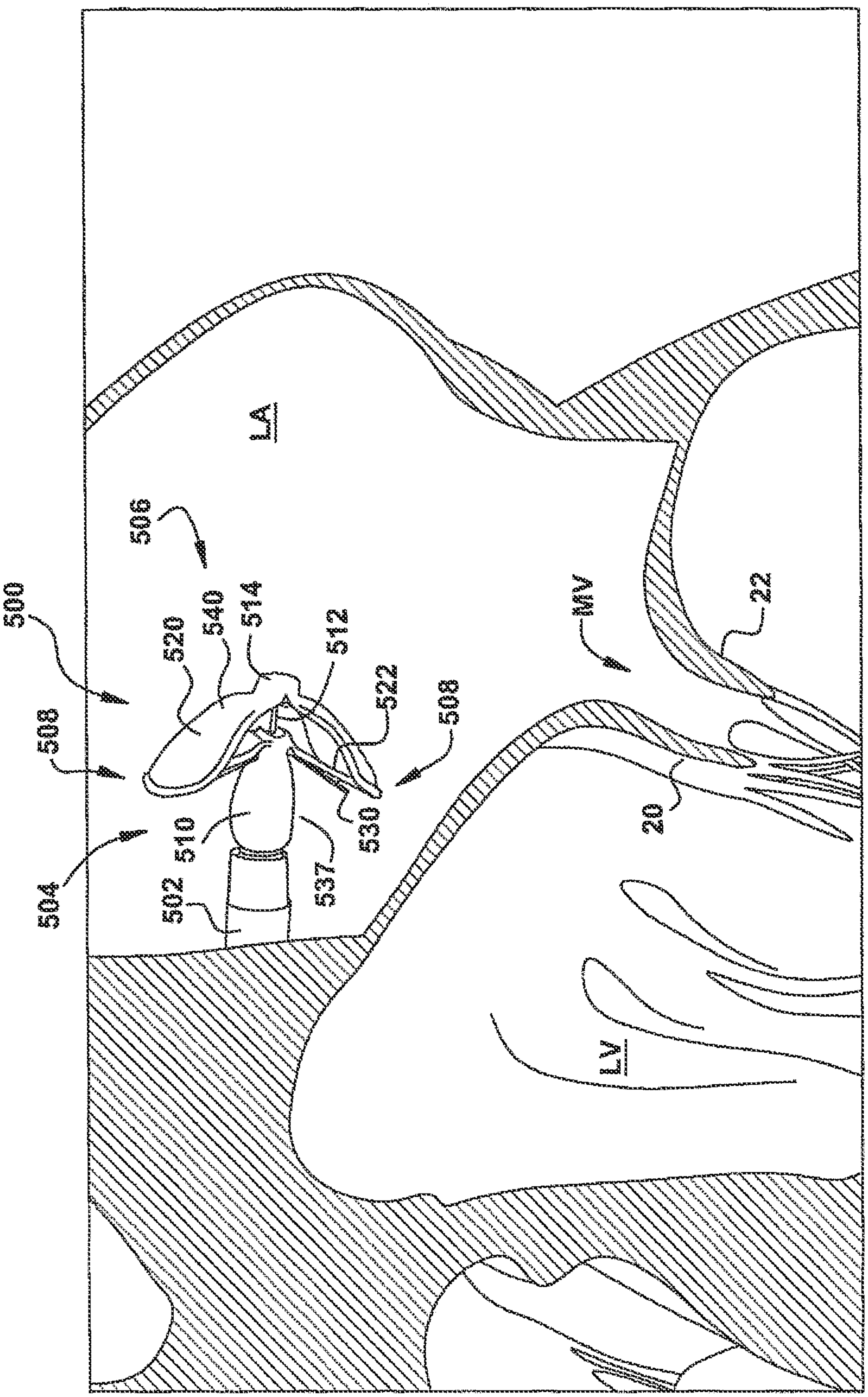
Figure 37:
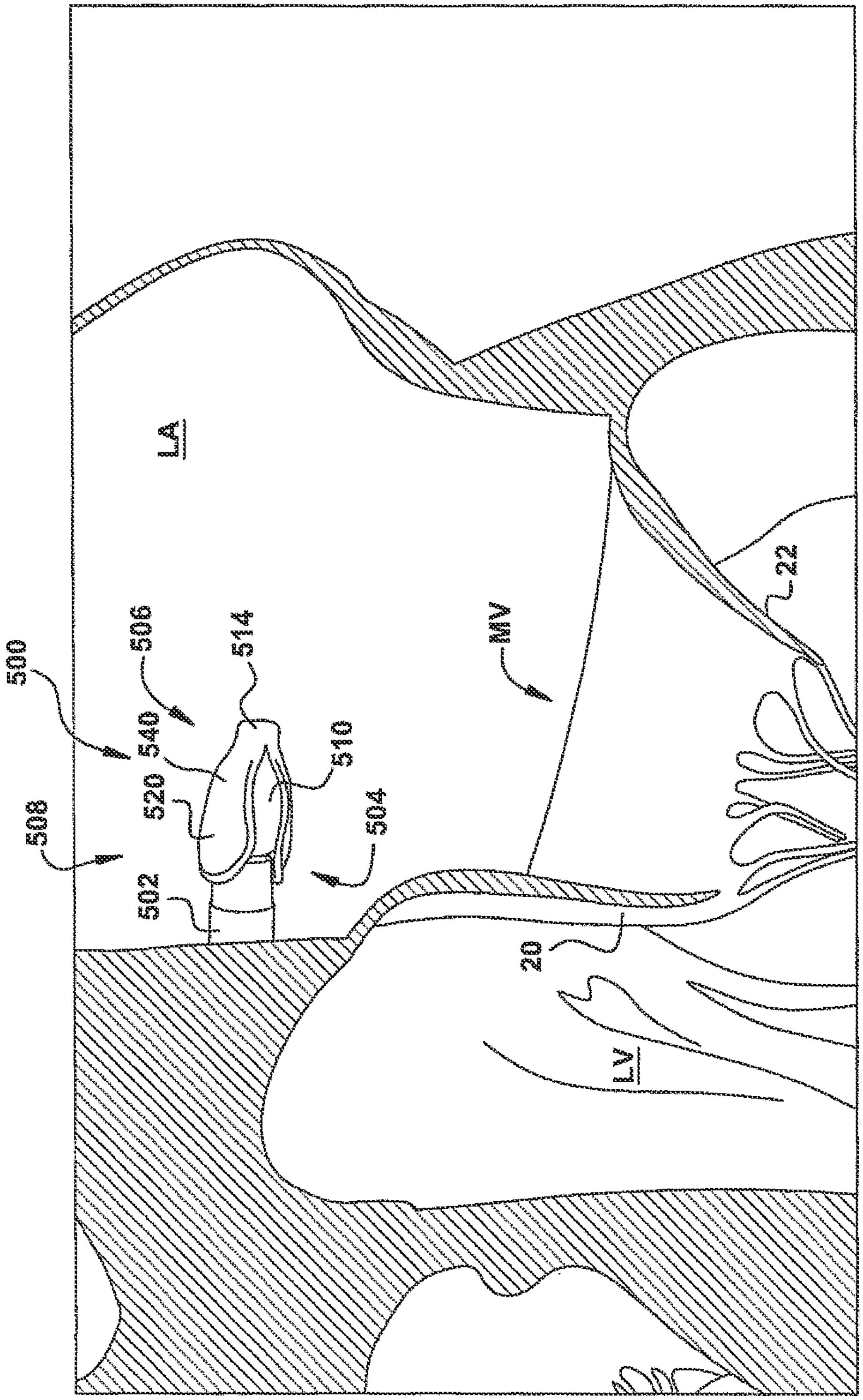
Figure 38:
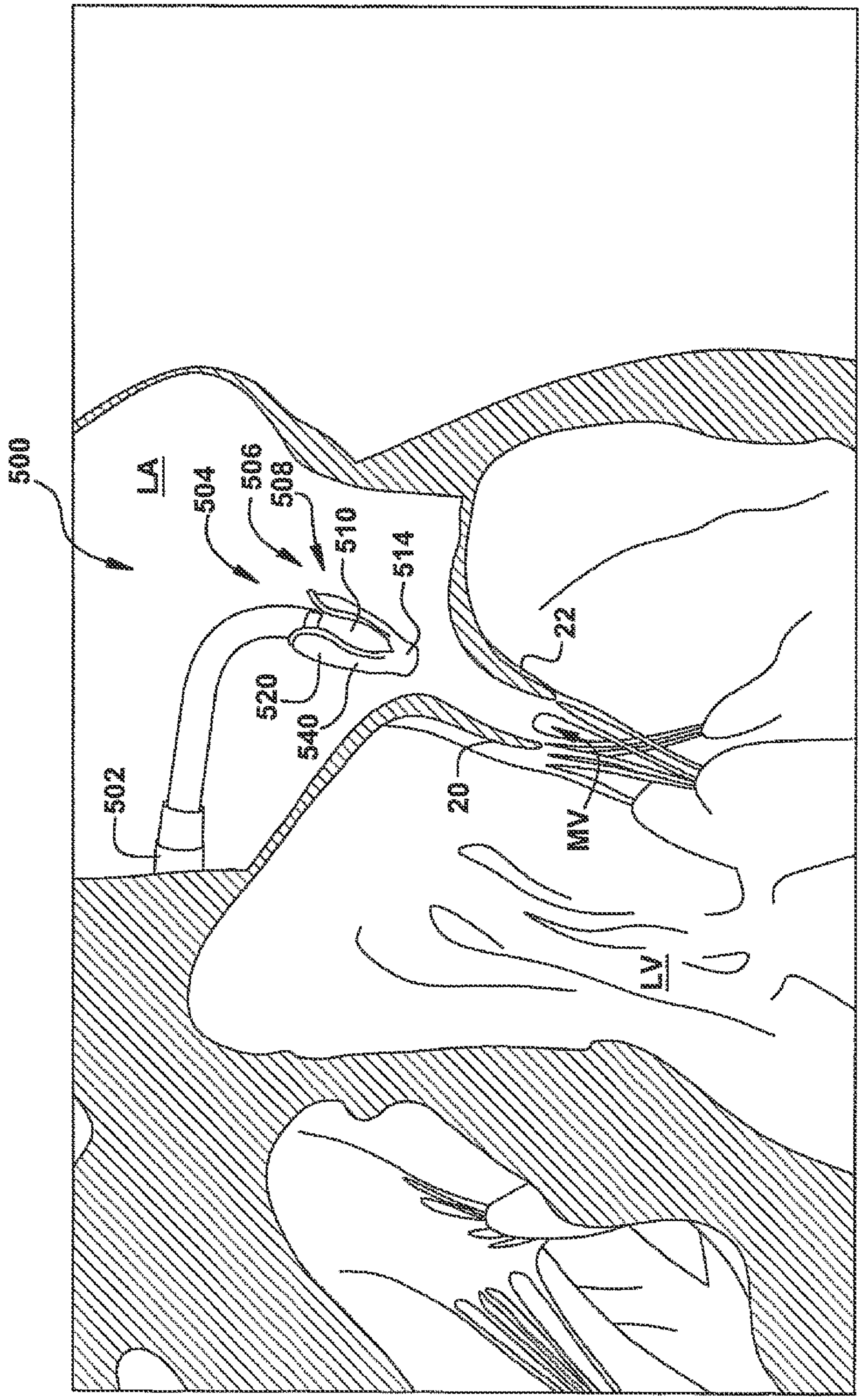
Figure 39:
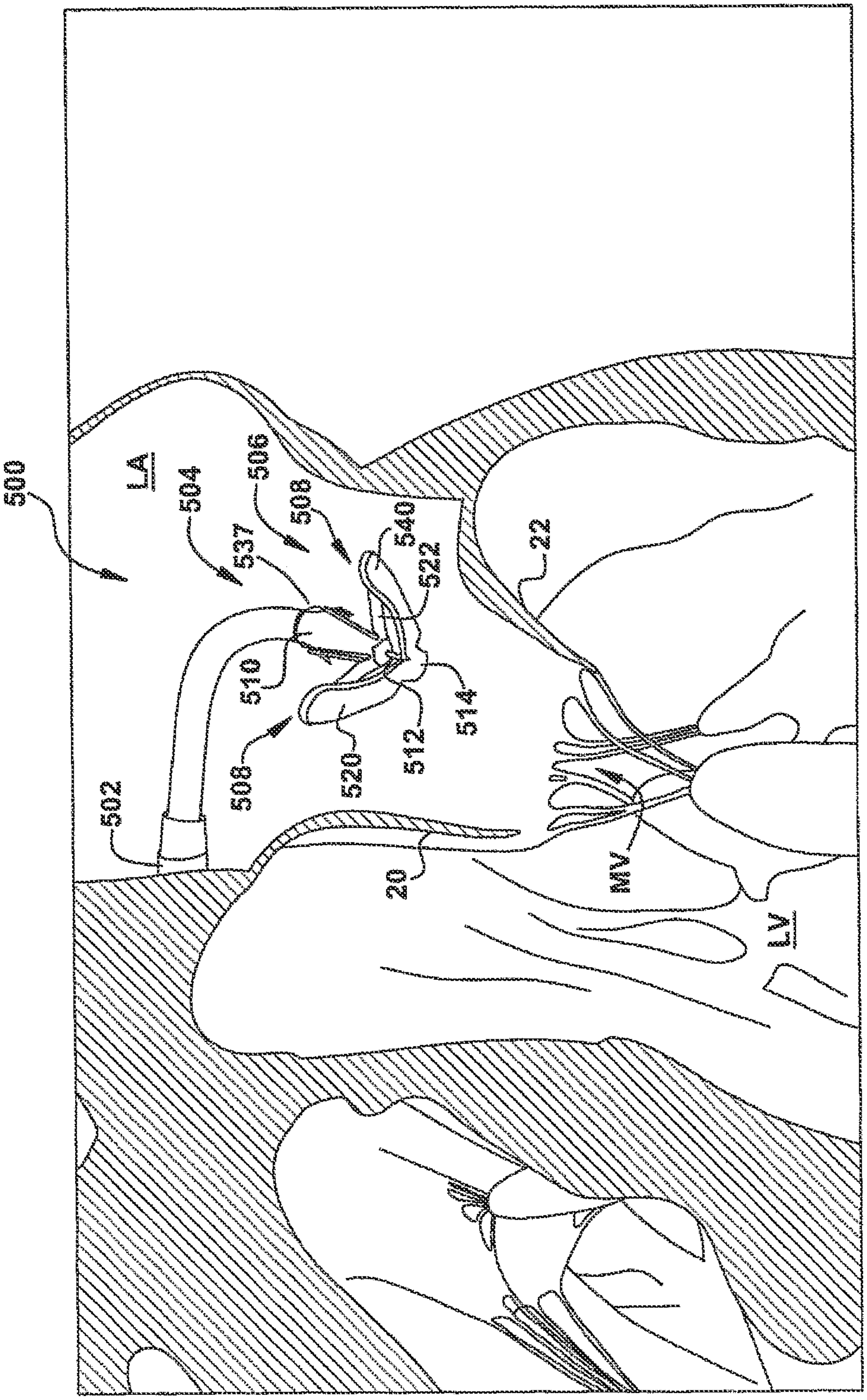
Figure 40:
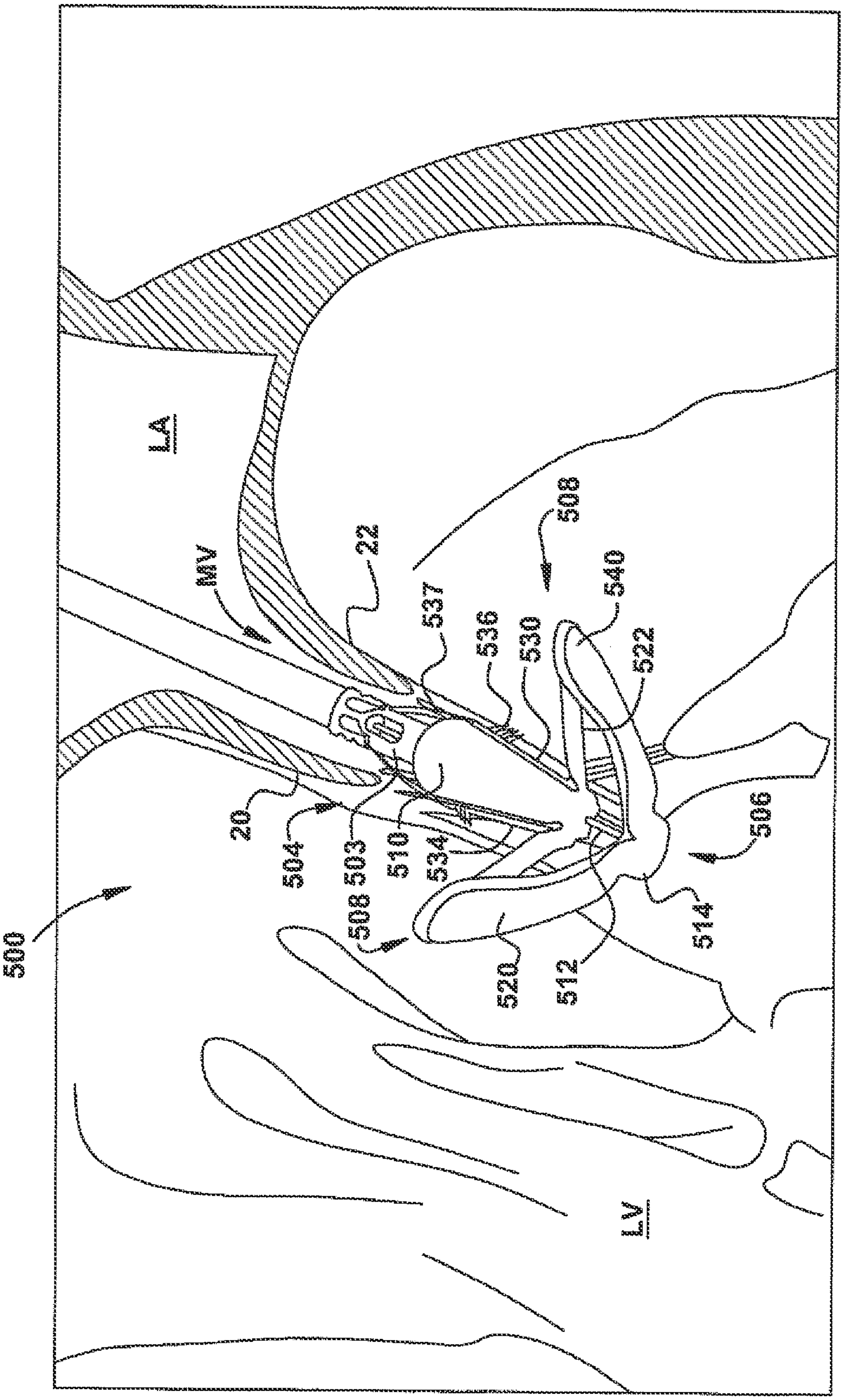
Figure 41:
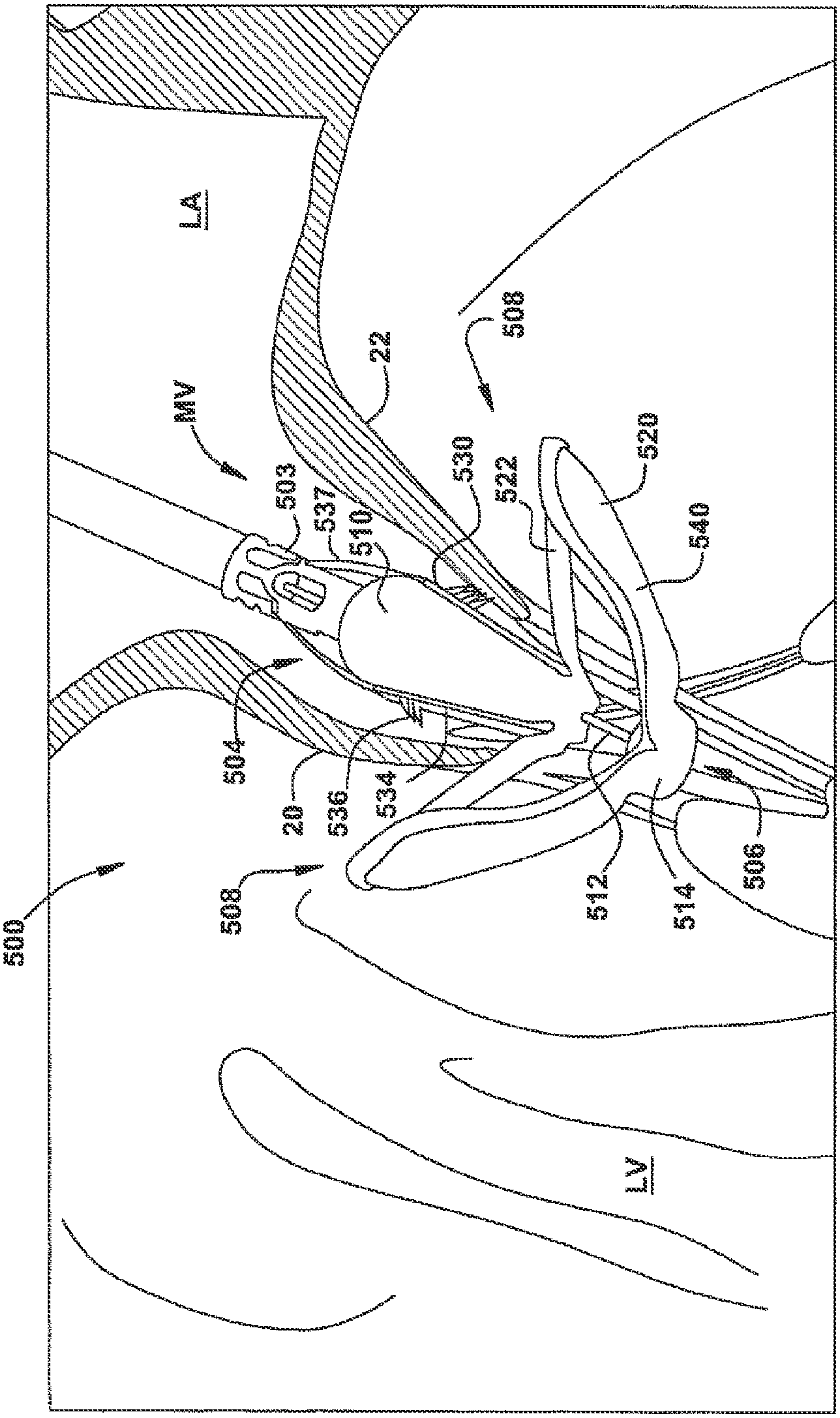
Figure 42:
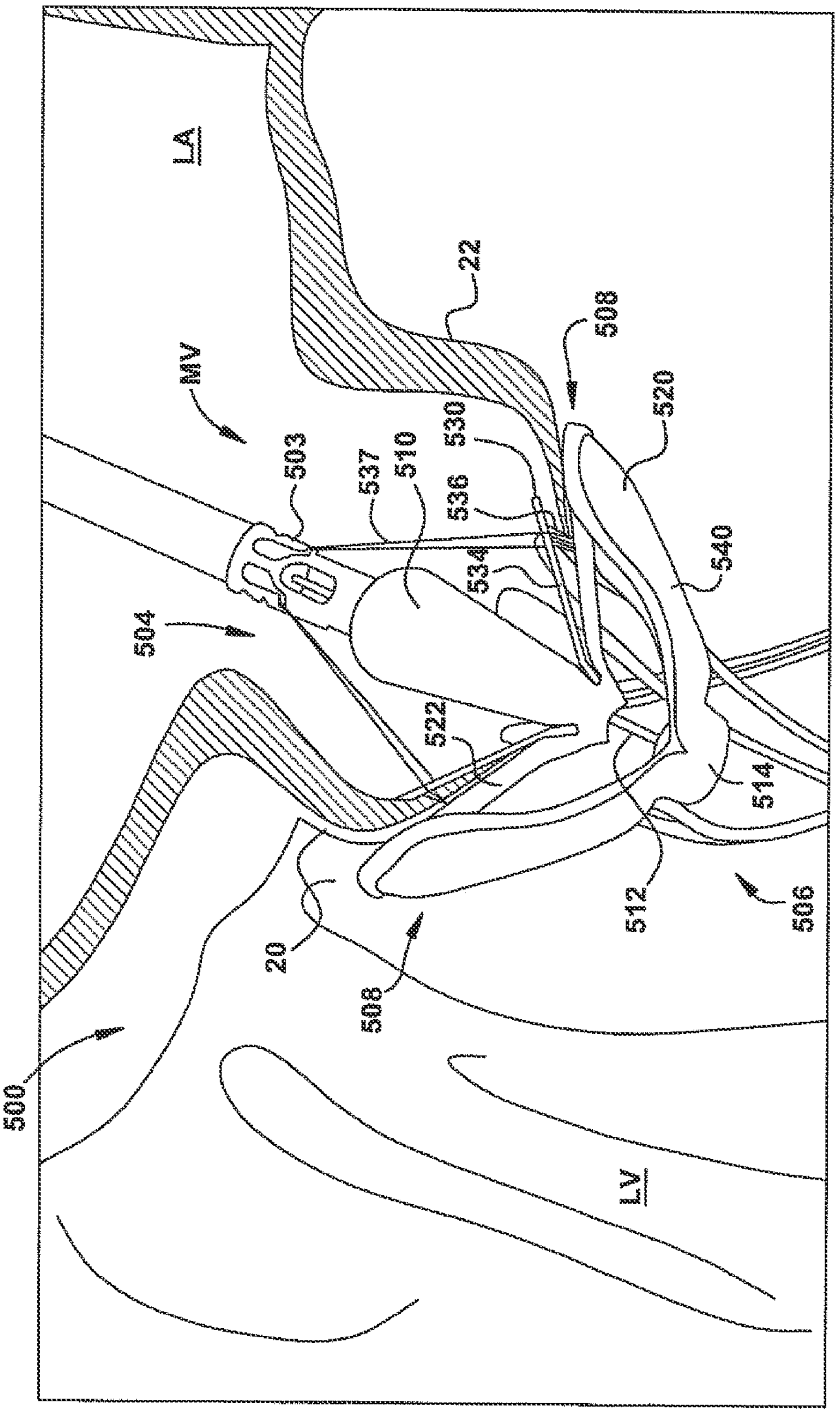
Figure 43:
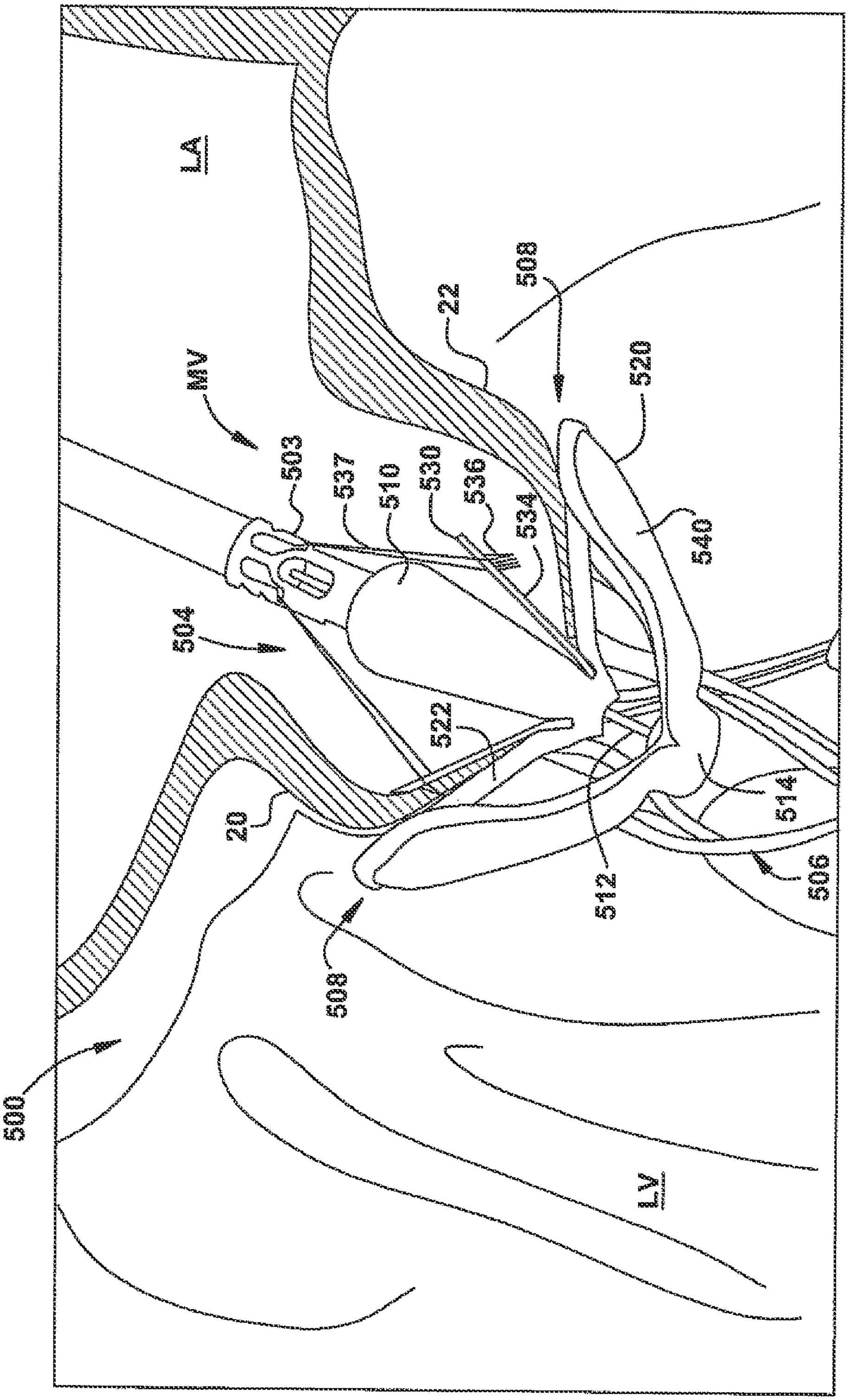
Figure 44:
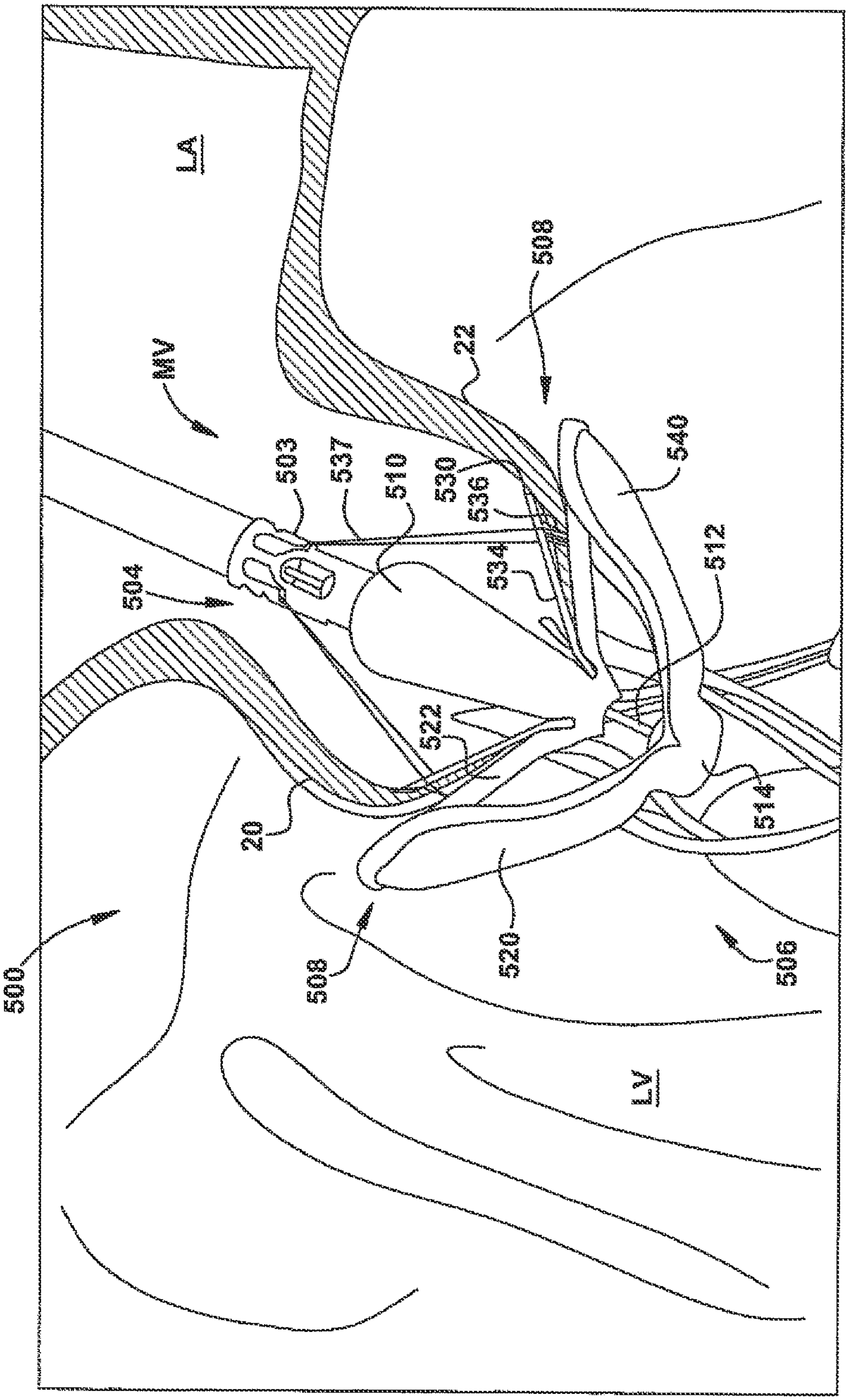
Figure 45:
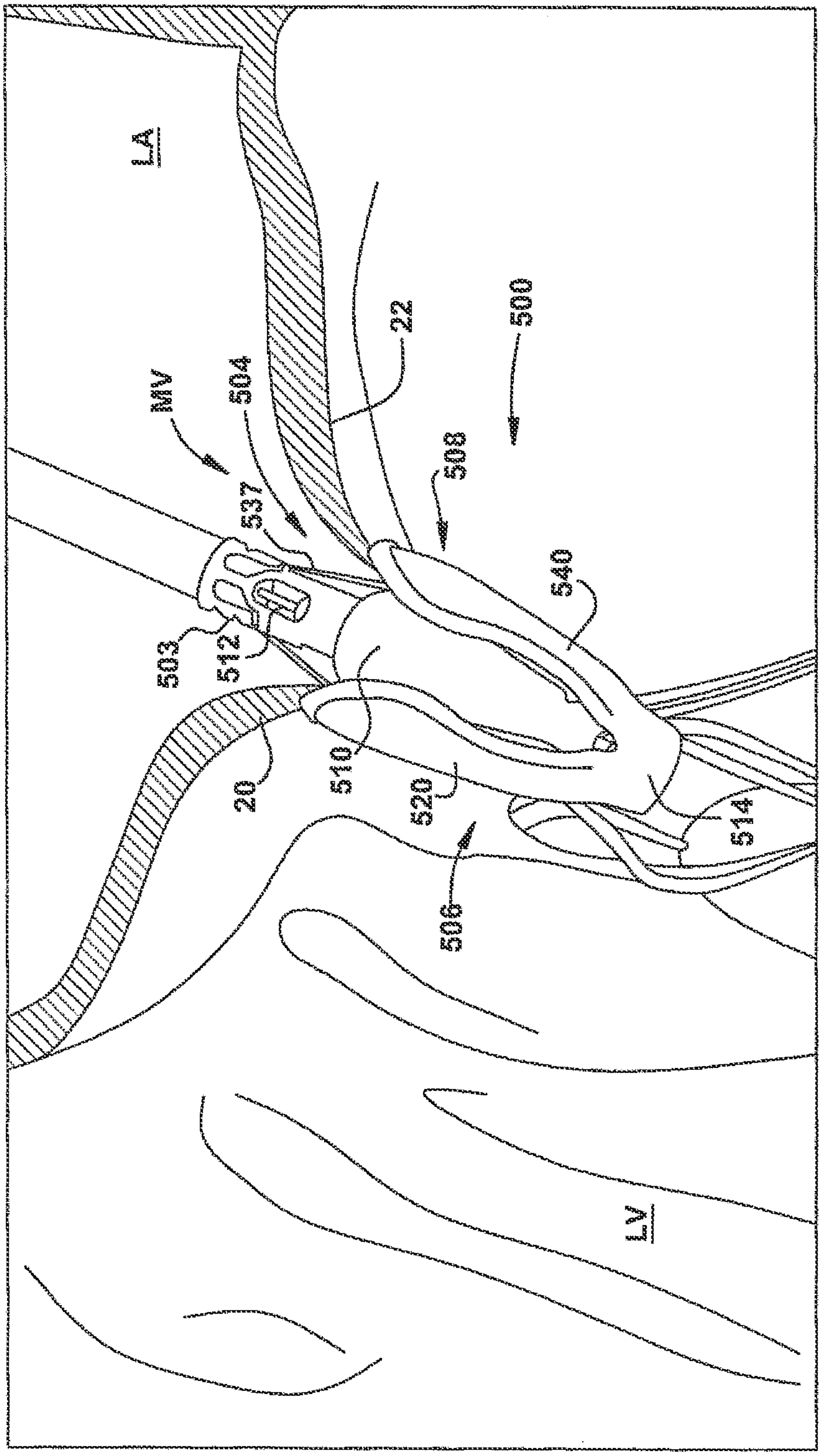
Figure 46:
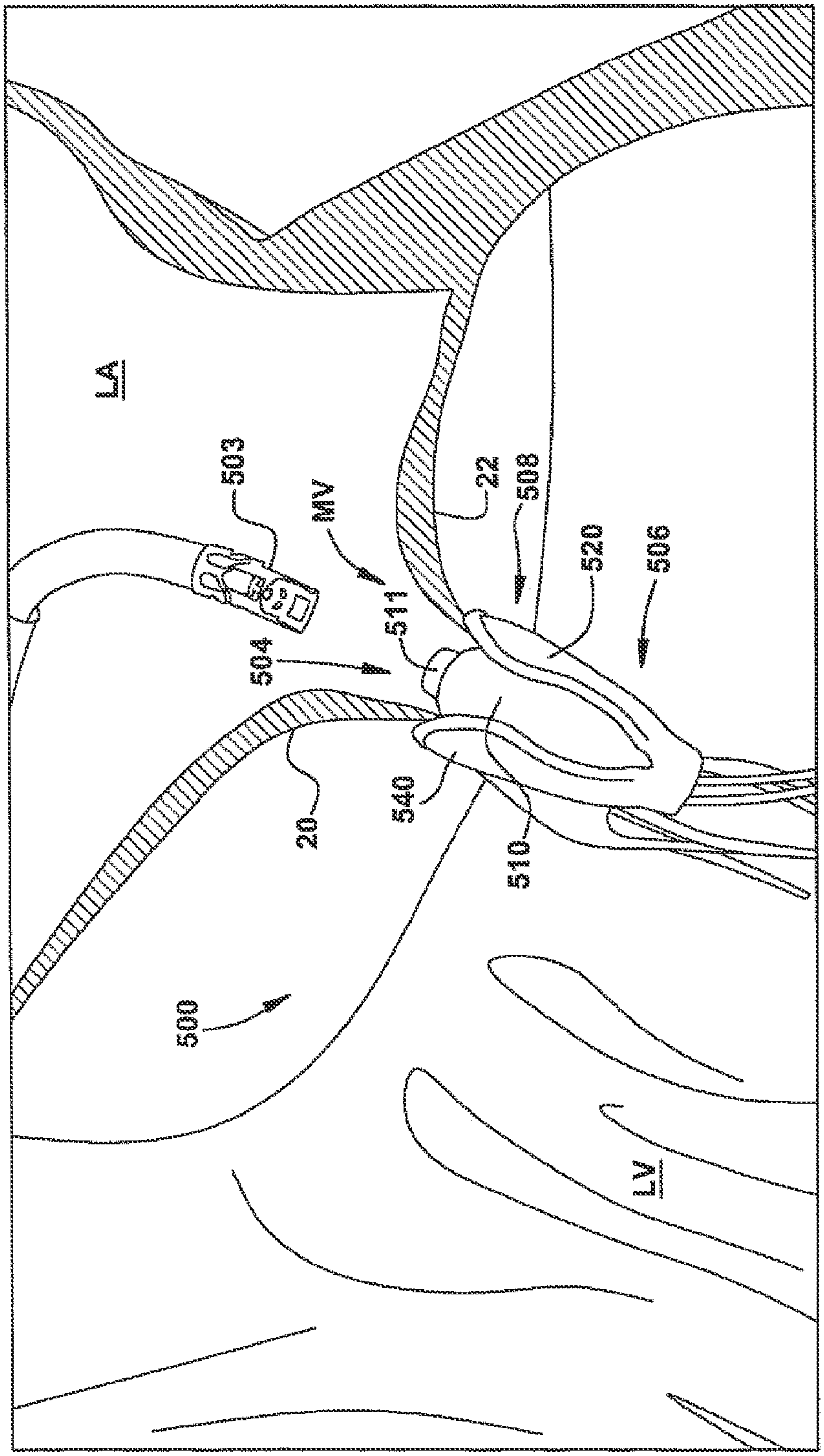

The device 500 is loaded in the delivery sheath in the fully open or fully extended position, because the fully open or fully extended position takes up the least space and allows the smallest catheter to be used (or the largest device 500 to be used for a given catheter size). Referring now to FIG. 35, the delivery sheath is inserted into the left atrium LA through the septum and the device 500 is deployed from the delivery sheath 502 in the fully open condition. The actuation element 512 is then retracted to move the device 500 into the fully closed condition shown in FIGS. 36-37 and then maneuvered towards the mitral valve MV (or other native valve, if implanted in another valve) as shown in FIG. 38. Referring now to FIG. 39, when the device 500 is aligned with the native valve or mitral valve MV, the actuation element 512 is extended to open the paddles 520, 522 into the partially opened position and the clasp control members or actuation lines 537 are retracted to open the clasps or barbed clasps 530 to prepare for leaflet grasp. Next, as shown in FIGS. 40-41, the partially open device 500 is inserted through the native valve or mitral valve MV until leaflets 20, 22 are properly positioned in between the inner paddles 522 and the coaption element 510 and inside the open clasps 530. FIG. 42 shows the device 500 with both clasps 530 closed, though the friction-enhancing elements or barbs 536 of one clasp 530 missed one of the leaflets 22. As can be seen in FIGS. 42-44, the out of position clasp 530 is opened and closed again to properly grasp the missed leaflet 22. When both leaflets 20, 22 are grasped properly, the actuation element 512 is retracted to move the device 500 into the fully closed position shown in FIG. 45. With the device 500 fully implanted in the native mitral valve MV, the actuation element 512 is withdrawn to release the capture mechanism 503 from the proximal collar 511. Once deployed, the device 500 can be maintained in the fully closed position with a mechanical means such as a latch or can be biased to remain closed through the use of spring material, such as steel, and/or shape-memory alloys such as Nitinol. For example, the paddles 520, 522 can be formed of steel or Nitinol shape-memory alloy—produced in a wire, sheet, tubing, or laser sintered powder—and are biased to hold the outer paddles 520 closed around the inner paddles 522, coaption element 510, and the clasps 530 pinched around native leaflets 20, 22.

Figure 6B:
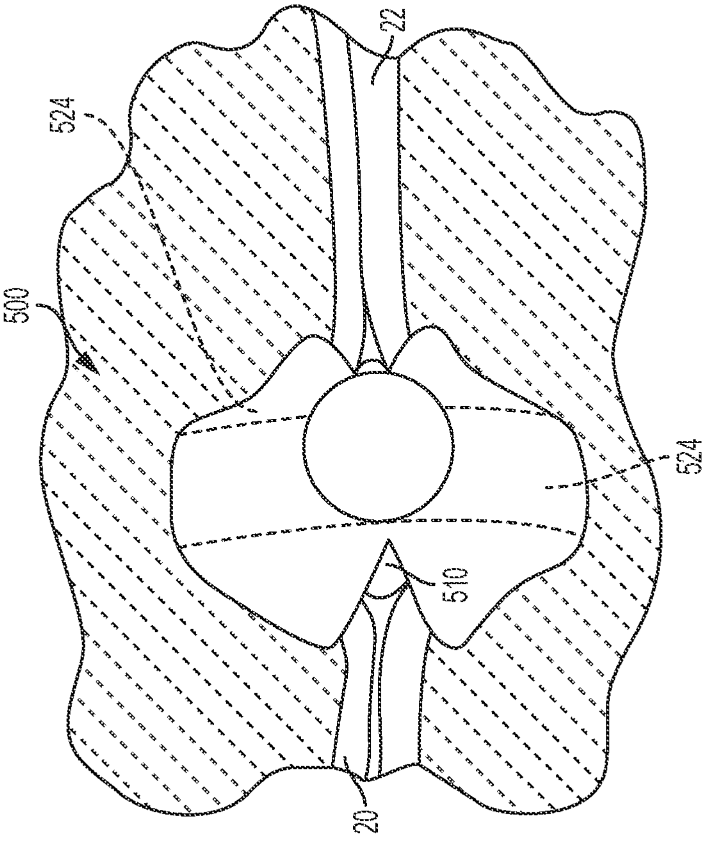
FIG. 6B illustrates a valve repair device attached to mitral valve leaflets with the coaption element in the gap of the mitral valve as viewed from a ventricular side of the mitral valve.
Figure 6A:
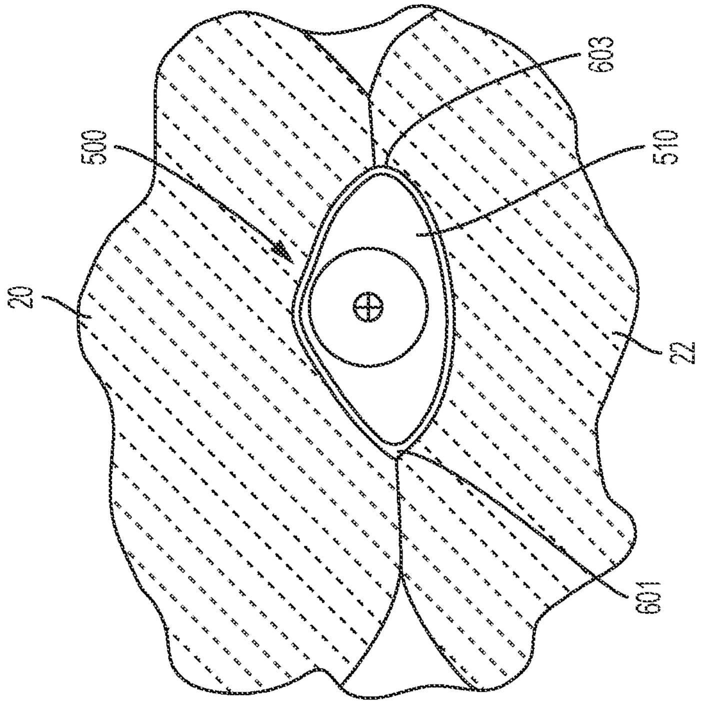
FIG. 6A illustrates a coaption element in the gap of the mitral valve as viewed from an atrial side of the mitral valve.

The device 500 can have a wide variety of different shapes and sizes. Referring to FIGS. 6 and 6A-6E, in an example embodiment, the coaption element 510 functions as a gap filler in the valve regurgitant orifice, such as the gap 26 in the native valve illustrated by FIG. 6. Referring to FIG. 6A, since the coaption element 510 is deployed between two opposing valve leaflets 20, 22, the leaflets will not coapt against each other in the area of the coaption element 510, but coapt against the coaption element 510 instead. This reduces the distance the leaflets 20, 22 need to be approximated. A reduction in leaflet approximation distance can result in several advantages. For example, the coaption element and resulting reduced approximation can facilitate repair of severe mitral valve anatomies, such as large gaps in functional valve disease (See for example, FIG. 6). Since the coaption element 510 reduces the distance the native valves have to be approximated, the stress in the native valves can be reduced or minimized. Shorter approximation distance of the valve leaflets 20, 22 can require less approximation forces which can result in less tension of the leaflets and less diameter reduction of the valve annulus. The smaller reduction of the valve annulus (or no reduction of the valve annulus) can result in less reduction in valve orifice area as compared to a device without a spacer. As a result, the coaption element 510 can reduce the transvalvular gradients.

Figure 6C:
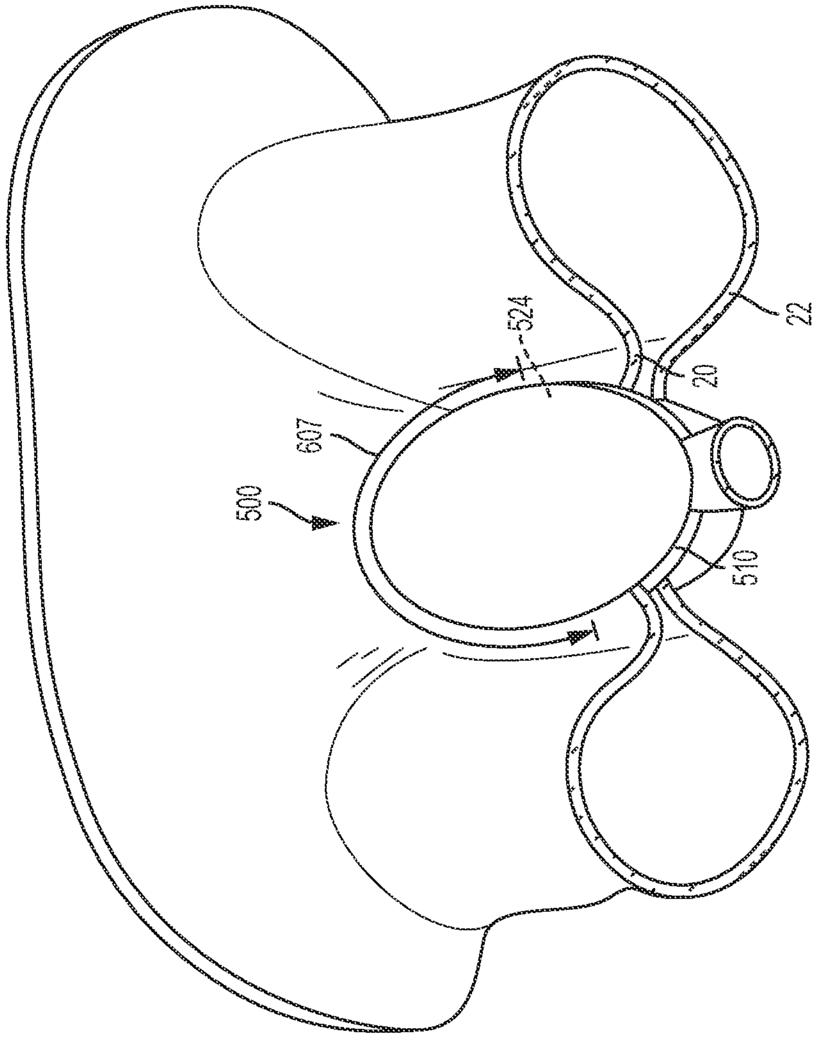
FIG. 6C is a perspective view of a valve repair device attached to mitral valve leaflets with the coaption element in the gap of the mitral valve shown from a ventricular side of the mitral valve.
Figure 6D:
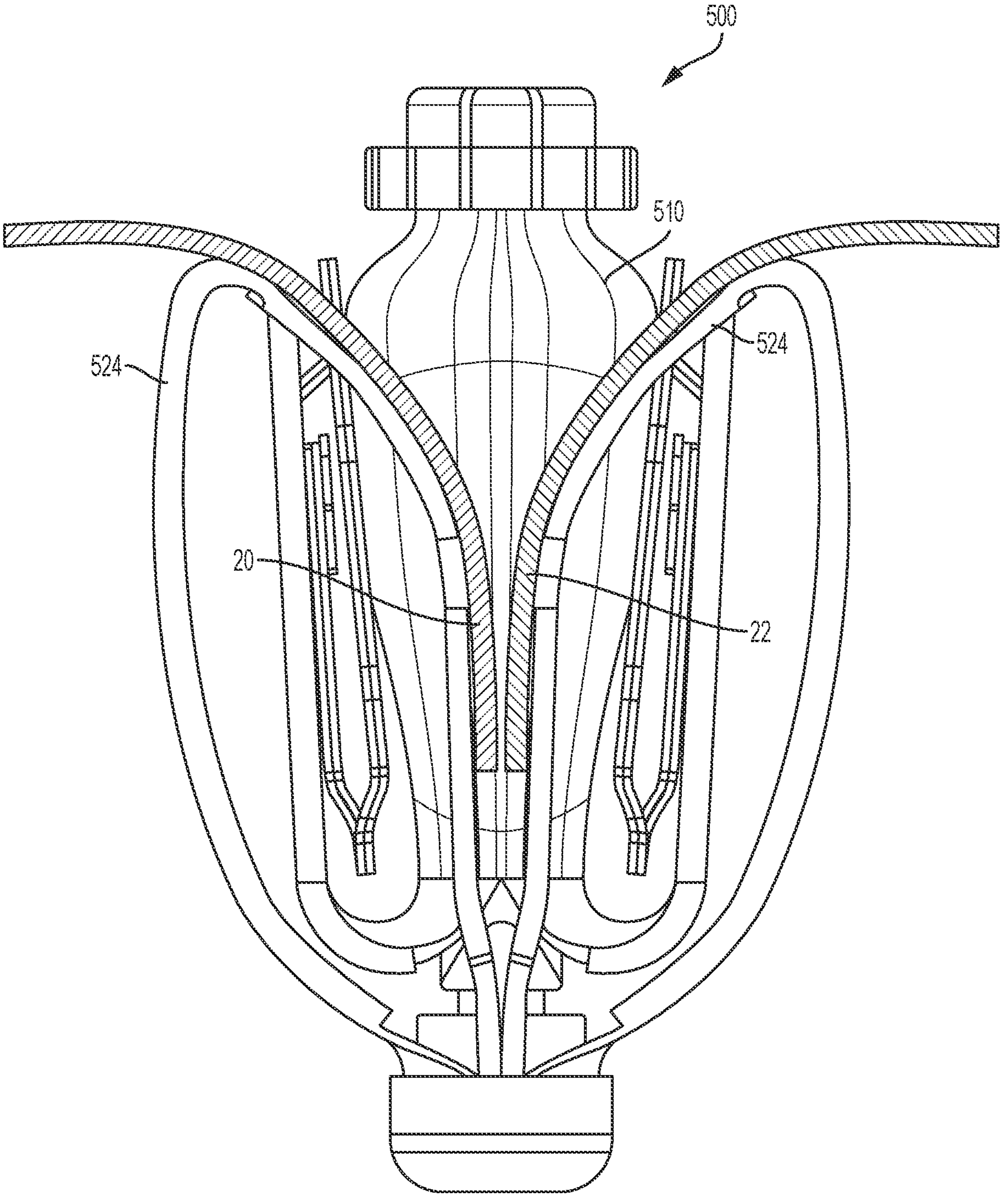
FIG. 6D is a schematic view illustrating a path of mitral valve leaflets along each side of a coaption element of an example mitral valve repair device.
Figure 6E:
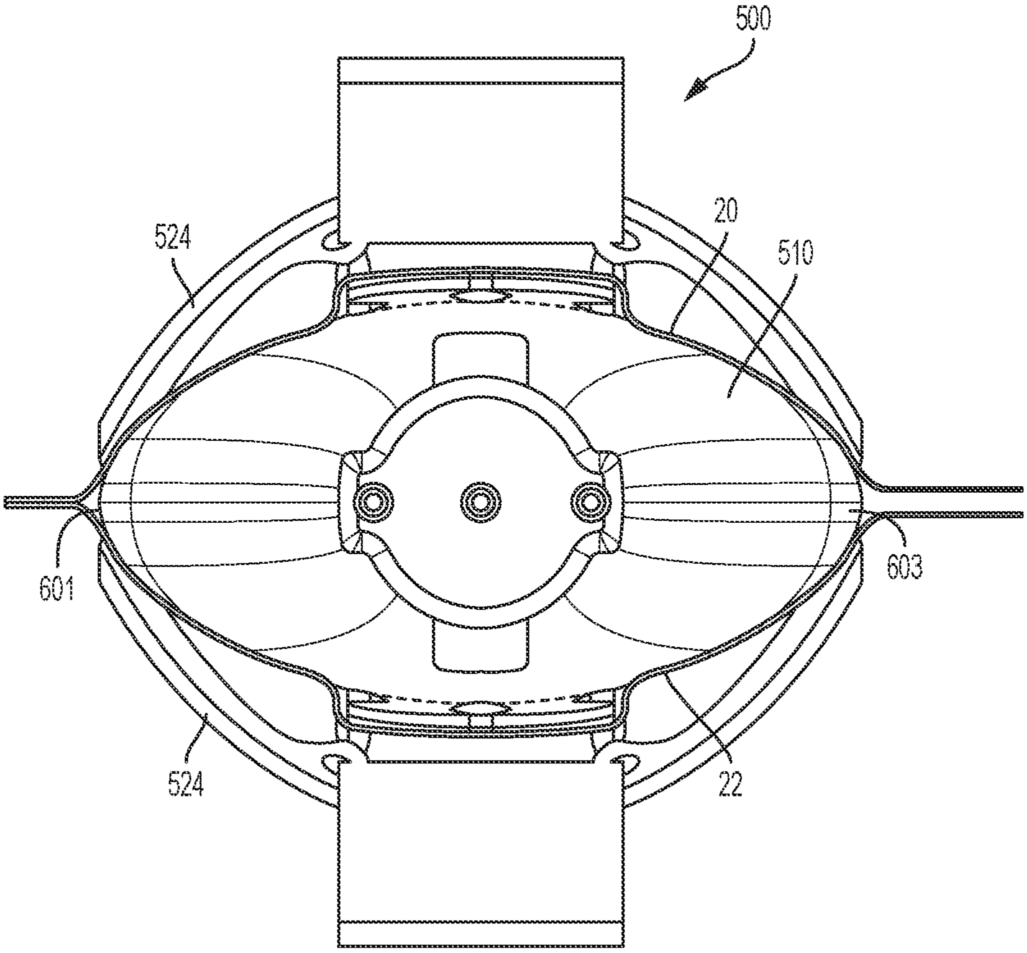
FIG. 6E is a top schematic view illustrating a path of mitral valve leaflets around a coaption element of an example native valve repair device.
Figure 7:
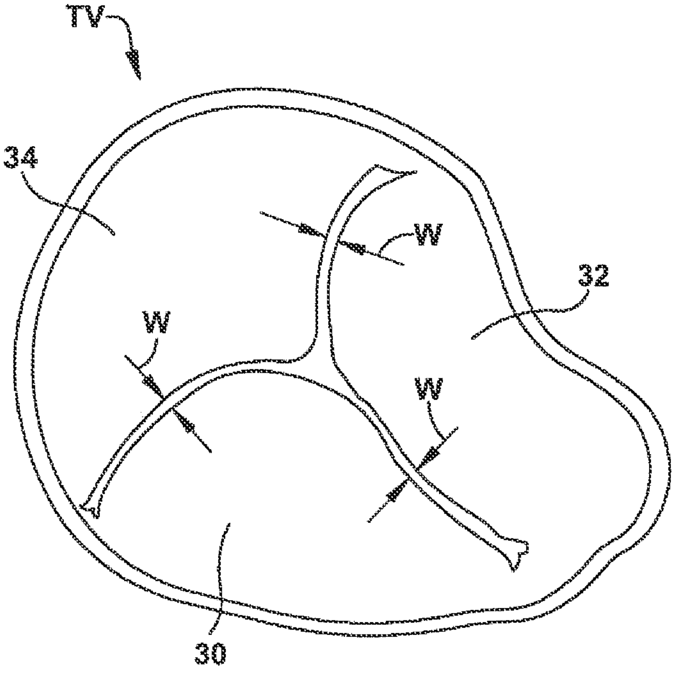
FIG. 7 illustrates a tricuspid valve viewed from an atrial side of the tricuspid valve.

In one example embodiment, the paddle frames 524 conform to the shape of the coaption element 510. In one example, if the coaption element 510 is wider than the paddle frames 524, a distance (gap) between the opposing leaflets 20, 22 can be created by the device 500. Referring to FIGS. 6A-6E, in one example embodiment the paddles are configured to conform to the shape or geometry of the coaption element 510. As a result, the paddles can mate with both the coaption element 510 and the native valve. Referring to FIGS. 6D and 6E, in one example embodiment the paddles 524 surround the coaption element 510. Thus, when the leaflets 20, 22 are coapted or pressed against the coaption element 510, the leaflets 20, 22 fully surround or "hug" the coaption element 510 in its entirety, thus small leaks on the medial and lateral aspects of the coaption element 510 can be prevented. FIGS. 6B and 6C illustrate the valve repair device 500 attached to native valve leaflets 20, 22 from the ventricular side of the mitral valve. FIG. 6A illustrates the valve repair device 500 attached to mitral valve leaflets 20, 22 from the atrial side of the mitral valve. Referring to FIGS. 6A and 6B, when the paddles have a geometry that conforms to the geometry of the coaption element 510, the leaflets 20, 22 can coapt around the coaption element and/or along the length of the spacer. Referring to FIG. 6E, a schematic atrial view/surgeons view depicts the paddle frames (which would not actually be visible from a true atrial view), conforming to the spacer geometry. The opposing leaflets 20, 22 (the ends of which would also not be visible in the true atrial view) being approximated by the paddles, to fully surround or "hug" the coaption element 510.

Referring to FIGS. 6B-6E, because the paddle frames 524 conform to the shape of the coaption element 510, the valve leaflets 20, 22 can be coapted completely around the coaption element by the paddle frames 524, including on the lateral and medial aspects 601, 603 of the coaption element 510. This coaption of the leaflets 20, 22 against the lateral and medial aspects of the coaption element 510 would seem to contradict the statement above that the presence of a coaption element 510 minimizes the distance the leaflets need to be approximated. However, the distance the leaflets 20, 22 need to be approximated is still minimized if the coaption element 510 is placed precisely at a regurgitant gap and the regurgitant gap is less than the width (medial–lateral) of the coaption element 510.

Referring to FIGS. 6A and 6E, the coaption element 510 can take a wide variety of different shapes. In one example embodiment, when viewed from the top (and/or sectional views from the top, the coaption element has an oval shape or an elliptical shape. The oval or elliptical shape can allow the paddle frames 524 to conform to the shape of the coaption element and/or can reduce lateral leaks (See FIGS. 48-66).

Figure 2A:
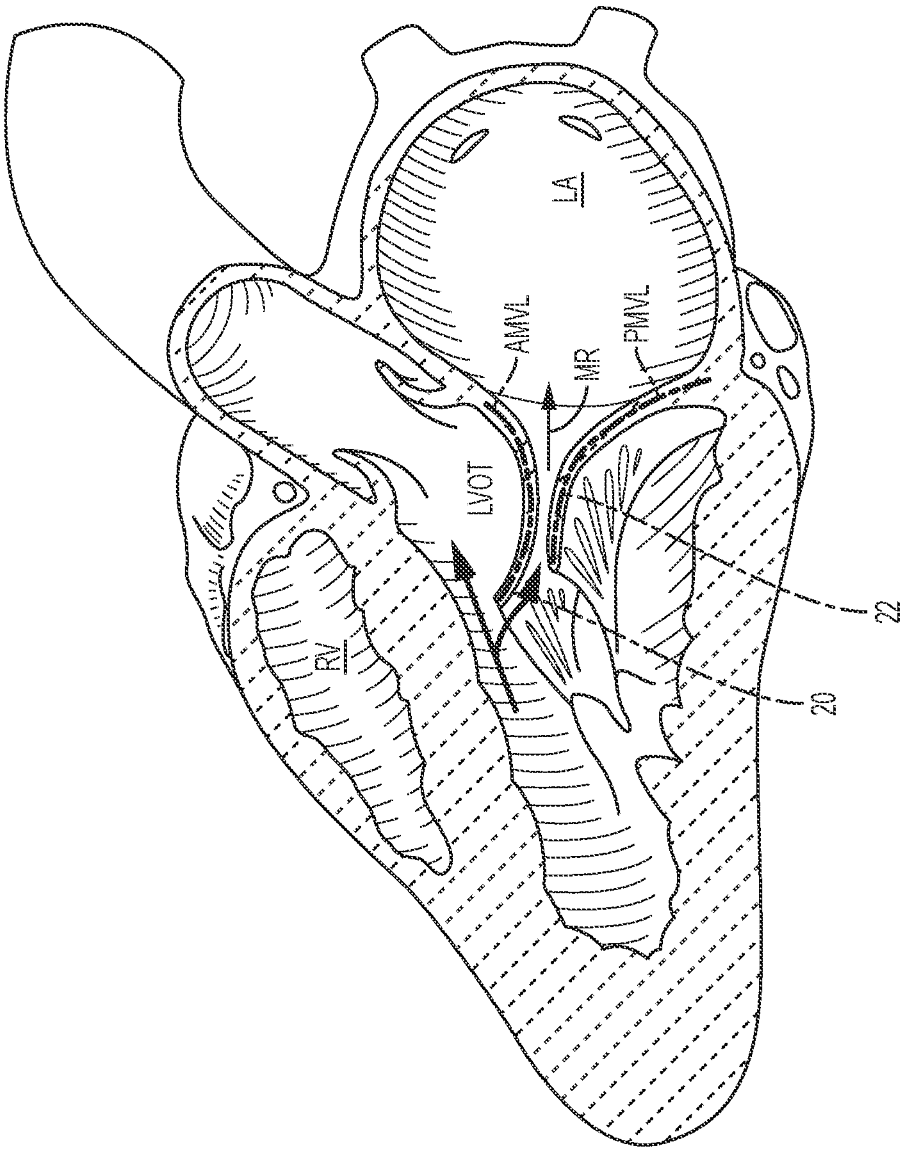
FIG. 2A is another cutaway view of the human heart in a systolic phase.

As mentioned above, the coaption element 510 can reduce tension of the opposing leaflets by reducing the distance the leaflets need to be approximated to the coaption element 510 at the positions 601, 603. The reduction of the distance of leaflet approximation at the positions 601, 603 can result in the reduction of leaflet stresses and gradients. In addition, as is also explained above, the native valve leaflets 20, 22 can surround or "hug" the coaption element in order to prevent lateral leaks. In one example embodiment, the geometrical characteristics of the coaption element can be designed to preserve and augment these two characteristics of the device 500. Referring to FIG. 2A, as seen from a Left Ventricular Outflow Tract (LVOT) view, the anatomy of the leaflets 20, 22 is such that the inner sides of the leaflets coapt at the free end portions and the leaflets 20, 22 start receding or spreading apart from each other. The leaflets 20, 22 spread apart in the atrial direction, until each leaflet meets with the mitral annulus.

Figure 2B:
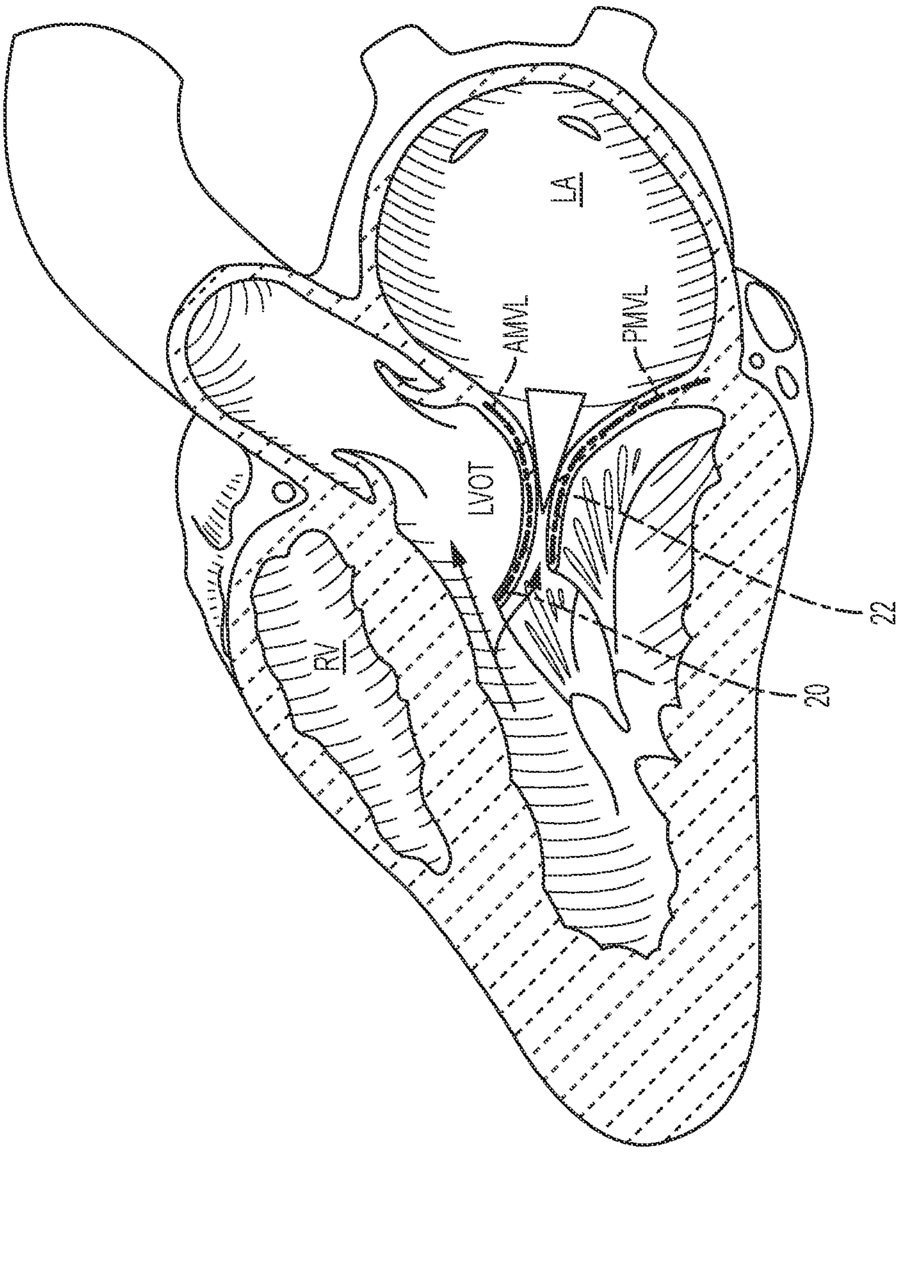
FIG. 2B is the cutaway view of FIG. 2A annotated to illustrate a natural shape of mitral valve leaflets in the systolic phase.

In one example embodiment, the valve repair device 500 and its coaption element 510 are designed to conform to the geometrical anatomy of the valve leaflets 20, 22. To achieve valve sealing, the valve repair device 500 can be designed to coapt the native leaflets to the coaption element, completely around the coaption element, including at the medial 601 and lateral 603 positions of the coaption element 510. Additionally, a reduction on forces required to bring the leaflets into contact with the coaption element 510 at the positions 601, 603 can minimize leaflet stress and gradients. FIG. 2B shows how a tapered or triangular shape of a coaption element 510 will naturally adapt to the native valve geometry and to its expanding leaflet nature (toward the annulus).

FIG. 6D illustrates the geometry of the coaption element 510 and the paddle frame 524 from an LVOT perspective. As can be seen in this view, the coaption element 510 has a tapered shape being smaller in dimension in the area closer to where the inside surfaces of the leaflets 20, 22 are required to coapt and increase in dimension as the coaption element extends toward the atrium. The depicted native valve geometry is accommodated by a tapered coaption element geometry. Still referring to FIG. 6D, the tapered coaption element geometry, in conjunction with the illustrated expanding paddle frame 524 shape (toward the valve annulus) can help to achieve coaptation on the lower end of the leaflets, reduce stress, and minimize transvalvular gradients.

Figure 67:
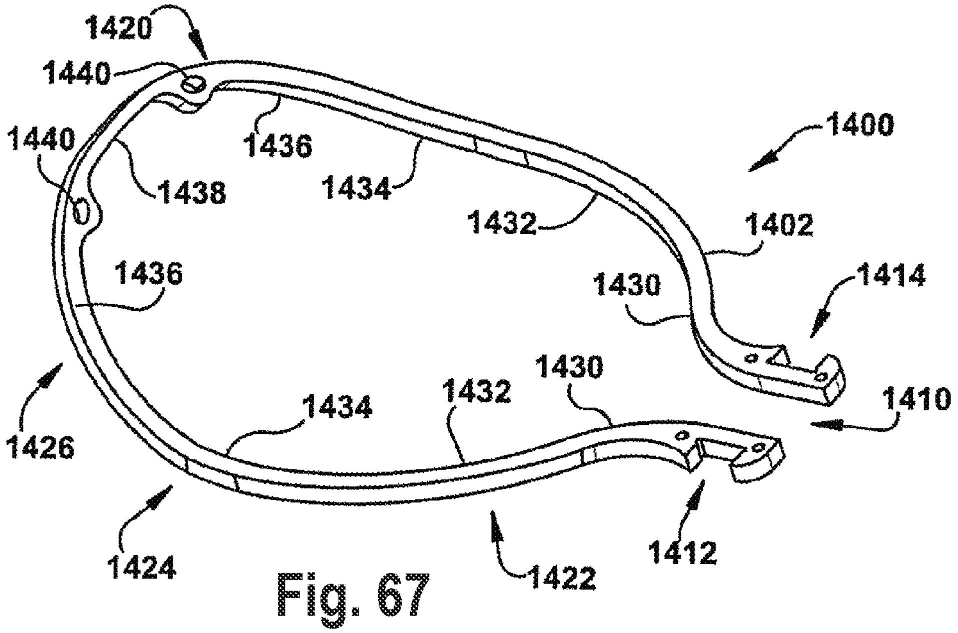
FIGS. 67-69 show perspective views of an example embodiment of a paddle frame for the implantable prosthetic device of FIG. 48.
Figure 67A:
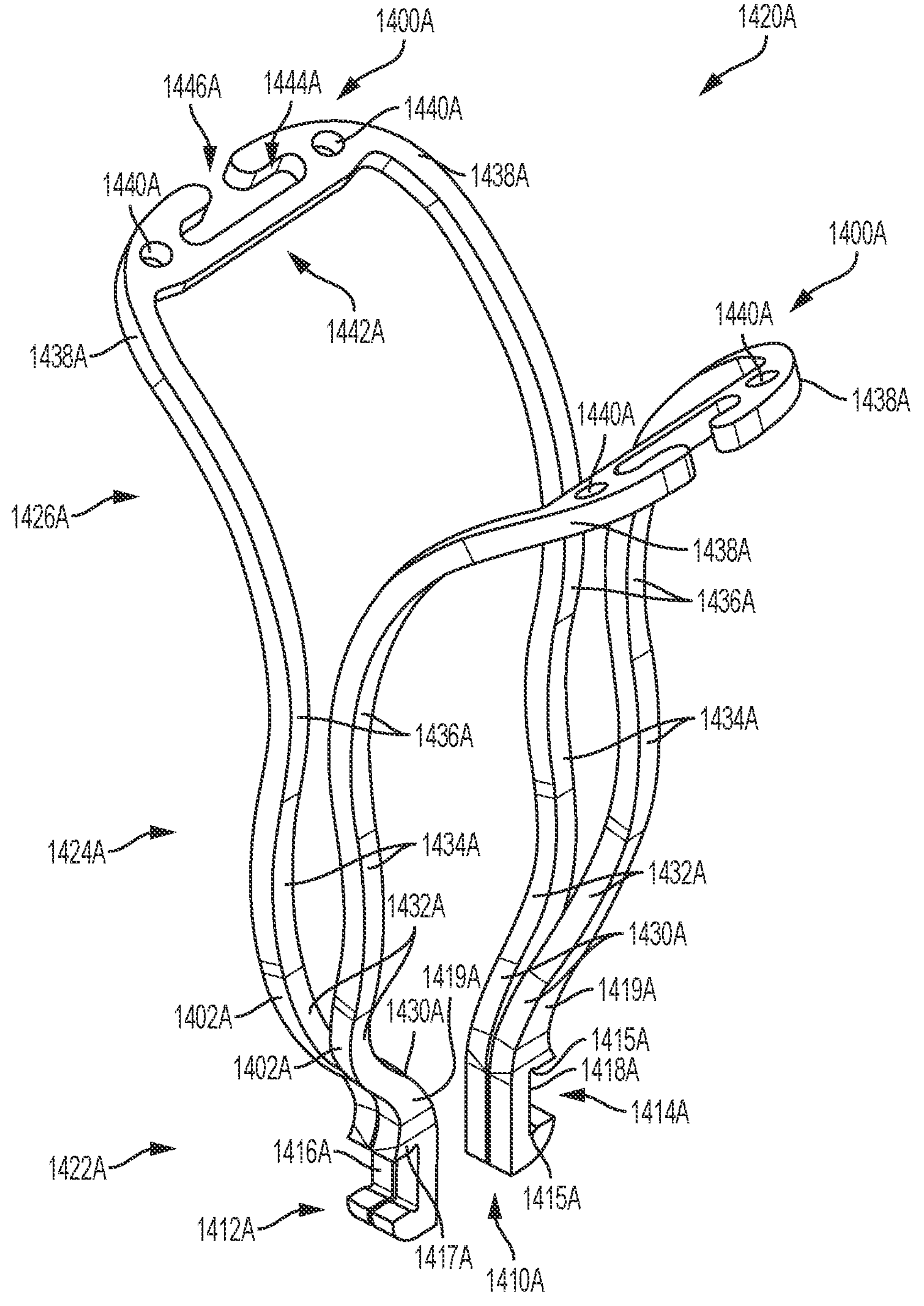
FIG. 67A shows a perspective view of an example embodiment of a paddle frame for the implantable prosthetic device of FIG. 48A.
Figure 68:
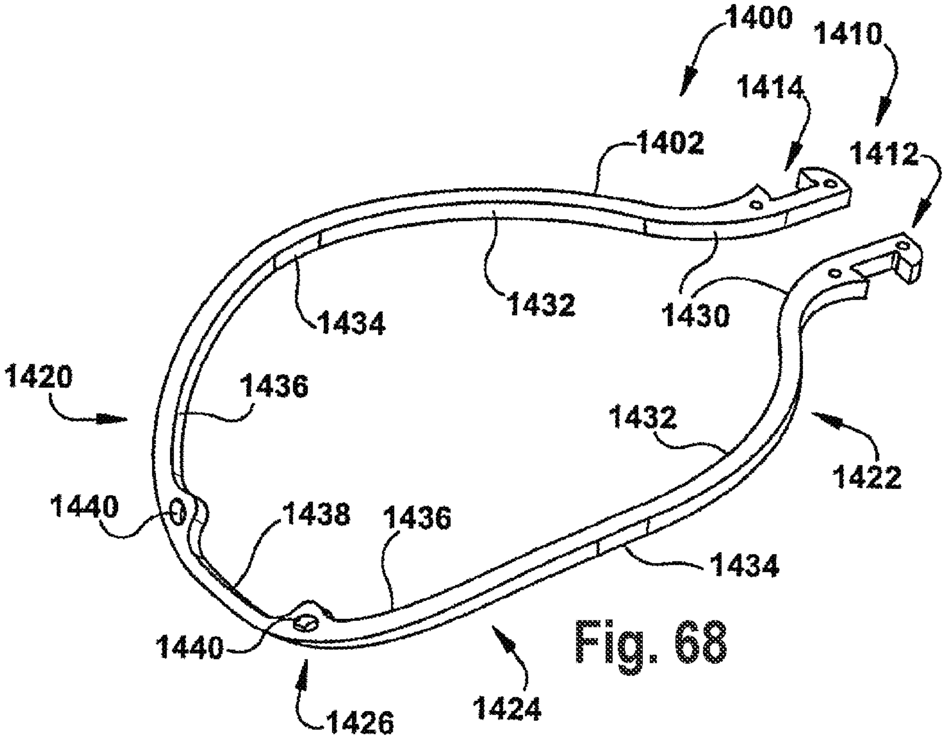

Referring to FIG. 6C, in one example embodiment remaining shapes of the coaption element 510 and the paddle frames 524 can be defined based on an Intra-Commissural view of the native valve and the device 500. Two factors of these shapes are leaflet coaptation against the coaption element 510 and reduction of stress on the leaflets due to the coaption. Referring to FIGS. 6C and 67, to both coapt the valve leaflets 20, 22 against the coaption element 510 and reduce the stress applied to the valve leaflets 20, 22 by the coaption element 510 and/or the paddles 524, the coaption element 510 can have a round or rounded shape and the paddle frame 524 can have a full radius that spans from one leg of the paddles to the other leg of the paddles. The round shape of the coaption element and/or the illustrated fully rounded shape of the paddle frame will distribute the stresses on the leaflets 20, 22 across a large, curved engagement area 607. For example, in FIG. 6C, the force on the leaflets 20, 22 by the paddle frames is spread along the entire rounded length of the paddle frame 524, as the leaflets 20 try to open during the diastole cycle.

Figure 50:
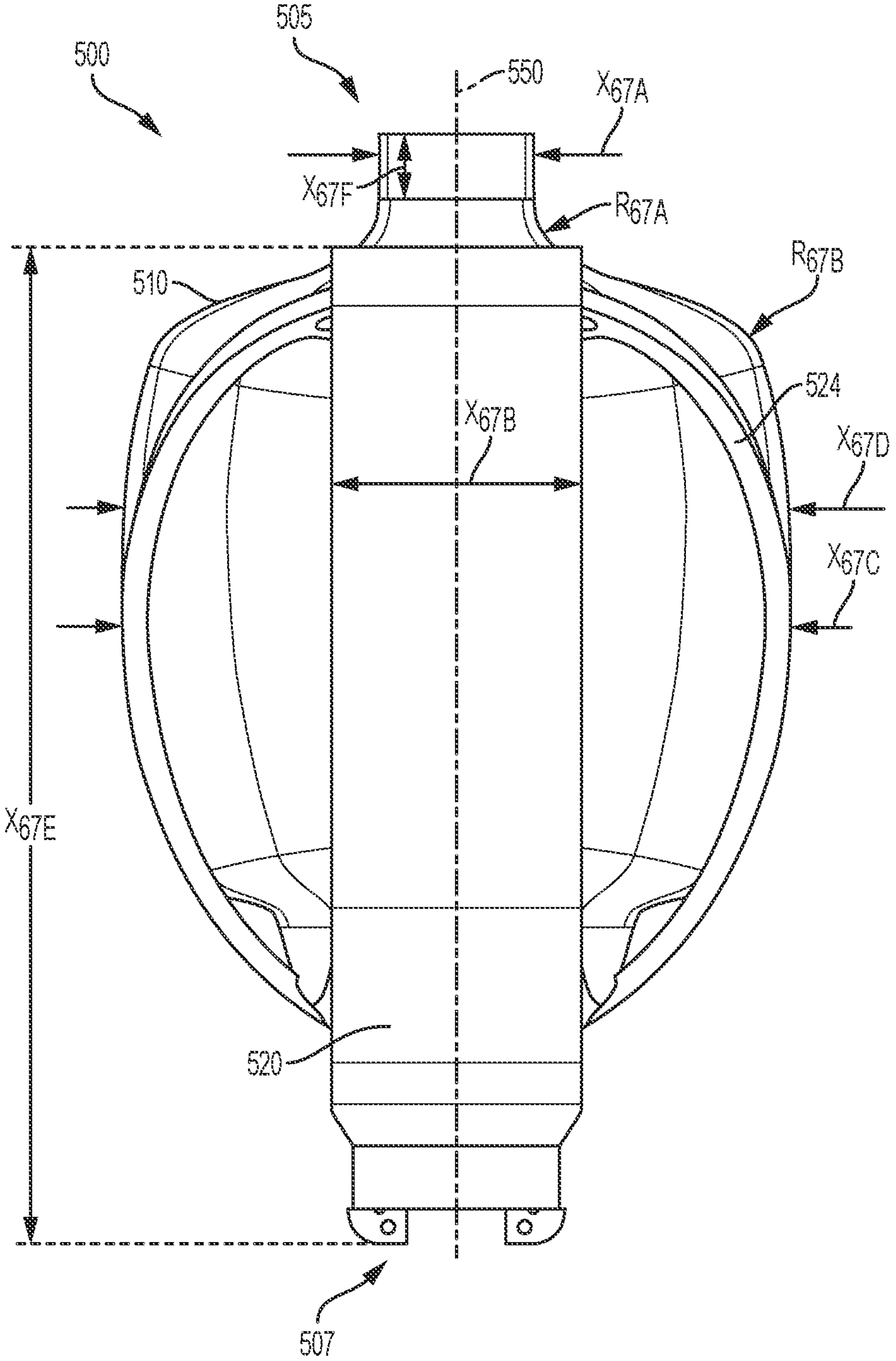
FIG. 50 shows a front view of the implantable prosthetic device of FIG. 48.

Referring to FIG. 50, in one example embodiment, to cooperate with the full rounded shape of the paddle frames 524, and/or in order to maximize leaflet coaptation against the coaption element 510 and leaflet-to-leaflet coaptation at the sides 601, 603 of the coaption element 510, the shape of the coaption element in the intra-commissural view follows a round shape. Referring to FIG. 50, the round shape of the coaption element in this view substantially follows or is close to the shape of the paddle frames 524.

Figure 51:
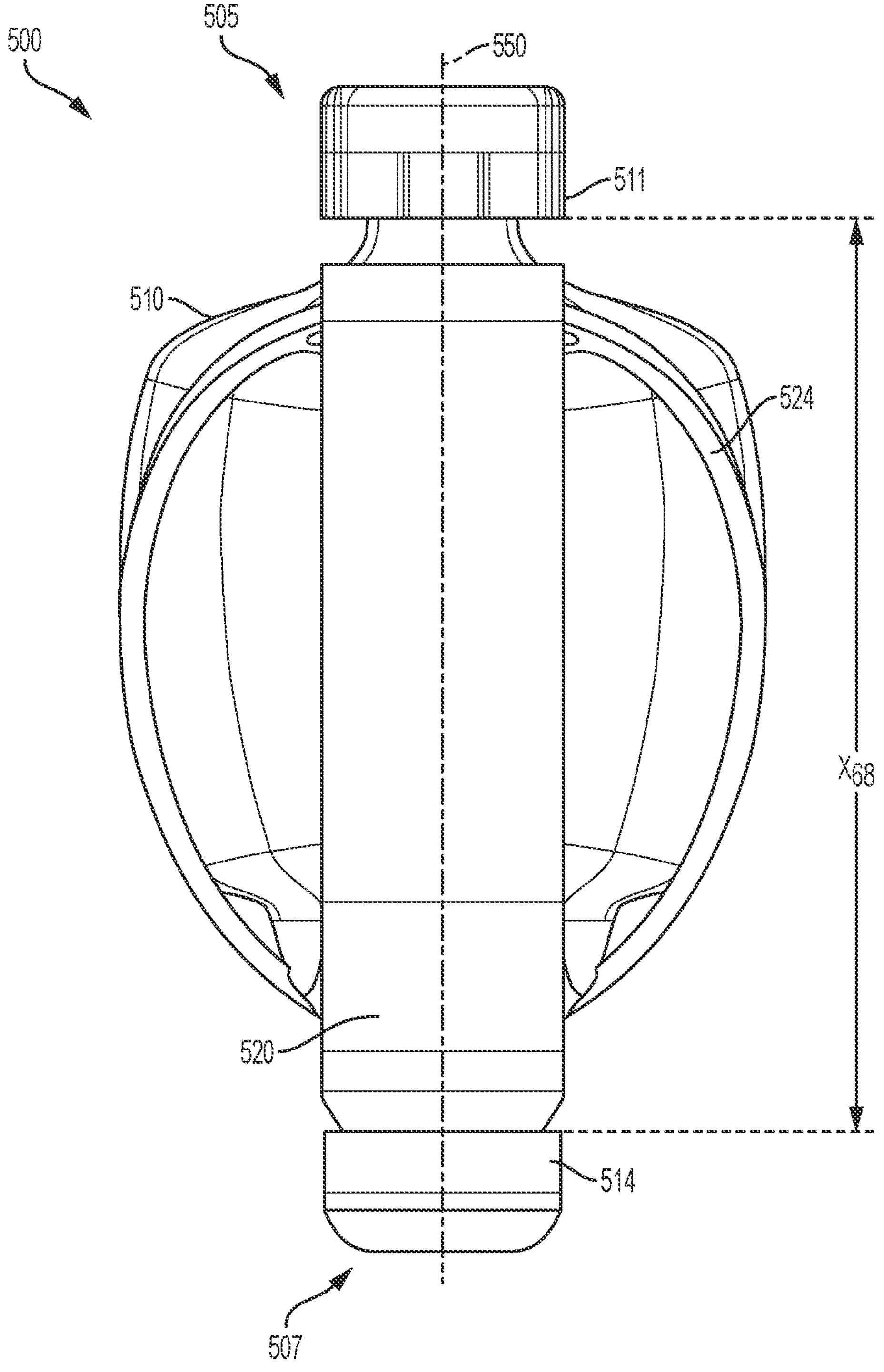
FIG. 51 shows a front view of the implantable prosthetic device of FIG. 48 with additional components.

In one example embodiment, the overall shape of the coaption element 510 is an elliptical or oval cross section when seen from the surgeon's view (top view—See FIG. 53), a tapered shape or cross section when seen from an LVOT view (side view—See FIG. 52), and a substantially round shape or rounded shape when seen from an intra-commissural view (See FIG. 51). In one example embodiment, a blend of these three geometries can result in the three-dimensional shape of the illustrated coaption element 510 that achieves the benefits described above.

In one example embodiment, the dimensions of the coaption element are selected to minimize the number of implants that a single patient will require (preferably one), while at the same time maintaining low transvalvular gradients. In one example embodiment, the anterior-posterior distance $X_{47B}$ at the top of the spacer is about 5 mm, and the medial-lateral distance $X_{67D}$ of the spacer at its widest is about 10 mm. In one example embodiment, the overall geometry of the device 500 can be based on these two dimensions and the overall shape strategy described above. It should be readily apparent that the use of other anterior-posterior distance $X_{47B}$ and medial-lateral distance $X_{67D}$ as starting points for the device will result in a device having different dimensions. Further, using other dimensions and the shape strategy described above will also result in a device having different dimensions.

Tables A, B, and C provide examples of values and ranges for dimensions of the device and components of the device for some example embodiments. However, the device can have a wide variety of different shapes and sizes and need not have all or any of the dimensional values or dimensional ranges provided in Tables A, B, and C. Table A provides examples of linear dimensions X in millimeters and ranges of linear dimensions in millimeters for the device and components of the device. Table B provides examples of radius dimensions R in millimeters and ranges of radius dimensions in millimeters for the device and components of the device. Table C provides examples of angular dimensions a in degrees and ranges of angular dimensions in degrees for the device and components of the device. The subscripts for each of the dimensions indicates the drawing in which the dimension first appears.

TABLE A

| Linear Dimensions (mm) | | | | | | | | | |
|---|---|---|---|---|---|---|---|---|---|
| | | Range A | | Range B | | Range C | Range D | | Range C |
| | Example | (max) | (min) | (max) | (min) | (max) | (min) | (max) | (min) |
| $X_{47A}$ | 2.8 | 1.4 | 4.2 | 2.1 | 3.5 | 2.52 | 3.08 | 2.66 | 2.94 |
| $X_{47B}$ | 5.3 | 2.65 | 7.95 | 3.975 | 6.625 | 4.77 | 5.83 | 5.035 | 5.565 |
| $X_{47C}$ | 2.8 | 1.4 | 4.2 | 2.1 | 3.5 | 2.52 | 3.08 | 2.66 | 2.94 |
| $X_{47D}$ | 3.3 | 1.65 | 4.95 | 2.475 | 4.125 | 2.97 | 3.63 | 3.135 | 3.465 |
| $X_{47E}$ | 5.4 | 2.7 | 8.1 | 4.05 | 6.75 | 4.86 | 5.94 | 5.13 | 5.67 |
| $X_{47F}$ | 8 | 4 | 12 | 6 | 10 | 7.2 | 8.8 | 7.6 | 8.4 |
| $X_{47G}$ | 1 | 0.5 | 1.5 | 0.75 | 1.25 | 0.9 | 1.1 | 0.95 | 1.05 |
| $X_{52A}$ | 12 | 6 | 18 | 9 | 15 | 10.8 | 13.2 | 11.4 | 12.6 |
| $X_{58A}$ | 11 | 5.5 | 16.5 | 8.25 | 13.75 | 9.9 | 12.1 | 10.45 | 11.55 |
| $X_{59A}$ | 27 | 13.5 | 40.5 | 20.25 | 33.75 | 24.3 | 29.7 | 25.65 | 28.35 |
| $X_{59B}$ | 8 | 4 | 12 | 6 | 10 | 7.2 | 8.8 | 7.6 | 8.4 |
| $X_{59C}$ | 7 | 3.5 | 10.5 | 5.25 | 8.75 | 6.3 | 7.7 | 6.65 | 7.35 |
| $X_{67A}$ | 2.4 | 1.2 | 3.6 | 1.8 | 3 | 2.16 | 2.64 | 2.28 | 2.52 |
| $X_{67B}$ | 3.7 | 1.85 | 5.55 | 2.775 | 4.625 | 3.33 | 4.07 | 3.515 | 3.885 |
| $X_{67C}$ | 10 | 5 | 15 | 7.5 | 12.5 | 9 | 11 | 9.5 | 10.5 |
| $X_{67D}$ | 10 | 5 | 15 | 7.5 | 12.5 | 9 | 11 | 9.5 | 10.5 |
| $X_{67E}$ | 15 | 7.5 | 22.5 | 11.25 | 18.75 | 13.5 | 16.5 | 14.25 | 15.75 |
| $X_{67F}$ | 1 | 0.5 | 1.5 | 0.75 | 1.25 | 0.9 | 1.1 | 0.95 | 1.05 |
| $X_{68}$ | 14.2 | 7.1 | 21.3 | 10.65 | 17.75 | 12.78 | 15.62 | 13.49 | 14.91 |
| $X_{70A}$ | 1.7 | 0.85 | 2.55 | 1.275 | 2.125 | 1.53 | 1.87 | 1.615 | 1.785 |
| $X_{70B}$ | 2.8 | 1.4 | 4.2 | 2.1 | 3.5 | 2.52 | 3.08 | 2.66 | 2.94 |
| $X_{71A}$ | 6.2 | 3.1 | 9.3 | 4.65 | 7.75 | 5.58 | 6.82 | 5.89 | 6.51 |
| $X_{71B}$ | 5.4 | 2.7 | 8.1 | 4.05 | 6.75 | 4.86 | 5.94 | 5.13 | 5.67 |
| $X_{71C}$ | 0.9 | 0.45 | 1.35 | 0.675 | 1.125 | 0.81 | 0.99 | 0.855 | 0.945 |
| $X_{71D}$ | 3.75 | 1.875 | 5.625 | 2.8125 | 4.6875 | 3.375 | 4.125 | 3.5625 | 3.9375 |
| $X_{71E}$ | 4.5 | 2.25 | 6.75 | 3.375 | 5.625 | 4.05 | 4.95 | 4.275 | 4.725 |
| $X_{72A}$ | 10.4 | 5.2 | 15.6 | 7.8 | 13 | 9.36 | 11.44 | 9.88 | 10.92 |

TABLE A-continued

| Linear Dimensions (mm) | | | | | | | | | |
|---|---|---|---|---|---|---|---|---|---|
| | | Range A | | Range B | | Range C Range D Range C | | | |
| | Example | (max) | (min) | (max) | (min) | (max) | (min) | (max) | (min) |
| $X_{91A}$ | 8.8 | 4.4 | 13.2 | 6.6 | 11 | 7.92 | 9.68 | 8.36 | 9.24 |
| $X_{91B}$ | 7.8 | 3.9 | 11.7 | 5.85 | 9.75 | 7.02 | 8.58 | 7.41 | 8.19 |
| $X_{91C}$ | 8.1 | 4.05 | 12.15 | 6.075 | 10.125 | 7.29 | 8.91 | 7.695 | 8.505 |
| $X_{91D}$ | 13.6 | 6.8 | 20.4 | 10.2 | 17 | 12.24 | 14.96 | 12.92 | 14.28 |
| $X_{92A}$ | 0.05 | 0.025 | 0.075 | 0.0375 | 0.0625 | 0.045 | 0.055 | 0.0475 | 0.0525 |
| $X_{92B}$ | 1.5 | 0.75 | 2.25 | 1.125 | 1.875 | 1.35 | 1.65 | 1.425 | 1.575 |
| $X_{92C}$ | 10.8 | 5.4 | 16.2 | 8.1 | 13.5 | 9.72 | 11.88 | 10.26 | 11.34 |
| $X_{95A}$ | 13.8 | 6.9 | 20.7 | 10.35 | 17.25 | 12.42 | 15.18 | 13.11 | 14.49 |
| $X_{96A}$ | 8.2 | 4.1 | 12.3 | 6.15 | 10.25 | 7.38 | 9.02 | 7.79 | 8.61 |
| $X_{96B}$ | 5.1 | 2.55 | 7.65 | 3.825 | 6.375 | 4.59 | 5.61 | 4.845 | 5.355 |
| $X_{96C}$ | 0.5 | 0.25 | 0.75 | 0.375 | 0.625 | 0.45 | 0.55 | 0.475 | 0.525 |
| $X_{97}$ | 10.8 | 5.4 | 16.2 | 8.1 | 13.5 | 9.72 | 11.88 | 10.26 | 11.34 |
| $X_{98A}$ | 9.8 | 4.9 | 14.7 | 7.35 | 12.25 | 8.82 | 10.78 | 9.31 | 10.29 |
| $X_{98B}$ | 5 | 2.5 | 7.5 | 3.75 | 6.25 | 4.5 | 5.5 | 4.75 | 5.25 |
| $X_{99}$ | 8 | 4 | 12 | 6 | 10 | 7.2 | 8.8 | 7.6 | 8.4 |
| $X_{100A}$ | 9.7 | 4.85 | 14.55 | 7.275 | 12.125 | 8.73 | 10.67 | 9.215 | 10.185 |
| $X_{100B}$ | 4 | 2 | 6 | 3 | 5 | 3.6 | 4.4 | 3.8 | 4.2 |
| $X_{101}$ | 5.2 | 2.6 | 7.8 | 3.9 | 6.5 | 4.68 | 5.72 | 4.94 | 5.46 |
| $X_{102A}$ | 8 | 4 | 12 | 6 | 10 | 7.2 | 8.8 | 7.6 | 8.4 |
| $X_{102B}$ | 2.9 | 1.45 | 4.35 | 2.175 | 3.625 | 2.61 | 3.19 | 2.755 | 3.045 |
| $X_{117A}$ | 4.2 | 2.1 | 6.3 | 3.15 | 5.25 | 3.78 | 4.62 | 3.99 | 4.41 |
| $X_{117B}$ | 14.5 | 7.25 | 21.75 | 10.875 | 18.125 | 13.05 | 15.95 | 13.775 | 15.225 |
| $X_{117C}$ | 13 | 6.5 | 19.5 | 9.75 | 16.25 | 11.7 | 14.3 | 12.35 | 13.65 |

TABLE B

| Radius Dimensions (degrees) | | | | | | | | | |
|---|---|---|---|---|---|---|---|---|---|
| | | Range A | | Range B | | Range C Range D Range C | | | |
| | Example | (max) | (min) | (max) | (min) | (max) | (min) | (max) | (min) |
| $R_{47A}$ | 1.3 | 0.65 | 1.95 | 0.975 | 1.625 | 1.17 | 1.43 | 1.235 | 1.365 |
| $R_{47B}$ | 1 | 0.5 | 1.5 | 0.75 | 1.25 | 0.9 | 1.1 | 0.95 | 1.05 |
| $R_{47C}$ | 0.6 | 0.3 | 0.9 | 0.45 | 0.75 | 0.54 | 0.66 | 0.57 | 0.63 |
| $R_{47D}$ | 5 | 2.5 | 7.5 | 3.75 | 6.25 | 4.5 | 5.5 | 4.75 | 5.25 |
| $R_{47E}$ | 0.75 | 0.375 | 1.125 | 0.5625 | 0.9375 | 0.675 | 0.825 | 0.7125 | 0.7875 |
| $R_{67A}$ | 0.75 | 0.375 | 1.125 | 0.5625 | 0.9375 | 0.675 | 0.825 | 0.7125 | 0.7875 |
| $R_{67B}$ | 0.9 | 0.45 | 1.35 | 0.675 | 1.125 | 0.81 | 0.99 | 0.855 | 0.945 |
| $R_{70A}$ | 1.4 | 0.7 | 2.1 | 1.05 | 1.75 | 1.26 | 1.54 | 1.33 | 1.47 |
| $R_{70B}$ | 0.4 | 0.2 | 0.6 | 0.3 | 0.5 | 0.36 | 0.44 | 0.38 | 0.42 |
| $R_{70C}$ | 0.6 | 0.3 | 0.9 | 0.45 | 0.75 | 0.54 | 0.66 | 0.57 | 0.63 |
| $R_{70D}$ | 7 | 3.5 | 10.5 | 5.25 | 8.75 | 6.3 | 7.7 | 6.65 | 7.35 |
| $R_{71A}$ | 1.6 | 0.8 | 2.4 | 1.2 | 2 | 1.44 | 1.76 | 1.52 | 1.68 |
| $R_{72A}$ | 1.85 | 0.925 | 2.775 | 1.3875 | 2.3125 | 1.665 | 2.035 | 1.7575 | 1.9425 |
| $R_{73A}$ | 1.9 | 0.95 | 2.85 | 1.425 | 2.375 | 1.71 | 2.09 | 1.805 | 1.995 |
| $R_{91A}$ | 9.2 | 4.6 | 13.8 | 6.9 | 11.5 | 8.28 | 10.12 | 8.74 | 9.66 |
| $R_{91B}$ | 0.3 | 0.15 | 0.45 | 0.225 | 0.375 | 0.27 | 0.33 | 0.285 | 0.315 |
| $R_{91C}$ | 0.3 | 0.15 | 0.45 | 0.225 | 0.375 | 0.27 | 0.33 | 0.285 | 0.315 |
| $R_{92A}$ | 0.75 | 0.375 | 1.125 | 0.5625 | 0.9375 | 0.675 | 0.825 | 0.7125 | 0.7875 |
| $R_{94A}$ | 1.65 | 0.825 | 2.475 | 1.2375 | 2.0625 | 1.485 | 1.815 | 1.5675 | 1.7325 |
| $R_{96A}$ | 1.7 | 0.85 | 2.55 | 1.275 | 2.125 | 1.53 | 1.87 | 1.615 | 1.785 |
| $R_{96B}$ | 4.7 | 2.35 | 7.05 | 3.525 | 5.875 | 4.23 | 5.17 | 4.465 | 4.935 |
| $R_{98A}$ | 1.3 | 0.65 | 1.95 | 0.975 | 1.625 | 1.17 | 1.43 | 1.235 | 1.365 |
| $R_{98B}$ | 7.6 | 3.8 | 11.4 | 5.7 | 9.5 | 6.84 | 8.36 | 7.22 | 7.98 |
| $R_{100A}$ | 0.9 | 0.45 | 1.35 | 0.675 | 1.125 | 0.81 | 0.99 | 0.855 | 0.945 |
| $R_{100B}$ | 9.6 | 4.8 | 14.4 | 7.2 | 12 | 8.64 | 10.56 | 9.12 | 10.08 |
| $R_{102A}$ | 0.45 | 0.225 | 0.675 | 0.3375 | 0.5625 | 0.405 | 0.495 | 0.4275 | 0.4725 |
| $R_{102B}$ | 8.5 | 4.25 | 12.75 | 6.375 | 10.625 | 7.65 | 9.35 | 8.075 | 8.925 |
| $R_{115A}$ | 9.3 | 4.65 | 13.95 | 6.975 | 11.625 | 8.37 | 10.23 | 8.835 | 9.765 |
| $R_{115B}$ | 7.8 | 3.9 | 11.7 | 5.85 | 9.75 | 7.02 | 8.58 | 7.41 | 8.19 |
| $R_{115C}$ | 7.8 | 3.9 | 11.7 | 5.85 | 9.75 | 7.02 | 8.58 | 7.41 | 8.19 |
| $R_{115D}$ | 6.7 | 3.35 | 10.05 | 5.025 | 8.375 | 6.03 | 7.37 | 6.365 | 7.035 |
| $R_{115E}$ | 1.5 | 0.75 | 2.25 | 1.125 | 1.875 | 1.35 | 1.65 | 1.425 | 1.575 |

TABLE C

| | Angular Dimensions (degrees) | | | | | | | | | |
|---|---|---|---|---|---|---|---|---|---|---|
| | | Range A | | Range B | | Range C | | Range D | | Range C |
| | Example | (max) | (min) | (max) | (min) | (max) | (min) | (max) | (min) | |
| $\alpha_{47}$ | 12 | 6 | 18 | 9 | 15 | 10.8 | 13.2 | 11.4 | 12.6 | |
| $\alpha_{91A}$ | 9 | 4.5 | 13.5 | 6.75 | 11.25 | 8.1 | 9.9 | 8.55 | 9.45 | |
| $\alpha_{91B}$ | 14 | 7 | 21 | 10.5 | 17.5 | 12.6 | 15.4 | 13.3 | 14.7 | |
| $\alpha_{91C}$ | 20 | 10 | 30 | 15 | 25 | 18 | 22 | 19 | 21 | |
| $\alpha_{117A}$ | 39 | 19.5 | 58.5 | 29.25 | 48.75 | 35.1 | 42.9 | 37.05 | 40.95 | |
| $\alpha_{117B}$ | 3 | 1.5 | 4.5 | 2.25 | 3.75 | 2.7 | 3.3 | 2.85 | 3.15 | |

Figure 47:
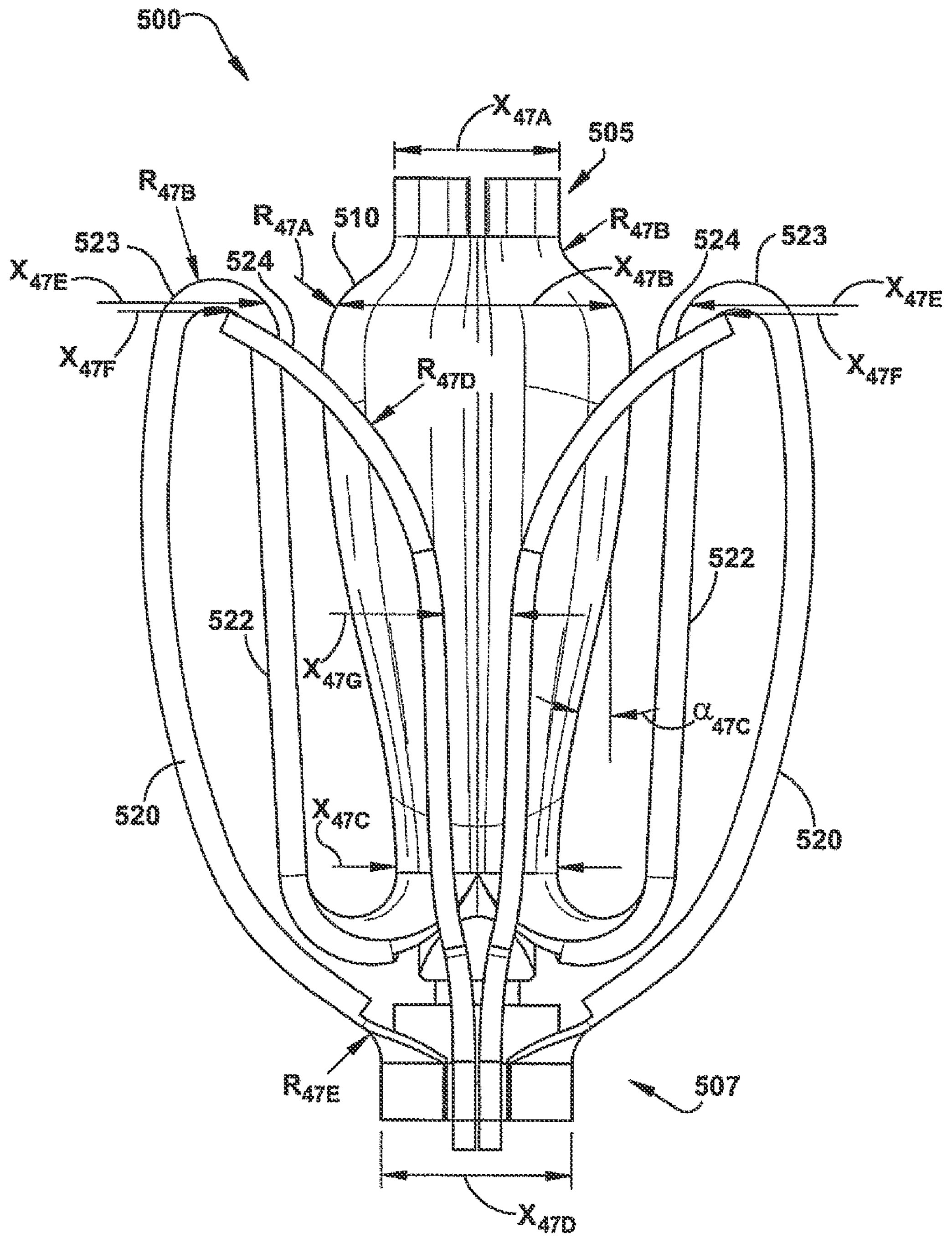
FIG. 47 shows a side view of an example implantable prosthetic device without clasps in a closed position.

Referring now to FIG. 47, an implantable device 500 can include any features for an implantable prosthetic device discussed in the present application, and the device 500 can be positioned to engage valve tissue 20, 22 as part of any suitable valve repair system (e.g., any valve repair system disclosed in the present application).

In some embodiments, the implantable device 500 has one, some, or all of a proximal or attachment portion 505, a coaption element 510 (e.g., a spacer, etc.), inner anchor portions or inner paddles 522, outer anchor portions or outer paddles 520, anchor extension members or paddle frames 524, and a distal portion 507. The inner paddles 522 are attached (e.g., jointably attached, etc.) between the coaption element 510 and the outer paddles 520. The outer paddles 520 are attached (e.g., jointably attached, etc.) between the inner paddles 522 and the distal portion 507. The paddle frames 524 are attached to the cap 514 at the distal portion 507 and extend to the joint portion 523 between the inner and outer paddles 522, 520. In some embodiments, the paddle frames 524 are formed of a material that is more rigid and stiff than the material forming the paddles 522, 520 so that the paddle frames 524 provide support for the paddles 522, 520. In one example embodiment, the inner paddles 522 are stiff, relatively stiff, rigid, have rigid portions and/or are stiffened by a stiffening member or the fixed portion of the clasps 530. The stiffening of the inner paddle allows the device to move to the various different positions shown and described herein. The inner paddle 522, the outer paddle 520, the coaption can all be interconnected as described herein, such that the device 500 is constrained to the movements and positions shown and described herein.

Figure 47A:
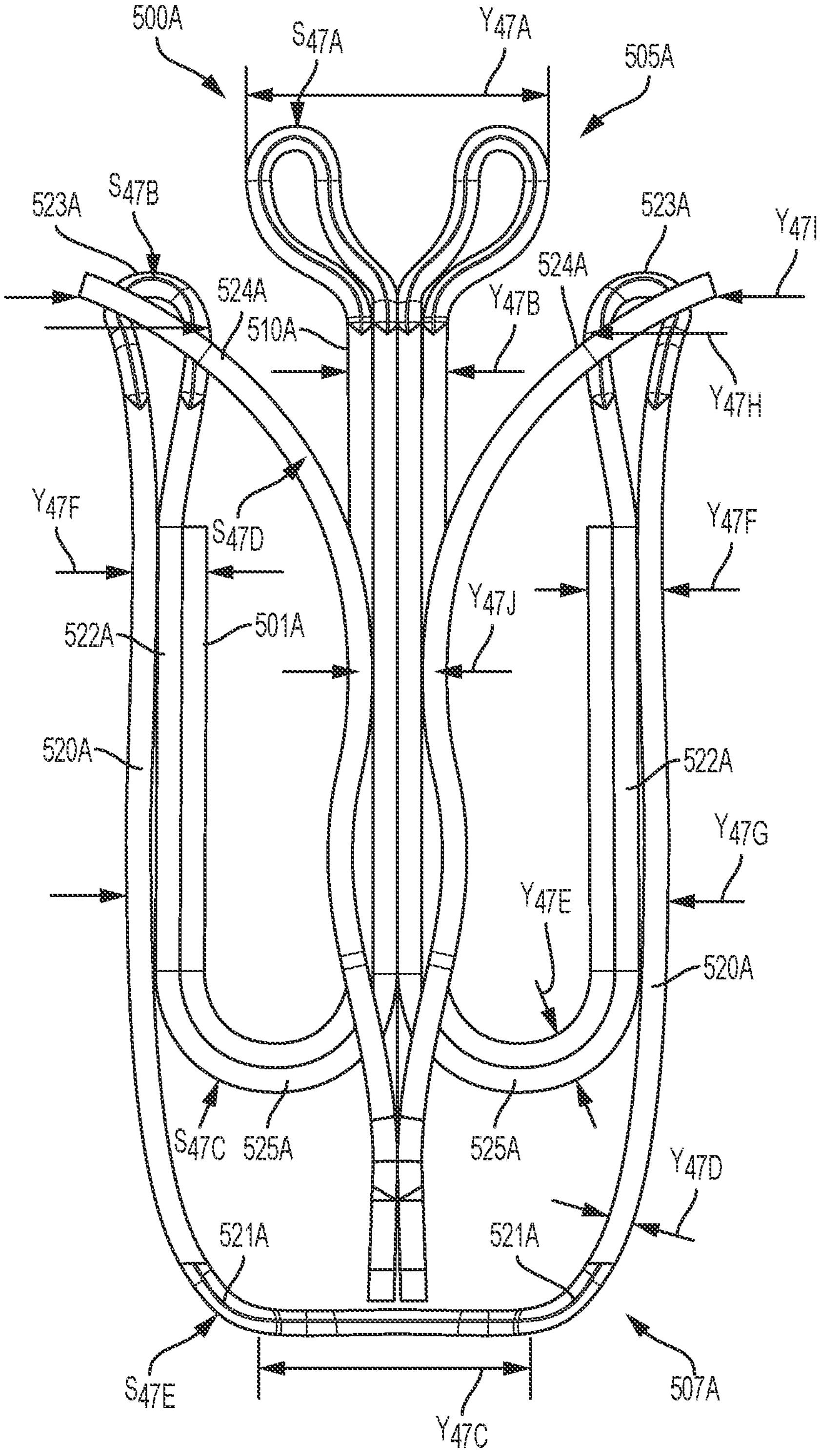
FIG. 47A shows a side view of an example implantable prosthetic device without clasps in a closed position.

Referring now to FIG. 47A, an implantable device 500A can include any other features for an implantable prosthetic device discussed in the present application, and the device 500A can be positioned to engage valve tissue 20, 22 as part of any suitable valve repair system (e.g., any valve repair system disclosed in the present application).

In some embodiments, the implantable device 500A has one, some, or all of a proximal or attachment portion 505A, a coaption element 510A, inner anchor portions or inner paddles 522A, outer anchor portions or outer paddles 520A, anchor extension members or paddle frames 524A, and a distal portion 507A. The inner paddles 522A are attached (e.g., jointably attached, etc.) between the coaption element 510A, e.g., by joint portions 525A and the outer paddles 520A by joint portions 523A. The outer paddles 520A are attached (e.g., jointably attached, etc.) between the inner paddles 522A, e.g., by joint portions 523A, and the distal portion 507A, e.g., by joint portions 521A. The paddle frames 524A are attached to the cap 514A at the distal portion 507A and extend to the joint portion 523A between the inner and outer paddles 522A, 520A. In some embodiments, the paddle frames 524A are formed of a material that is more rigid and stiff than the material forming the paddles 522A, 520A so that the paddle frames 524A provide support for the paddles 522A, 520A. The paddle frames 524A include an opening or slot 524B for receiving the joint portions 523A. In some embodiments, the inner paddles 522A are stiff, relatively stiff, rigid, have rigid portions and/or are stiffened by a stiffening member or the fixed portion of the clasps 530C. The stiffening of the inner paddle allows the device to move to the various different positions shown and described herein. The inner paddle 522A, the outer paddle 520A, and the coaption element can all be interconnected as described herein, such that the device 500A is constrained to the movements and positions shown and described herein.

The coaption element 510A, inner paddles 522A, outer paddles 520A can be attached together by integrally forming the coaption element 510A and the paddles 520A, 522A as a single, unitary component. This can be accomplished, for example, by forming the coaption element 510A and the paddles 520A, 522A from a continuous strip 501A of a braided or woven material, such as braided or woven nitinol wire.

The continuous strip 501A is attached to a collar 511D, a cap 514A, paddle frames 524A, clasps 530C. The coaption element 510A, hinge portions 521A, 523A, 525A, outer paddles 520A, and/or inner paddles 522A can be formed from the continuous strip 501A. The continuous strip 501A can be a single layer of material or can include two or more layers. In certain embodiments, portions of the device 500A have a single layer of the strip of material 501A and other portions are formed from multiple overlapping or overlying layers of the strip of material 501A. For example, FIG. 47A shows the coaption element 510A and inner paddles 522A formed from multiple overlapping or overlying layers of the strip of material 501A. Consequently, the coaption element 510A and inner paddle 522A have an increased stiffness relative to the outer paddles 520A that are formed from a single layer of material 501A. The single continuous strip of material 501A can start and end in various locations of the device 500A. The ends of the strip of material 501A can be in the same location or different locations of the device 500A. For example, in the illustrated embodiment of FIG. 47A, the strip of material begins and ends in the location of the inner paddles 522.

The clasps 530C can comprise attachment or fixed portions 532C, arm or moveable portions 534C, barbs 536C, and joint portions 538C. The attachment or fixed portions 532C can be coupled to the inner paddles 522A in various ways such as with sutures, adhesive, fasteners, welding, stitching, swaging, friction fit and/or other means for coupling with the joint portions 538C disposed proximate the coaption element 510A. The clasps 530C can be similar to clasps 430.

The moveable portions 534C can pivot or flex relative to the fixed portions 532C between an open configuration and a closed configuration. In some embodiments, the clasps 530C can be biased to the closed configuration. In the open configuration, the fixed portions 532C and the moveable portions 534C pivot or flex away from each other such that native leaflets can be positioned between the fixed portions 532C and the moveable portions 534C. In the closed configuration, the fixed portions 532C and the moveable portions 534C pivot or flex toward each other, thereby clamping the native leaflets between the fixed portions 532C and the moveable portions 534C. The fixed arms 532C remain stationary or substantially stationary when the moveable arms 534C are opened to open the clasps 530C and expose the friction-enhancing elements or barbs 536C. The clasps 530C are opened by applying tension to actuation lines 537A attached to the moveable arms 534C, thereby causing the moveable arms 534C to move, pivot, or flex on the joint portions 538C.

In some embodiments, the device 500A is narrower when viewed from the front than the side. From the side, the device 500A has a generally inverted trapezoidal shape that is rounded and tapers toward the distal portion 507A of the device 500A. From the front, the device 500A has a generally rounded rectangle shape that tapers somewhat toward the distal portion 507A. As seen from a bottom view of the device 500A, the device 500A can have a generally rounded rectangle shape when viewed from below (and when viewed from above as can be seen in, for example, FIG. 53A).

In the closed configuration of the device 500A, the inner paddles 522A are disposed between the outer paddles 520A and the coaption element 510A. In some embodiments, the device 500A includes clasps or gripping members 530C that can be opened and closed to grasp the native leaflets 20, 22 of the mitral valve MV. The clasps 530C are attached to and move with the inner paddles 522A and are disposed between the inner paddles 522A and the coaption element 510A.

Extending the actuation element 512A pulls down on the bottom portions of the outer paddles 520A and paddle frames 524A to transition the device 500A from a closed to partially open position. The outer paddles 520A and paddle frames 524A pull down on the inner paddles 522A where the inner paddles 522A are connected to the outer paddles 520A and the paddle frames 524A. Because the attachment portion 505A and coaption element 510A are held in place, the inner paddles 522A are caused to move, pivot, or flex in an opening direction. The inner paddles 522A, the outer paddles 520A, and the paddle frames all flex in opening direction. Opening the paddles 522A, 520A and frames 524 forms a gap 520D between the coaption element 510A and the inner paddle 522A that can receive and grasp the native leaflets 20.

Continuing to extend the actuation element 512A pulls down on the outer paddles 520A and paddle frames 524A, thereby causing the inner paddles 522A to spread apart further from the coaption element 510A. In the laterally extended or open position, the inner paddles 522A extend horizontally more than in other positions of the device 500A and form an approximately 90-degree angle with the coaption element 510A. Similarly, the paddle frames 524A are at their maximum spread position when the device 500A is in the laterally extended or open position. The increased gap 520D formed in the laterally extended or open position allows clasps 530C to open further before engaging the coaption element 510A, thereby increasing the size of the gap 530D as compared to the partially open position.

As is described above, some embodiments of the device 500A include clasps or gripping members 530C. When the device 500A is opened the clasps 530C are exposed. In some embodiments, the closed clasps 530C can be opened, thereby creating a second opening or gap 530D for receiving and capturing the native leaflets 20, 22. The extent of the gap 530D in the clasps 530C is limited to the extent that the inner paddle 522A has spread away from the coaption element 510A.

In some embodiments, the device 500A can be moved into the fully extended position by continuing to extend the actuation element 512A described above, thereby increasing the distance D2 between the attachment portion 505A and distal portion 507A to a maximum distance allowable by the device 500A. Continuing to extend the actuation element 512A pulls down on the outer paddles 520A and paddle frames 524A, thereby causing the inner paddles 522A to extend further away from the coaption element 510A. The outer paddles 520A and paddle frames 524A move to a position where they are close to the actuation element. In the fully extended position, the inner paddles 522A are open to an approximately 180-degree angle with the coaption element 510A. The inner and outer paddles 522A, 520A are stretched straight or substantially straight in the fully extended position to form an approximately 180-degree angle between the paddles 522A, 520A. The fully extended position of the device 500A provides the maximum size of the gap 520D between the paddles, and, in some embodiments, allows clasps 530C to also open fully to approximately 180 degrees between portions of the clasp 530C. The position of the device 500A is the narrowest configuration. Thus, the fully extended position of the device 500A may be a desirable position for bailout of the device 500A from an attempted implantation or may be a desired position for placement of the device in a delivery catheter, or the like.

Figure 90:
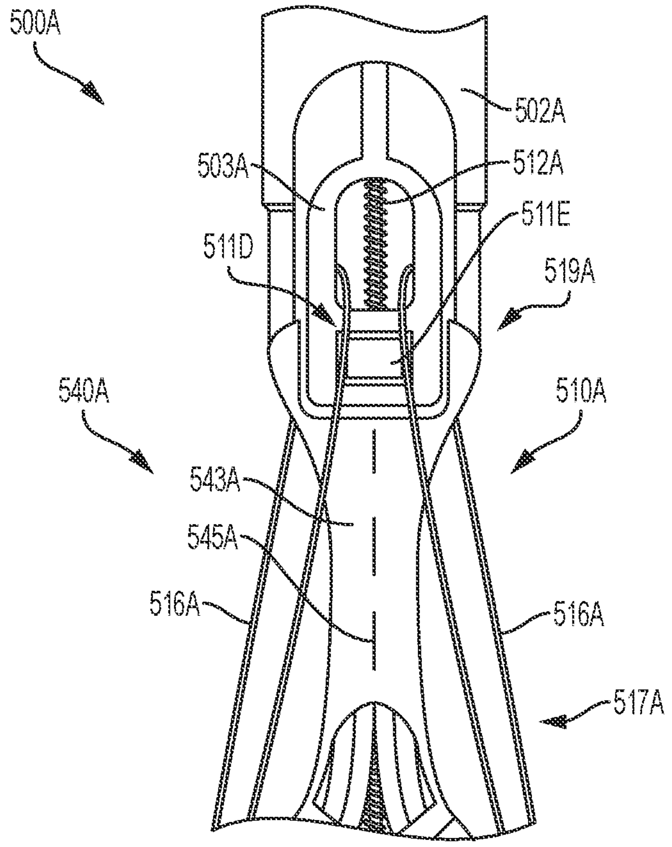
FIG. 90 is an enlarged side view of an example device showing the cover.
Figure 91:
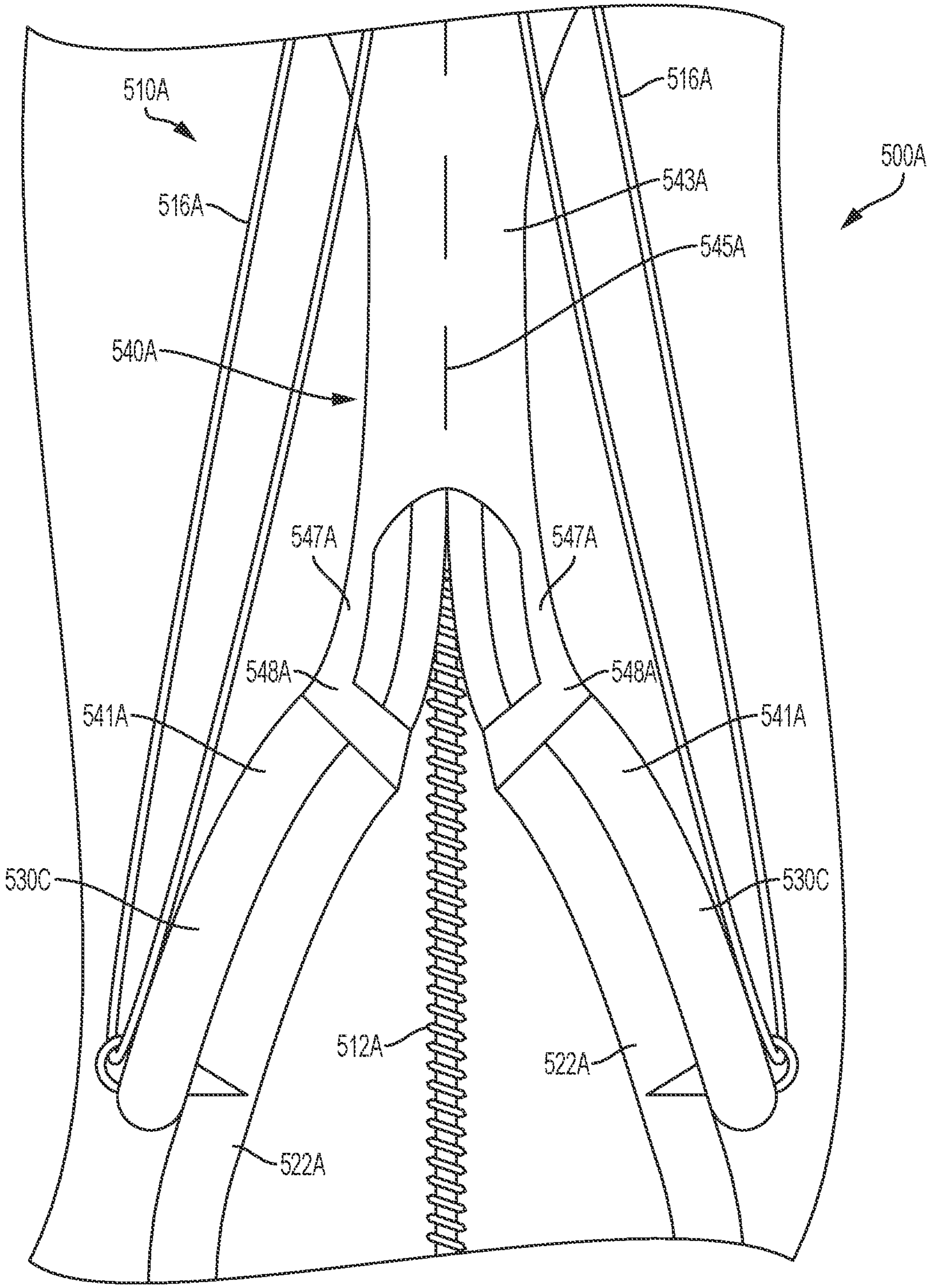
FIG. 91 is an enlarged side view of the example device of FIG. 90 showing the cover.

Referring now to FIGS. 90-91, enlarged views of portions of FIG. 60C are shown. Referring now to FIG. 90, the inner cover 543A can be seen covering the coaption element 510A from the proximal portion 519B to the distal portion 517A. In some embodiments, the inner cover 543A is formed from a flat sheet (see FIG. 94) of a cloth material such as polyethylene cloth of a fine mesh and is folded around the coaption element 510A and held in place by stitches 545A. Referring now to FIG. 91, the outer cover 541A can be seen covering the clasps 530C and inner paddles 522A. Collar portions 548A of inner cover 543A cover the portion of the clasps 530C and inner paddles 522A closest to the coaption element 510A. Transition portions 547A of the inner cover 543A extend from the coaption element 510A to the collar portions 548A to provide a smooth transition between the coaption element 510A and the clasps 530C and inner paddles 522A so that native tissue is not caught on the device 500A during implantation.

Figure 92:
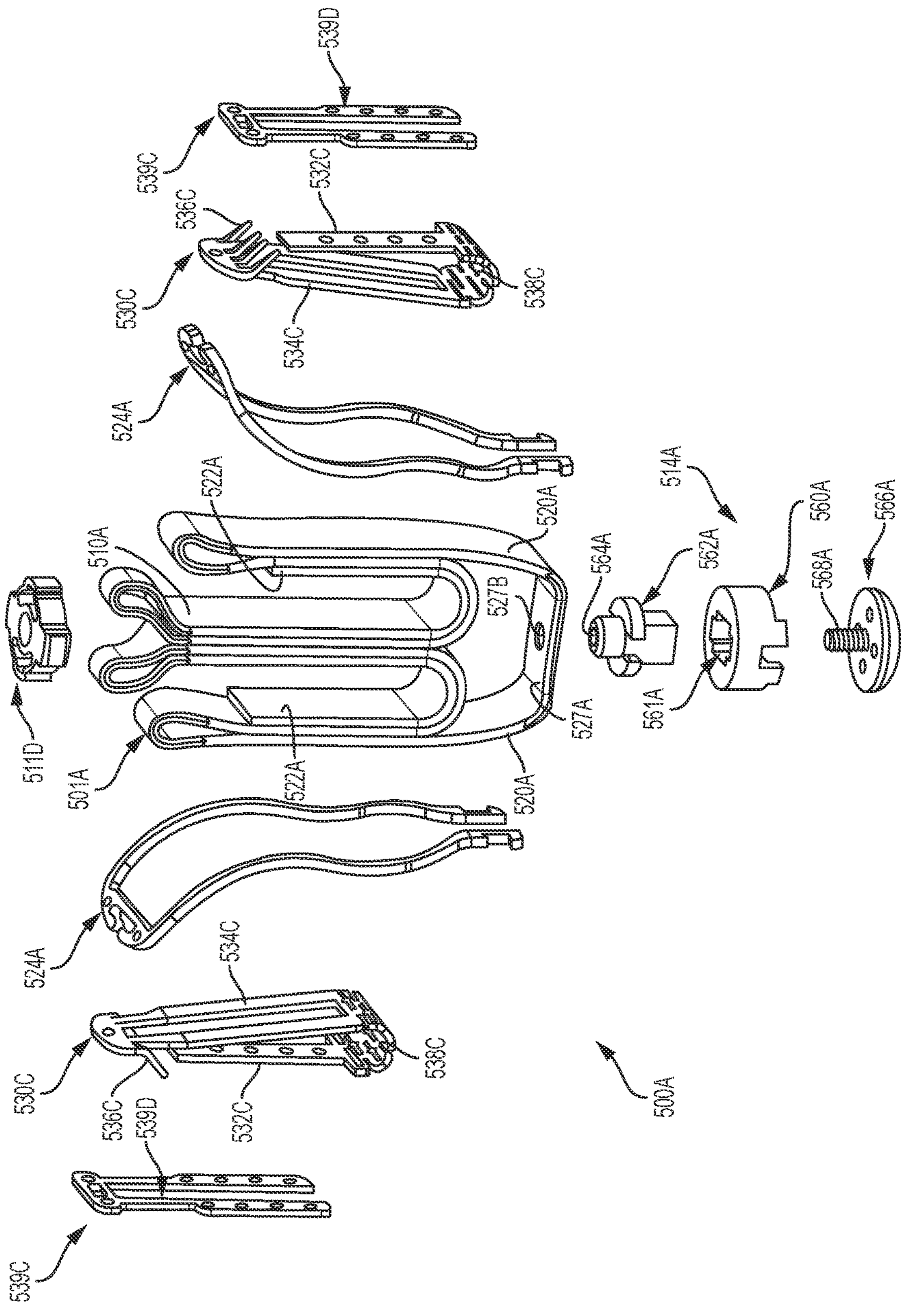
FIG. 92 shows an exploded view of an example prosthetic device.

Referring now to FIG. 92, an exploded view of the device 500A is shown. The coaption element 510A, outer paddles 520A, and inner paddles 522A are formed from a single strip of material 501A, as described above. The collar 511D, cap 514A, paddle frames 524A, and clasps 530C are assembled to the strip of material 501A to form the device 500A. The cap 514A includes a retention body 560A with a locking aperture 561A for receiving a retaining nut 562A having a threaded bore 564A that engages a threaded portion 568A of a retaining bolt 566A. The threaded portion 568A of the retaining bolt 566A is inserted through the opening 527B to engage the retention body and nut 560A, 562A to attach the cap 514A to the strip of material 501A.

In some embodiments, a stiffening member 539C is attached to the inner paddle 522A to stiffen the inner paddle 522A to maintain the inner paddle in a straight or substantially straight configuration as the inner paddle is moved between the various positions. A cutout 539D in the stiffening member 539C is shaped to receive the fixed arm 532C of the clasp 530C so that the stiffening member 539C can fit around the fixed arm 532C when both the stiffening member 539C and clasp 530C are attached to the inner paddle 522A. Like the fixed arm 532C, the stiffening member 539C can be coupled to the inner paddles 522A in various ways such as with sutures, adhesive, fasteners, welding, stitching, swaging, friction fit and/or other means for coupling.

Figure 93:
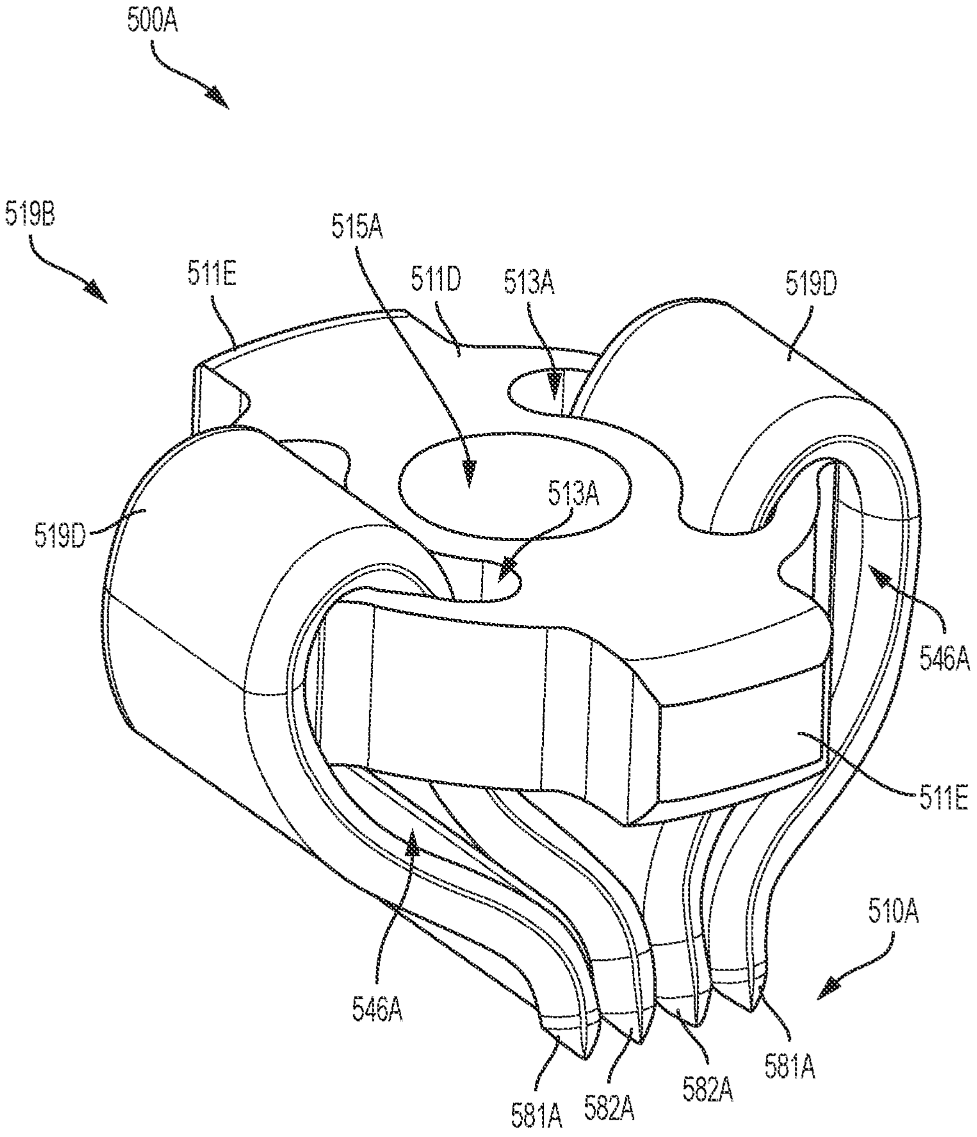
FIG. 93 shows an enlarged perspective view of the collar of an example prosthetic device.

Referring now to FIG. 93, an enlarged view of the collar 511D attached to the proximal portion 519B of the coaption element 510A is shown. The collar 511D includes protrusions 511B for releasably engaging the fingers 503A of the delivery device 502A. An aperture 515A in the collar 511D receives the actuation element 512A. The proximal portion 519B of the coaption element 510A flares outward to form two loops 519D that are inserted through the arcuate openings 513A of the collar 511D to attach the collar 511D to the proximal portion 519B of the coaption element 510A. The loops 519D are formed by folding the strip of material 501A to form first and second layers 581A, 582A.

Figure 94:
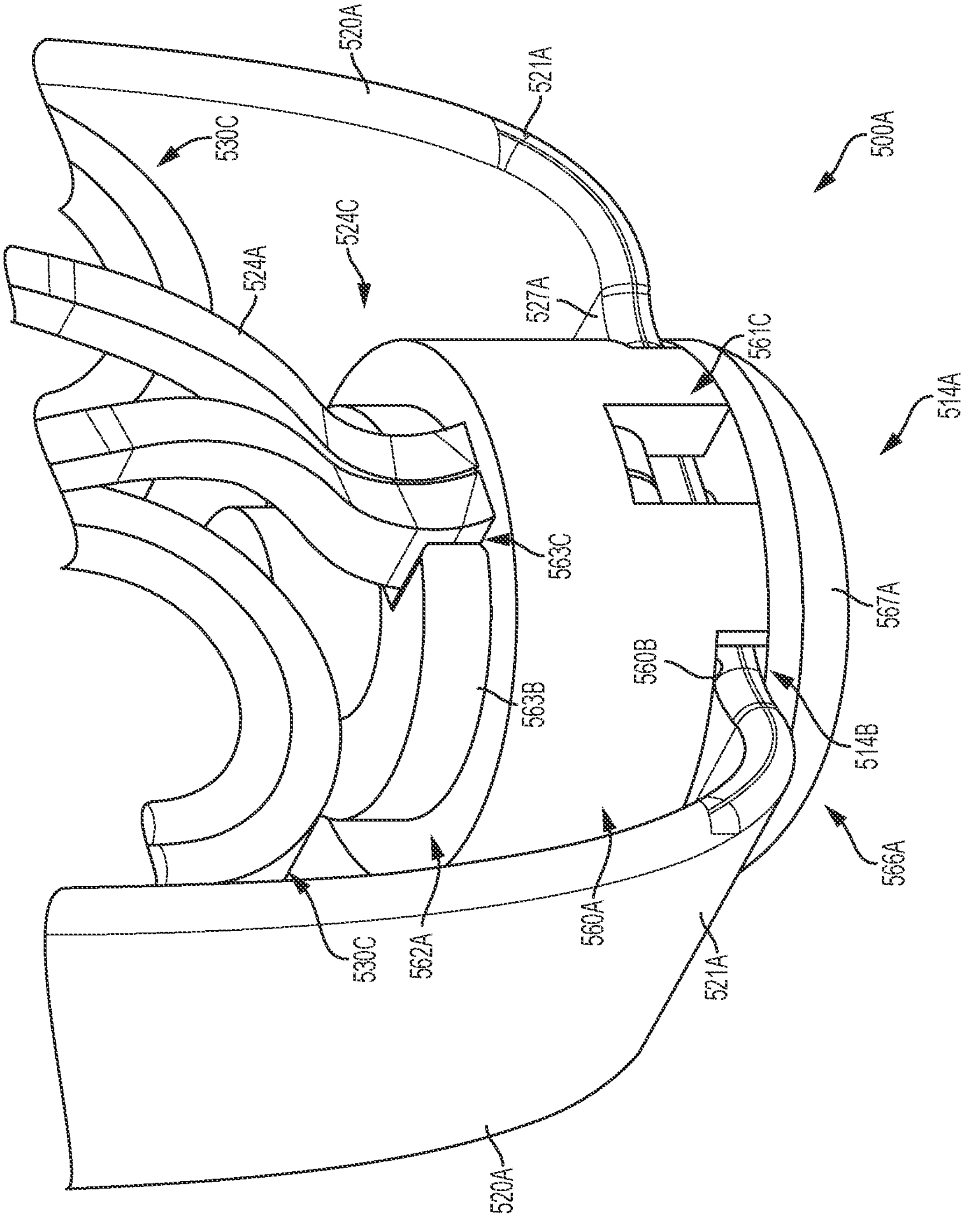
FIG. 94 shows an enlarged perspective view of the cap of an example prosthetic device.
Figure 95:
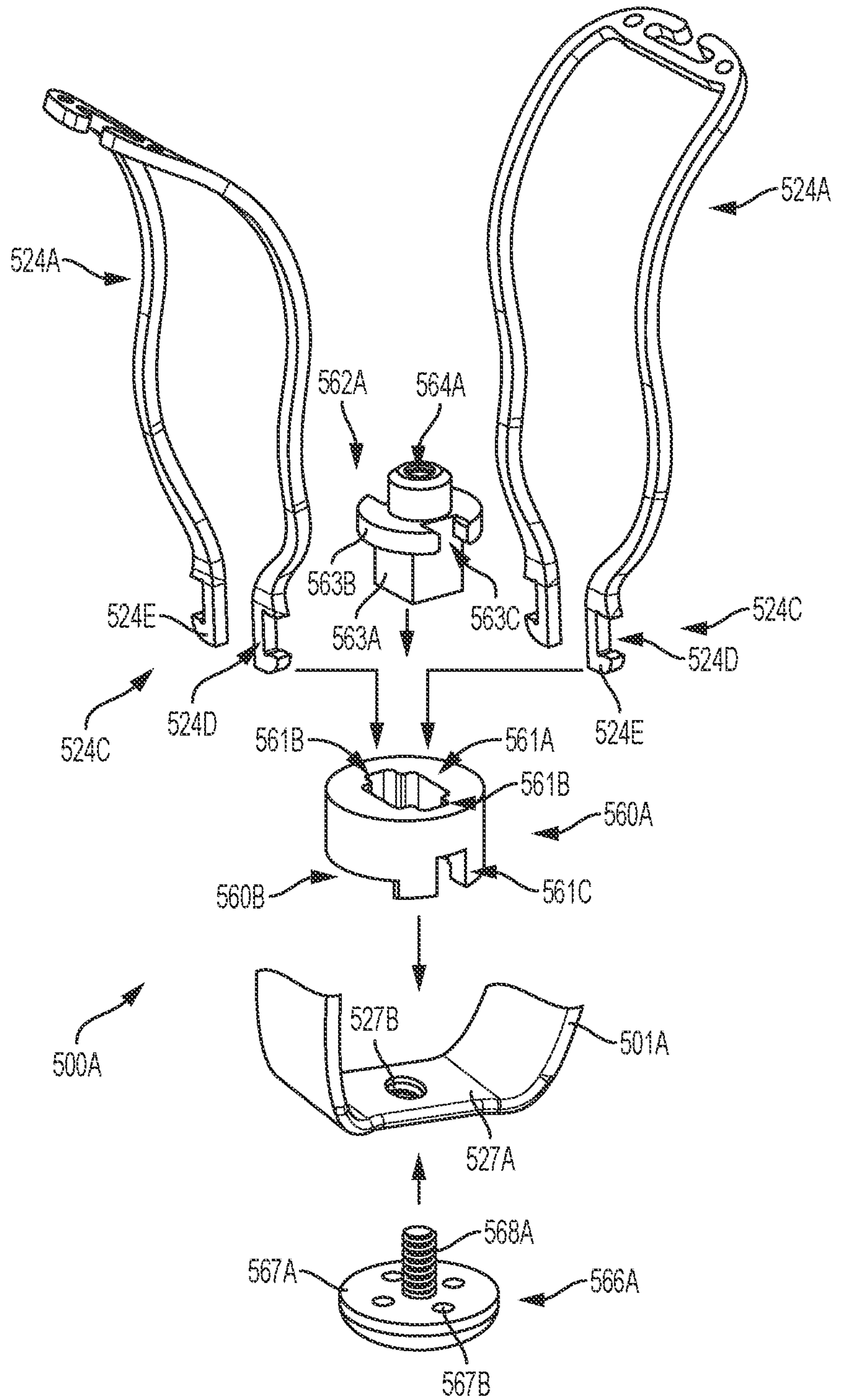
FIG. 95 shows an exploded view of the cap of FIG. 94.

Referring now to FIGS. 94-95, enlarged and exploded views of the cap 514A are shown, respectively. FIG. 94 shows an enlarged view of the cap 514A attached to the distal portion 527A of the strip of material 501A. The retention body 560A, retaining nut 562A, and retaining bolt 566A cooperate to attach the paddle frames 524A to the distal portion 527A of the strip of material 501A. In particular, the retaining bolt 566A is inserted through the opening 527B of the distal portion 527A (FIG. 95) to prohibit movement of the cap 514A along the strip of material 501A. A channel 560B in the retention body 560A and a flange 567A of the bolt 566A form a passageway 514B through the cap 514A for the distal portion 527A.

Referring now to FIG. 95, the components of the cap 514A are shown in an exploded view to better illustrate the features of the components of the cap 514A and paddle frames 524A and to show how those features interlock during assembly of the cap 514A to the distal portion 527A. Forming the cap 514A from multiple components that can be assembled around the strip of material 501A allows the cap 514A to be attached after the strip of material 501A has been folded to form the coaption element 510A and paddles 520A, 522A and been woven through the collar 511D and paddle frames 524A.

The retention body 560A includes a locking aperture 561A for receiving the retaining nut 562A. The locking aperture 561A has a generally rectangular shape and includes two opposing locking channels 561B that receive the attachment portions 524C of the paddle frames 524A. A transverse locking channel 561C formed in the bottom of the retention body 560A has the same width as the locking channels 561B. The paddle frames 524A include notches 524D in the attachment portions 524C that form hook portions 524E that engage the transverse locking channel 561C to secure the paddle frames 524A to the cap 514A.

The retaining nut 562A includes a rectangular locking body 563A extending distally from a flange 563B. The locking body 563A is configured to slidably engage the locking aperture 561A of the retention body 560A while leaving the locking channels 561B unobstructed. Thus, the locking body 563A can be inserted into the locking aperture 561A to lock the attachment portions 524C of the paddle frames 524A within the locking channels 561B. Notches 563C in the flange 563B accommodate the attachment portions 524C of the paddle frames 524A. The threaded bore 564A is formed through the retaining nut 562A to receive the retaining bolt 566A.

The retaining bolt 566A includes a threaded portion 568A extending from the flange 567A. The threaded portion 568A is inserted through the opening 527B in the distal portion 527A to threadedly engage the threaded bore 564A of the retaining nut 562A. The flange 567A has a rounded shape that provides a rounded end to the distal portion 507A of the device 500A. The flange 567A includes openings 567B for receiving a tool (not shown) that engages the bolt 566A so that the bolt 566A can be turned during assembly to couple the components of the cap 514A together.

To assemble the paddle frames 524A and cap 514A to the distal portion 527A, the paddle frames 524A are squeezed to narrow the width of the attachment portion 524C so that the attachment portions 524C can be inserted into the locking channels 561B of the locking aperture 561A. When the paddle frames 524A are allowed to expand, the attachment portions 524C expand outward so that the notches 524D engage the retention body 560A and the hook portions 524E engage the transverse locking channel 561C. The retaining nut 562A is then inserted into the locking aperture 561A with the locking portion 563A arranged between the two attachment portions 524C of each paddle frame 524A, thereby locking the paddle frames 524A in engagement with the retention body 560A. The assembled paddle frames 524A, retention body 560A, and retaining nut 562A are placed on the distal portion 527A so that the threaded bore 564A aligns with the opening 527B and the threaded portion 568A of the bolt 566A is inserted through the opening 527B to threadedly engage the threaded bore 564A. The bolt 566A is then tightened until the flange 567A engages the retention body 560A and the cap 514A is securely assembled to the distal portion 527A.

Figure 96:
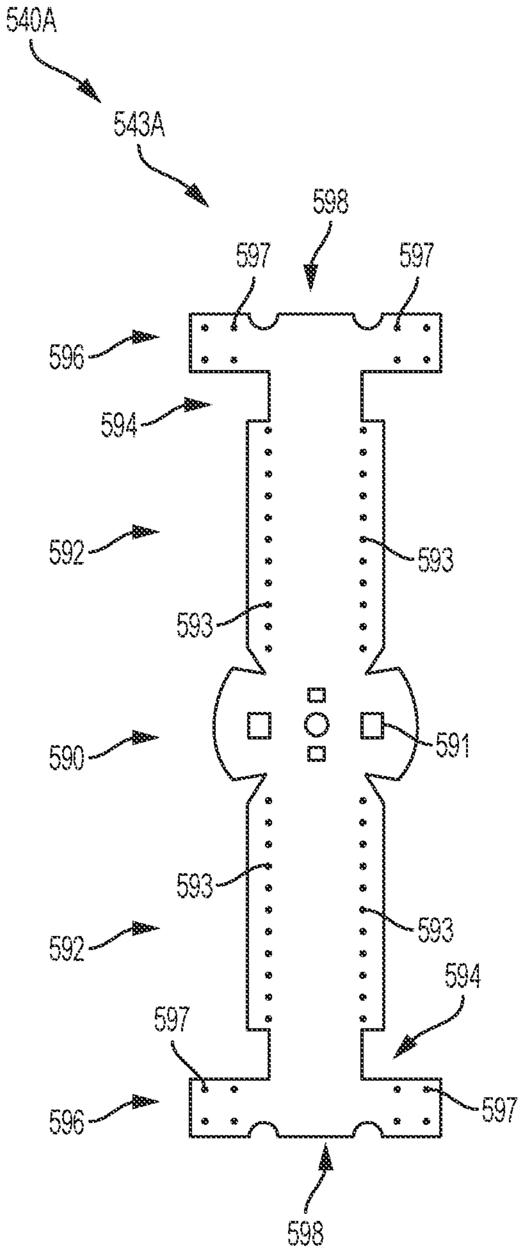
FIG. 96 shows a plan view of an inner cover for an example prosthetic device.
Figure 97:
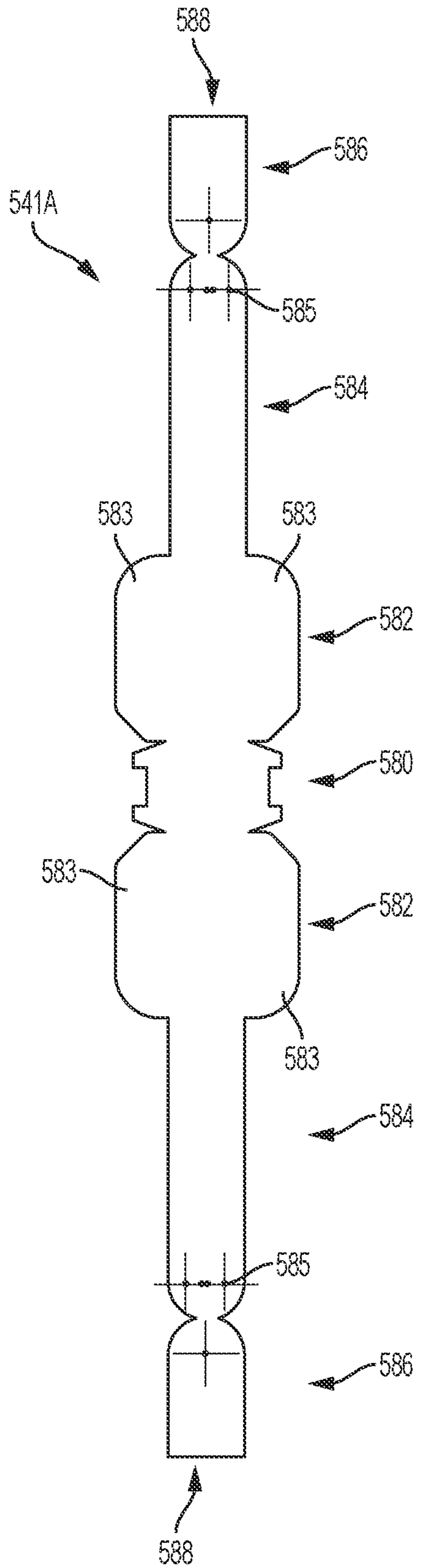
FIG. 97 shows a plan view of an outer cover for an example prosthetic device.

Referring now to FIGS. 96 and 97, portions of the cover 540A are shown cut from flat sheets of material. The cover 540A includes the outer cover 541A and the inner cover 543A. Each of the covers 541A, 543A include different shaped segments or portions to attach to different portions of the device 500A. In particular, the covers 541A, 543A are shaped to smooth transitions between portions of the device 500A to reduce catch points and provide a smoother exterior to the device 500. These covers can incorporate elements and/or techniques described with respect to other covers herein, e.g., cover 5000 in FIGS. 104A-111. The various covers described herein can be used on any of the devices (or components thereof) herein and other medical devices.

The various segments of the covers 541A, 543A extend from a middle portion that is shaped to attach to an end of the device 500A. In some embodiments, the portion of the cover 541A, 543A that attaches to an end of the device 500A is located at an end of the covers 541A, 543A or can be located anywhere between the middle and ends of the covers 541A, 543A. Various portions of the covers 541A, 543A can be shaped to wrap around portions of the device 500A. The cover 540A can be made of any suitable material, such as a polyethylene cloth of a fine mesh. In some embodiments, the cover is formed out of a single piece of material. In some embodiments, the cover can be formed of any number of pieces of material that are attached to the device and/or joined together by any suitable means, such as by stitching, adhesives, welding, or the like.

In some embodiments, the outer cover 541A extends outward from a middle portion 580 to end portions 588. The middle portion 580 is shaped to be attached to the cap 514A of the device 500A. Outer paddle portions 582 extend from the middle portion 580 to inner paddle and inside clasp portions 584. The inner paddle and inside clasp portions 584 extend from the outer paddle portions 582 to outside moveable clasp portions 586. The outside moveable clasp portions 586 extend from the inner paddle portions 584 to the end portions 588.

The outer paddle portions 582 include wing portions 583 that extend laterally to a width that is wider than the other portions of the outer cover 541A so that the outer paddle portions 582 can attach to the outer paddles 520A and paddle frames 524A of the device 500A. The inner paddle portions 584 attach to the inner paddles 522A, stationary arms 532C, and the inside surface (the side with the friction-enhancing elements or barbs) of the moveable arms 534C. The outside clasp portions 586 attach to the outside surface (the side without the friction-enhancing elements or barbs) of the moveable arms 534C of the clasps 530C. The ends 588 of the outer cover 541A terminate near the joint portion 538C of the clasp 530C on the outside of the clasps 530C. The inner paddle and inside clasp portions 584 include openings 585 that allow the friction-enhancing elements or barbs 536C of the clasps 530C to protrude through the outer cover 541A to engage tissue of the native heart valve.

In some embodiments, the inner cover 543A extends outward from a middle portion 590 to end portions 598. The middle portion 590 is configured to be attached to the collar 511D of the device 500A. Openings 591 in the middle portion 590 expose the protrusions 511E from the collar 511D when the middle portion 590 is attached to the collar 511D so that the protrusions 511E can be engaged by the delivery device 502A. Coaption portions 592 extend from the middle portion 590 to flexible hinge portions 594. Holes 593 along the edges of the coaption portions 592 allow each of the coaption portions 592 to be joined together after being folded around the coaption element 510A, such as, for example, by stitches 545A. The flexible hinge portions 594 extend from the coaption portions 592 to transition portions 596. The transition portions 596 extend from the flexible hinge portions 594 to the end portions 598. Holes 597 along the edges of the transition portions 596 allow each of the transition portions 596 to be wrapped around the inner paddle 522A and ends of the clasp 530C and secured to itself by stitches or other suitable securing means. The flexible hinge portions 594 bridge the gaps between the coaption element 510A and the clasps 530C when the device 500A is opened, as can be seen in FIG. 91.

In some embodiments, the device 500 extends from a proximal portion 505 to a distal portion 507 and can include one or more of a coaption portion 510, inner paddles 522, outer paddles 520, and paddle frames 524. In some embodiments, the outer paddles 520 extend to and/or around the paddle frames 524 and can have more than one layer to surround the paddle frames 524. The proximal portion 505 can include a collar 511 for attaching a delivery device (not shown). The distal portion 507 can include a cap 514 that is attached (e.g., jointably attached, etc.) to the outer paddles 520 and is engaged by an actuation element (not shown) to open and close the device 500 to facilitate implantation in the native valve as described in the present application.

In some embodiments, the device 500 has a shape that is symmetrical or substantially symmetrical around a vertical front-to-back plane 550 and is narrower or generally narrower at the distal portion 507 than the proximal portion 505. The shape of the coaption element 510 and paddle frames 524 is rounded or generally rounded to prevent the device 500 from catching or snagging on structures of the heart, such as the chordae tendineae, during implantation. For this reason, the proximal collar 511 and cap 514 can also have round edges. When viewed from the front or back, the paddle frames 524 can be seen to have a rounded or generally rounded shape, extending upwards and outwards from the distal portion 507 to approximately coincide with the shape of the coaption element 510 when viewed from the front or back. Thus, the coaption element 510 and paddle frames 524 generally define the shape of the device 500 when viewed from the front or back. In addition, the rounded shape of the paddle frames 524 and the corresponding rounded shape of the coaption element can distribute leaflet stress across a wider surface. In some embodiments, the paddle frames 524 and/or the coaption element 510 can have other shapes.

Figure 52:
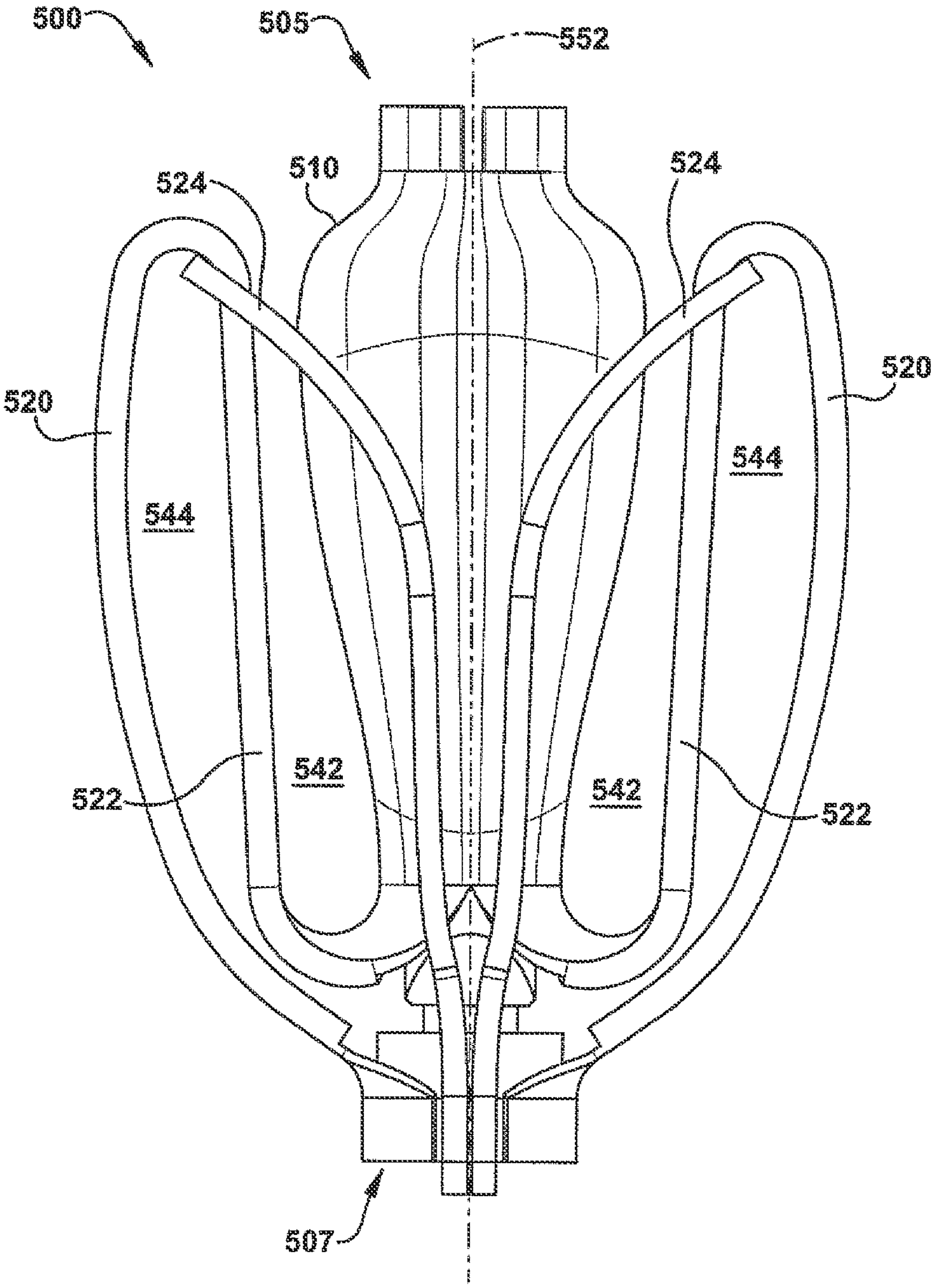
FIG. 52 shows a side view of the implantable prosthetic device of FIG. 48.

Referring now to FIG. 52, a side view of the device 500 is shown. As with the front and back views (FIGS. 50-51), the device 500 has a shape that is symmetrical or substantially symmetrical around a vertical side-to-side plane 552 when viewed from the side. The distal portion 507 is also generally narrower than the proximal portion 505 when the device 500 is viewed from the side. The coaption element 510 optionally also has a tapering or generally tapering shape that narrows toward the distal portion 507 of the device 500. However, in some example embodiments, the coaption element does not taper as it extends from the proximal portion of the device to the distal portion of the device.

The rounded features of the device 500 are further demonstrated by the round shape of the paddles 520, 522 where the inner and outer paddles 520, 522 are joined together and the round shape of the paddle frames 524. However, the paddles 520, 522 and paddle frames 524 can take a wide variety of different forms. For example, the paddles 520, 522 and the paddle frames 524 can be rounded along the top edges but be flat or substantially flat on the sides of the paddles 520, 522 and/or the paddle frames. By making the paddles 520, 522 flat or substantially flat on the sides, two devices can be implanted side-by-side on the native valve leaflet, with the two devices sitting flush or substantially flush against each other.

The closed paddles 520, 522 form gaps 542 between the inner paddles 522 and the coaption element 510 that are configured to receive native tissue. As can be seen in FIG. 52, the narrowing of the coaption element 510 gives the gaps 542 a somewhat teardrop shape that increases in width as the gaps 542 approach the distal portion 507 of the device. The widening of the gaps 542 toward the distal portion 507 allows the paddles 520,522 to contact tissue grasped in the gaps 542 nearer to the proximal portion 505.

The paddle frames 524 extend vertically from the distal portion 507 toward the proximal portion 505 until approximately a middle third of the device 500 before bending or flaring outward so that the connection portion of the frames 524 passes through gaps 544 formed by the inner paddles 522 folded inside of the outer paddles 520. However, in some embodiments the connection of the frames is positioned inside the inner paddles 522 or outside the outer paddles 520. The outer paddles 520 have a rounded shape that is similar to that of the coaption element 510 when viewed from the front or back (FIGS. 50-51). Thus, the device 500 has a rounded shape or substantially round shape.

Figure 54:
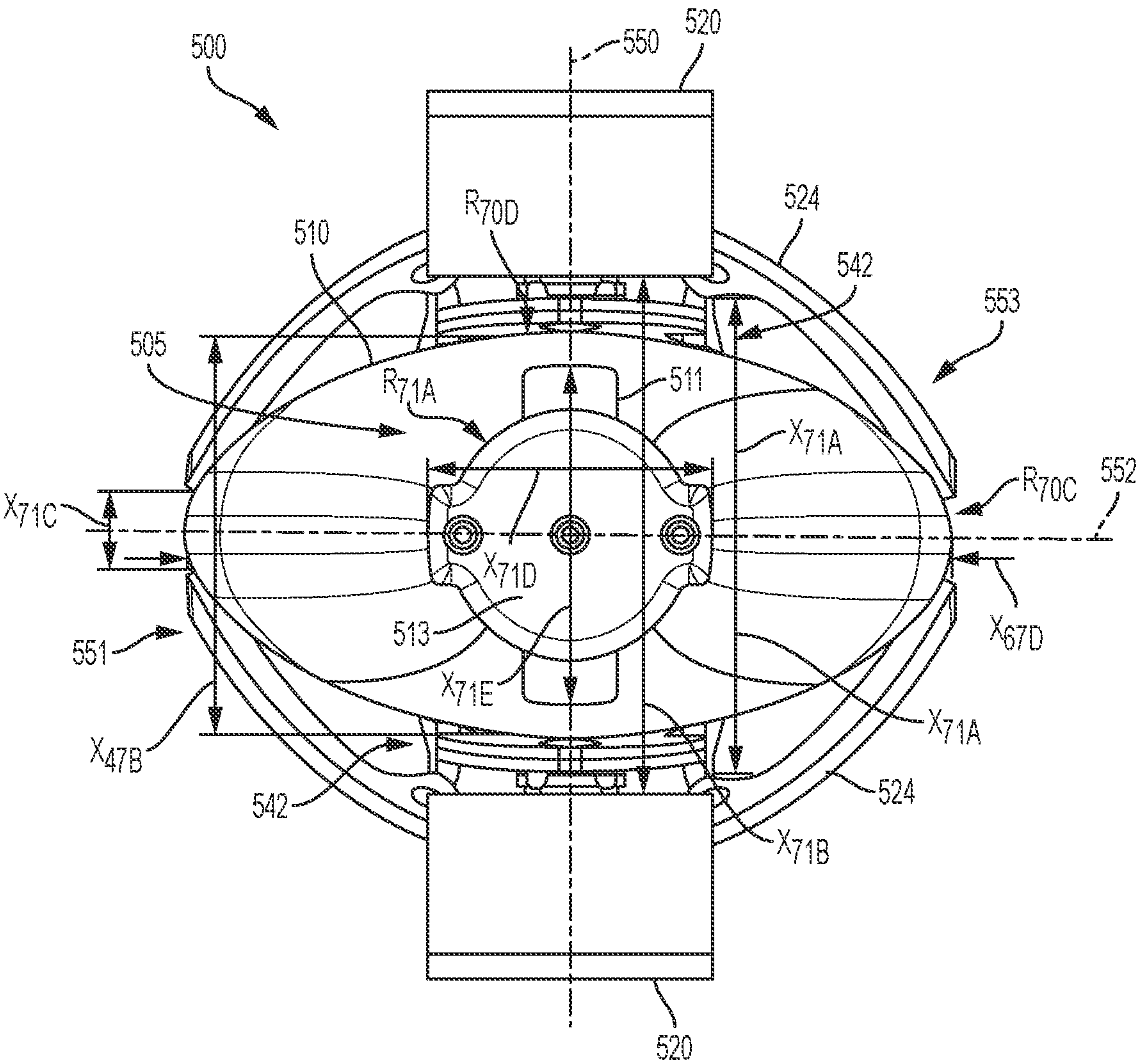
FIG. 54 shows a top view of the implantable prosthetic device of FIG. 48 with a collar component.
Figure 55:
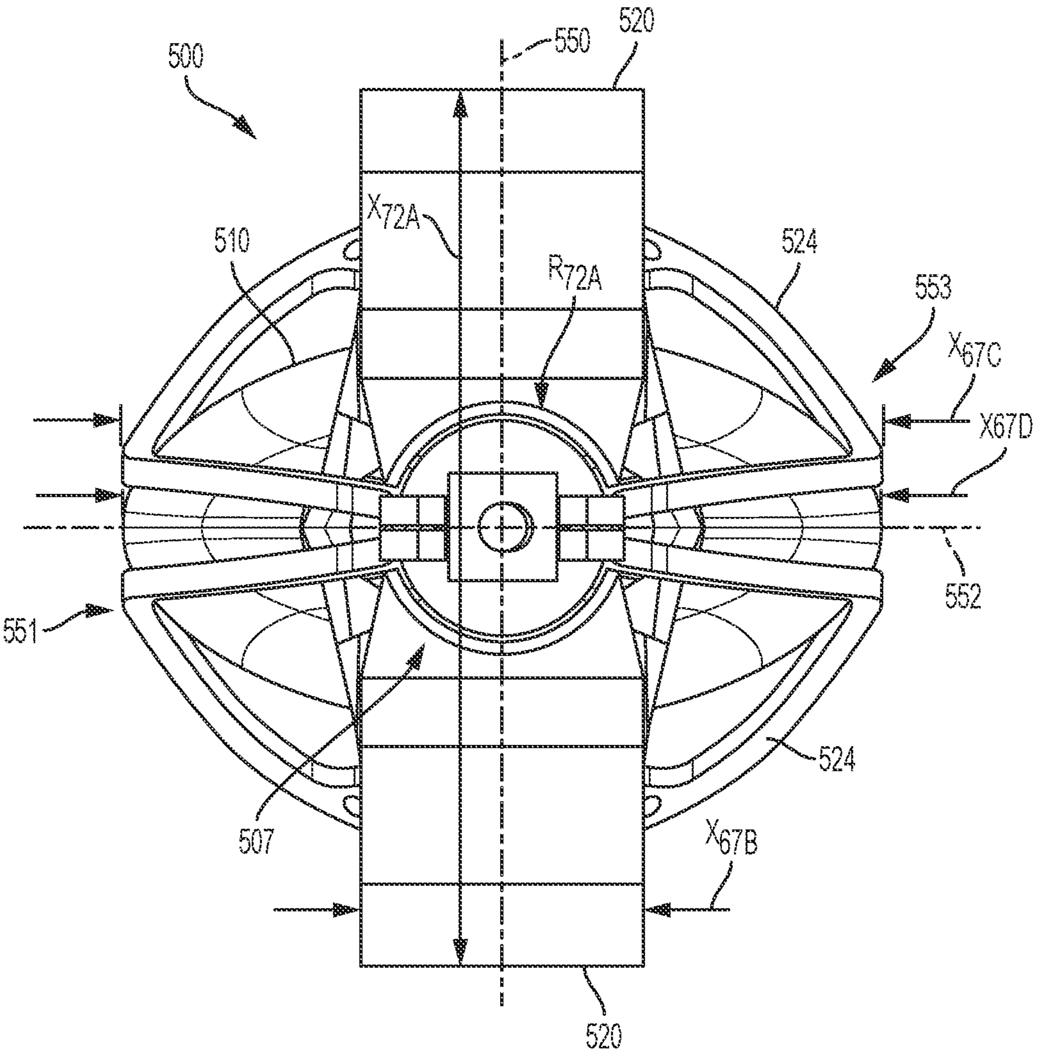
FIG. 55 shows a bottom view of the implantable prosthetic device of FIG. 48.
Figure 56:
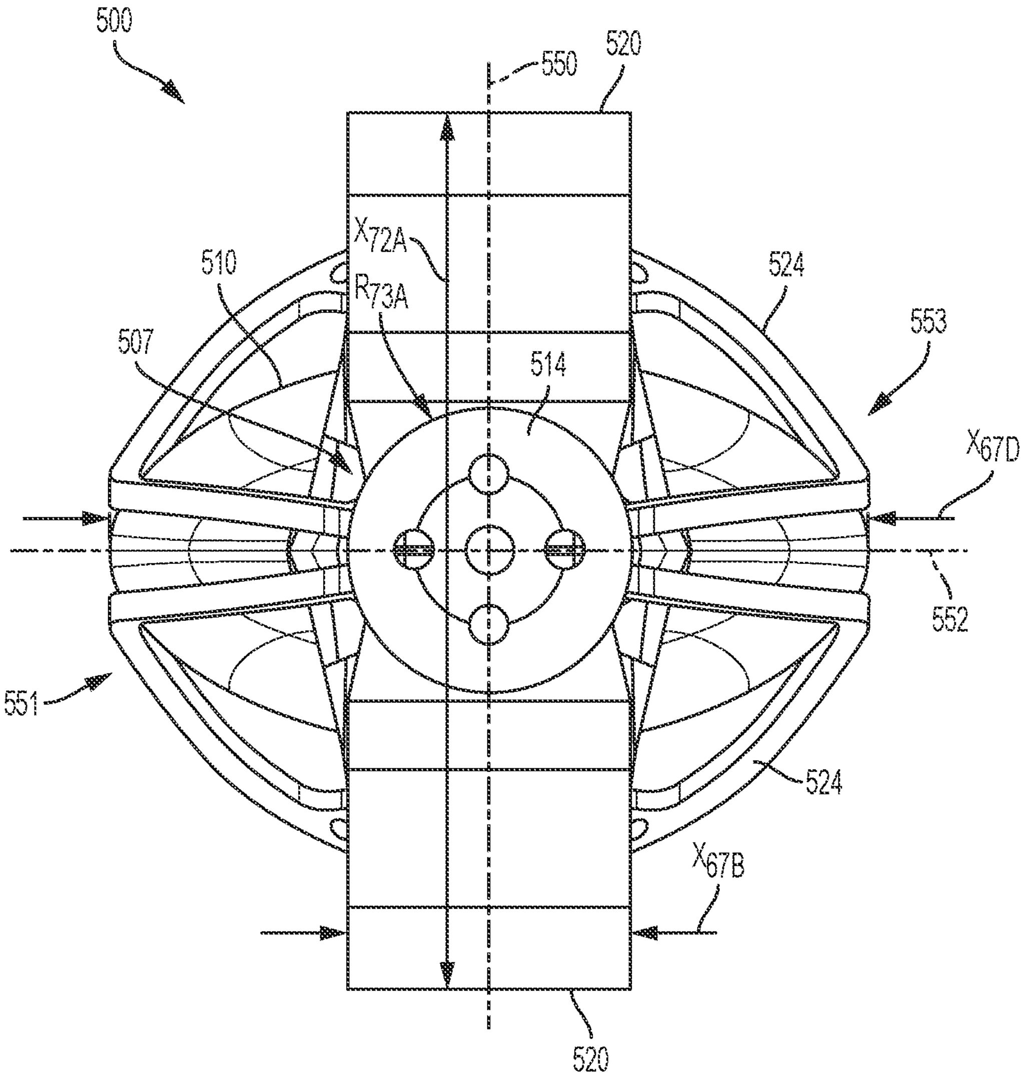
FIG. 56 shows a bottom view of the implantable prosthetic device of FIG. 48 with a cap component.

The round shape of the device 500 is particularly visible when the device 500 is viewed from the top (FIGS. 53-54) or bottom (FIGS. 55-56).

Figure 53:
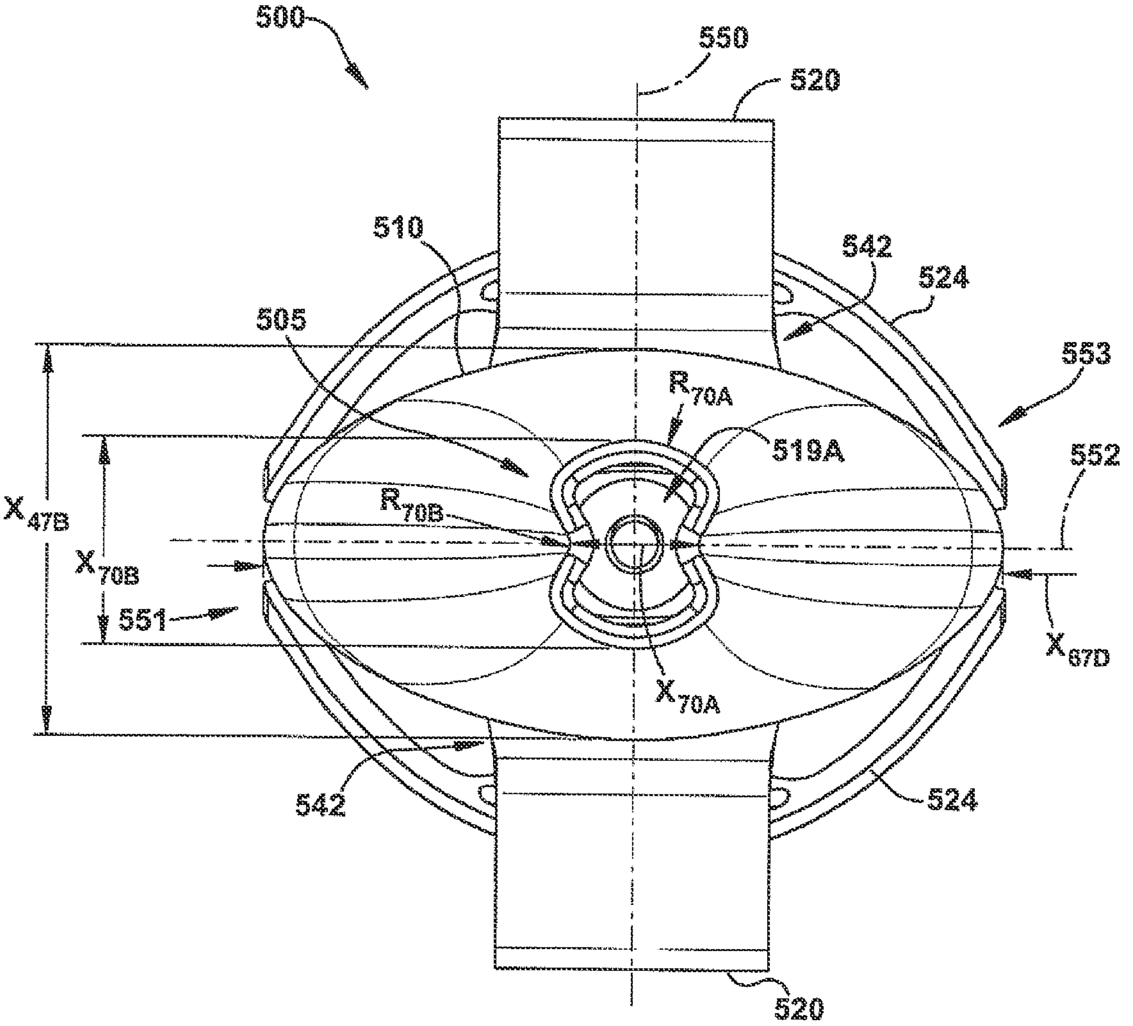
FIG. 53 shows a top view of the implantable prosthetic device of FIG. 48.

Referring now to FIGS. 53-54, top views of the device 500 are shown. The device 500 has a shape that is symmetrical or substantially symmetrical around a front-to-back plane 550 and is also symmetrical or substantially symmetrical around a side-to-side plane 552 when viewed from the top. An opening 519A in the coaption element 510 is visible at the proximal portion 505 of the device 500. As can be seen in FIG. 53, the coaption element 510 can be hollow inside. The proximal collar 511 shown in FIG. 54 can be secured to the coaption element 510 to close off the coaption element 510.

In one example embodiment, the coaption element is not planar and has all curved surfaces. For example, the coaption elements 510 illustrated herein can be formed of a series of blended surfaces have a variety of different radii of curvature. The coaption element 510 has an oval or generally oval shape when viewed from the top. However, in some example embodiments, the coaption element 510 can have other shapes when viewed from the top. For example, the coaption element can have a rectangular, square, diamond, elliptical, or any other shape. The paddle frames 224 each have an arcuate shape with a smaller radius than the coaption element 510 so that the gaps 542 formed between the inner paddles 522 and paddle frames 524 and the coaption element 510 taper as they approach left 551 and right 553 sides of the device 500. Thus, native tissue, such as the leaflets 20,22 tend to be pinched between the paddle frames 524 and the coaption element 510 towards the left and right sides 551,553 of the device 500.

Referring now to FIGS. 55-56, bottom views of the device 500 are shown. As with the top views (FIGS. 53-54), the device 500 has a shape that is symmetrical or substantially symmetrical around the front-to-back plane 550 and is also symmetrical or substantially symmetrical around the side-to-side plane 552 when viewed from the bottom. The cap 514 is shown in FIG. 56 and can attach (e.g., jointably attach, etc.) to the outer paddles 520 and the paddle frames 524.

The paddle frames 524 extend outward from the distal portion 507 of the device 500 to the left and right sides 551,553 at a narrow or slight angle from the side-to-side plane 552. The paddle frames 524 extend further away from the side-to-side plane 552 as the paddle frames 524 extend toward the proximal portion of the device 500 (FIG. 52) to ultimately form the arcuate shape seen in FIGS. 53-54.

Figure 57A:
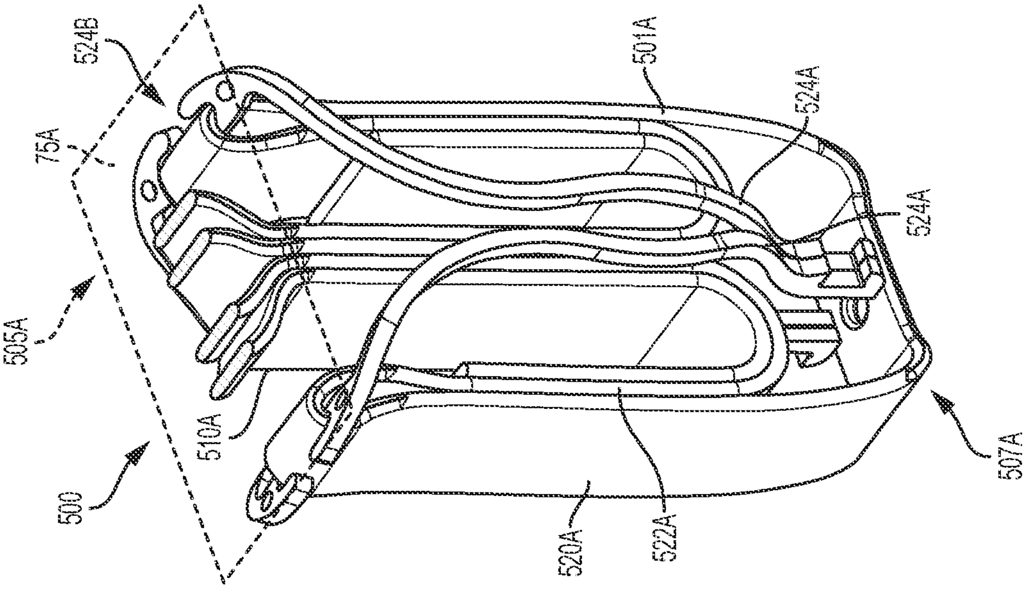
FIG. 57A shows a sectioned perspective view of the implantable prosthetic device of FIG. 48A sectioned by cross-section plane 75A.
Figure 57:
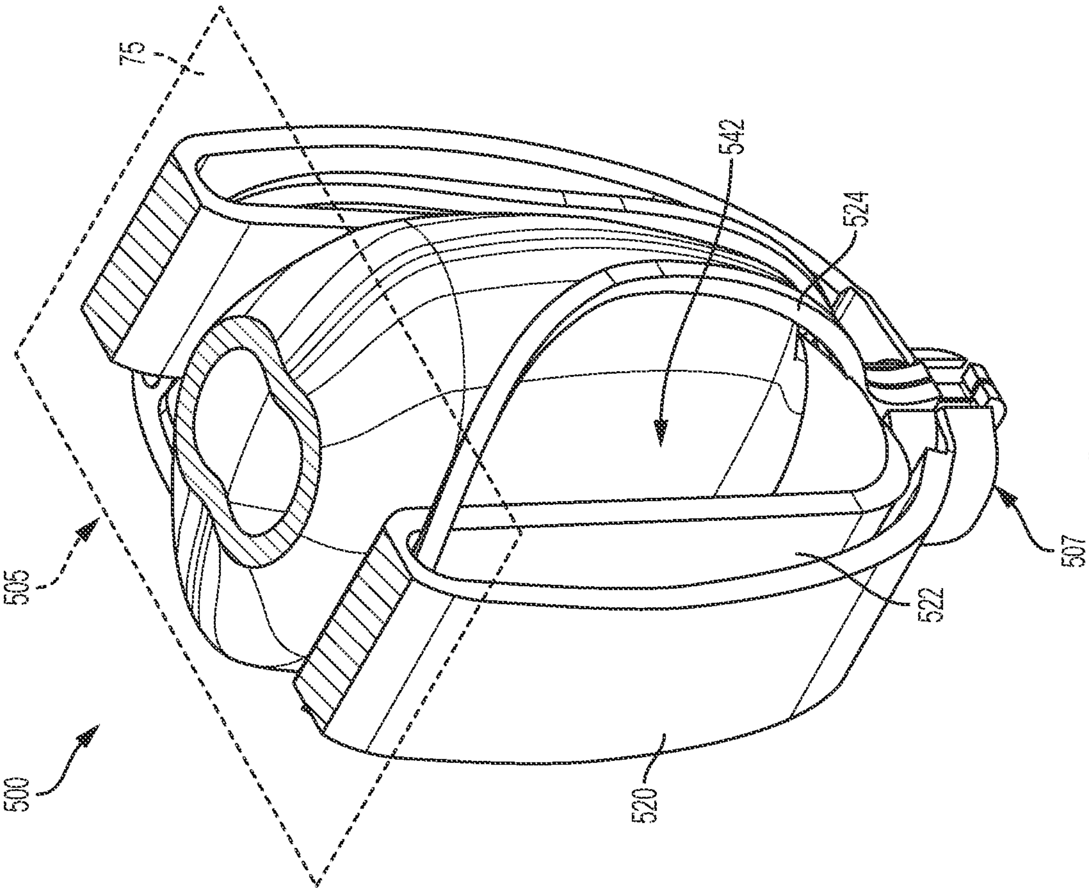
FIG. 57 shows a sectioned perspective view of the implantable prosthetic device of FIG. 48 sectioned by cross-section plane 75.
Figure 58A:
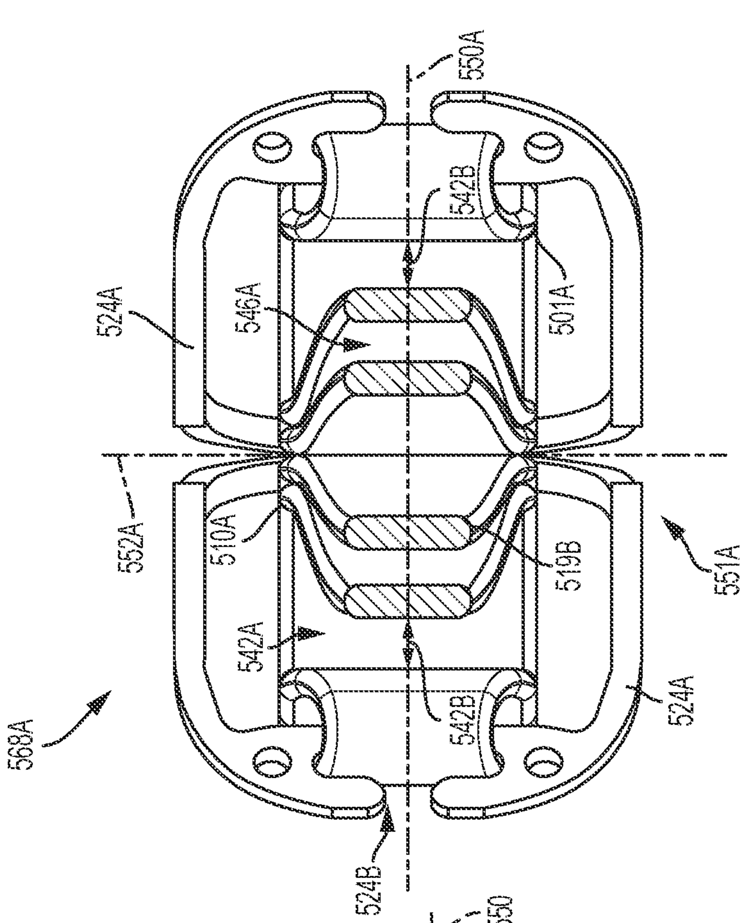
FIG. 58A shows a top cross-section view of the example prosthetic device illustrated by FIG. 57A.
Figure 58:
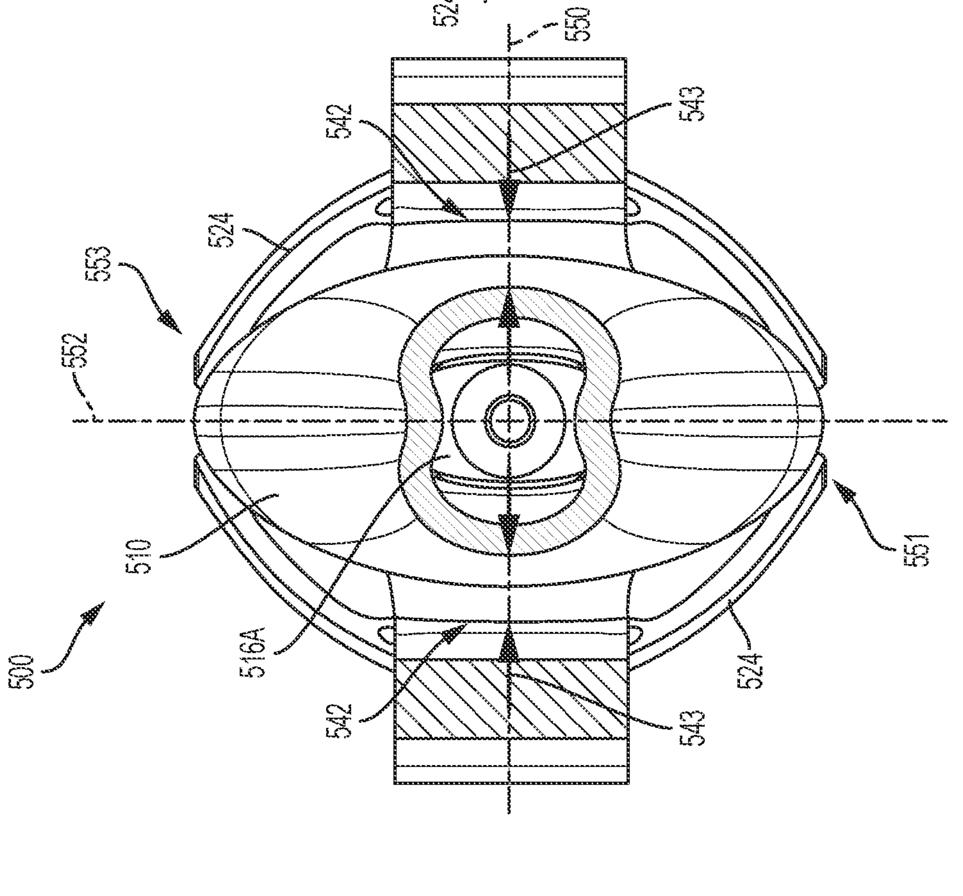
FIG. 58 shows a top cross-section view of the example prosthetic device illustrated by FIG. 57.

Referring now to FIGS. 57-66, perspective and cross-sectional views of the device 500 are shown. Referring now to FIG. 57, the device 500 is shown sliced by cross-section plane 75 near the proximal portion of the coaption element 510. Referring now to FIG. 58, a cross-sectional view of the device 500 is shown as viewed from cross-section plane 75 in FIG. 57. At the location of the plane 75, the coaption element 510 has a round or generally round shape with lobes arranged along the front-to-back plane 550. The gaps 542 between the paddle frames 524 and coaption element 510 form a crescent-like shape with a central width 543. As noted above, the gaps 542 narrow as the gaps 542 approach the left and right sides 551,553.

Figure 59A:
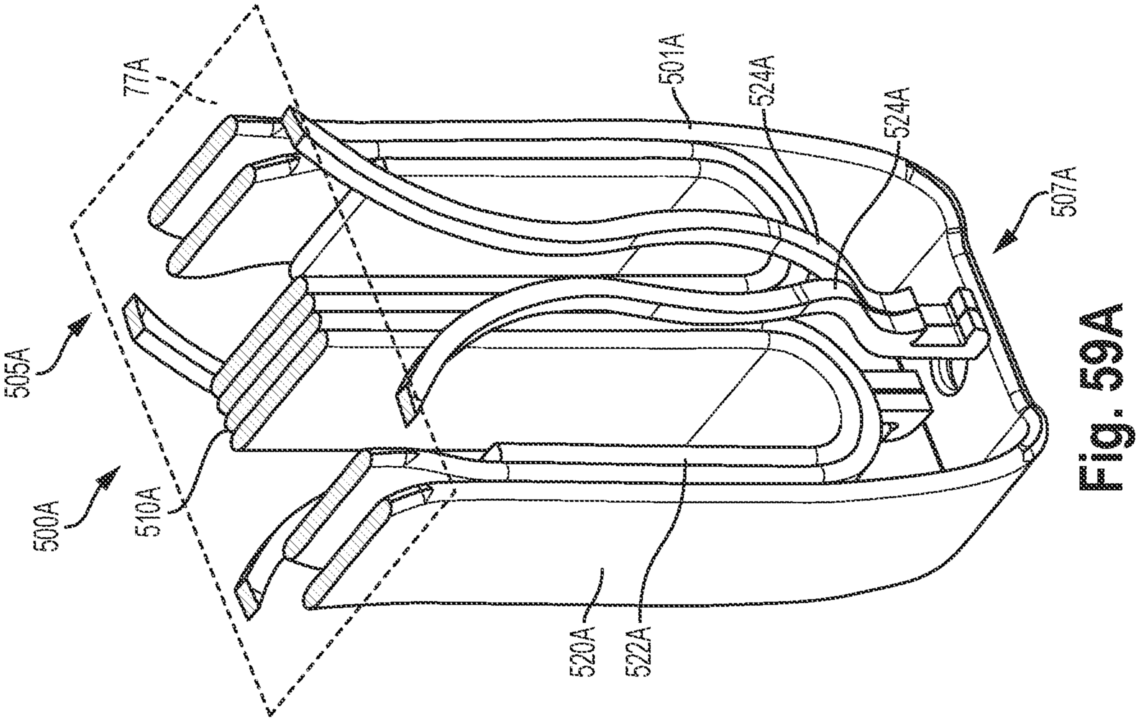
FIG. 59A shows a sectioned perspective view of the implantable prosthetic device of FIG. 48A sectioned by cross-section plane 77A.
Figure 59:
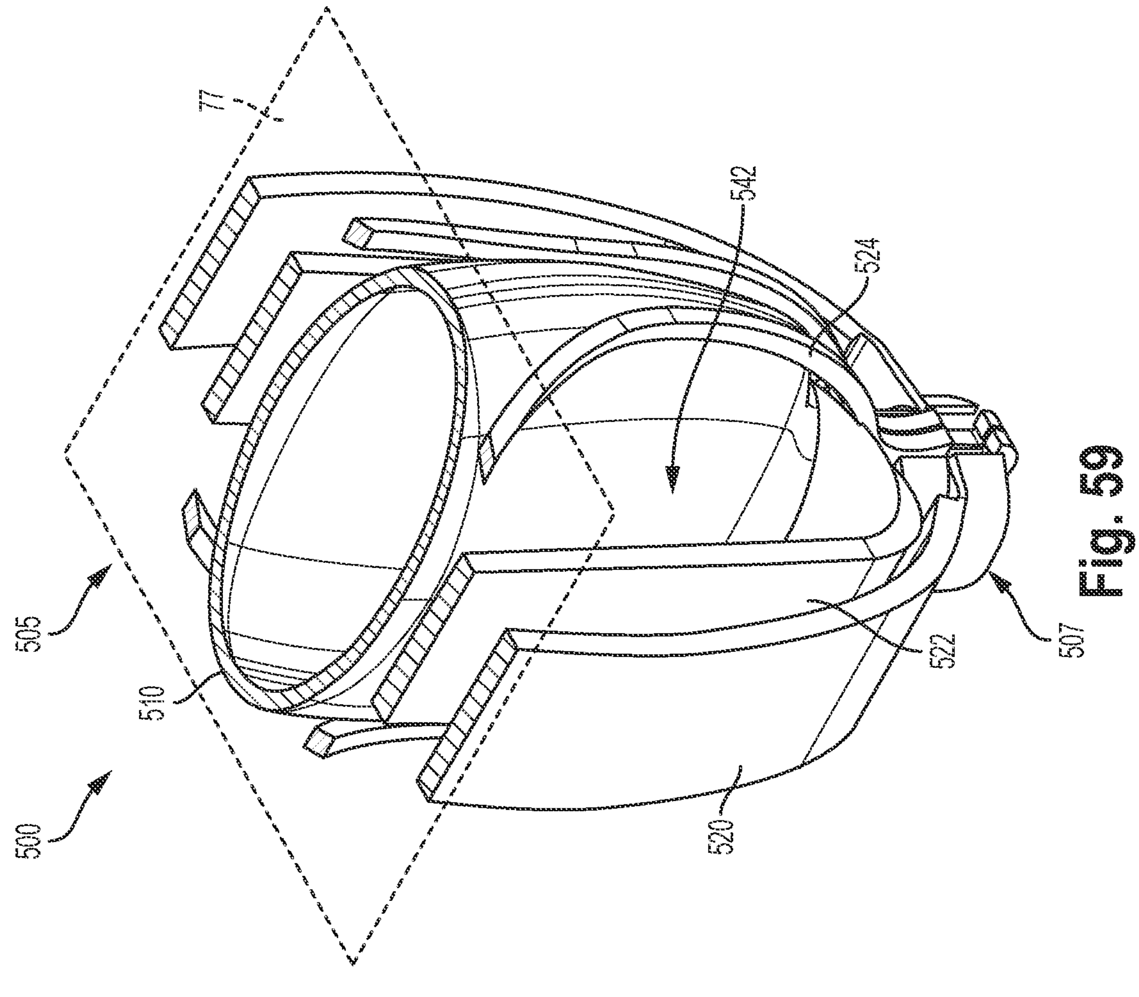
FIG. 59 shows a sectioned perspective view of the implantable prosthetic device of FIG. 48 sectioned by cross-section plane 77.
Figure 60A:
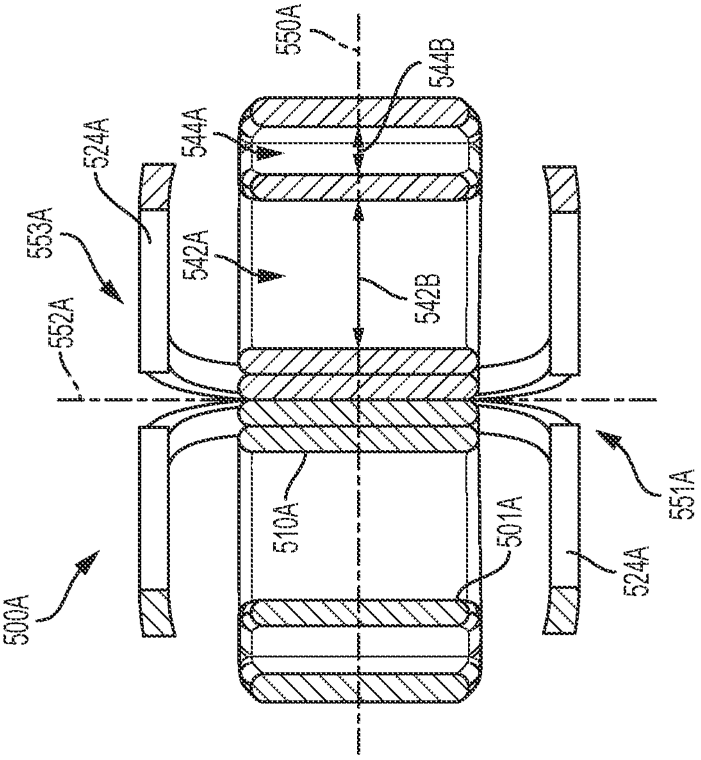
FIG. 60A shows a top cross-section view of the example prosthetic device illustrated by FIG. 59A.
Figure 60:
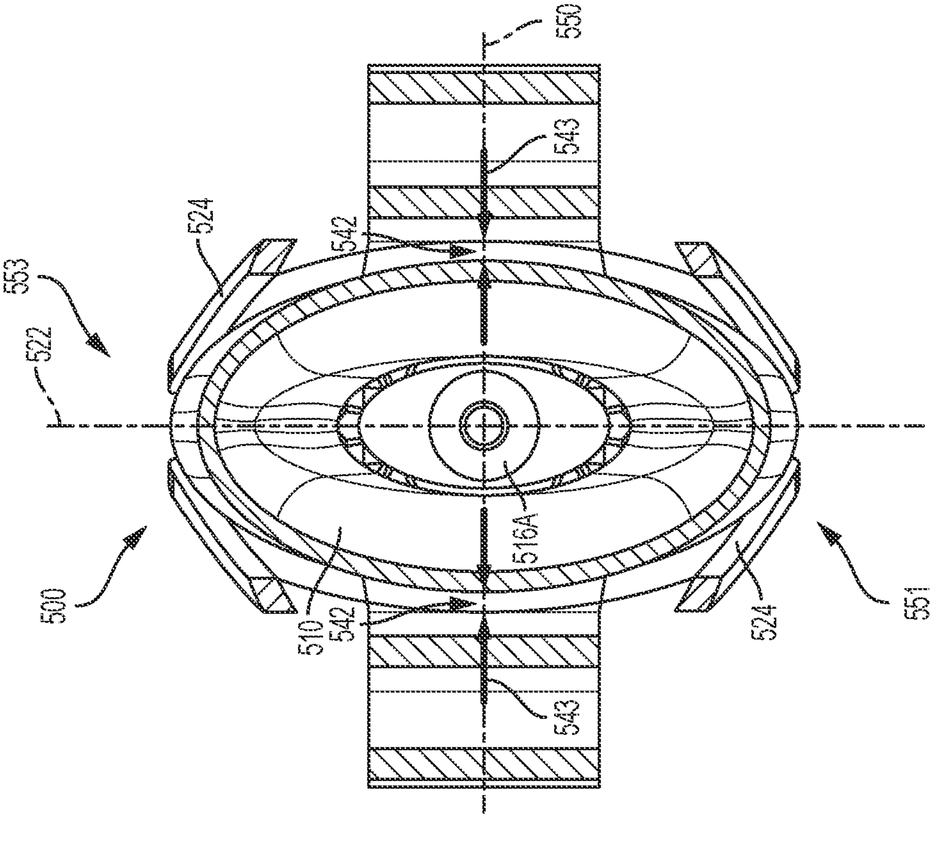
FIG. 60 shows a top cross-section view of the example prosthetic device illustrated by FIG. 59.

Referring now to FIG. 59, the device 500 is shown sliced by cross-section plane 77 positioned about three-quarters of the way between the distal portion 507 and the proximal portion 505 of the coaption element 510. Referring now to FIG. 60, a cross-sectional view of the device 500 is shown as viewed from cross-section plane 77 in FIG. 59. At the location of the plane 75, the coaption element 510 has an oval or generally oval shape oriented along the side-to-side plane 552. The gaps 542 between the paddle frames 524 and coaption element 510 form a crescent or crescent-like shape with a central width 543 that is less than the central width 543 seen in FIG. 58. At the location of the plane 77, the width 543 of the gaps 542 is narrower towards the center of the device, widens somewhat as the gaps 542 approach the left and right sides 551,553 before narrowing again. Thus, the native tissue is pinched in the center of the gaps 542 about three-quarters of the way up the coaption element 510.

Figure 61A:
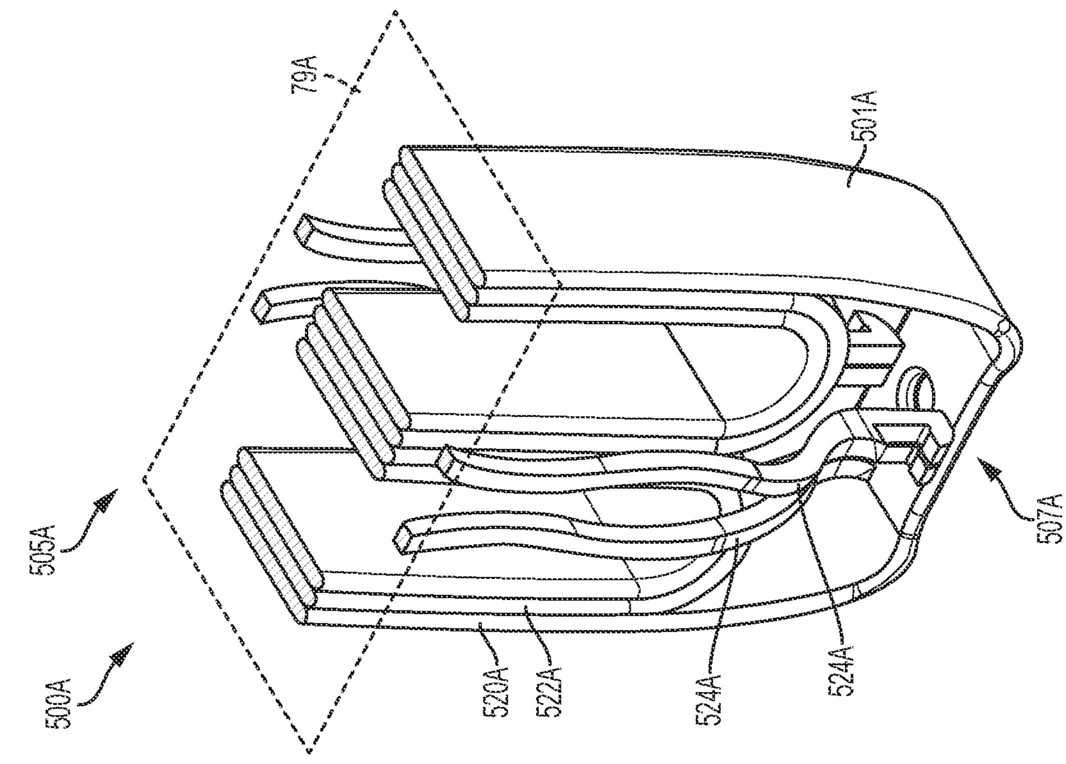
FIG. 61A shows a sectioned perspective view of the implantable prosthetic device of FIG. 48A sectioned by cross-section plane 77A.
Figure 61:
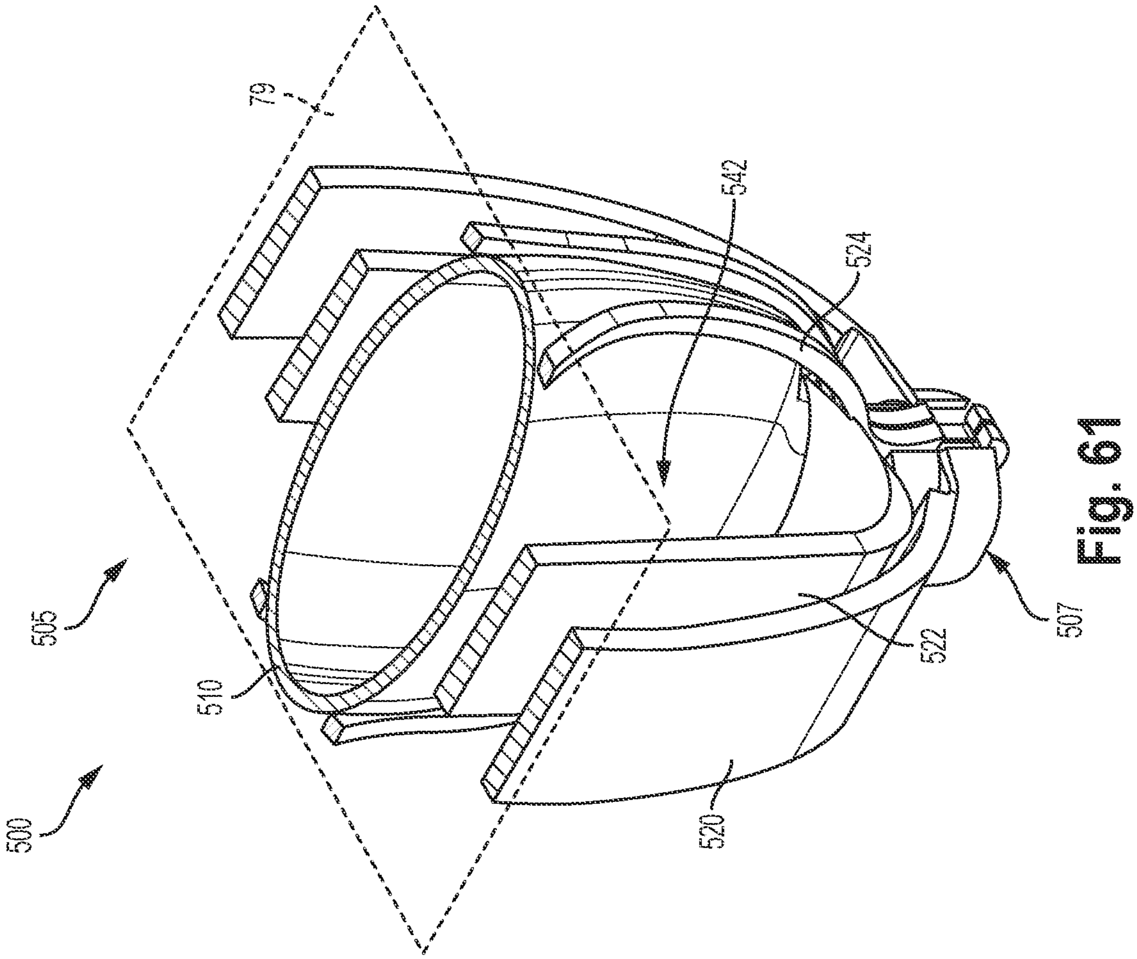
FIG. 61 shows a sectioned perspective view of the implantable prosthetic device of FIG. 48 sectioned by cross-section plane 77.
Figure 62A:
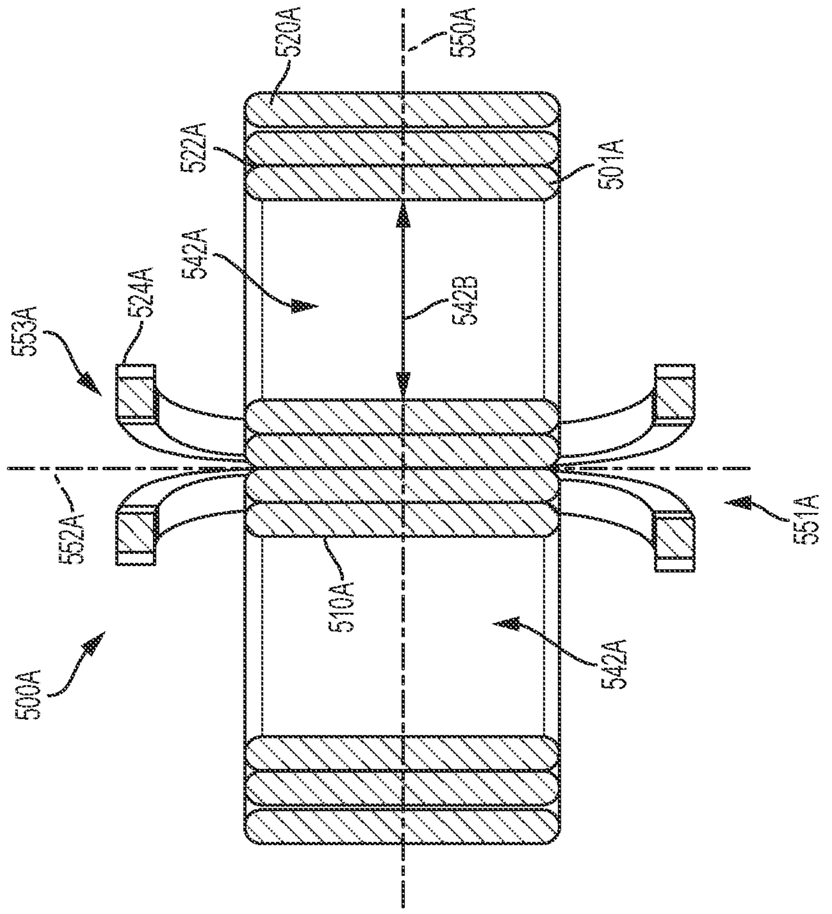
FIG. 62A shows a top cross-section view of the example prosthetic device illustrated by FIG. 61A.
Figure 62:
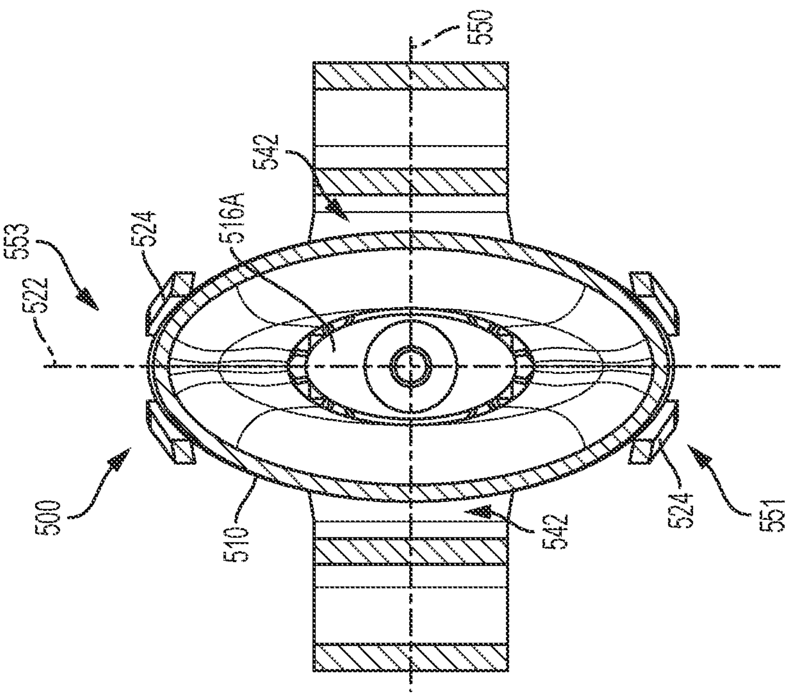
FIG. 62 shows a top cross-section view of the example prosthetic device illustrated by FIG. 61.

Referring now to FIG. 61, the device 500 is shown sliced by cross-section plane 79 positioned about half of the way between the distal portion 507 and the proximal portion 505 of the coaption element 510. Referring now to FIG. 62, a cross-sectional view of the device 500 is shown as viewed from cross-section plane 79 in FIG. 61. At the location of the plane 79, the coaption element 510 has an oval or generally oval shape oriented along the side-to-side plane 552. The paddle frames 524 can be seen near the left and right sides 551, 553 very close to or in contact with the coaption element 510. The gaps 542 are crescent or generally crescent shaped and are wider than the gaps 542 viewed along the plane 77 (FIG. 60.)

Figure 63A:
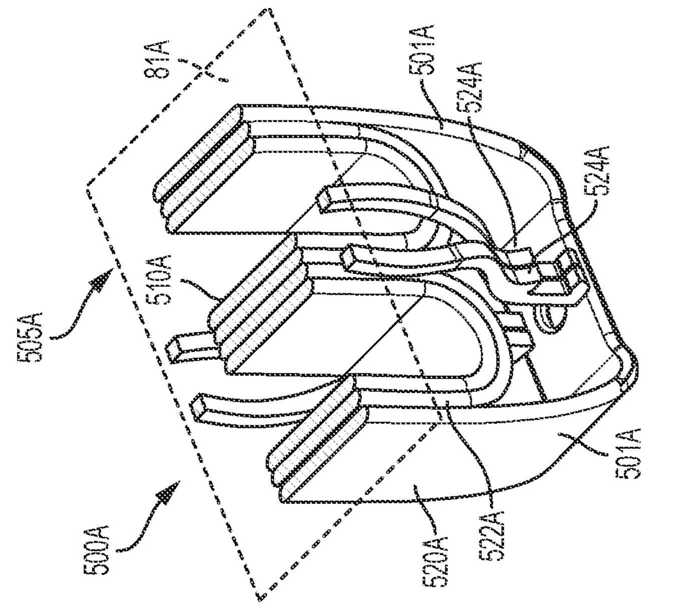
FIG. 63A shows a sectioned perspective view of the implantable prosthetic device of FIG. 48A sectioned by cross-section plane 81A.
Figure 63:
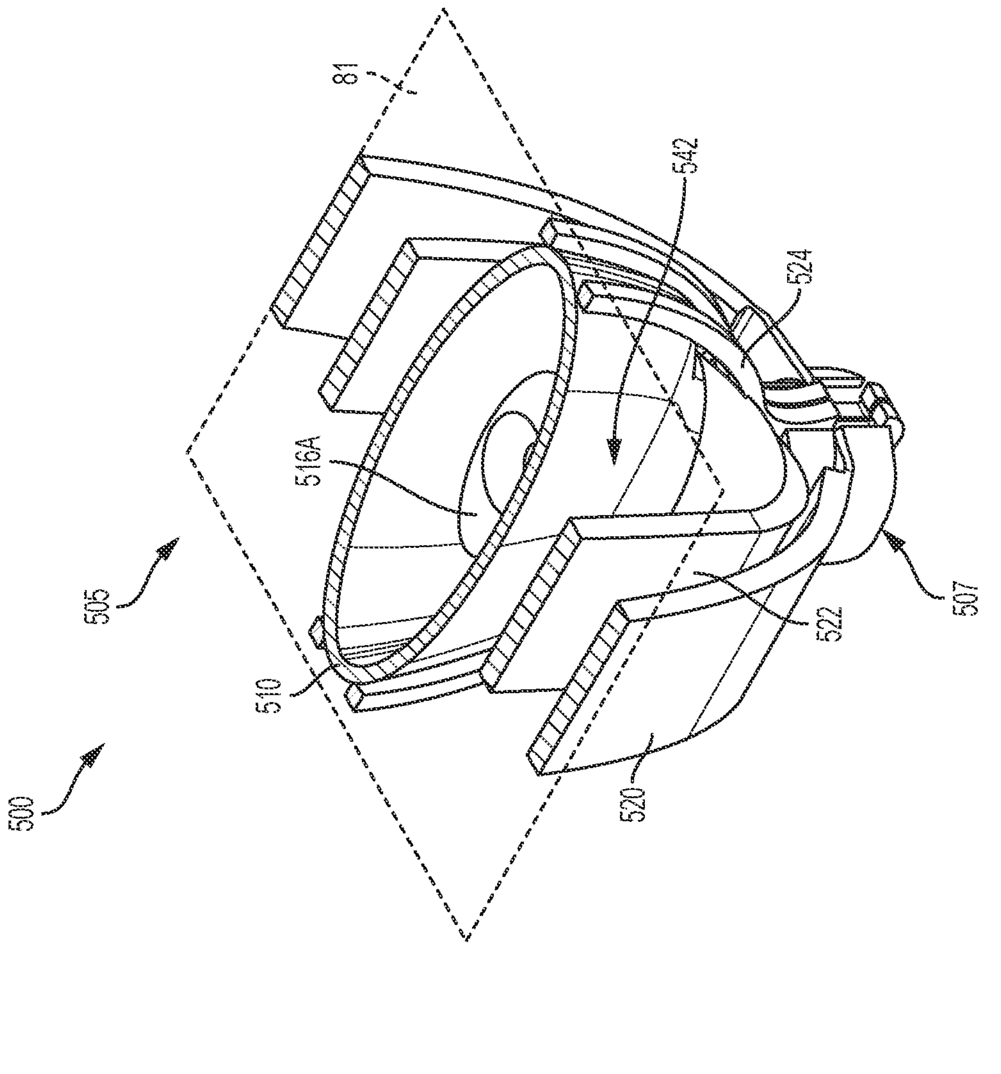
FIG. 63 shows a sectioned perspective view of the implantable prosthetic device of FIG. 48 sectioned by cross-section plane 81.
Figure 64A:
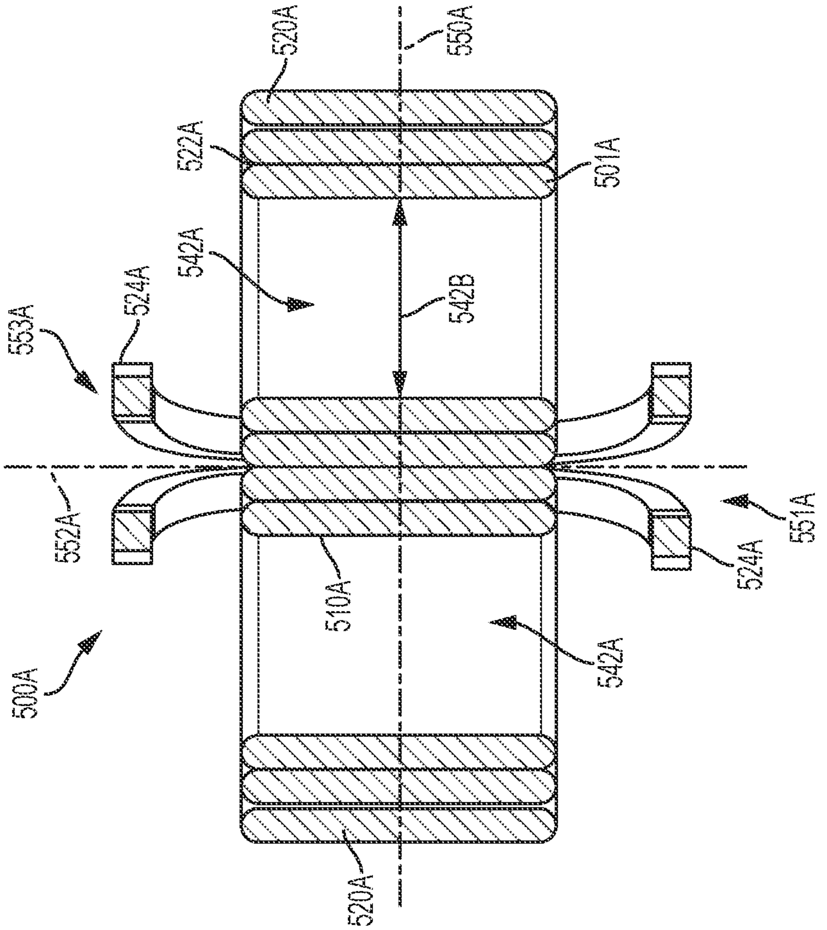
FIG. 64A shows a top cross-section view of the example prosthetic device illustrated by FIG. 63A.
Figure 64:
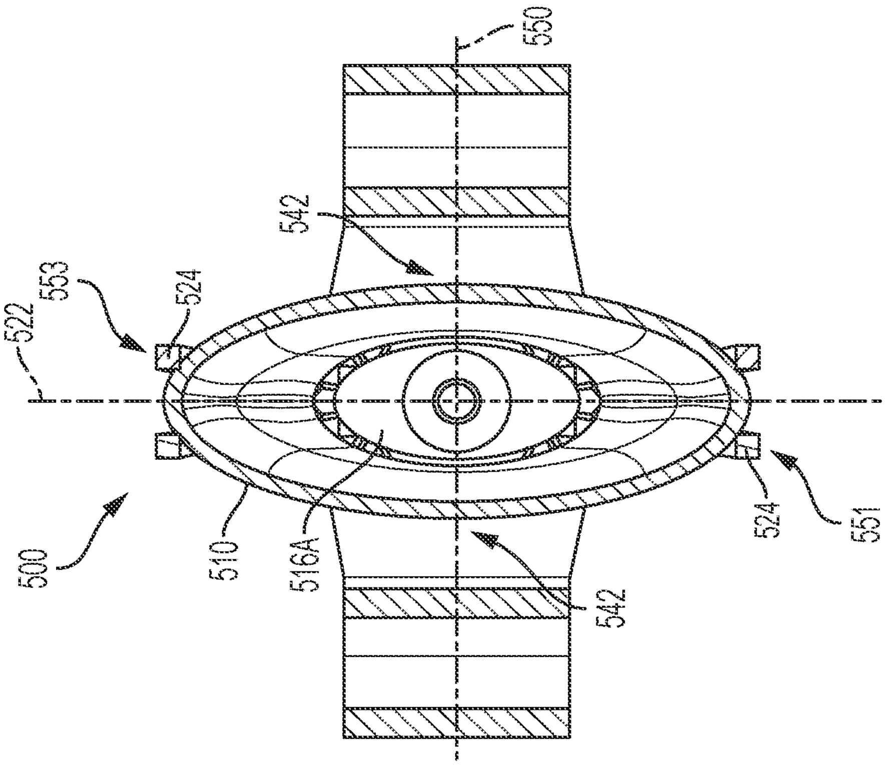
FIG. 64 shows a top cross-section view of the example prosthetic device illustrated by FIG. 63.

Referring now to FIG. 63, the device 500 is shown sliced by cross-section plane 81 positioned about one-quarter of the way between the distal portion 507 and the proximal portion 505 of the coaption element 510. Referring now to FIG. 64, a cross-sectional view of the device 500 is shown as viewed from cross-section plane 81 in FIG. 63. At the location of the plane 81, the coaption element 510 has an oval or generally oval shape oriented along the side-to-side plane 552 that is narrower than the oval shape seen in FIG. 60. The paddle frames 524 can be seen near the left and right sides 551, 553 very close to or in contact with the coaption element 510. The gaps 542 are crescent or generally crescent shaped and are wider than the gaps 542 viewed along the plane 79 (FIG. 62.)

Figure 65A:
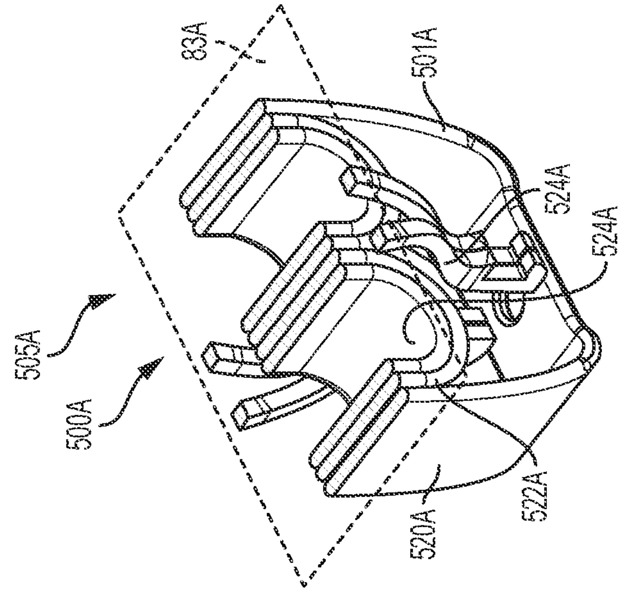
FIG. 65A shows a sectioned perspective view of the implantable prosthetic device of FIG. 48A sectioned by cross-section plane 83A.
Figure 65:
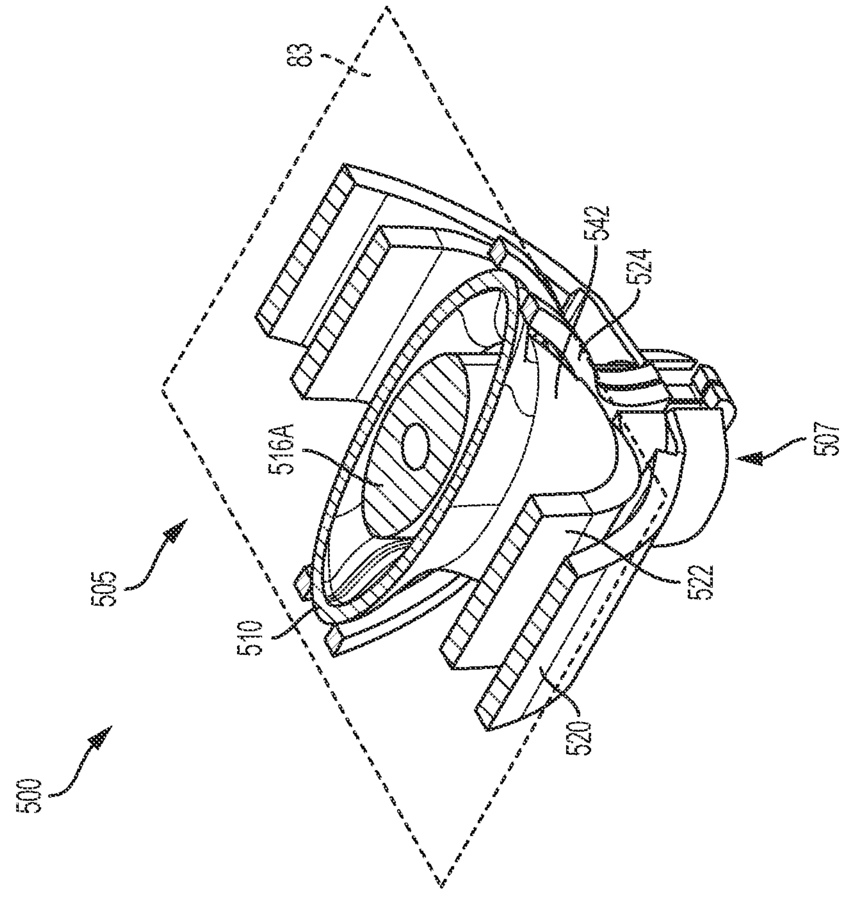
FIG. 65 shows a sectioned perspective view of the implantable prosthetic device of FIG. 48 sectioned by cross-section plane 83.
Figure 66A:
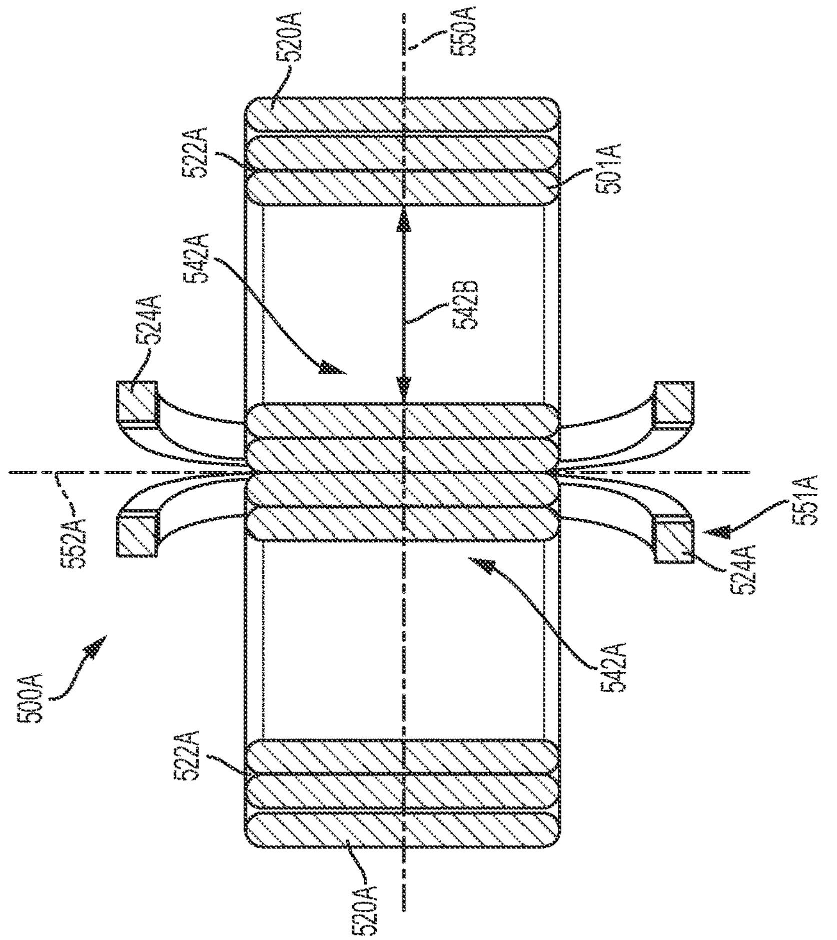
FIG. 66A shows a top cross-section view of the example prosthetic device illustrated by FIG. 65A.
Figure 66:
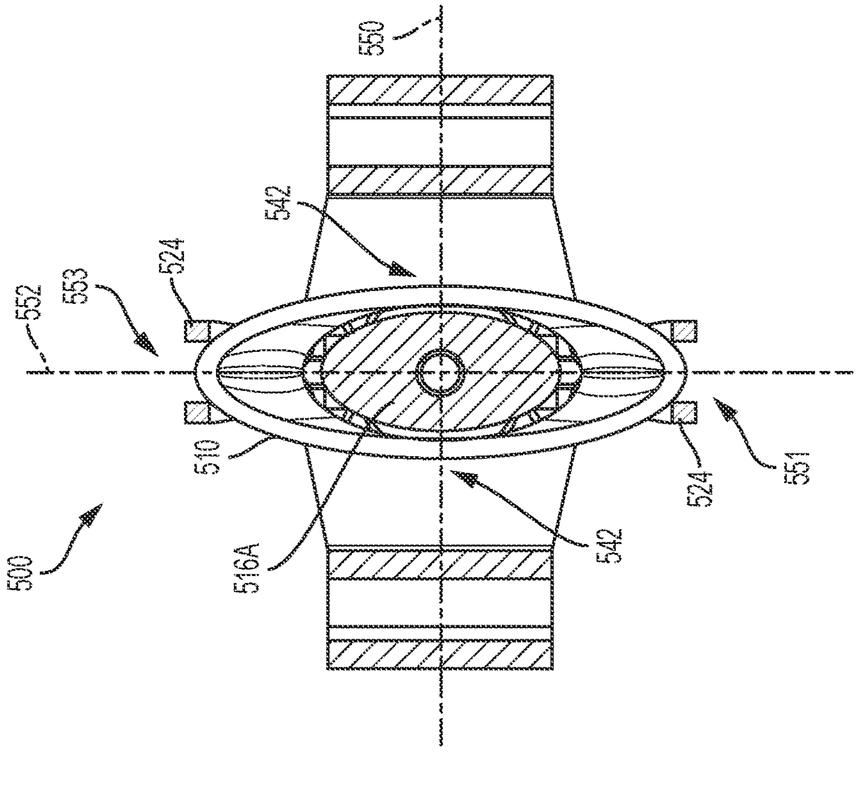
FIG. 66 shows a top cross-section view of the example prosthetic device illustrated by FIG. 65.

Referring now to FIG. 65, the device 500 is shown sliced by cross-section plane 83 positioned near the distal portion 507 of the coaption element 510. Referring now to FIG. 66, a cross-sectional view of the device 500 is shown as viewed from cross-section plane 83 in FIG. 65. At the location of the plane 83, the coaption element 510 has an oval or generally oval shape oriented along the side-to-side plane 552 that is narrower than the oval shape seen in FIG. 62 as the coaption element 510 tapers toward the distal portion 507 of the device 500. The paddle frames 524 can be seen near the left and right sides 551, 553 very close to or in contact with the coaption element 510. While the inner paddles 522 are not visible in FIG. 64, the gaps 542 are crescent or generally crescent shaped and are wider than the gaps 542 viewed along the plane 81 (FIG. 64.)

Figure 48:
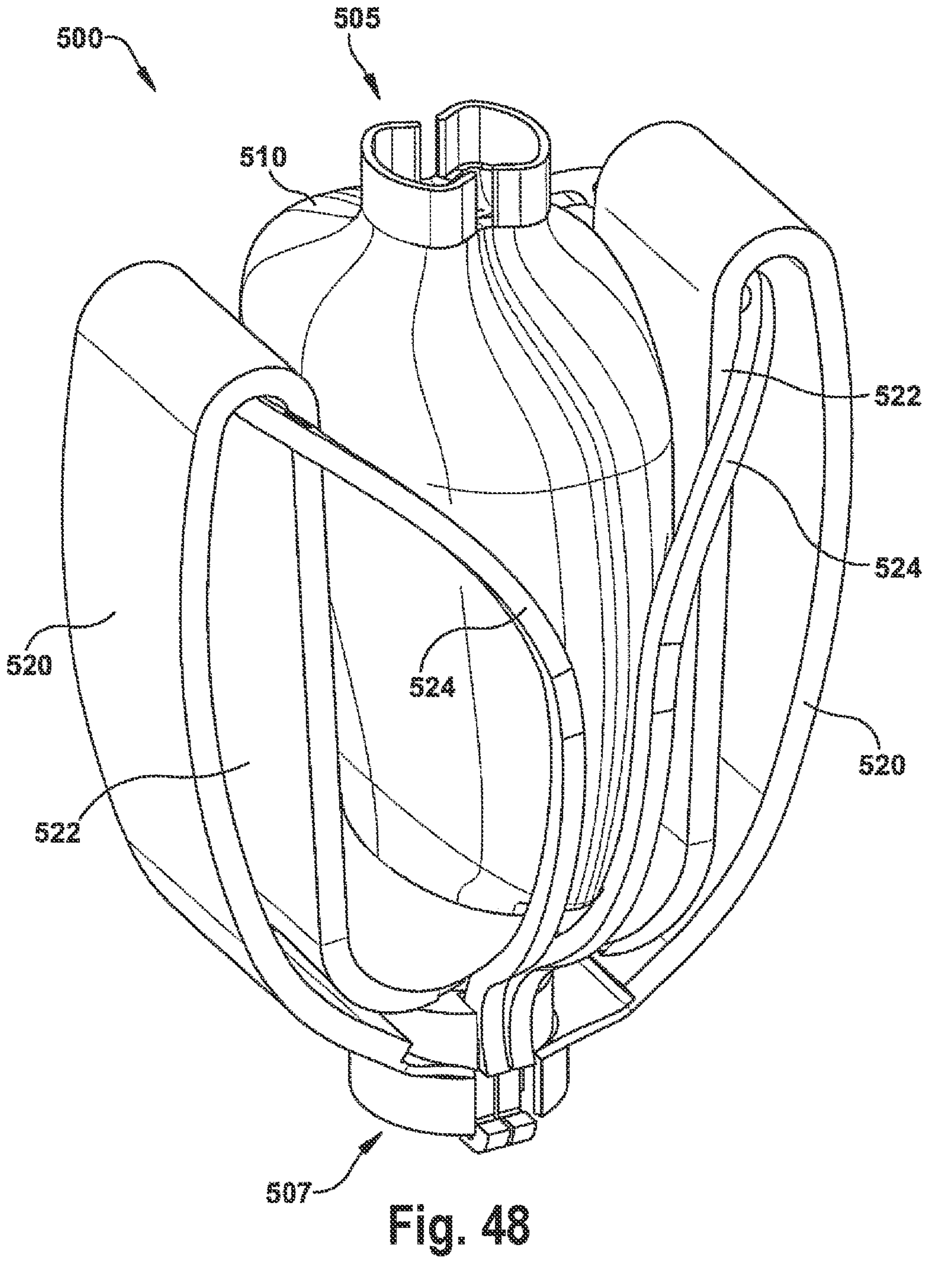
FIG. 48 shows a perspective view of an example implantable prosthetic device in a closed position.
Figure 48A:
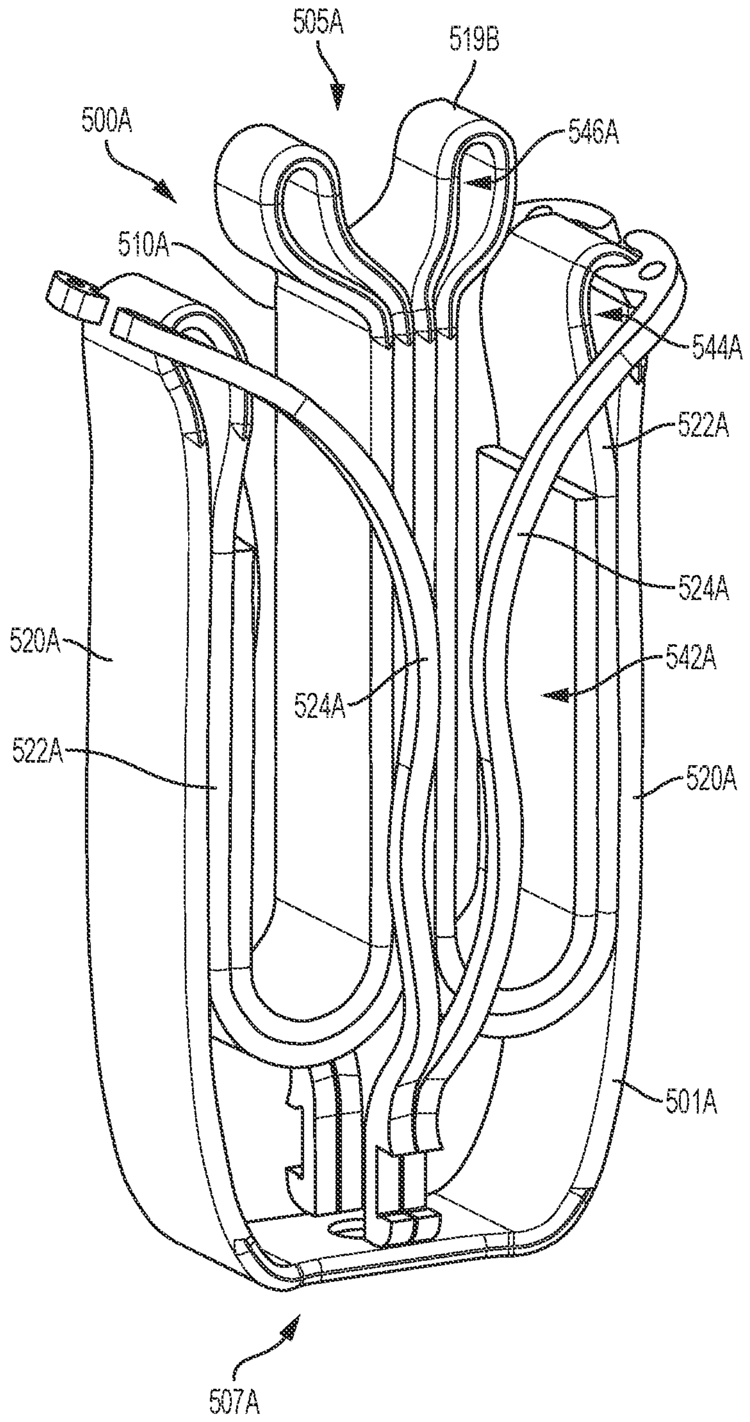
FIG. 48A shows a perspective view of an example implantable prosthetic device in a closed position.
Figure 49:
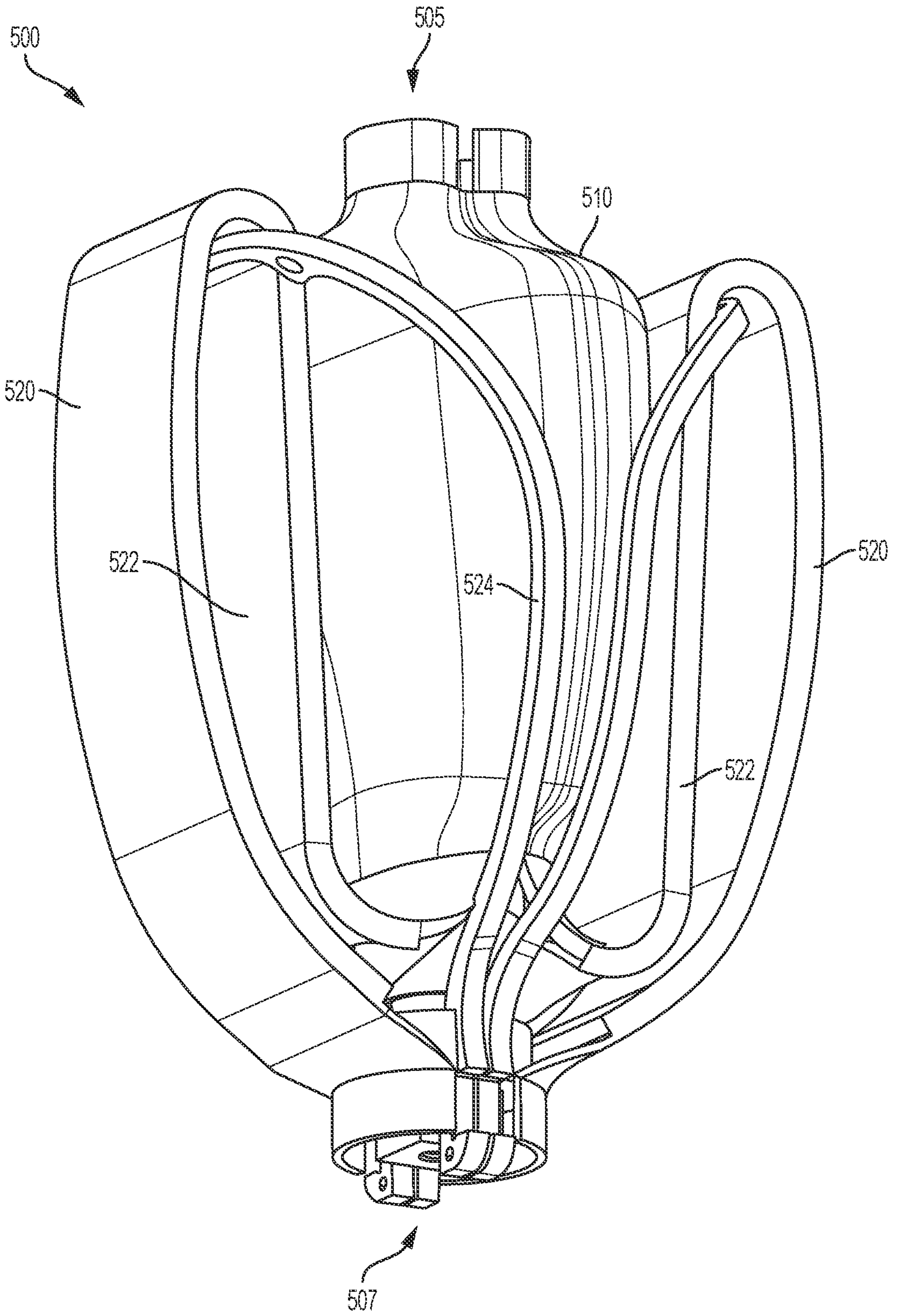
FIG. 49 shows a perspective view of the implantable prosthetic device of FIG. 48.
Figure 49A:
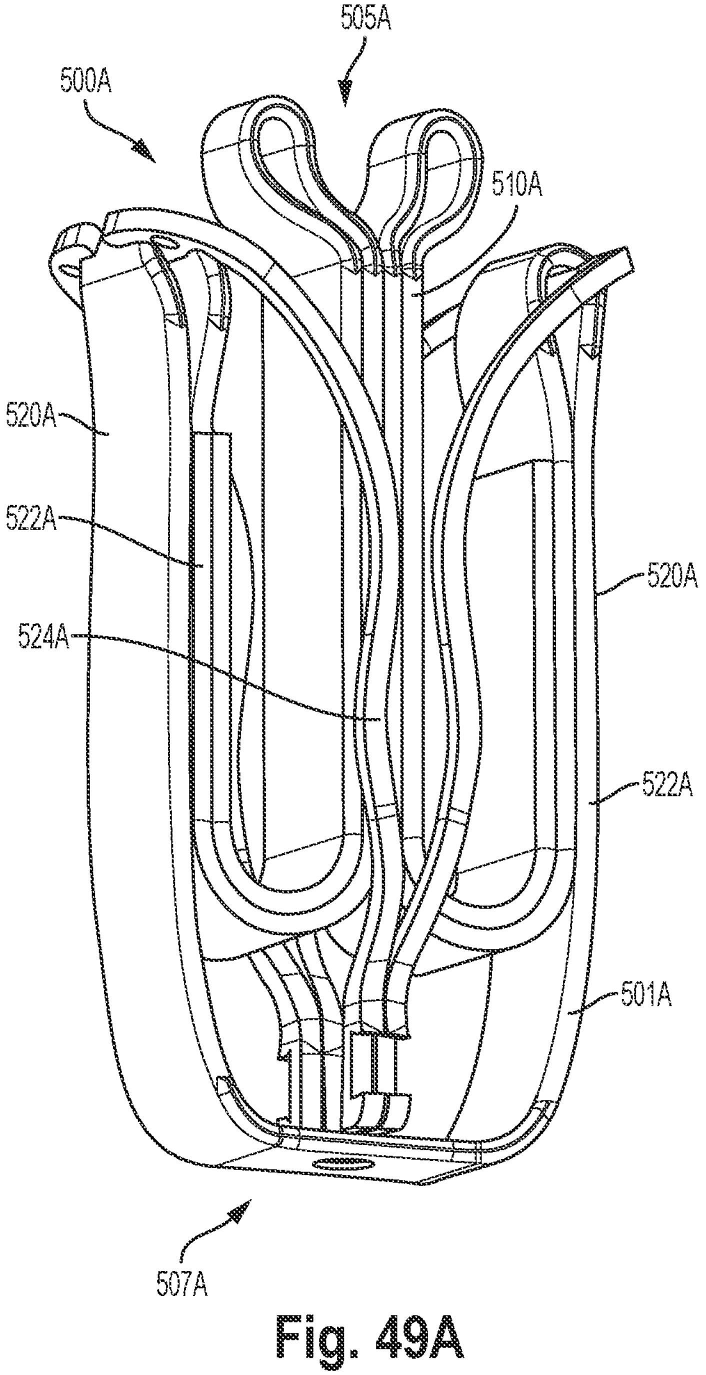
FIG. 49A shows a perspective view of the implantable prosthetic device of FIG. 48A.

Referring now to FIGS. 48A, 49A, 50A, 51A, 53A, 54A, 55A, 56A, 57A, 58A, 59A, 60A, 61A, 62A, 63A, 64A, 65A, and 66A, the example implantable device 500A is shown in the closed condition. Referring now to FIGS. 48A and 49A, the device 500A extends from a proximal portion 505A to a distal portion 507A and includes a coaption portion 510A, inner paddles 522A, outer paddles 520A, and paddle frames 524A. The proximal portion 505A can include a collar 511D for attaching a delivery device (not shown). The distal portion 507A can include a cap 514A that is attached (e.g., jointably attached, etc.) to the outer paddles 520A and is engaged by an actuation element (not shown) to open and close the device 500A to facilitate implantation in the native valve as described in the present application.

Figure 50A:
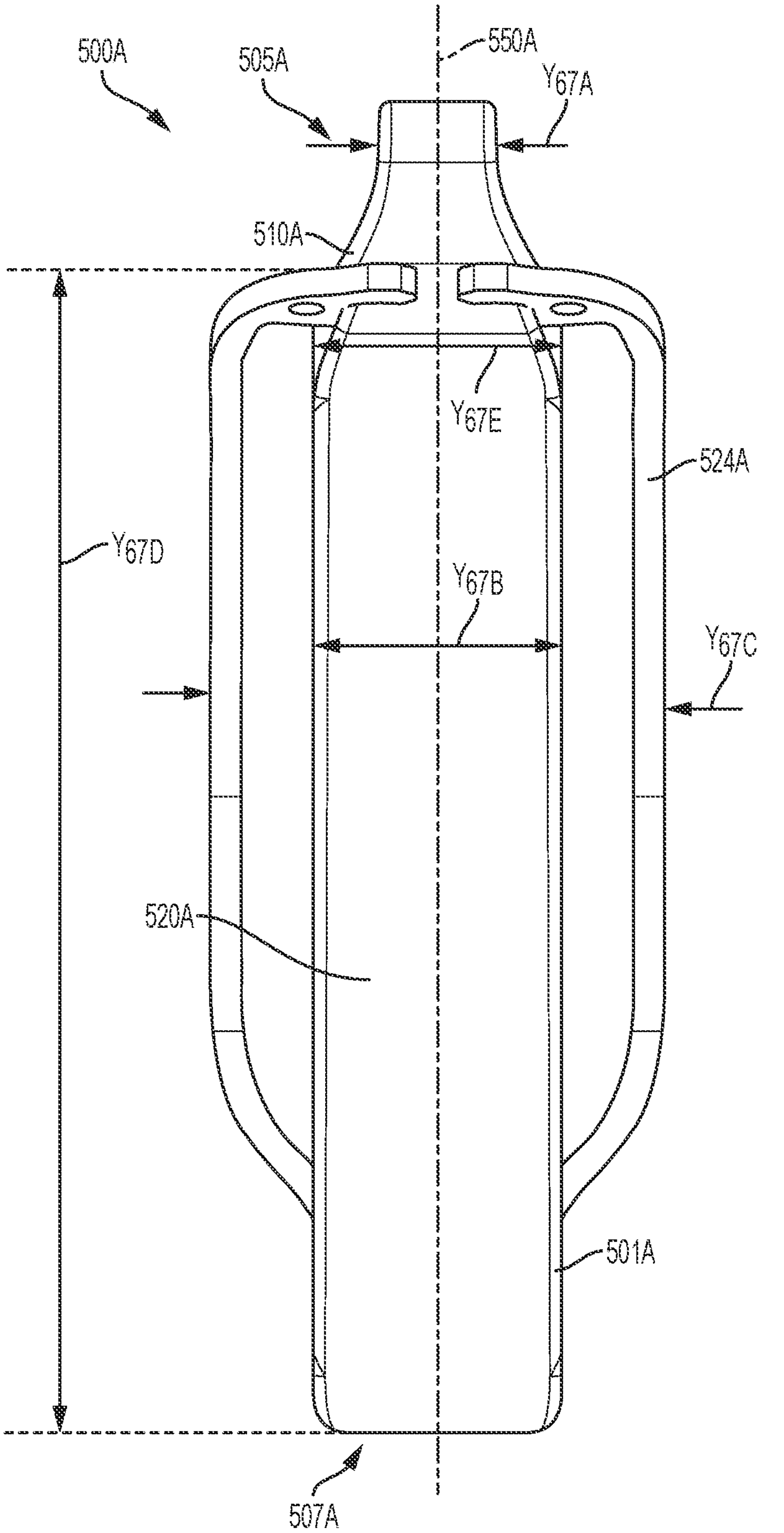
FIG. 50A shows a front view of the implantable prosthetic device of FIG. 48A.
Figure 51A:
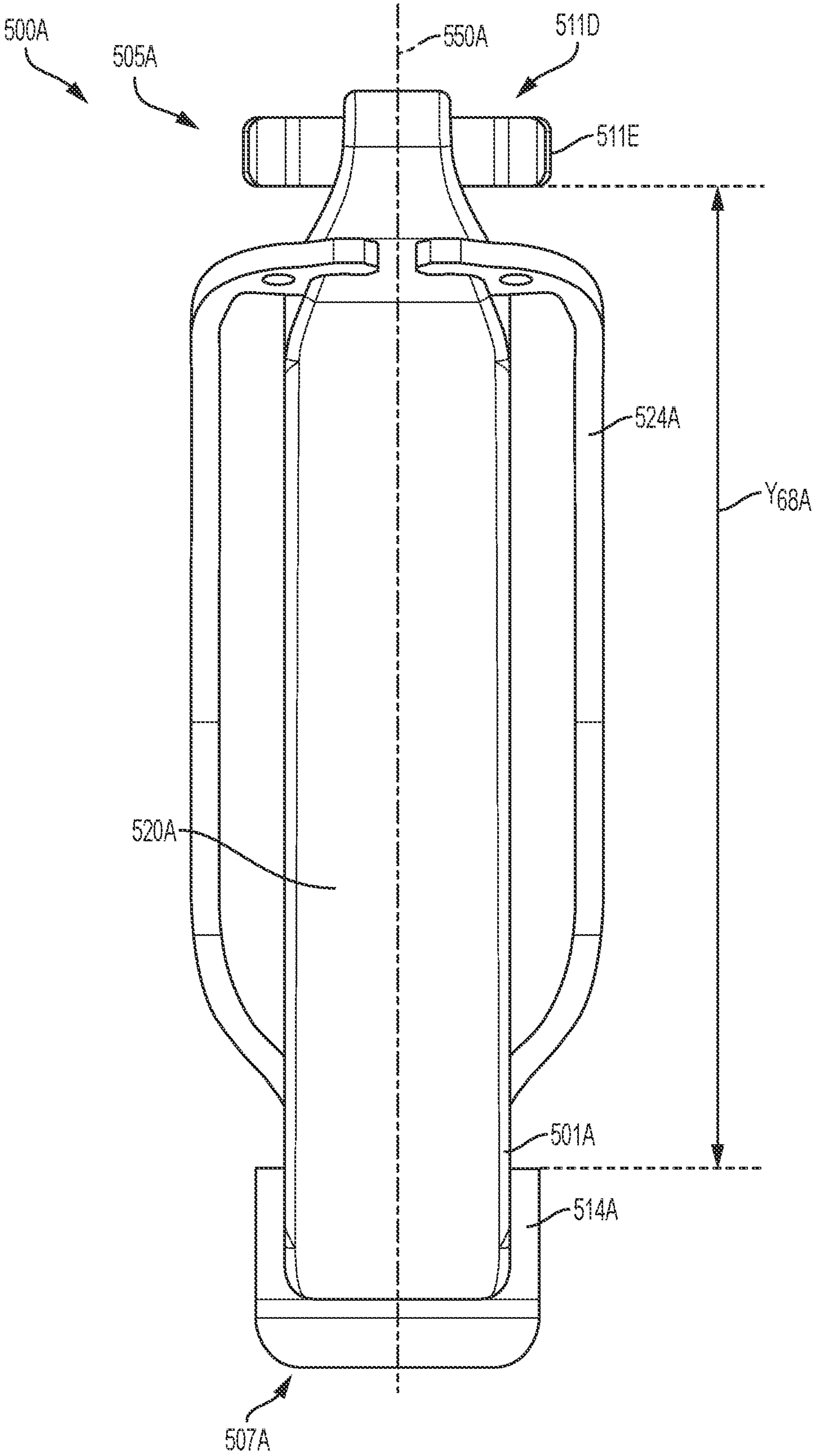
FIG. 51A shows a front view of the implantable prosthetic device of FIG. 48A with additional components.

Referring now to FIGS. 50A and 51A, front views of the device 500A are shown. The device 500A has a shape that is symmetrical or substantially symmetrical around a vertical front-to-back plane 550A and is generally narrower at the distal portion 507A than along the paddle frames 524A. The shape of the coaption element 510A and paddle frames 524A is a generally rounded rectangular shape to prevent the device 500A from catching or snagging on structures of the heart, such as the chordae tendineae, during implantation. For this reason, the proximal collar 511D (FIG. 51A) and cap 514A (FIG. 51A) can also have round edges. When viewed from the front or back, the paddle frames 524A can be seen to have a generally rounded rectangular shape, extending upwards and outwards from the distal portion 507A to a shape that has sides that are wider than and approximately parallel to the coaption element 510A when viewed from the front or back. Thus, the paddle frames 524A generally define the shape of the device 500A when viewed from the front or back. In addition, the rounded rectangular shape of the paddle frames 524A can distribute leaflet stress across a wider surface. In some example embodiments, the paddle frames 524A and/or the coaption element 510A can have other shapes.

As with the front and back views (FIGS. 50A and 51A), the device 500A has a shape that is symmetrical or substantially symmetrical around a vertical side-to-side plane 552A (FIG. 53A) when viewed from the side (e.g., FIG. 47A). The distal portion 507A is also generally narrower than the proximal portion 505A when the device 500A is viewed from the side. In the embodiment illustrated in FIG. 48B, the coaption element 510A does not taper as it extends from the proximal portion 505A of the device 500A to the distal portion 507A of the device 500A. However, in some example embodiments, the coaption element does taper as it extends from the proximal portion of the device to the distal portion of the device (e.g., FIG. 47).

The generally rounded features of the device 500A are further demonstrated by the rounded shape of the paddles 520A, 522A where the inner and outer paddles 520A, 522A are joined together. However, the paddles 520A, 522A and paddle frames 524A can take a wide variety of different forms. For example, the paddles 520A, 522A and the paddle frames 524A can be rounded along the top edges and be flat or substantially flat on the sides (e.g., the sides of the paddle frames 524A arranged at the front and back sides of the device 500A). By making the paddles 520A, 522A flat or substantially flat on the sides, two devices can be implanted side-by-side on the native valve leaflet, with the two devices sitting flush or substantially flush against each other.

The closed paddles 520A, 522A form gaps 542A between the inner paddles 522A and the coaption element 510A that are configured to receive native tissue. In some embodiments, the proximal end of the coaption element 510A has an approximately dog-bone shape so that the gaps 542A are narrower toward the proximal portion 505A as the gaps 542A approach the distal portion 507A of the device. The narrowing of the gaps 542A toward the attachment portion 505A allows the paddles 520A, 522A to contact tissue grasped in the gaps 542A nearer to the proximal portion 505A.

The paddle frames 524A extend vertically from the distal portion 507A toward the proximal portion 505A until approximately a middle third of the device 500A before bending or flaring outward so that a connection portion 524B of the frames 524A passes through gaps 544A formed by the inner paddles 522A folded inside of the outer paddles 520A. However, in some embodiments the connections of the frames are positioned inside the inner paddles 522A or outside the outer paddles 520A. The outer paddles 520A have a rounded rectangular shape that is similar to that of the coaption element 510A when viewed from the front or back (FIGS. 50A and 51A). Thus, the device 500A has a rounded rectangular shape. The rounded rectangular shape of the device 500A is particularly visible when the device 500A is viewed from the top (FIGS. 53A and 54A) or bottom (FIGS. 55A and 56A).

Figure 53A:
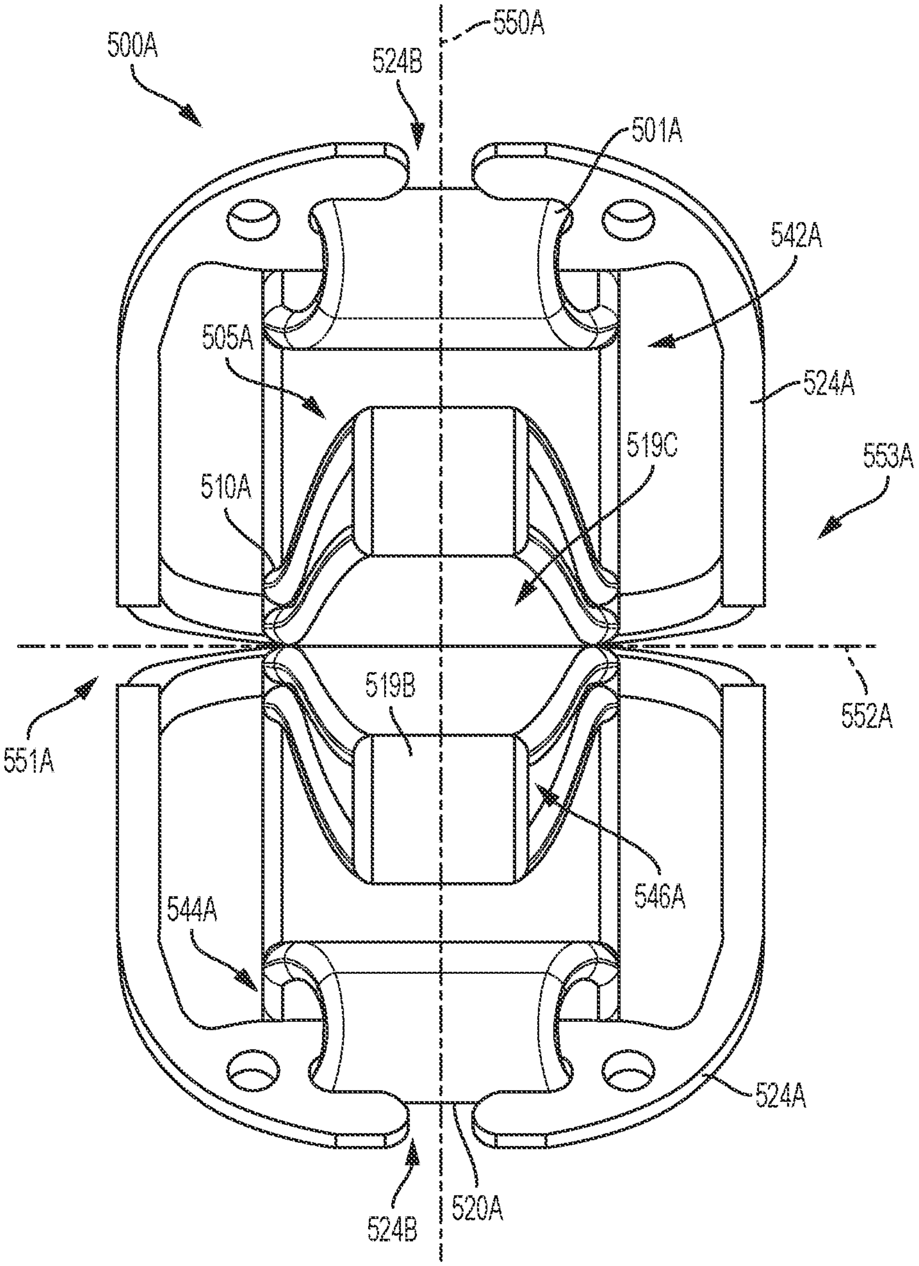
FIG. 53A shows a top view of the implantable prosthetic device of FIG. 48A.
Figure 54A:
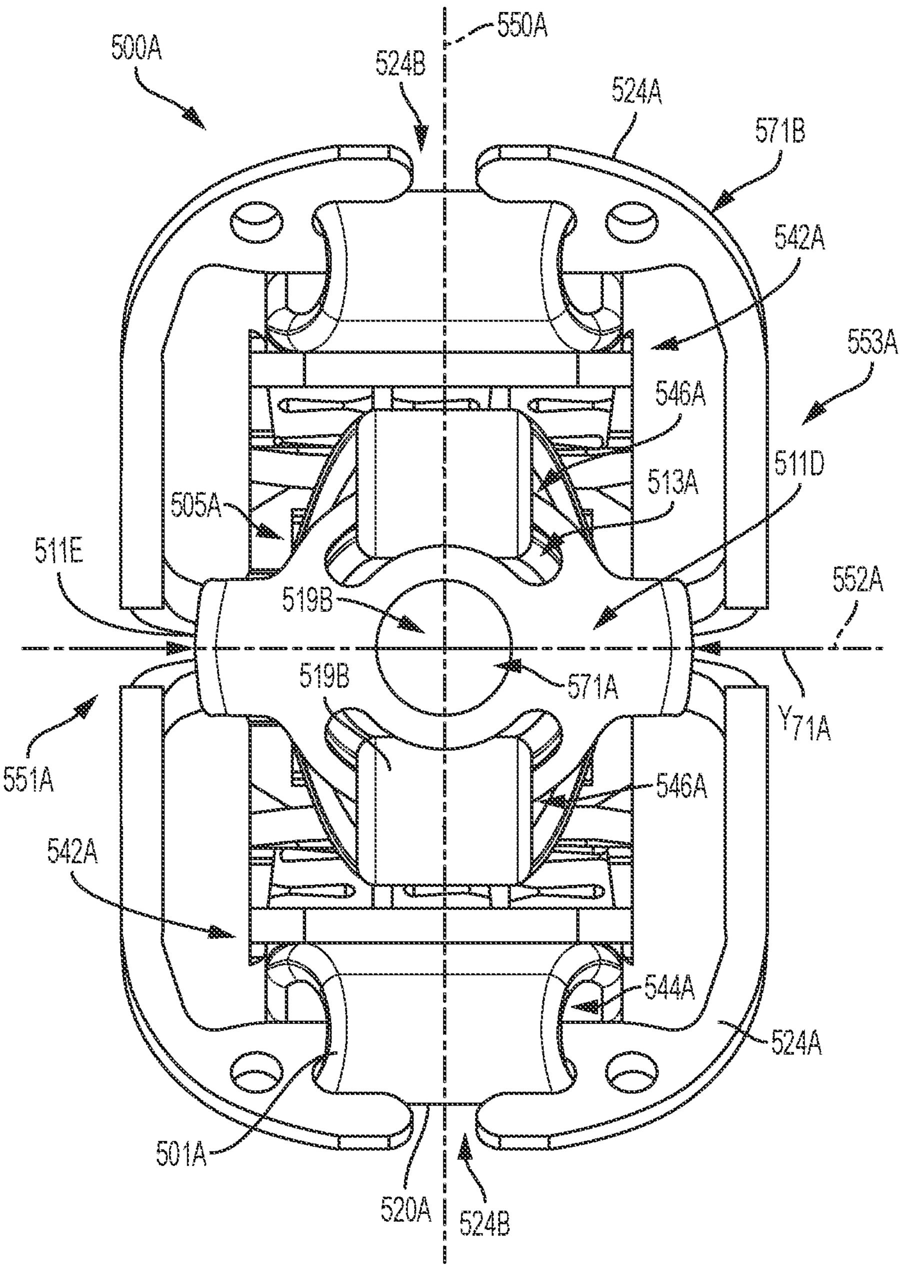
FIG. 54A shows a top view of the implantable prosthetic device of FIG. 48A with a collar component.

Referring now to FIGS. 53A and 54A, top views of the device 500A are shown. The device 500A has a shape that is symmetrical or substantially symmetrical around a front-to-back plane 550A and is also symmetrical or substantially symmetrical around a side-to-side plane 552A when viewed from the top. A proximal opening 519C in the coaption element 510A is visible at the proximal portion 505A of the device 500A. The actuation element 512A is received through the opening 519C so that the coaption element 510A wraps around the actuation element 512A. In some embodiments, the opening 519C is formed by inserting the actuation element 512A between the folded and overlapping layers of the strip of material 501A (described in detail below). In some embodiments, the opening 519C is formed by shape-setting the folded layers of the strip of material 501A forming the coaption element 510A around a blank or jig to give the coaption element 510A a rounded or generally rounded shape. The proximal collar 511D shown in FIG. 54A can be secured to the coaption element 510A to close off the coaption element 510A. The proximal collar 511D includes attachment portions 513A that engage with openings 546A formed by the folded layers of the strip of material 501A that form the coaption element 510A. In some embodiments, the attachment portions 513A are holes in the collar 511D so that the strip of material 501A must be inserted through the collar 511D before folding the strip of material 501A during assembly of the device 500A. In some embodiments, the attachment portions 513A are open slots (e.g., the attachment portions 524B of the paddle frames 524A) that receive the strip of material 501A before or after folding the strip of material 501A.

As is noted above, the coaption element 510A has a generally rectangular shape when viewed from the top. In some example embodiments, the coaption element 510A can have other shapes when viewed from the top. For example, the coaption element can have a round, square, diamond, elliptical, or any other shape. The paddle frames 224A each have a rounded rectangular shape when viewed from the top so that the paddle frames 224A surround the rectangular coaption element 510A. Thus, native tissue, such as the leaflets 20, 22 tend to be pinched or compressed evenly in the gaps 542A formed between the inner paddles 522A and paddle frames 524A and the coaption element 510A.

Figure 55A:
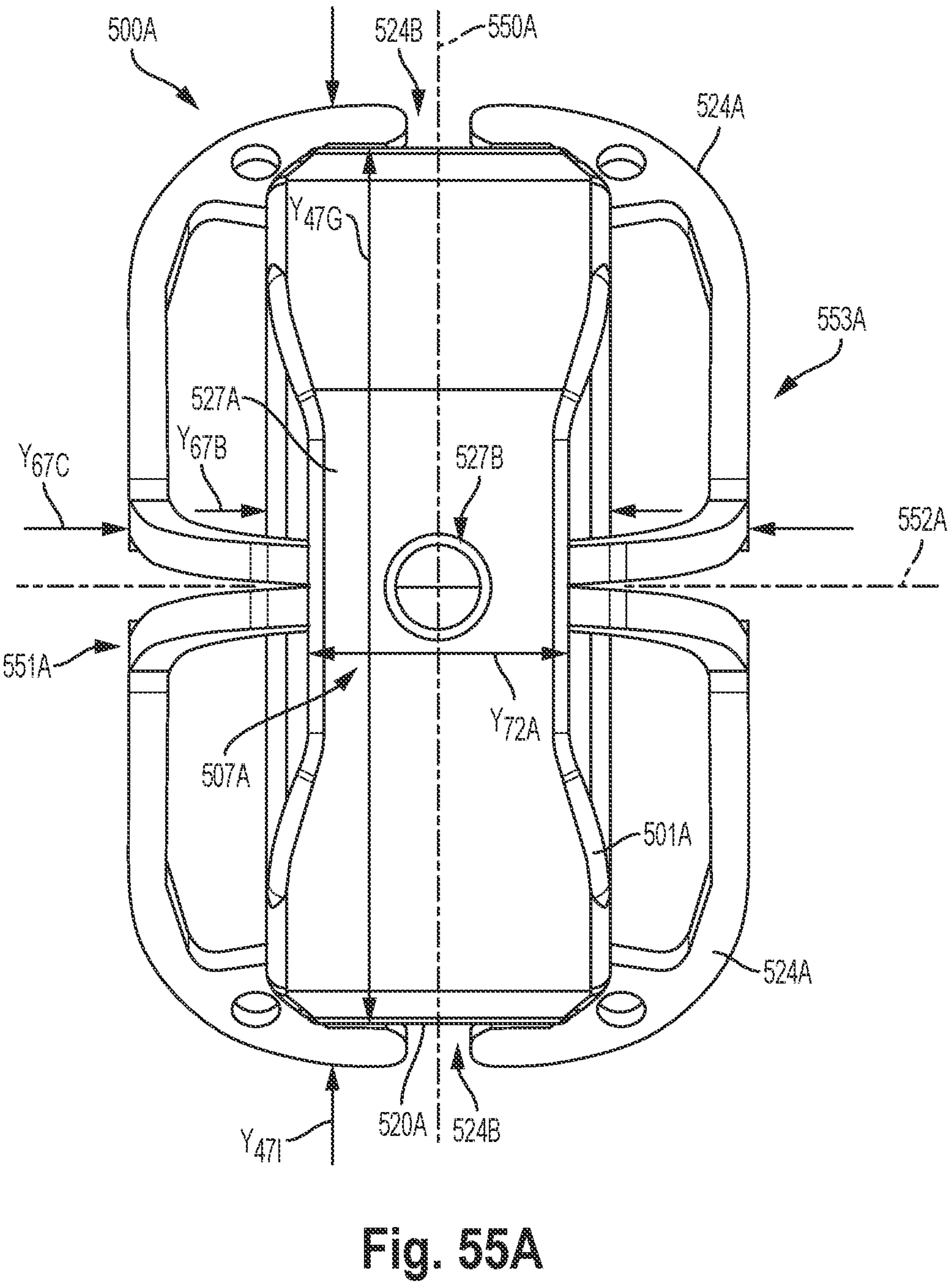
FIG. 55A shows a bottom view of the implantable prosthetic device of FIG. 48A.
Figure 56A:
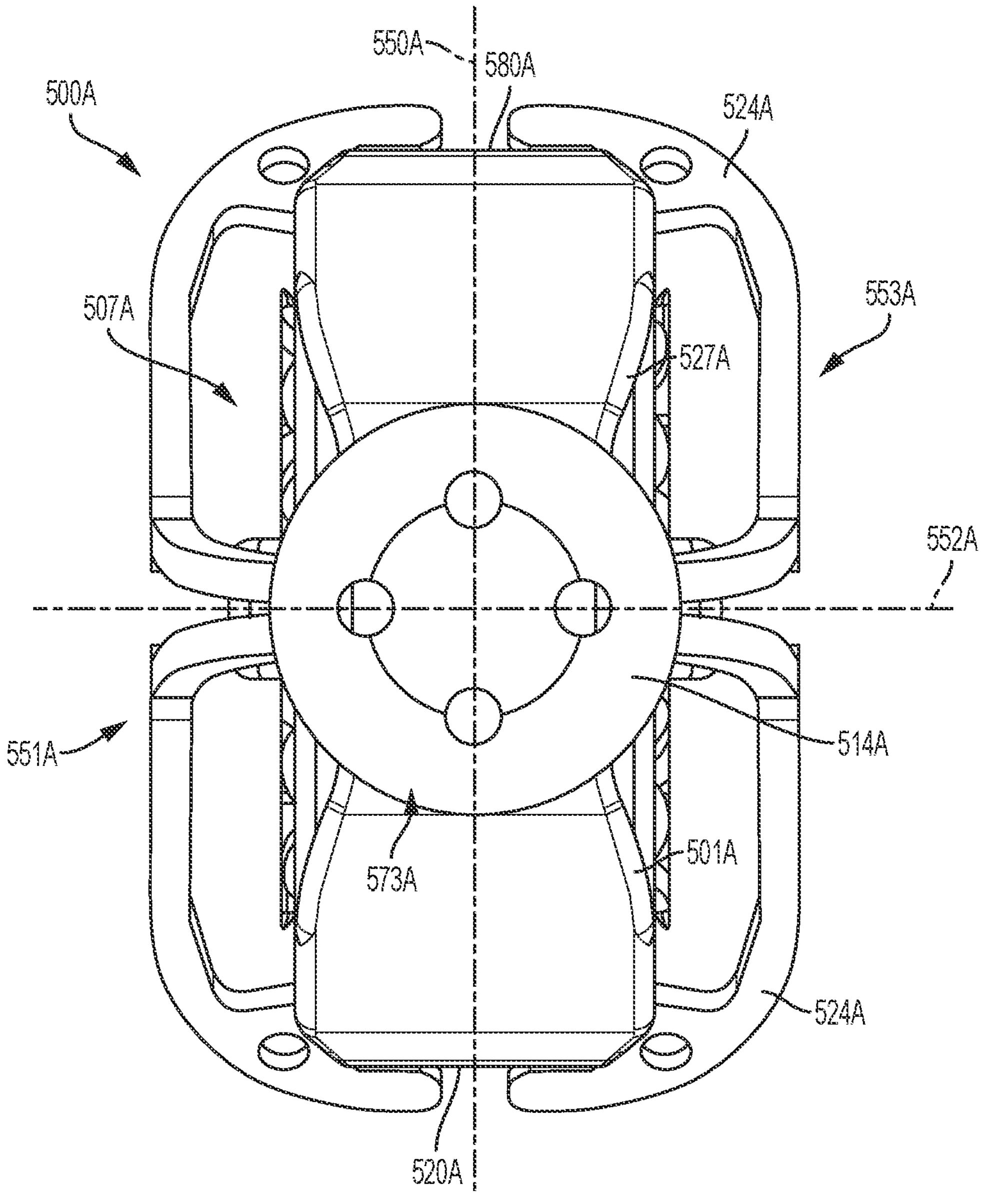
FIG. 56A shows a bottom view of the implantable prosthetic device of FIG. 48A with a cap component.

Referring now to FIGS. 55A and 56A, bottom views of the device 500A are shown. As with the top views (FIGS. 53A and 54A), the device 500A has a shape that is symmetrical or substantially symmetrical around the front-to-back plane 550A and is also symmetrical or substantially symmetrical around the side-to-side plane 552A when viewed from the bottom. A distal portion 527A of the strip of material 501A includes an aperture 527B for receiving the cap 514A shown in FIG. 56A.

The paddle frames 524A extend outward from the distal portion 507A of the device 500A to the left and right sides 551A, 553A at a narrow or slight angle from the side-to-side plane 552A. The paddle frames 524A extend further away from the side-to-side plane 552A while maintaining a generally constant distance relative to the front-to-back plane 550A as the paddle frames 524A extend toward the proximal portion 505A of the device 500A (FIG. 48A) to ultimately form the rounded rectangle shape seen in FIGS. 53A and 54A.

In one example embodiment, the dimensions of the device 500A are selected to minimize the number of implants that a single patient will require (preferably one), while at the same time maintaining low transvalvular gradients. In one example embodiment, the anterior-posterior distance Y47I of the device 500A at the widest is less than 10 mm, and the medial-lateral distance Y67C of the spacer at its widest is less than 6 mm. In one example embodiment, the overall geometry of the device 500A can be based on these two dimensions and the overall shape strategy described above. It should be readily apparent that the use of other anterior-posterior distance Y47I and medial-lateral distance Y67C as starting points for the device 500A will result in a device having different dimensions. Further, using other dimensions and the shape strategy described above will also result in a device having different dimensions.

Tables D and E provide examples of values and ranges for dimensions of the device 500A and components of the device 500A for some example embodiments. However, the device 500A can have a wide variety of different shapes and sizes and need not have all or any of the dimensional values or dimensional ranges provided in Tables D and E. Table D provides examples of linear dimensions Y in millimeters and ranges of linear dimensions in millimeters for the device 500A and components of the device 500A. Table B provides examples of radius dimensions S in millimeters and ranges of radius dimensions in millimeters for the device 500A and components of the device 500A. The subscripts for each of the dimensions indicates the drawing in which the dimension first appears.

TABLE D

| Linear Dimensions (mm) | | | | | | | | | |
|---|---|---|---|---|---|---|---|---|---|
| | | Range A | | Range B | | Range C | | Range D | |
| | Example | (max) | (min) | (max) | (min) | (max) | (min) | (max) | (min) |
| $Y_{47A}$ | 2.58 | 1.29 | 3.87 | 1.94 | 3.23 | 2.32 | 2.84 | 2.45 | 2.71 |
| $Y_{47B}$ | 1.43 | 0.72 | 2.15 | 1.07 | 1.79 | 1.29 | 1.57 | 1.36 | 1.50 |
| $Y_{47C}$ | 3.75 | 1.88 | 5.63 | 2.81 | 4.69 | 3.38 | 4.13 | 3.56 | 3.94 |
| $Y_{47D}$ | 0.35 | 0.18 | 0.53 | 0.26 | 0.44 | 0.32 | 0.39 | 0.33 | 0.37 |
| $Y_{47E}$ | 0.71 | 0.36 | 1.07 | 0.53 | 0.89 | 0.64 | 0.78 | 0.67 | 0.75 |
| $Y_{47F}$ | 1.07 | 0.54 | 1.61 | 0.80 | 1.34 | 0.96 | 1.18 | 1.02 | 1.12 |
| $Y_{47G}$ | 7.68 | 3.84 | 11.52 | 5.76 | 9.60 | 6.91 | 8.45 | 7.30 | 8.05 |
| $Y_{47H}$ | 5.41 | 2.71 | 8.12 | 4.06 | 6.76 | 4.87 | 5.95 | 5.14 | 5.68 |
| $Y_{47I}$ | 9.16 | 4.58 | 13.74 | 6.87 | 11.45 | 8.24 | 10.08 | 8.70 | 9.62 |
| $Y_{47J}$ | 0.72 | 0.36 | 1.08 | 0.54 | 0.90 | 0.65 | 0.79 | 0.68 | 0.75 |
| $Y_{67A}$ | 1.61 | 0.81 | 2.42 | 1.21 | 2.01 | 1.45 | 1.77 | 1.53 | 1.69 |
| $Y_{67B}$ | 3.25 | 1.63 | 4.88 | 2.44 | 4.06 | 2.93 | 3.58 | 3.09 | 3.41 |
| $Y_{67C}$ | 5.90 | 2.95 | 8.85 | 4.43 | 7.38 | 5.31 | 6.49 | 5.61 | 6.20 |
| $Y_{67D}$ | 15.21 | 7.60 | 22.81 | 11.41 | 19.01 | 13.69 | 16.73 | 14.45 | 15.97 |
| $Y_{67E}$ | 3.25 | 1.63 | 4.88 | 2.44 | 4.06 | 2.93 | 3.58 | 3.09 | 3.41 |
| $Y_{68A}$ | 14.04 | 7.02 | 21.06 | 10.53 | 17.55 | 12.64 | 15.44 | 13.34 | 14.74 |
| $Y_{73A}$ | 4.50 | 2.25 | 6.75 | 3.38 | 5.63 | 4.02 | 4.95 | 4.28 | 4.73 |
| $Y_{72A}$ | 2.50 | 1.25 | 3.75 | 1.88 | 3.13 | 2.25 | 2.75 | 2.38 | 2.63 |
| $Y_{114A}$ | 4.34 | 2.17 | 6.50 | 3.25 | 5.42 | 3.90 | 4.77 | 4.12 | 4.55 |
| $Y_{114B}$ | 13.28 | 6.64 | 19.92 | 9.96 | 16.60 | 11.95 | 14.61 | 12.62 | 13.94 |
| $Y_{116A}$ | 14.79 | 7.39 | 22.18 | 11.0 | 18.48 | 13.31 | 16.27 | 14.05 | 15.53 |

TABLE E

| Radius Dimensions (mm) | | | | | | | | | |
|---|---|---|---|---|---|---|---|---|---|
| | | Range A | | Range B | | Range C | | Range D | |
| | Example | (max) | (min) | (max) | (min) | (max) | (min) | (max) | (min) |
| $S_{47A}$ | 0.74 | 0.37 | 1.11 | 0.56 | 0.93 | 0.67 | 0.81 | 0.70 | 0.78 |
| $S_{47B}$ | 0.68 | 0.34 | 1.02 | 0.51 | 0.85 | 0.61 | 0.75 | 0.65 | 0.71 |
| $S_{47C}$ | 1.10 | 0.55 | 1.65 | 0.83 | 1.38 | 0.99 | 1.21 | 1.05 | 1.16 |
| $S_{47D}$ | 5.62 | 2.81 | 8.43 | 4.22 | 7.03 | 5.06 | 6.18 | 5.34 | 5.90 |
| $S_{47E}$ | 0.96 | 0.48 | 1.44 | 0.72 | 1.20 | 0.86 | 1.06 | 0.91 | 1.01 |
| $S_{71A}$ | 0.63 | 0.31 | 0.94 | 0.47 | 0.78 | 0.56 | 0.69 | 0.59 | 0.66 |
| $S_{71B}$ | 2.07 | 1.04 | 3.11 | 1.55 | 2.59 | 1.86 | 2.28 | 1.97 | 2.17 |
| $S_{73A}$ | 1.88 | 0.94 | 2.81 | 1.41 | 2.34 | 1.69 | 2.06 | 1.78 | 1.97 |
| $S_{114A}$ | 5.62 | 2.81 | 8.43 | 4.22 | 7.03 | 5.06 | 6.18 | 5.34 | 5.90 |
| $S_{114B}$ | 6.00 | 3.00 | 9.00 | 4.50 | 7.50 | 5.40 | 6.60 | 5.70 | 6.30 |
| $S_{114C}$ | 3.15 | 1.58 | 4.73 | 2.36 | 3.94 | 2.84 | 3.47 | 2.99 | 3.31 |
| $S_{117A}$ | 1.15 | 0.58 | 1.73 | 0.86 | 1.44 | 1.04 | 1.27 | 1.09 | 1.21 |
| $S_{117B}$ | 2.69 | 1.35 | 4.04 | 2.02 | 3.36 | 2.42 | 2.96 | 2.56 | 2.82 |

Referring now to FIGS. 57A, 58A, 59A, 60A, 61A, 62A, 63A, 64A, 65A, and 66A, perspective and cross-sectional views of the device 500A are shown. Referring now to FIG. 74A, the device 500A is shown sliced by cross-section plane 75A near the proximal portion of the coaption element 510A. Referring now to FIG. 58A, a cross-sectional view of the device 500A is shown as viewed from cross-section plane 75A in FIG. 57A. At the location of the plane 75A, the coaption element 510A has a generally rounded rectangular shape. The gaps 542A between the inner paddles 522A and coaption element 510A have a width 542B. As noted above, the gaps 542A have a consistent or generally consistent width.

Referring now to FIG. 59A, the device 500A is shown sliced by cross-section plane 77A positioned about three-quarters of the way between the distal portion 507A and the proximal portion 505A of the coaption element 510A. Referring now to FIG. 60A, a cross-sectional view of the device 500A is shown as viewed from cross-section plane 77A in FIG. 59A. As can be seen in FIGS. 59A and 60A, the strip of material 501A forming the device 500A is overlapped to form four layers in the area of the coaption element 510A. A single layer of the strip of material 501A forms each of the inner paddle 522A and the outer paddle 520A. At the location of the plane 75A, the coaption element 510A has a generally rectangular shape oriented along the side-to-side plane 552A. The gaps 542A between the inner paddle 522A and the coaption element 510A are visible. The gaps 542A between the inner paddles 522A and coaption element 510A have a width 542B that is greater than the width 542B seen in FIG. 58A. The gaps 544A between the outer and inner paddles 520A, 522A have a consistent or generally consistent width 544B for receiving the attachment portion 524B of the paddle frames 524A.

Referring now to FIG. 61A, the device 500A is shown sliced by cross-section plane 79A positioned about half of the way between the distal portion 507A and the proximal portion 505A of the device 500A. Referring now to FIG. 62A, a cross-sectional view of the device 500A is shown as viewed from cross-section plane 79A in FIG. 61A. As can be seen in FIGS. 61A and 62A, the strip of material 501A forming the device 500A is overlapped to form four layers in the area of the coaption element 510A, two layers in the area of the inner paddle 522A, and one layer in the area of the outer paddle 520A. At the location of the plane 79A, the coaption element 510A has a generally rectangular shape oriented along the side-to-side plane 552A. The gaps 542A between the inner paddles 522A and the coaption element 510A have a width 542B that is the same or about the same as the width 542B seen in FIG. 60A.

Referring now to FIG. 63A, the device 500A is shown sliced by cross-section plane 81A positioned about one-quarter of the way between the distal portion 507A and the proximal portion 505A of the device 500A. Referring now to FIG. 64A, a cross-sectional view of the device 500A is shown as viewed from cross-section plane 81A in FIG. 63A. As can be seen in FIGS. 63A and 64A, the strip of material 501A forming the device 500A is overlapped to form four layers in the area of the coaption element 510A, two layers in the area of the inner paddle 522A, and the outer paddle 520A is formed by a single layer. At the location of the plane 81A, the coaption element 510A has a generally rectangular shape oriented along the side-to-side plane 552A. The gaps 542A between the inner paddle 522A and coaption element 510A have a width 542B that is about the same as the central width 542B seen in FIG. 62A.

Referring now to FIG. 65A, the device 500A is shown sliced by cross-section plane 83A positioned about one-quarter of the way between the distal portion 507A and the proximal portion 505A of the device 500A. Referring now to FIG. 66A, a cross-sectional view of the device 500A is shown as viewed from cross-section plane 83A in FIG. 65A. As can be seen in FIGS. 65A and 66A, the strip of material 501A forming the device 500A is overlapped to form four layers in the area of the coaption element 510A, two layers in the area of the inner paddle 522A, and a single layer forms the outer paddle 520A. At the location of the plane 83A, the coaption element 510A has a generally rectangular shape oriented along the side-to-side plane 552A. The gaps 542A between the inner paddles 522A and coaption element 510A form an arcuate shape with a width 542B that is about the same as the central width 542B seen in FIG. 64A.

In some embodiments, portions of the device 500A are formed by the strip of material 501A (e.g., a single, continuous strip of material, a composite strip of material, etc.), such as the coaption element 510A and paddles 520A, 522A. The coaption element 510A and the paddles can be made from a wide variety of different materials. The coaption element 510A, and paddles 520A, 522A can be formed from a material that can be a metal fabric, such as a mesh, woven, braided, electrospun, deposited or formed in any other suitable way, laser cut, or otherwise cut material or flexible material. The material can be cloth, shape-memory alloy wire—such as Nitinol—to provide shape-setting capability, or any other flexible material suitable for implantation in the human body.

In one example embodiment, the coaption element 510A, inner paddle 522A, and outer paddle 520A are made from a single, continuous strip of material 501A. The strip of material 501A can be formed from a material that can be a metal fabric, such as a mesh, woven, braided, electrospun, deposited or formed in any other suitable way, laser cut, or otherwise cut material or flexible material. The material can be cloth, shape-memory alloy wire—such as Nitinol—to provide shape-setting capability, or any other flexible material suitable for implantation in the human body. In one example embodiment, the strip of material 501A is made of a braided mesh of between 25 and 100 strands, such as between 40 and 85 strands, such as between 45 and 60 strands, such as about 48 Nitinol wires or 50 Nitinol wires.

As is discussed in the present disclosure, the coaption element 510A of the device 500A can be formed from four layers of material, such as the material 4000. When layers of the material 4000 are used to form the coaption element 510A, the actuation element 512A of the device 500A can be inserted through the middle gap 4001B formed in the center of the four layers of material 4000. The actuation element 512A can have a larger diameter than the width of the gap 4001B, so that inserting the actuation element 512A causes the middle gap 4001B to stretch open and adjacent outer gaps 4001A, 4001C to reduce in size. In some embodiments, inserting the actuation element 512A causes the center body portions 4006 on either side to bulge outward to a thickness that is greater than the thickness of the four stacked edge portions 4002, 4004.

The coaption element 510A and paddle portions 520A, 522A can be covered in a cloth, such as a polyethylene cloth. The coaption element 510A and paddles 520A, 522A can be surrounded in their entirety with a cloth cover (e.g., cover 540A), such as a polyethylene cloth of a fine mesh. The cloth cover can provide a blood seal on the surface of the spacer, and/or promote rapid tissue ingrowth.

The use of a shape memory material, such as braided Nitinol wire mesh, for the construction of the coaption element 510A and paddles 520A, 522A results in a coaption element and paddles that can be self-expandable, flexible in all directions, and/or results in low strains when crimped and/or bent. The material can be a single piece, two halves joined together, or a plurality of sections or pieces that are fastened or joined together in any suitable manner, such as, by welding, with adhesives, or the like.

In some embodiments, the device 500A extends from a proximal portion 505A to a distal portion 507A and includes a coaption element 510A, inner paddles 522A, and outer paddles 520A. The single, continuous strip of material 501A extends between two ends 501B and is folded to form the coaption element 510A, inner paddles 522A, and outer paddles 520A. Some portions of the device 500A are formed from multiple layers of the strip of material 501A. For example, the strip of material 501A is overlapped to form four layers in the area of the coaption element 510A and two layers in the area of the inner paddle 522A.

The coaption element 510A and paddles 520A, 522A are connected (e.g., jointably connected, etc.) together, e.g., by joint portions of the strip of material 501A. The coaption element 510A is connected (e.g., jointably connected, etc.) to the inner paddles 522A, e.g., by joint portions 525A. The inner paddles 522A are connected (e.g., jointably connected, etc.) to the outer paddles 520A, e.g., by joint portions 523A. The outer paddles 520A are attached (e.g., jointably attached, etc.) to the distal portion 527A, e.g., by joint portions 521A. The aperture 527B in the distal portion 527A engages the cap 514A.

Various gaps are formed between portions of the device 500A when the strip of material 501A is folded into the desired shape. In some embodiments, coaption gaps 542A are formed between the inner paddles 522A and the coaption element 510A. Paddle gaps 544A are formed between the inner and outer paddles 520A, 522A when the paddles 520A, 522A are folded. Collar gaps 546A are formed when the strip of material 501A is folded to form the proximal portions 519B of the coaption element 510A.

Referring now to FIGS. 67-83, an example paddle frame 1400 for an implantable prosthetic device is shown. The paddle frame 1400 can be used with any of the implantable prosthetic devices described in the present application. The paddle frame 1400 is formed from a piece of material 1402, such as nitinol, or any other suitable material. The paddle frame 1400 extends from a cap attachment portion 1410 to a paddle connection portion 1420 and has a proximal portion 1422, a middle portion 1424, and a distal portion 1426. In some embodiments, the paddle frame 1400 includes attachment portions 1440 for securing a cover (see FIG. 30), the inner paddle portion 522, and/or the outer paddle portion 520 to the paddle frame 1400. Any of the covers and associated techniques described herein can be used and/or adapted to cover paddle frame 1400 and/or other portions of a device including paddle frame 1400. In some embodiments, the paddle frame 1400 is thinner in the location of the fifth curve 1438 to facilitate bending of both sides of the paddle frame 1400 toward the center plane 1404 during, for example, crimping of the device.

The paddle frame 1400 extends from a first attachment portion 1412 in a rounded, three-dimensional shape through the proximal, middle, and distal portions 1422, 1424, 1426 and returns to a second attachment portion 1414. To form a rounded three-dimensional shape, the paddle frame 1400 is bent or curved in multiple locations as the paddle frame 1400 extends between the first and second attachment portions 1412, 1414. The attachment portions 1412, 1414 include notches 1416, 1418 respectively for attachment to the cap. The paddle frame 1400 flexes at the area 1419. The area 1419 can include a wider portion 1417 to distribute the stress that results from flexing the paddle frame 1400 over a greater area. Also, notches 1416, 1418 can include radiused notches 1415 at each end of the notches. The radiused notches 1415 serve as strain reliefs for the bending area 1419 and the area where the paddle frame 1400 connects to the cap.

Figure 71:
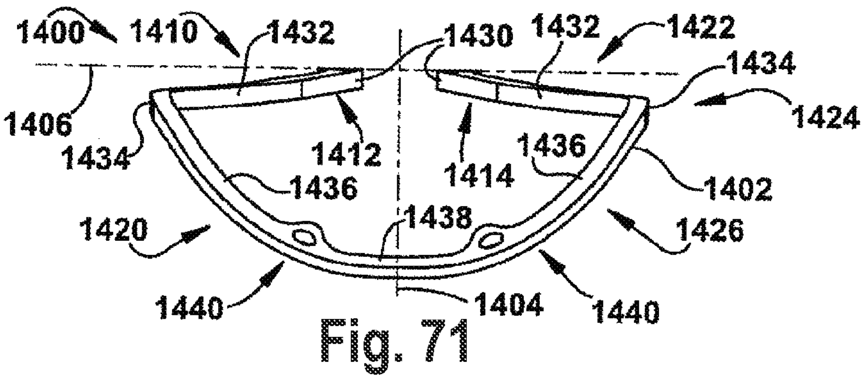
FIG. 71 shows a top view of the paddle frame of FIGS. 67-69.
Figure 72:
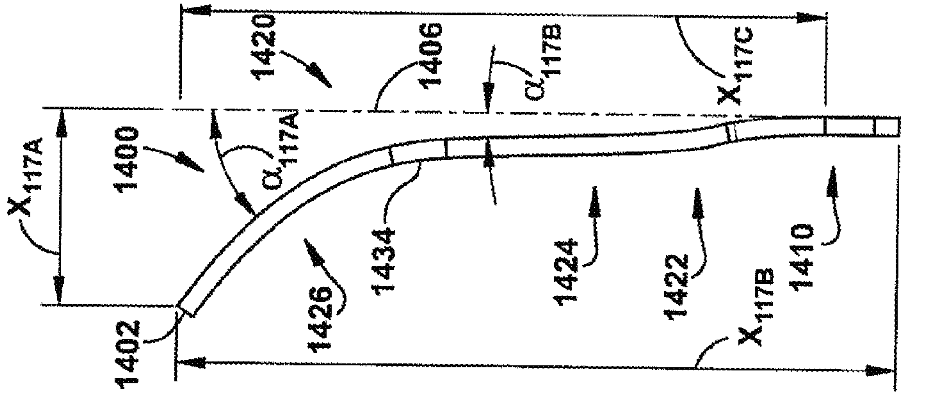
FIG. 72 shows a side view of the paddle frame of FIGS. 67-69.
Figure 73:
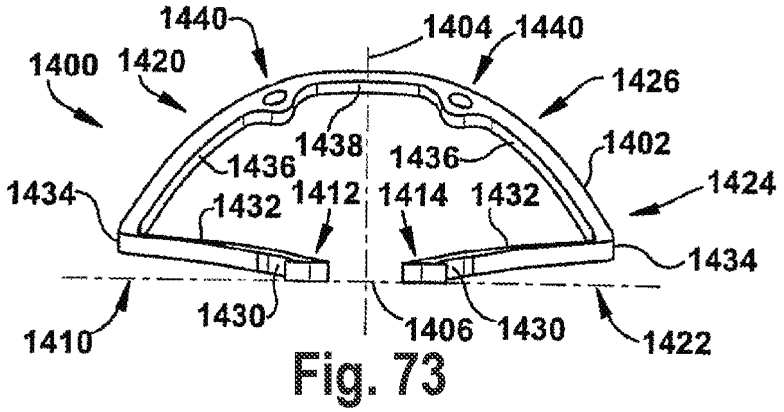
FIG. 73 shows a bottom view of the paddle frame of FIGS. 67-69.
Figure 73A:
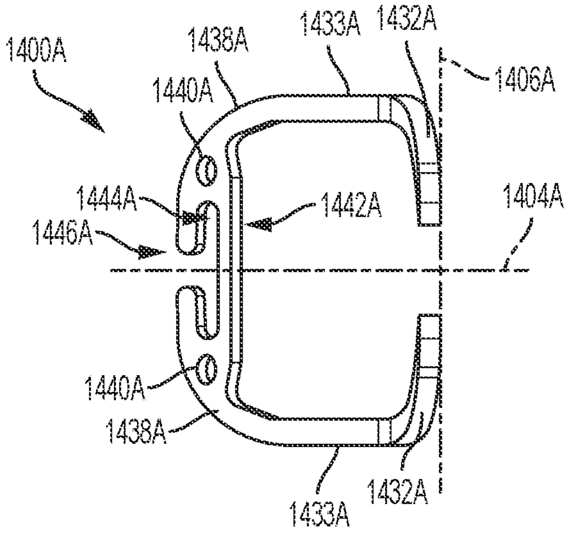
FIG. 73A shows a bottom view of the paddle frame of FIG. 67A.

The paddle frame 1400 curves away from a median or central plane 1404 (FIG. 70) at a first curve 1430 to widen the shape of the paddle frame 1400. As can be seen in FIG. 72, the paddle frame 1400 also curves away from a frontal plane 1406 in the location of the first curve 1430. The paddle frame 1400 curves away from the outward direction of the first curve 1430 at a second curve 1432 to form sides of the frame 1400. The paddle frame continues to slope away from the frontal plane 1406 in the location of the second curve 1432. In some embodiments, the second curve 1432 has a larger radius than the first curve 1430. The paddle frame 1400 curves away from the frontal plane 1406 at a third curve 1434 as the paddle frame 1400 continues to curve in the arc of the second curve 1432 when viewed from the frontal plane 1406. This curvature at the third curve 1434 results in a gradual departure of the frame 1400, and thus the native valve leaflet from the centerline 1406. This departure from the centerline results in spreading of the leaflet tissue toward the valve annulus, which can result in less stress on the leaflet tissue. The paddle frame 1400 curves toward the lateral plane 1404 at a fourth curve 1436 as the frame 1400 continues to curve away from the frontal plane 1406. The rounded three-dimensional shape of the paddle frame 1400 is closed with a fifth curve 1438 that joins both sides of the paddle frame 1400. As can be seen in FIGS. 71 and 73, the paddle frame 1400 has an arcuate or generally arcuate shape as the frame 1400 extends away from the attachment portion 1420 and to the closed portion 1424. The middle portion 1424 of the frame is closer to the frontal plane 1406 than the closed portion 1424, giving the sides of the middle portion 1424 a rounded, wing-like shape that engages the curved surface of coaption element (not shown) during grasping of native tissue between a paddle (not shown) and coaption element of an implantable device of the present invention.

Figure 84:
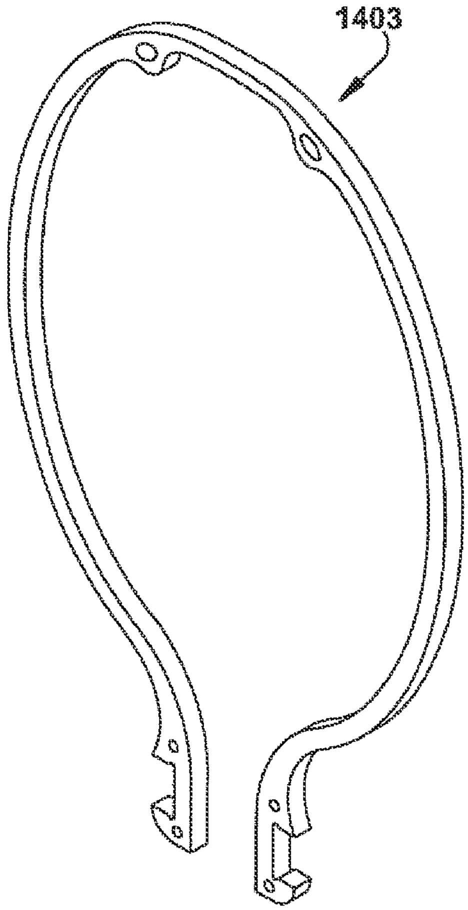
FIG. 84 is a perspective view of a blank used to make a paddle frame.
Figure 85:
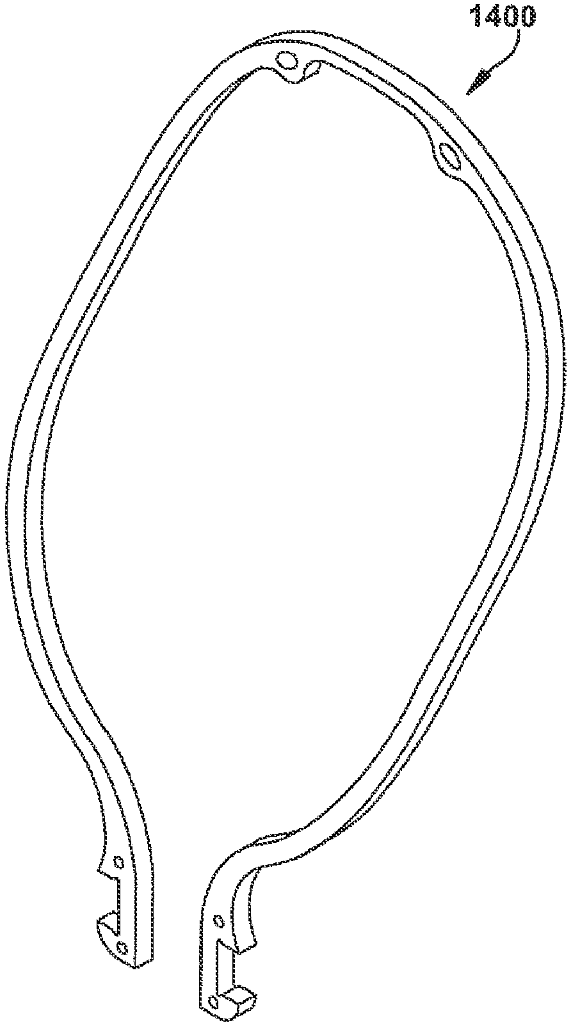
FIG. 85 is a perspective view of the blank of FIG. 84 bent to make a paddle frame.

Referring to FIG. 84, in an example embodiment, a flat blank 1403 of paddle frame 1400 can be cut, for example laser cut, from a flat sheet of material. Referring to FIG. 85, the cut blank 1403 can then be bent to form the three-dimensional shaped paddle frame 1400.

Figure 86:
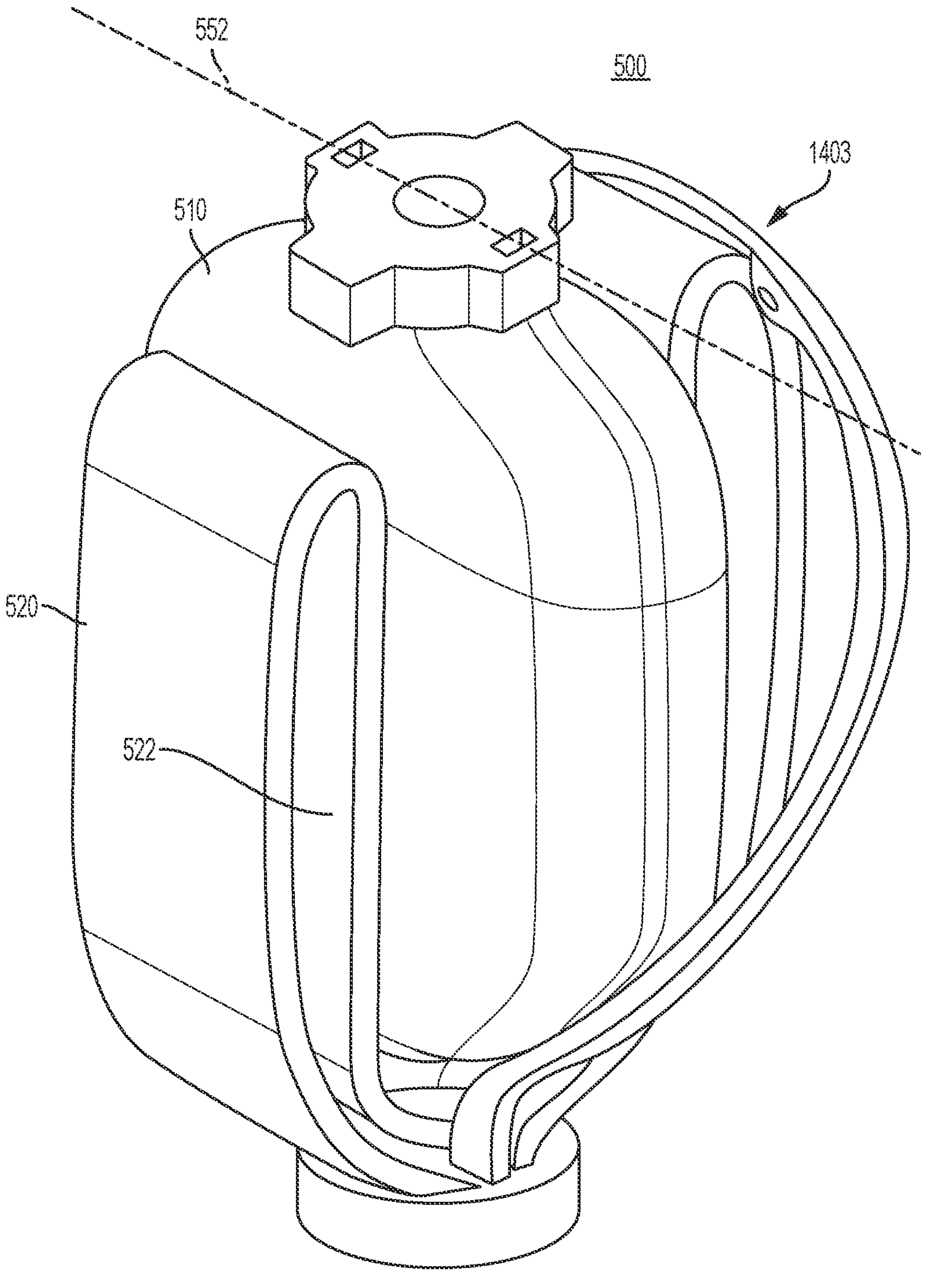
FIG. 86 is a perspective view of a shape-set paddle frame attached to a cap of a valve repair device.
Figure 87:
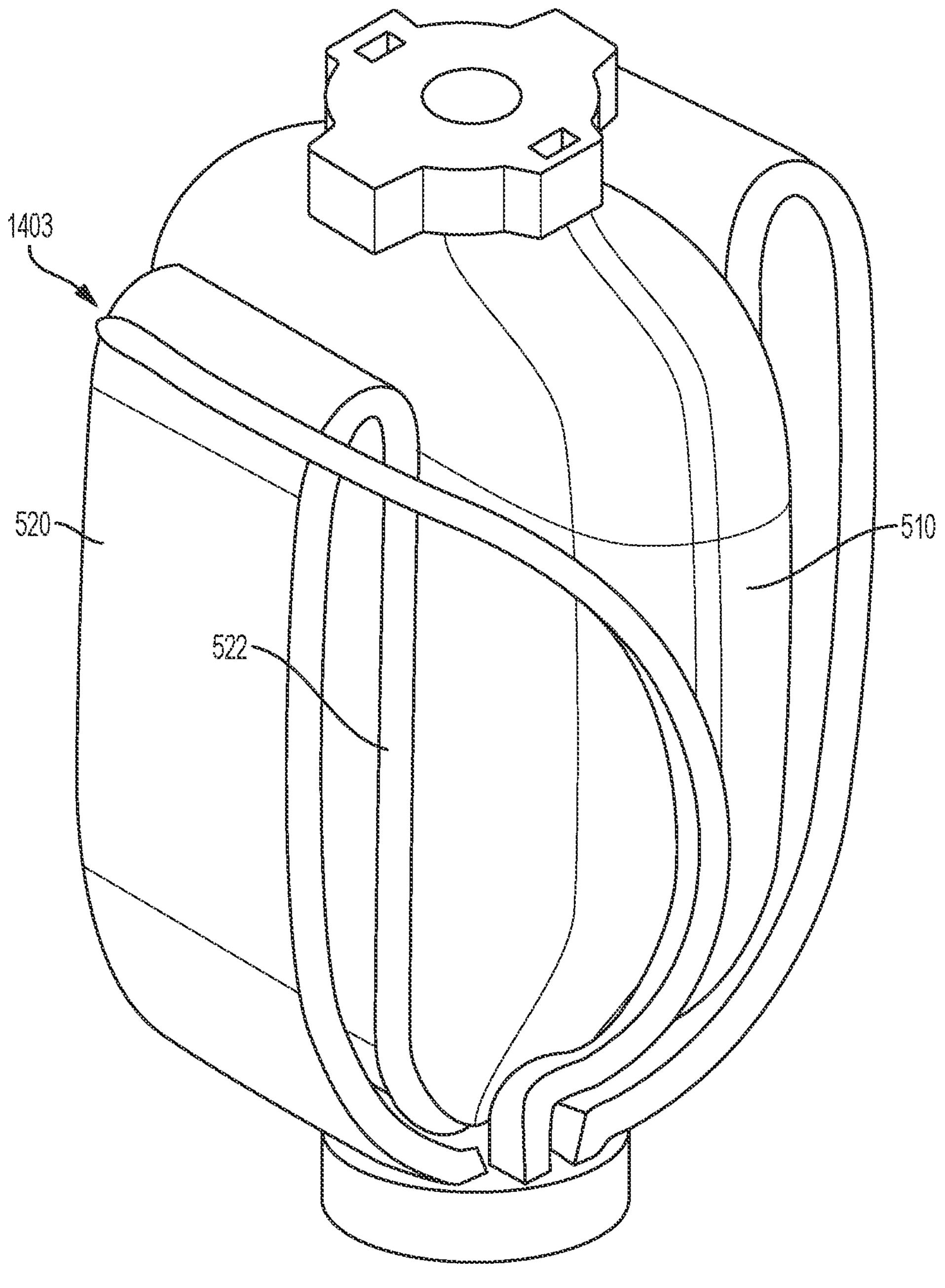
FIG. 87 is a perspective view of the paddle frame of FIG. 86 flexed and attached to inner and outer paddles at a closed position.

Referring to FIGS. 86 and 87, in one example embodiment, the paddle frames 1400 can be shape-set to provide increased clamping force against or toward the coaption element 510 when the paddles 520, 522 are in the closed configuration. This is because the paddle frames are shape-set relative to the closed position (e.g. FIG. 87) to a first position (e.g., FIG. 86) which is beyond the position where the inner paddle 522 would engage the coaption element, such as beyond the central plane 552 of the device 500, such as beyond the opposite side of the coaption element, such as beyond the outer paddle on the opposite side of the coaption element. Referring to FIG. 87, the paddle frame 1400 is flexed and attached to the inner and outer paddles 522, 520, for example by stitching. This results in the paddle frames having a preload (i.e., the clamping force against or toward the coaption element is greater than zero) when the paddle frames 1400 are in the closed configuration. Thus, shape-setting the paddle frames 1400 in the FIG. 86 configuration can increase the clamping force of the paddle frames 1400 compared to paddle frames that are shape-set in the closed configuration (FIG. 87).

The magnitude of the preload of the paddle frames 1400 can be altered by adjusting the degree to which the paddle frames 1400 are shape-set relative to the coaption element 510. The farther the paddle frames 1400 are shape-set past the closed position, the greater the preload.

The curves of the paddle frame 1400 can be independent from one another, that is, one curve is complete before another curve starts, or can be combined, that is, the paddle frame 1400 curves in multiple directions simultaneously.

Referring now to FIGS. 67A, 69A, 70A, 71A, 72A, and 73A, example paddle frames 1400A for an implantable prosthetic device are shown. The paddle frames 1400A can be used with any of the implantable prosthetic devices described in the present application. Each paddle frame 1400A is formed from a piece of material 1402A, such as nitinol, or any other suitable material. Each paddle frame 1400A extends from a cap attachment portion 1410A to a paddle connection portion 1420A and has a proximal portion 1422A, a middle portion 1424A, and a distal portion 1426A. Any of the covers and associated techniques described herein can be used and/or adapted to cover paddle frame 1400A and/or other portions of a device including paddle frame 1400A.

Each paddle frame 1400A extends from a first attachment portion 1412A in a rounded, three-dimensional shape through the proximal, middle, and distal portions 1422, 1424, 1426 and returns to a second attachment portion 1414. To form a rounded three-dimensional shape, each paddle frame 1400A is bent or curved in multiple locations as the paddle frame 1400A extends from the first and second attachment portions 1412A, 1414A. The attachment portions 1412A, 1414A include notches 1416A, 1418A respectively for attachment to the cap. The paddle frames 1400A flex at the area 1419A. The area 1419A can include a wider portion 1417A to distribute the stress that results from flexing the paddle frame 1400A over a greater area. Also, notches 1416A, 1418A can include radiused notches 1415A at each end of the notches 1416A, 1418A. The radiused notches 1415A serve as strain reliefs for the bending area 1419A and the area where the paddle frame 1400A connects to the cap.

Figure 69:
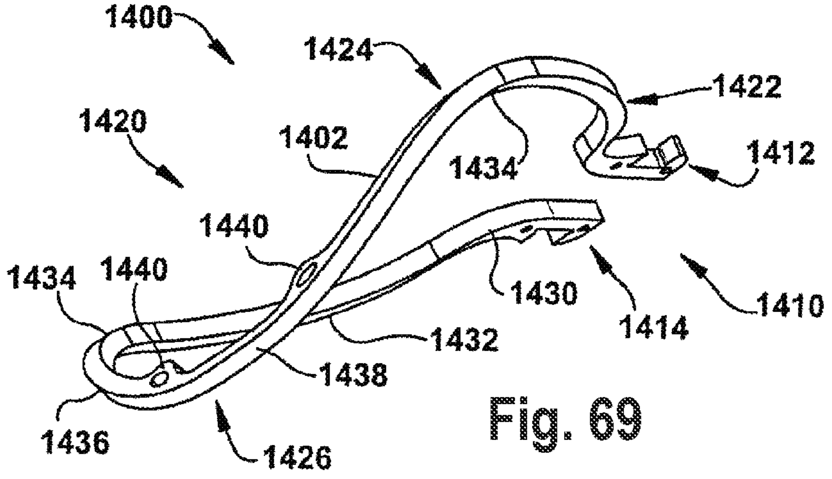
Figure 69A:
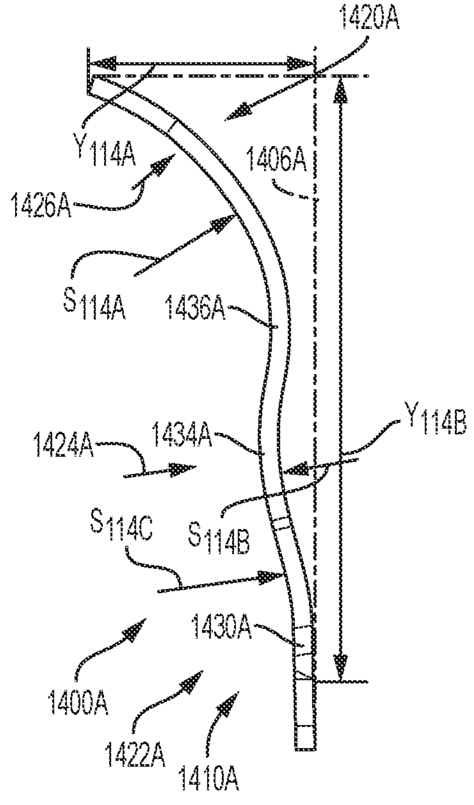
FIG. 69A shows a side view of the paddle frame of FIG. 67A.
Figure 70:
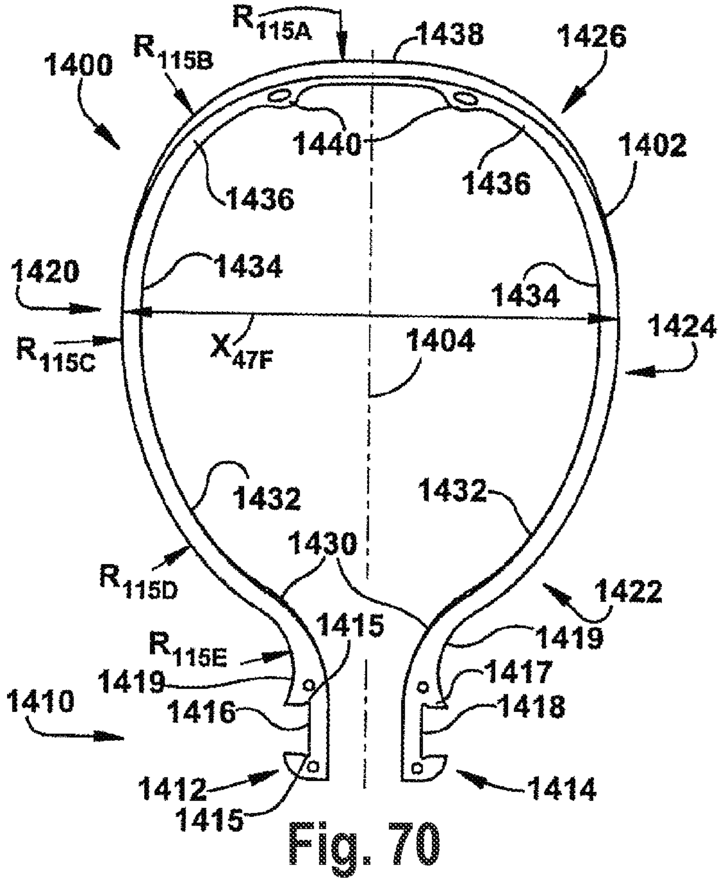
FIG. 70 shows a front view of the paddle frame of FIGS. 67-69.
Figure 70A:
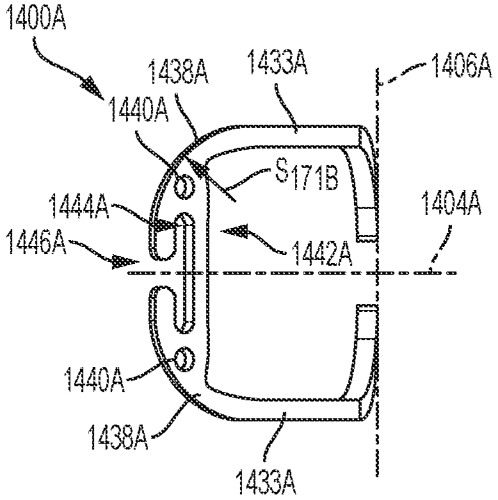
FIG. 70A shows a top view of the paddle frame of FIG. 67A.

Each paddle frame 1400A curves away from a median or central plane 1404A (FIG. 71A) at a first curve 1430A to widen the shape of the paddle frame 1400A. As can be seen in FIG. 69A, the paddle frame 1400A also curves away from a frontal plane 1406A in the location of the first curve 1430A. The paddle frame 1400A curves away from the outward direction of the first curve 1430A at a second curve 1432A to form sides 1433A of the frame 1400A that are parallel or substantially parallel to the central plane 1404A when viewed from the frontal plane 1406A. The paddle frame continues to slope away from the frontal plane 1406A in the location of the second curve 1432A. In some embodiments, the second curve 1432A has a larger radius than the first curve 1430A. The paddle frame 1400A curves back toward the frontal plane 1406A at a third curve 1434A in the middle portion 1424A while the sides 1433A of the paddle frame 1400A remain parallel or substantially parallel to the central plane 1404A. The paddle frame 1400A curves away from the central plane 1404A a second time at a fourth curve 1436A and continues to curve away from the central plane 1404A through the remainder of the middle and distal portions 1424A, 1426A. The rounded three-dimensional shape of the paddle frame 1400A is closed by an end portion 1442A connected to the sides 1433A by fifth curves 1438A that form rounded corners of the distal end 1426A of the paddle frame 1400A.

The end portion 1442A can be wider than the remainder of the paddle frame 1400A to accommodate features that allow the paddle frames 1400A to be attached to the paddles (not shown) and cover (not shown). For example, the end portion 1442A can include a slot 1444A for receiving a portion of a strip of material, such as the strip of material 401A, 501A described above. An opening 1446A in the end portion 1442A allows a strip of material to be inserted into the slot 1444A. The end portion 1442A can also include attachment holes 1440A for securing a cover (see FIG. 30A) to the paddle frame 1400A.

Figure 71A:
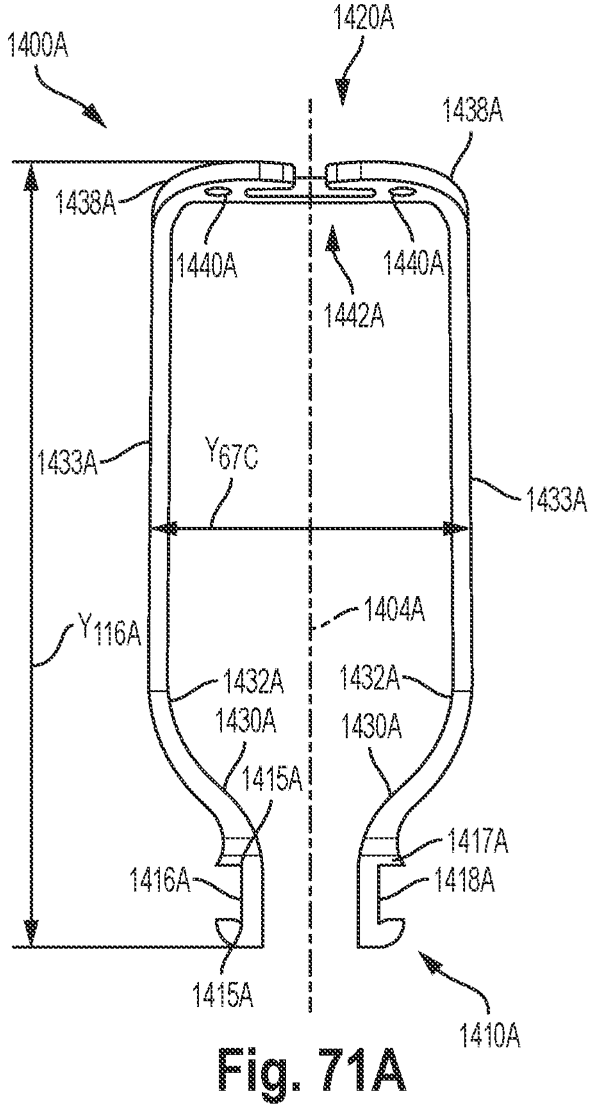
FIG. 71A shows a front view of the paddle frame of FIG. 67A.
Figure 72A:
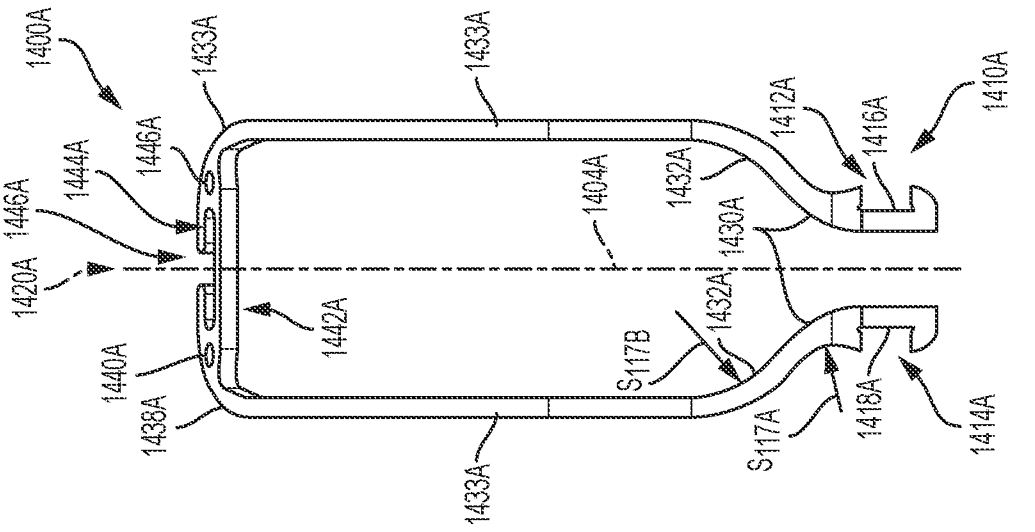
FIG. 72A shows a rear view of the paddle frame of FIG. 67A.

As can be seen in FIGS. 71A and 72A, the paddle frame 1400A has a generally rounded rectangle shape as the frame extends away from the attachment portion 1410A to the closed end of the paddle connection portion 1420A. The middle portion 1424A of the frame is closer to the frontal plane 1406A than the distal portion 1426A, giving the sides of the middle portion 1424A a rounded, wing-like shape that engages the front and back surfaces of the coaption element (not shown) during grasping of native tissue between a paddle (not shown) and coaption element of an implantable device described herein.

Figure 88:
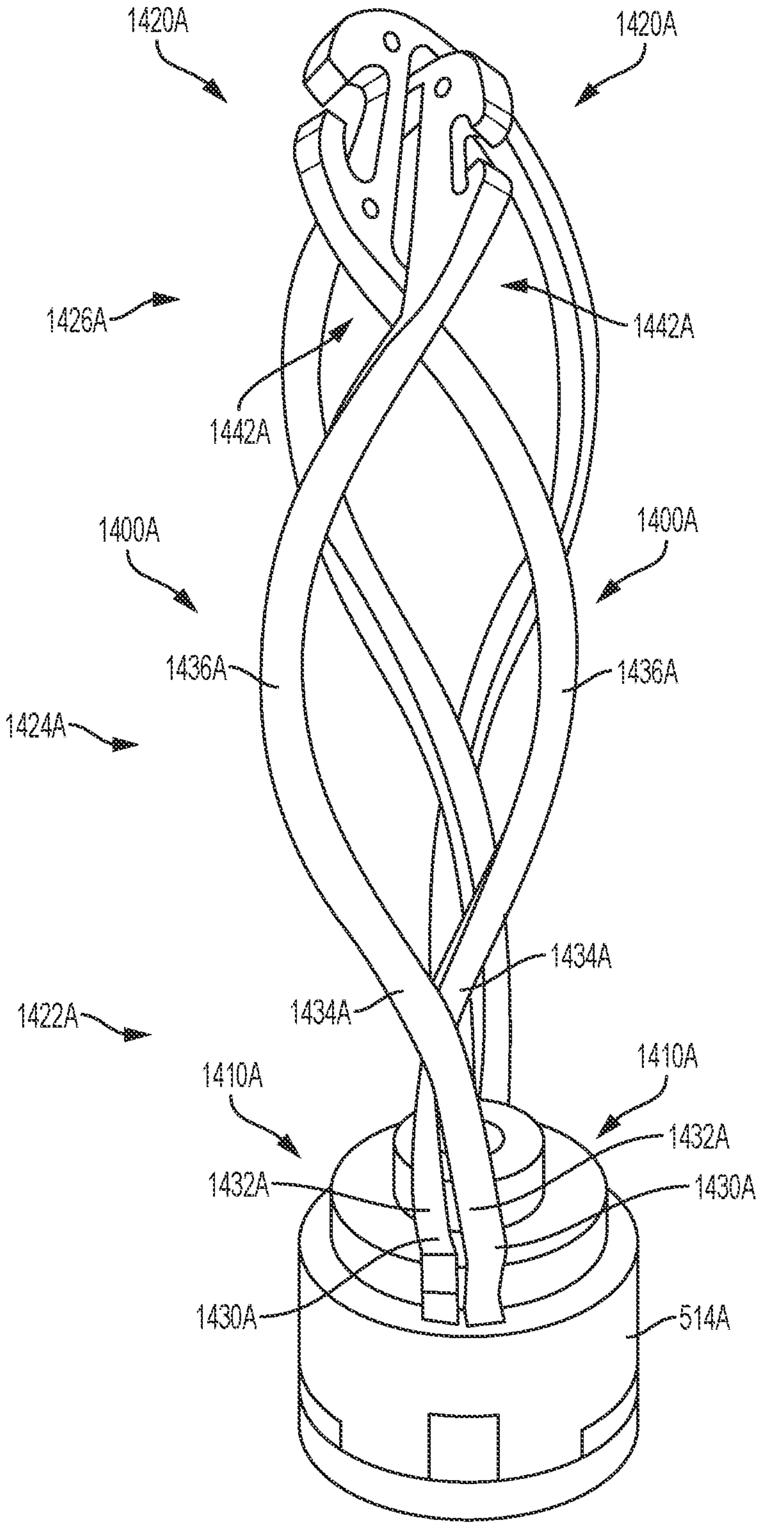
FIG. 88 is a perspective view of two of the paddle frames of FIG. 67A showing the paddle frames in a shape-set position.
Figure 89:
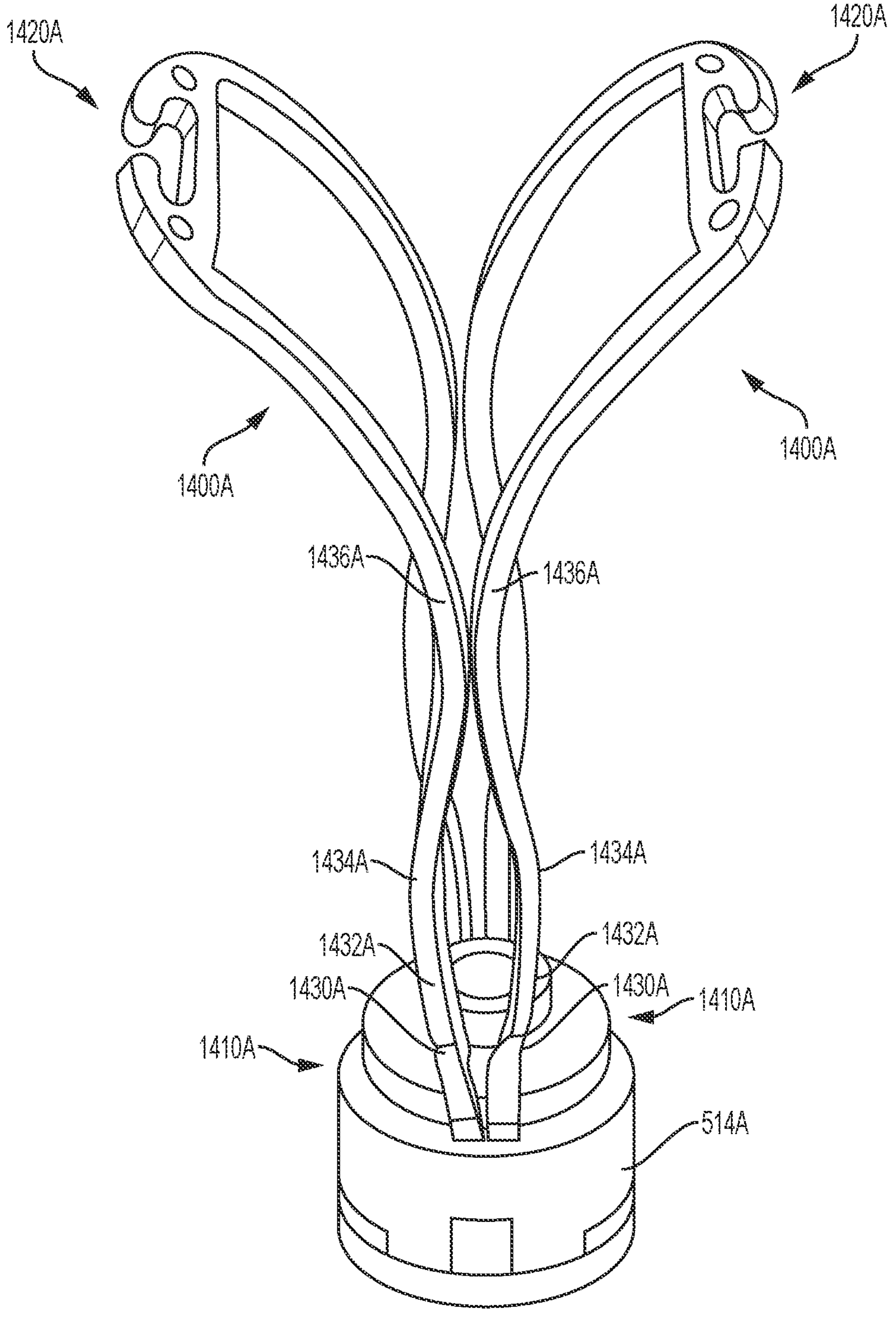
FIG. 89 is a perspective view of the paddle frames of FIG. 88 showing the paddle frames in a loaded position.

Referring to FIGS. 88 and 89, the paddle frames 1400A are shown assembled to the cap 514A of an example implantable device, such as the device 500A described above. In one example embodiment, the paddle frames 1400A can be shape-set to provide increased clamping force against or toward a coaption element 510A when the paddles 520A, 522A are in the closed configuration. This is because the paddle frames 1400A are shape-set relative to the closed position (e.g., FIG. 89) to a first position (e.g., FIG. 88) which is beyond the position where the inner paddle 522A would engage the coaption element 510A, such as beyond the central plane 552A of the device 500A (e.g., FIG. 53A), such as beyond the opposite side of the coaption element, such as beyond the outer paddle on the opposite side of the coaption element. In the first position the sides 1433A of the paddle frames 1400A are intertwined in that the sides 1433A of one paddle frame 1400A are moved slightly laterally to allow movement past the sides 1433A of the other paddle frame 1400A until the end portions 1442A of each frame 1400A contact each other and the sides 1433A and prevent further movement.

The magnitude of the preload of the paddle frames 1400A can be altered by adjusting the degree to which the paddle frames 1400A are shape-set relative to the coaption element 510A. The farther the paddle frames 1400A are shape-set past the closed position, the greater the preload force when the paddle frames 1400A are moved into the open position.

The curves of the paddle frame 1400A can be independent from one another, that is, one curve is complete before another curve starts, or can be combined, that is, the paddle frame 1400A curves in multiple directions simultaneously.

Like the paddle frame 1400 shown in FIGS. 84 and 85, in an example embodiment, the paddle frame 1400A can be formed from a flat blank that is cut from a flat sheet of material, for example, by laser cutting. The cut blank can then be bent to form the three-dimensional shape of the paddle frame 1400A.

Figure 74:
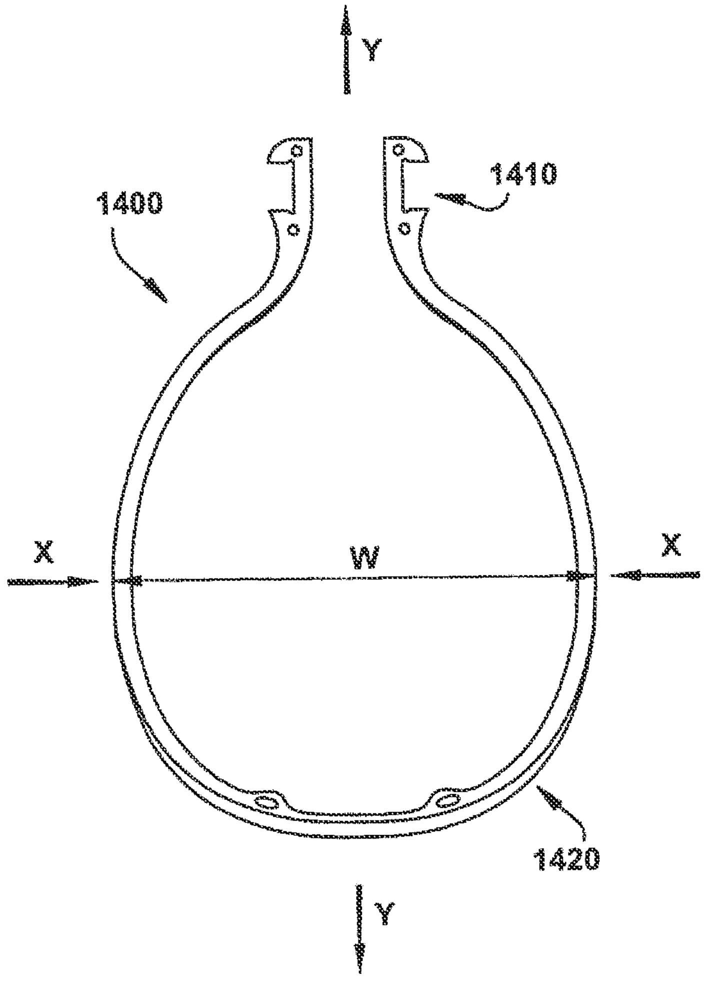
FIG. 74 shows a front view of the paddle frame of FIGS. 67-69.
Figure 75:
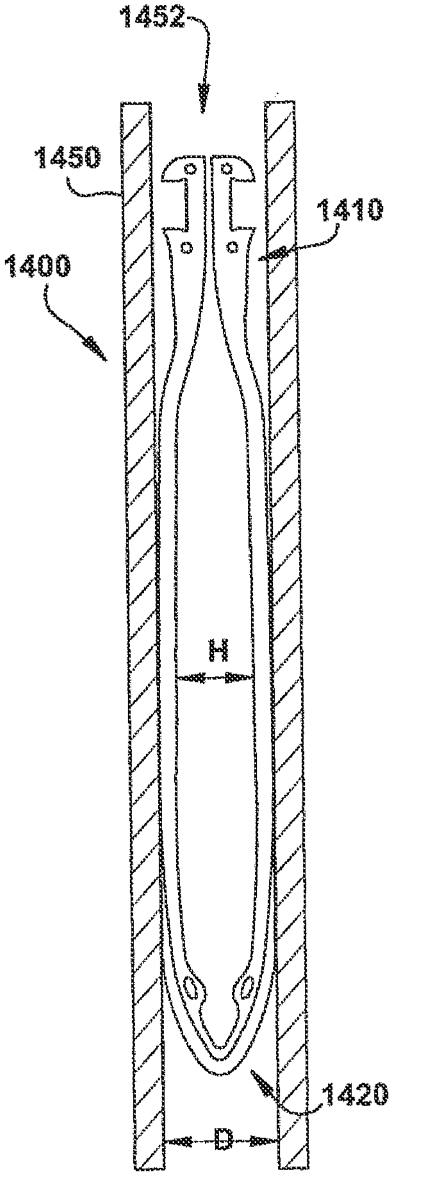
FIG. 75 shows a front view of the paddle frame of FIGS. 67-69 in a compressed condition inside a delivery device.

Referring now to FIGS. 74-75, the paddle frame 1400 is shown in an expanded condition (FIG. 74) and a compressed condition (FIG. 75). The paddle frame 1400 is in a compressed condition when the paddles are disposed in a delivery device 1450. Referring to FIG. 74, the paddle frame 1400 is moved from the expanded condition to the compressed condition by compressing the paddle in the direction X and extending a length of the paddle in the direction Y. When the paddles 1400 are in the compressed condition, the paddles have a width H. The width H can be, for example between about 4 mm and about 7 mm, such as, between about 5 mm and about 6 mm. In alternative embodiments, the width H can be less than 4 mm or more than 7 mm. In certain embodiments, the width H of the compressed paddles 1400 is equal or substantially equal to a width D of the delivery opening 1452 of the delivery device 1450. The ratio between the width W of the paddles in the expanded condition and the width H of the paddles in the compressed condition can be, for example, about 4 to 1 or less, such as about 3 to 1 or less, such as about 2 to 1 or less, such as about 1.5 to 1, such as about 1.25 to 1, such as about 1 to 1. In alternative embodiments, the ratio between the width W and the width H can be more than 4 to 1. FIG. 75 illustrates the connection portions 1410 compressed from the positions illustrated by FIG. 74. However, in some example embodiments, the connection portions 1410 will not be compressed. For example, the connection portions 1410 will not be compressed when the connection portions 1410 are connected to a cap 514. The paddle frame 1400A shown in FIGS. 67A and 69A-73A can be similarly compressed.

Figure 76:
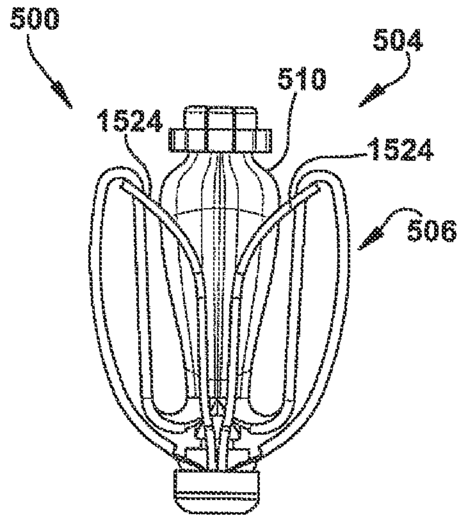
FIG. 76 shows a side view of an example embodiment of an implantable prosthetic device in a closed condition.
Figure 77:
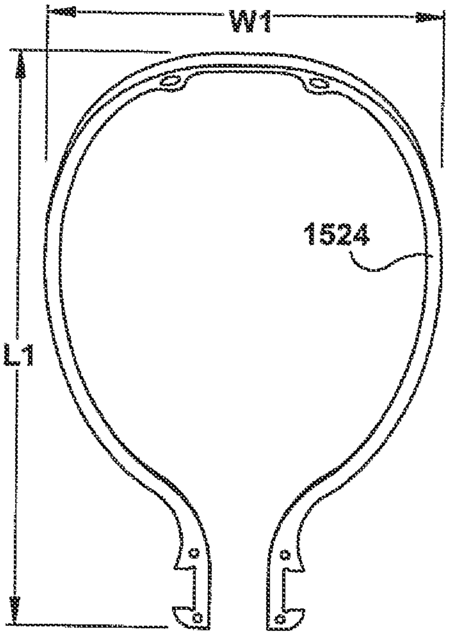
FIG. 77 shows a front view of a paddle frame of the example prosthetic device of FIG. 76.
Figure 78:
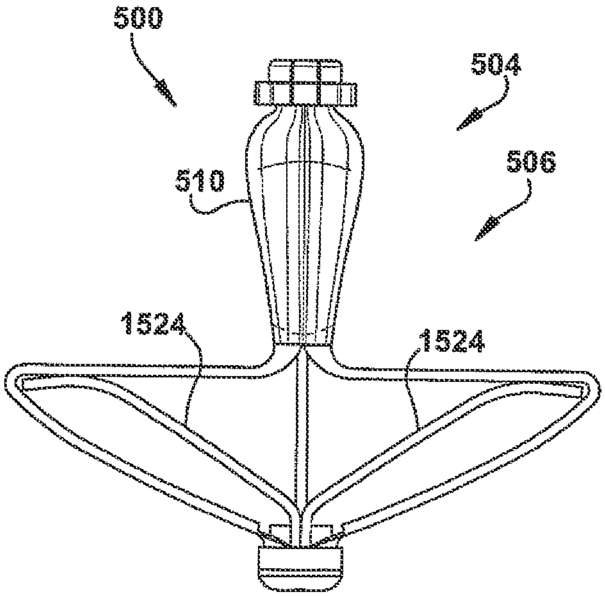
FIG. 78 shows a side view of the implantable prosthetic device of FIG. 76 in an open condition.
Figure 79:
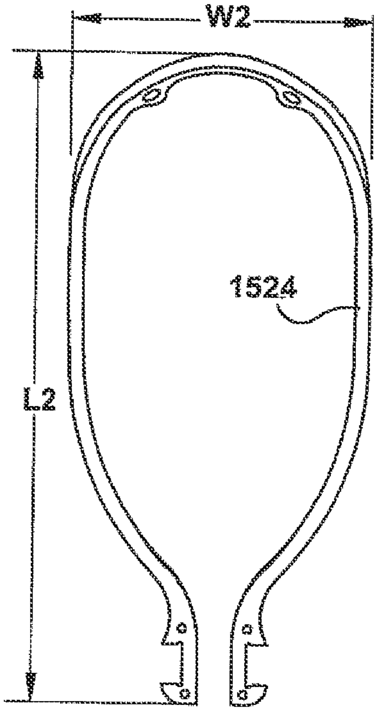
FIG. 79 shows a front view of the paddle frame of the open prosthetic device of FIG. 78.

Referring now to FIGS. 76-79, the example implantable device 500 is shown in open and closed conditions with paddle frames that are compressed or stretched as the anchor portion 506 of the device is opened and closed. The paddle frames 1524 are like the paddle frame 1400 described above. Referring now to FIG. 76, the anchor portion 506 is shown in a closed condition. Referring now to FIG. 77, the paddle frames 1524 have a first width W1 and a first length L1. Referring now to FIG. 78, the anchor portion 506 is shown in an open condition and the paddle frames 1524 are in an extended condition (FIG. 79). Opening the anchor portion 506 of the device 500 causes the paddle frames 1524 to move, extend, or pivot outward from the coaption portion 510 and transition to the extended condition. In the extended condition, the paddle frames 1524 have a second or extended length L2 and a second or extended width W2. In the extended condition, the paddle frame 1524 lengthens and narrows such that the second length L2 is greater than the first length L1 and the second width W2 is narrower than the first width W1. One advantage of this embodiment is that the paddle frames become narrower and can have less chordal engagement during grasping of the leaflets. However, the paddle frames become wide when the implant is closed to enhance support of the leaflet. Another advantage of this embodiment is that the paddle frames also become narrower and longer in the bailout position. The narrower paddle size in the extended, elongated, or bailout position can allow for less chordal entanglement and increased ease of bailout.

Figure 80:
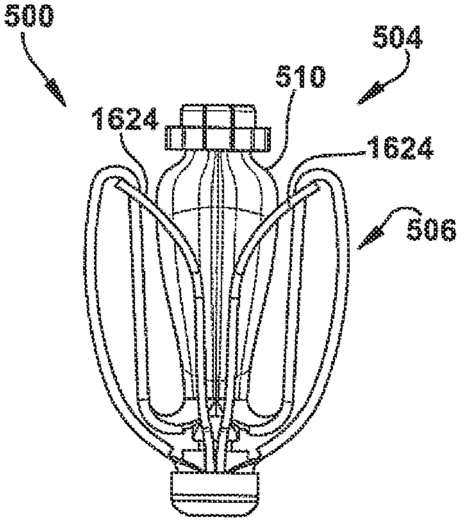
FIG. 80 shows a side view of an example embodiment of an implantable prosthetic device in a closed condition.
Figure 81:
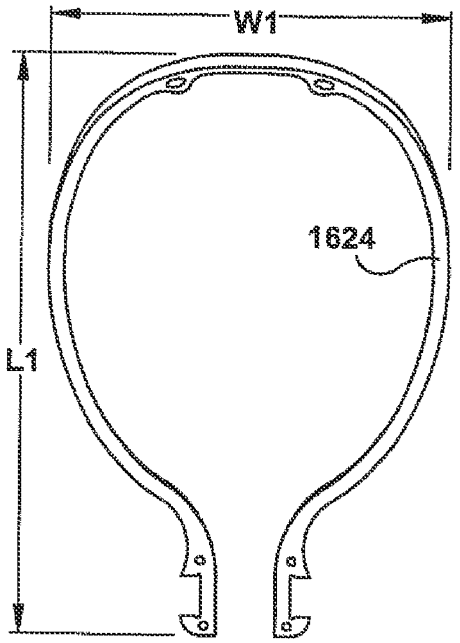
FIG. 81 shows a front view of a paddle frame of the example prosthetic device of FIG. 80.
Figure 82:
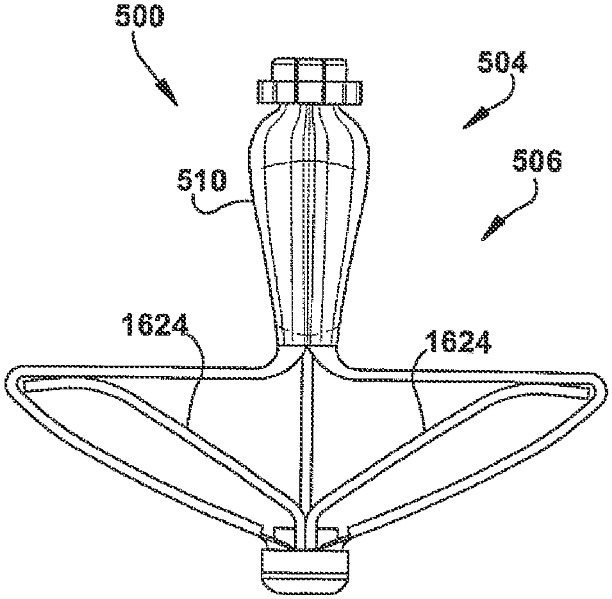
FIG. 82 shows a side view of the implantable prosthetic device of FIG. 80 in a closed condition.
Figure 83:
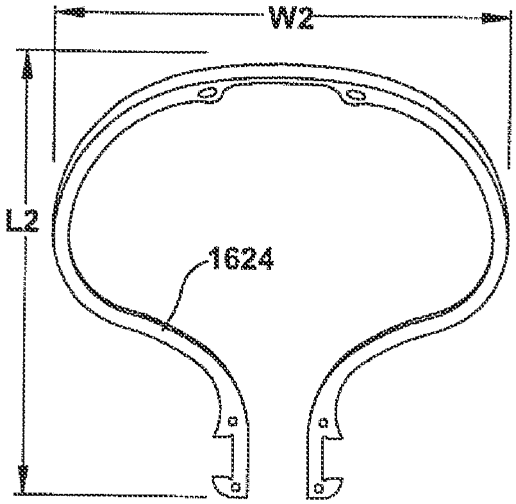
FIG. 83 shows a front view of the paddle frame of the open prosthetic device of FIG. 82.

Referring now to FIGS. 80-83, the example implantable device 500 is shown in open and closed conditions with paddle frames that are compressed or stretched as the anchor portion 506 of the device is opened and closed. The paddle frames 1624 are similar to the paddle frame 1400 described above. Referring now to FIG. 80, the anchor portion 506 is shown in a closed condition. Referring now to FIG. 81, the paddle frames 1624 have a first width W1 and a first length L1. Referring now to FIG. 82, the anchor portion 506 is shown in an open condition and the paddle frames 1624 are in a compressed condition (FIG. 83). Opening the anchor portion 506 of the device 500 causes the paddle frames 1624 to move, extend, or pivot outward from the coaption portion 510 and transition to the compressed condition. In the compressed condition, the paddle frames 1624 have a second or compressed length L2 and a second or compressed width W2. In the compressed condition, the paddle frame 1624 shortens and widens such that the second length L2 is less than the first length L1 and the second width W2 is wider than the first width W1.

Referring now to FIGS. 104A through 105H, example methods of stitching or sewing a cover 5000 or similar device using a thread 5100 are depicted. The cover 5000 can be any cover and can include any other features for a cover as discussed in the present application. The cover 5000 can be a cloth or fabric such as PET, velour, or other suitable fabric. In some embodiments, in lieu of or in addition to a fabric, the cover 5000 can include a coating (e.g., polymeric, etc.). In some embodiments, the cover comprises a polymer or polymeric material. The cover 5000 can be formed from a single piece of material, or from multiple segments abutting or joined to each other. In the illustrated embodiment, the cover 5000 is substantially rectangular. However, the cover 5000 can be any shape or size.

As shown in FIGS. 104A through 105H, the cover 5000 has a first side 5002, a second side 5004, a first end 5006, a second end 5008, a first surface 5010, a second surface 5012 opposite the first surface 5010, a first portion 5014 near the first side 5002, and a second portion 5016 near the second side 5004. The thread 5100 can have a first end 5102 and a second end 5104. The thread 5100 can be any fiber, cord, string, strand, other similar thread, or any combination thereof. The thread 5100 can be a single thread or comprise multiple threads, such as in a braided configuration. The front end 5102 of the thread 5000 can be secured to a needle 5200 and the second end 5104 can be knotted or otherwise configured such that the diameter of the second end 5104 is larger than the diameter of the needle 5200 and/or that the second end 5104 remains secure within the cover 5000 when stitched, as discussed below.

The cover 5000 is positioned or otherwise configured such that the first and second sides 5002, 5004 of the cover 5000 are opposite one another and the thread 5100 is passed through and between the first and second sides 5002, 5004 of the cover 5000 to secure the first and second sides 5002, 5004 together. The thread 5100 can be secured to a needle 5200 and passed through cover 5000 near the first and second ends 5002, 5004. However, the thread 5100 can be passed through the cover 5000 by other means. For example, holes, such as laser-cut holes, can be pre-cut in the first and second portions 5014, 5016 of the cover 5000 near the first and second sides 5002, 5004 and extending from the first surface 5010 to the second surface 5012 such that the thread 5100 can be passed through the holes.

Figure 104A:
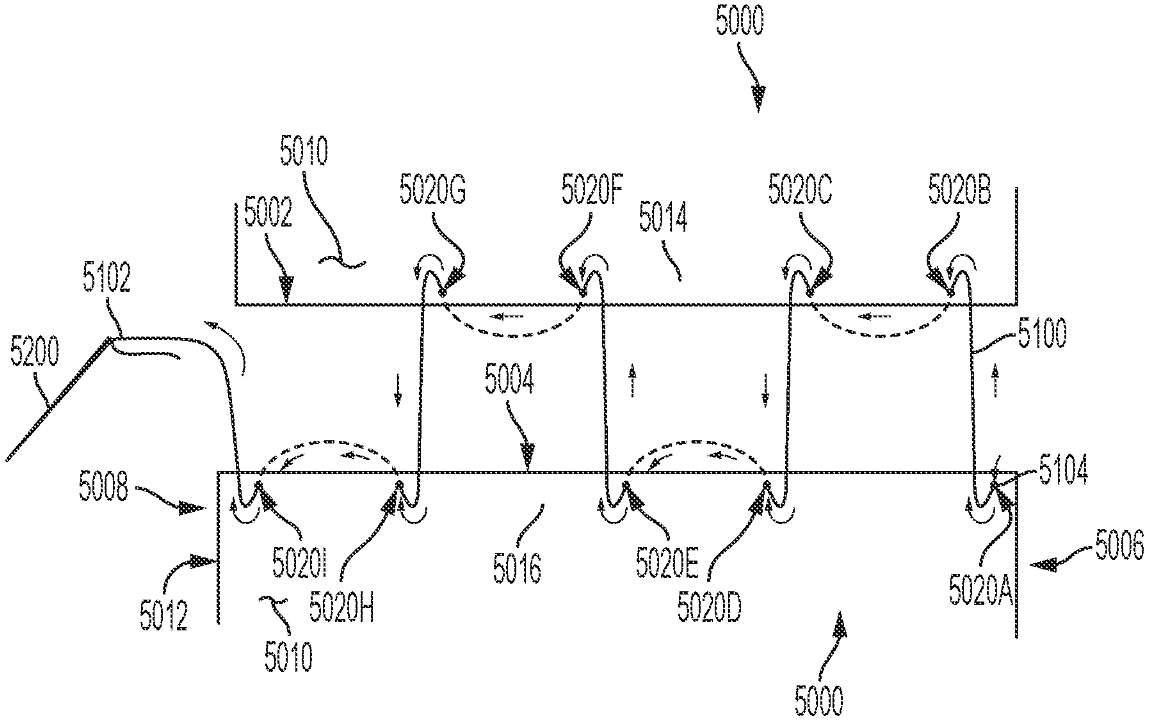
FIG. 104A is an illustrative view of a first example method of stitching a cover.
Figure 104B:
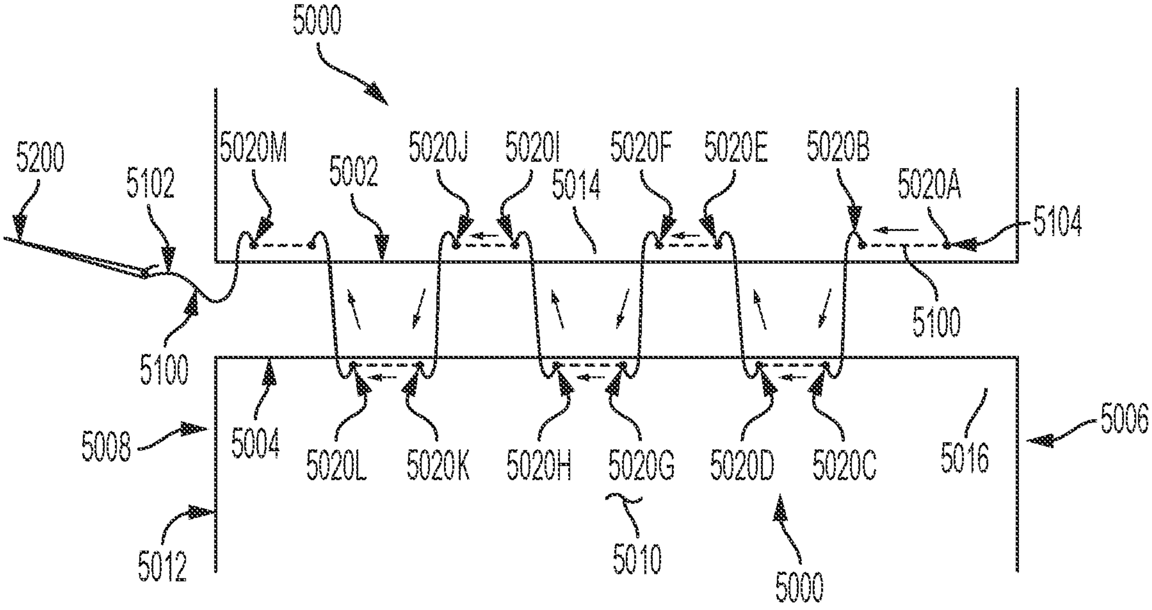
FIG. 104B is an illustrative view of a second example method of stitching a cover.

As shown in FIG. 104A, the thread 5100 can be passed through the cover 5000 from the second surface 5004 to the first surface 5006 at a first point 5020A in the first or second portions 5014, 5016 near the first or second side 5002, 5004, respectively. In the illustrated embodiment, the first point 5020A is in the second portion 5016 near the second side 5004. However, the thread 5100 can be first passed from the second surface 5004 to the first surface 5002 in the first portion 5014 near the first side 5002 (FIG. 104B). The second end 5104 of the thread 5100 can be knotted or otherwise configured at the end such that the end of the thread 5100 remains flush with the second surface 5012 of the cover 5000 and will not slide or otherwise move through the cover 5000 at the first point 5020A.

In the illustrated embodiment, the first point 5020A is near the first end 5006 of the cover 5000. However, the thread 5100 can be first passed from the second surface 5012 to the first surface 5010 at any point in the first or second portions 5014, 5016 along the first or second side 5002, 5004, respectively. For example, the first point 5020A can be near the second end 5008 of the cover 5000 or at any point between the first and second ends 5006, 5008 of the cover 5000.

Once the thread 5100 has been passed from the second surface 5012 to the first surface 5010 at the first point 5020A in either the first or second portion 5014, 5016 near the sides 5002, 5004 of the cover 5000 (the second portion 5016 near the second side 5004 in FIG. 104A), the thread 5100 can be passed through the cover 5000 from the first surface 5010 to the second surface 5012 at a second point 5020B. The second point 5020B is in the portion 5014, 5016 opposite the first point 5020A and near the respective side 5002, 5004 (the first portion 5014 near the first side 5002 in FIG. 104A). The second point 5020B can be substantially opposite the first point 5020A when the first and second sides 5002, 5004 are brought together. The thread 5100 can then be passed beneath and along the second surface 5012 and through the cover 5000 from the second surface 5012 to the first surface 5010 at a third point 5020C in the same portion 5014, 5016 and near the same side 5002, 5004 of the cover 5000 as the second point 5020B (the first portion 5014 near the first side 5002 in FIG. 104A). The third point 5020C can be substantially the same distance from the side 5002, 5004 as the second point 5020B. The thread 5100 can then be passed through the cover 5000 from the first surface 5010 to the second surface 5012 at a fourth point 5020D in the portion 5014, 5016 opposite the third point 5020C and near the respective side 5002, 5004 (the second portion 5016 near the second side 5004 in FIG. 104A). The fourth point 5020D can be substantially the same distance from the side 5002, 5004 as the first point 5020A. This alternating in and out pattern can be continued and repeated as desired.

To continue the pattern, once the thread 5100 is passed through the cover 5000 from the first surface 5010 to the second surface 5012 at the fourth point 5020D, the thread 5100 can be passed beneath and along the second surface 5012 and through the cover 5000 from the second surface 5012 to the first surface 5010 at a fifth point 5020E in the same portion 5014, 5016 and near the same side 5002, 5004 as the fourth point 5020D (the second portion 5016 near the second side 5004 in FIG. 104A). The fifth point 5020E can be substantially in line with the first and fourth points 5020A, 5020D. The thread 5100 can then be passed through the cover 5000 from the first surface 5010 to the second surface 5012 at a sixth point 5020F in the portion 5014, 5016 opposite the fifth point 5020E and near the respective side 5002, 5004 (the first portion 5014 near the first side 5002 in FIG. 104A). The sixth point 5020F can be substantially opposite the fifth point 5020E and substantially in line with the second and third points 5020B, 5020C. This pattern can be repeated by passing the thread 5100 out though the cover 5000 (from second surface 5012 to first surface 5010) at a point subsequent to and along the same side 5002, 5004 as the sixth point 5020F, then passing the thread in through the cover 5000 (from the first surface 5010 to the second surface 5012) at a point in the opposite portion 5014, 5016, and then out of the cover 5000 at a subsequent point along the same side 5002, 5004.

The pattern can be continued to any length by alternating such in and out stitches along the sides 5002, 5004 of the cover 5000. This alternating in and out pattern can be repeated along the lengths of the first and second sides 5002, 5004 until the thread 5100 connects the first and second sides 5002, 5004 for a desired length. For example, pattern can be repeated such that the thread 5100 extends substantially from the first end 5006 of the cover 5000 to the second end 5008 of the cover 5000.

In the illustrated embodiment, the alternating in and out pattern is repeated by passing the thread beneath and along the second surface 5012 and out through the cover 5000 from the second surface 5012 to the first surface 5010 at a seventh point 5020G, in through the cover 5000 from the first surface 5010 to the second surface 5012 at an eighth point 5020H, and along the second surface 5012 and out through the cover 5000 from the second surface 5012 to the first surface 5010 at a ninth point 5020I. The seventh point 5020G is in the same portion 5014, 5016 as the second point 5020B (first portion 5014 in FIG. 104A) and substantially in line with the second, third, and sixth points 5020B, 5020C, 5020F. The eighth and ninth points 5020H, 5020I are in the same portion 5014, 5016 as the first point 5020A (second portion 5016 in FIG. 104A) and substantially in line with the first, fourth, and fifth points 5020A, 5020D, 5020E. The eighth point 5020H can be substantially opposite the seventh point 5020G when the first and second sides 5002, 5004 are brought together. This pattern can then be repeated as desired.

In some embodiments, a pattern, as shown in FIG. 104B, can be used. The first point 5020A can be in the first portion 5014 near the first side 5002 of the cover 5000. Additionally, to begin the pattern, the thread 5100 can be passed through the cover 5000 at the first point 5020A from the first surface 5010 to the second surface 5012, beneath and along the second surface 5012, and from the second surface 5012 to the first surface 5010 at a second point 5020B in the same portion 5014, 5016 and near the same side 5002, 5004 as the first point 5020A. In such an embodiment, the thread 5100 is then passed in through the cover 5000 from the first surface 5010 to the second surface 5012 at the third point 5020C in the portion 5014, 5016 opposite the second point 5020B. The pattern can then follow a similar pattern of alternating in and out stitches as described above.

Additionally or alternatively, as shown in FIG. 104B, when the thread 5100 is passed from a point in one portion 5014, 5016 of the cover 5000 to a point in the opposite portion 5014, 5016, the subsequent point may not be substantially opposite the prior point but can be farther along the length of the side 5002, 5004. For example, as illustrated in FIG. 104B, after the thread 5100 is passed from the second surface 5012 to the first surface 5010 at the second point 5020B, the thread 5100 is then passed in through the cover 5000 from the first surface 5010 to the second surface 5012 at the third point 5020C which is farther away from the first end 5006 than the second point 5020B. In such an embodiment, when the thread 5100 is passed from a point in one portion 5014, 5016 of the cover 5000 to a point in the opposite portion 5014, 5016, the subsequent point is preferably spaced laterally from the prior point such that the thread 5100 is substantially not exposed when the thread 5100 is pulled tight and the first and second sides 5002, 5004 are brought together, as described below.

Referring to FIGS. 105A through 105H, the method of stitching can be used to sew or otherwise secure the cover 5000 around a component 5300 (e.g., a strut, arm, leg, anchor, paddle, extension, body, coaption element, or other component of a medical device. The stitching method can secure the cover 5000 around the component 5300 to reduce catch points and provide a smoother exterior to the cover 5000 when secured around the component 5300.

In the illustrated embodiment, the thread 5100 has a first end 5102 and a second end 5104. The first end 5102 is secured to a needle 5200 having a pointed front end 5202 and a rear end 5204. The second end 5104 of the thread 5100 can be knotted or otherwise increased in size such that the second end 5104 of the thread 5100 has a larger diameter than the needle 5200. The first end 5102 of the thread 5100 can be secured to the needle 5200 by tying or otherwise securing the first end 5100 around an eye (not pictured) of the needle 5200. However, it will be appreciated that the first end 5102 of the thread 5100 can be secured to the needle 5200 by other suitable means and/or the second end 5104 of the thread 5100 may not be knotted or otherwise increased in size. Further, the thread 5100 may not be attached to a needle and another or no device can be used to pass the thread 5100 through the cover 5000.

Figure 105A:
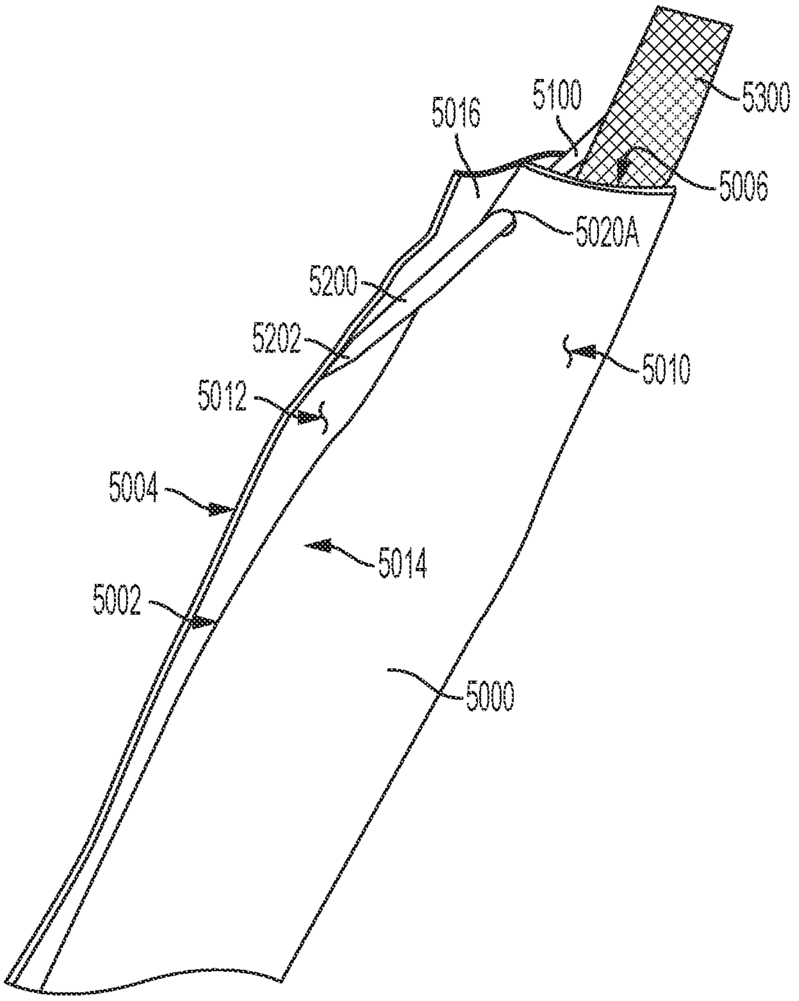
FIGS. 105A through 105H are perspective views of an example method of stitching a cover around a portion of an implantable device.

As shown in FIG. 105A, the cover 5000 can be positioned along a length or axis of the device component 5300 such that the first and second sides 5002, 5004 of the cover 5000 are generally parallel to the length of the component 5300. The cover 5000 can be disposed around the component 5300 such that the second surface 5012 is directed toward the component 5300 and the first side 5002 is adjacent to the second side 5004. The first and second sides 5002, 5004 can be positioned such that at least part of the first and second portions 5014, 5016 are not in contact with the component 5300.

The front end 5202 of the needle 5200 may be passed out through the cover 5000 from the second surface 5012 to the first surface 5014 at a first point 5020A in one of the portions 5014, 5016 near the respective side 5002, 5004. As shown, the first point 5020A is between the side 5002, 5004 of the cover 5000 and the device component 5300. In the illustrated embodiment, the first point 5020A is in the first portion 5014 near the first side 5002 and near the first end 5006 of the cover 5000. However, the first point 5020A can be at any location along either the first or second side 5002, 5004. The needle 5200 can be pulled out through the cover 5000 at the first point 5020A such that at least a portion of the thread 5100 is passed through the cover 5000.

Figure 105B:
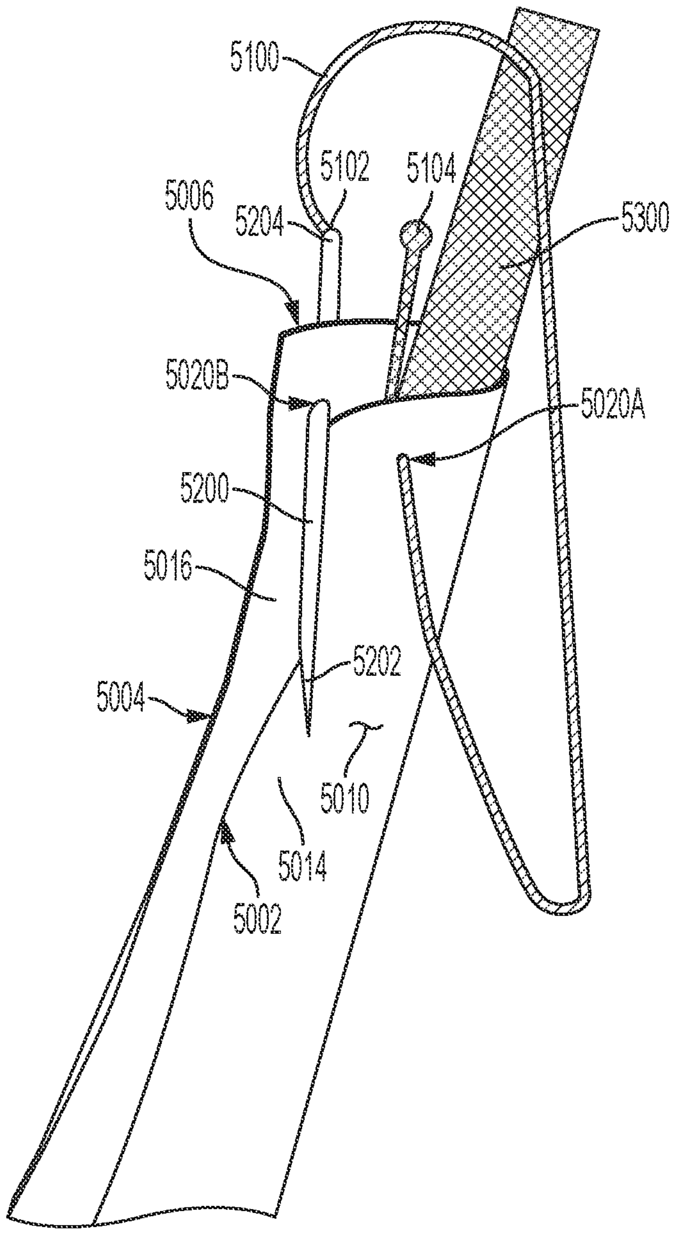

As shown in FIG. 105B, the front end 5202 of the needle 5200 can then be passed in through the cover 5000 from the first surface 5010 to the second surface 5012 at a second point 5020B in the portion 5014, 5016 opposite the first point 5020A (the second portion 5016 in FIG. 105B) between the respective side 5002, 5004 and the device component 5300. The second point 5020B may be substantially directly across from the first point 5020A when the first and second sides 5002, 5004 are brought together. The needle 5200 can be pulled out through the cover 5000 at the second point 5020B such that at least a portion of the thread 5100 is pulled in through the cover 5000.

Figure 105C:
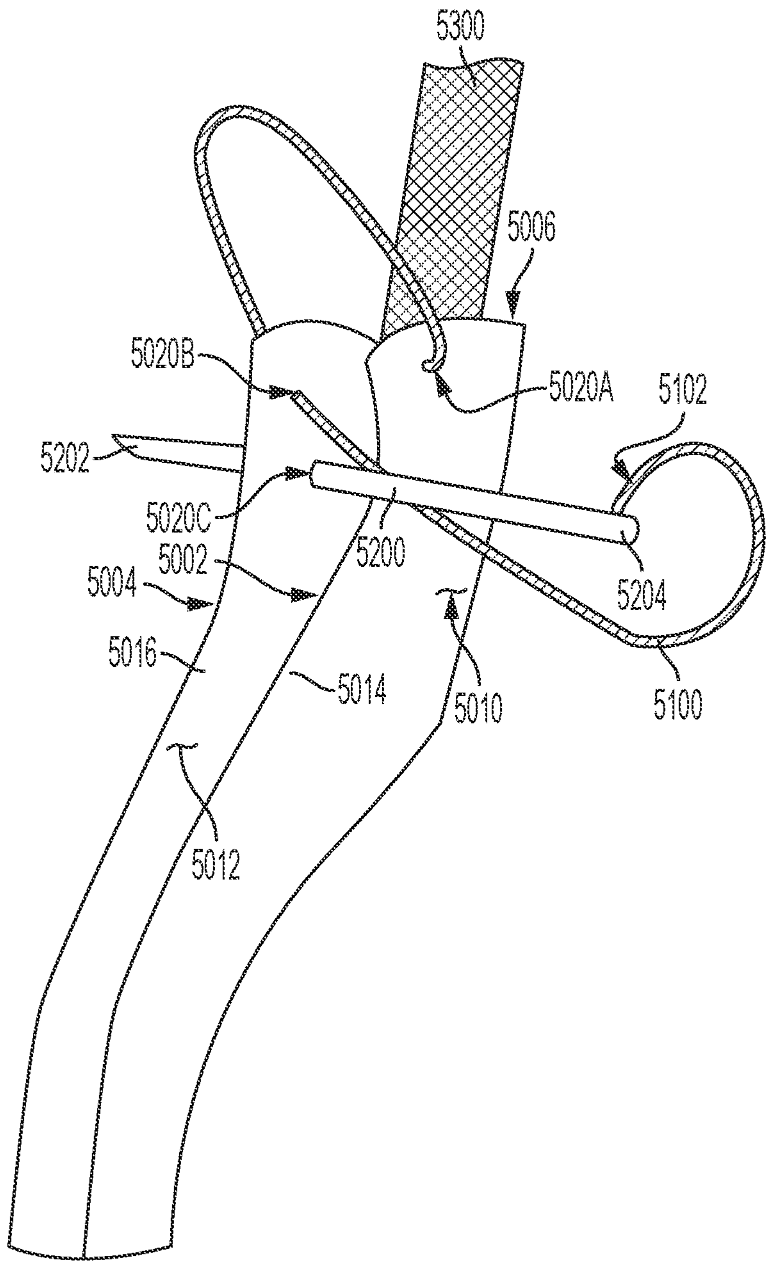

As shown in FIG. 105C, the front end 5202 of the needle 5200 can then be passed out through the cover 5000 from the second surface 5012 to the first surface 5010 at a third point 5020C in the same portion 5014, 5016 as the second point 5020B (the second portion 5016 in FIG. 105C) between the side 5002, 5004 and the component 5300. The third point 5020C can be substantially the same distance from the side 5002, 5004 as the second point 5020B. The needle 5200 may be pulled through the cover 5000 at the third point 5020C such that at least a portion of the thread 5100 is pulled out through the cover 5000.

Figure 105D:
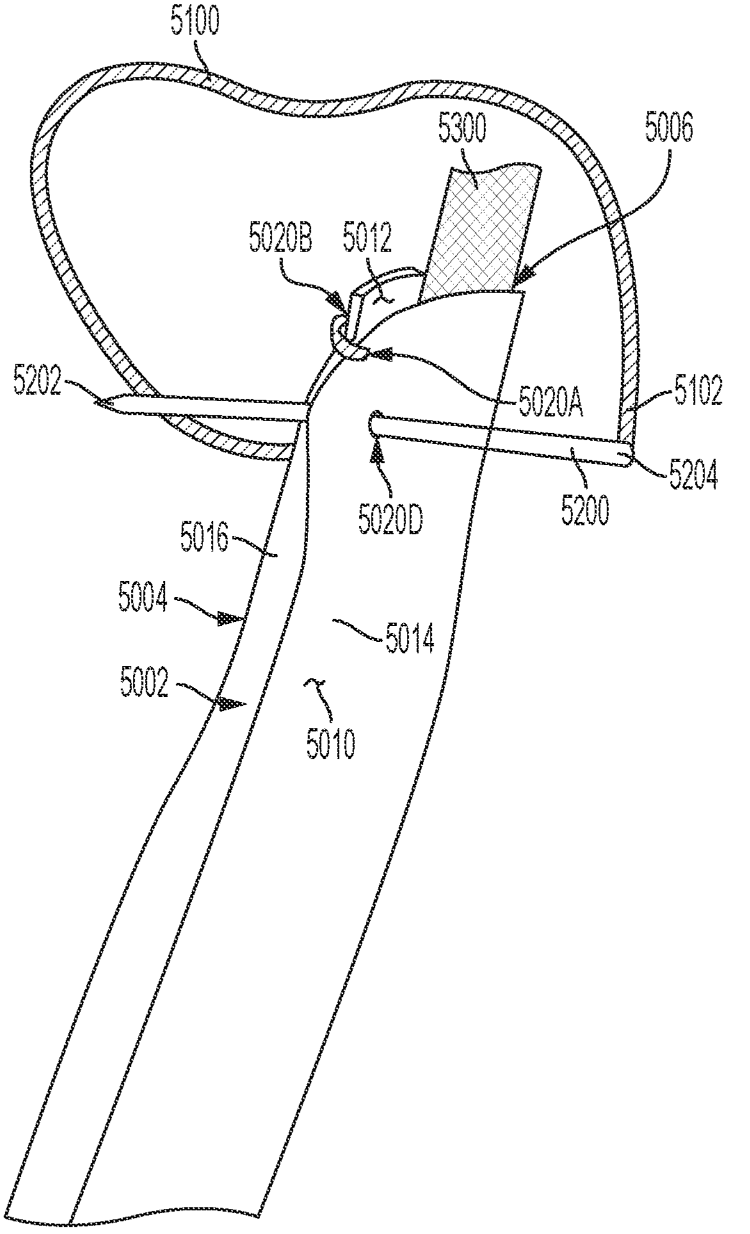

As shown in FIG. 105D, the front end 5202 of the needle 5200 can then be passed in through the cover 5000 from the first surface 5010 to the second surface 5012 at a fourth point 5020D in the portion 5014, 5016 opposite the third point 5020C (first portion 5014 in FIG. 105D) between the side 5002, 5004 and the component 5300. The fourth point 5020D can be substantially directly across from the third point 5020C when the first and second sides 5002, 5004 are brought together and the fourth point 5020D can be substantially the same distance from the side 5002, 5004 as the first point 5020A. The needle 5200 can be pulled in through the cover 5000 at the fourth point 5020D such that at least a portion of the thread 5100 is pulled in through the cover 5000.

Figure 105E:
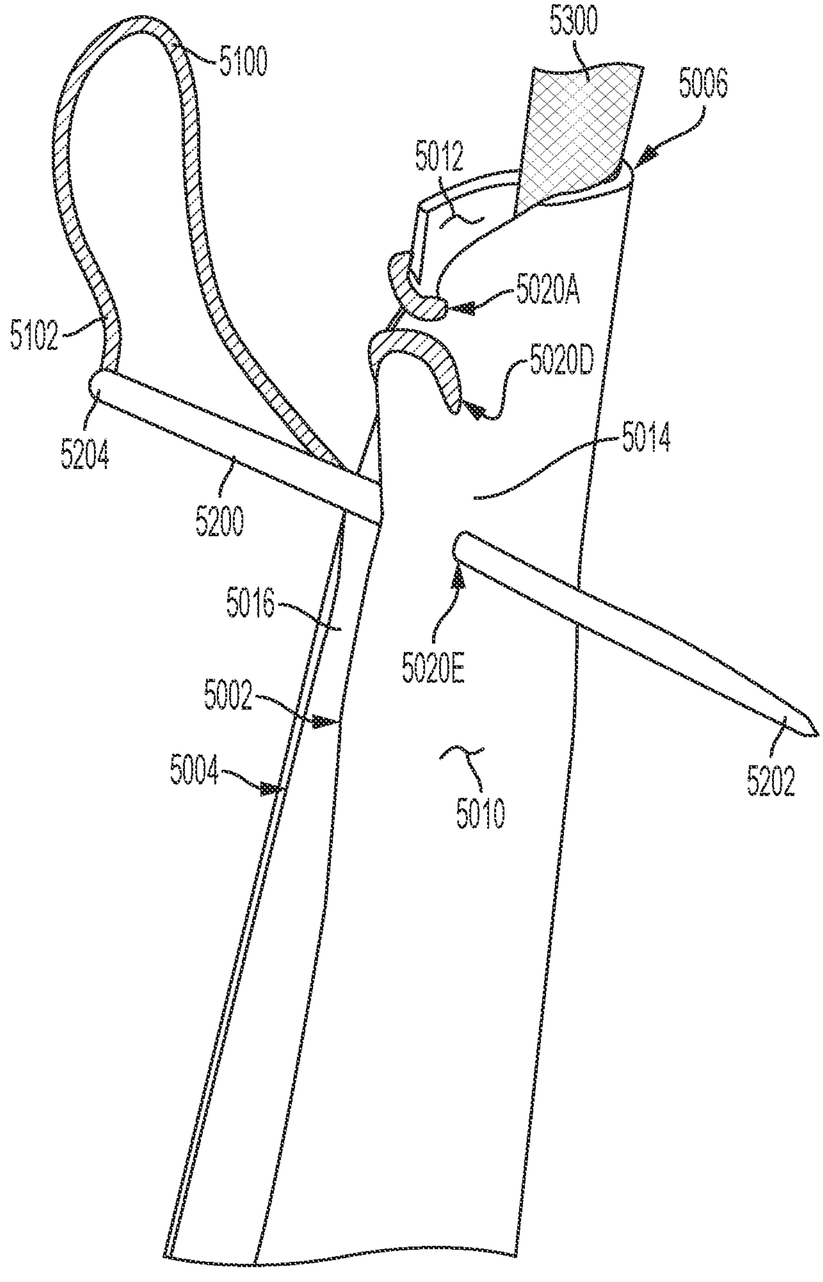

As shown in FIG. 105E, the front end 5202 of the needle 5200 can then be passed out through the cover 5000 from the second surface 5012 to the first surface 5010 at a fifth point 5020E in the same portion 5014, 5016 as the fourth point 5020D (first portion 5014 in FIG. 105E) between the respective side 5002, 5004 and the strut 5300. The fifth point 5020E can be substantially in line with the first point and fourth points 5020A, 5020D. The needle 5200 can then be pulled out through the cover 5000 at the fifth point 5020E such that at least a portion of the thread 5100 is pulled out through the cover 5000.

Figure 105F:
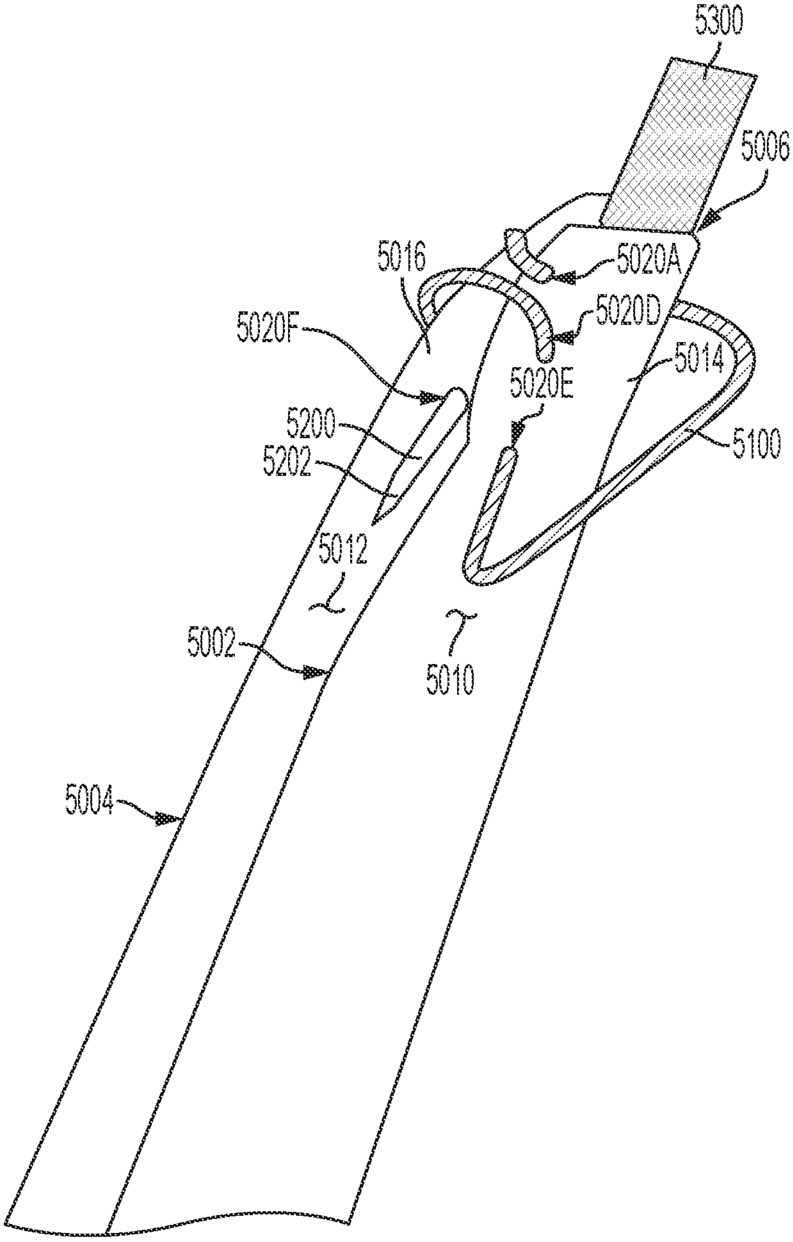

As shown in FIG. 105F, the front end 5202 of the needle 5200 can then be passed in through the cover 5000 from the first surface 5010 to the second surface 5012 at a sixth point 5020F in the portion 5014, 5016 opposite the fifth point 5020E (the second portion 5016 in FIG. 105F) between the side respective side 5002, 5004 and the component 5300. The sixth point 5020F can be substantially directly across from fifth point 5020E when the first and second sides 5002, 5004 are brought together and the sixth point 5020F can be in line with the second and third points 5020B, 5020C. The needle 5200 can then be pulled in through the cover 5000 at the sixth point 5020F such that at least a portion of the thread 5100 is pulled in through the cover 5000.

Figure 105G:
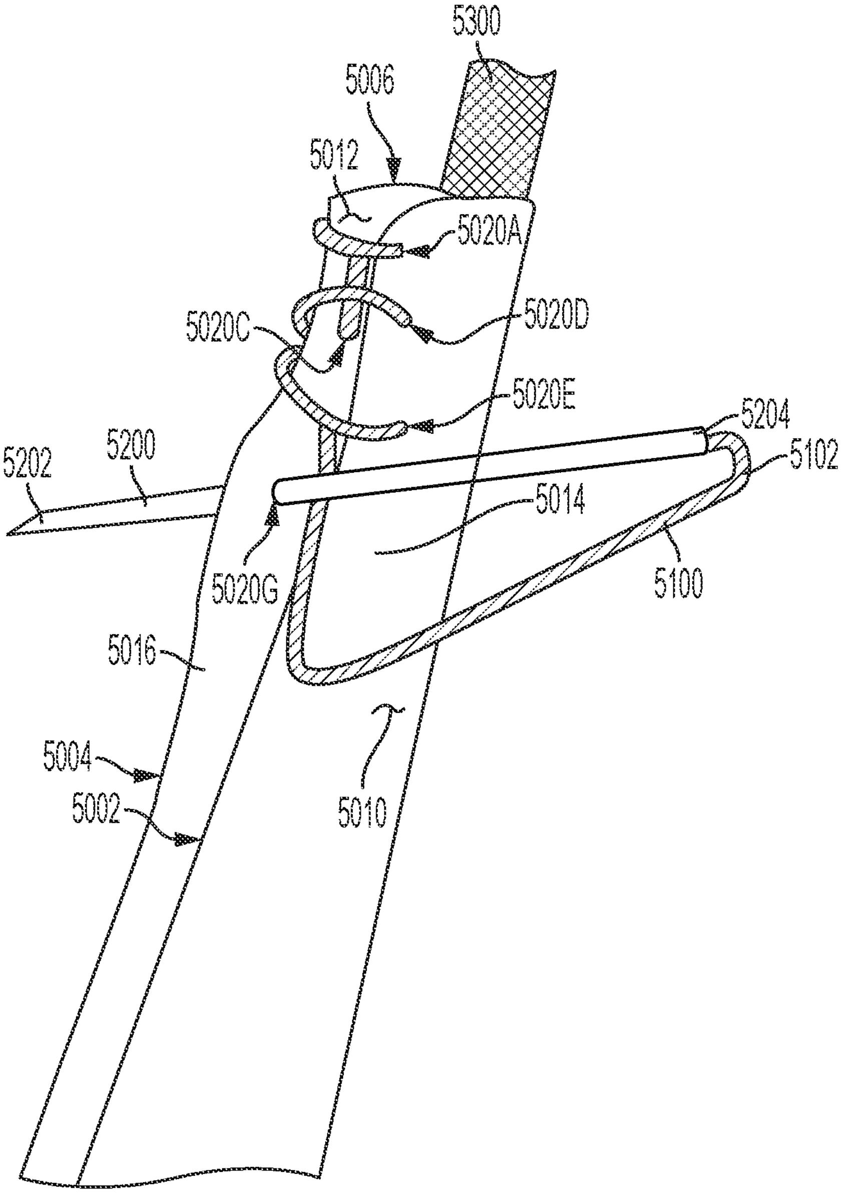

As shown in FIG. 105G, the front end 5202 of the needle 5200 can then be passed out through the cover 5000 from the second surface 5012 to the first surface 5010 at a seventh point 5020G in the same portion 5014, 5016 as the sixth point 5020F (the second portion 5016 in FIG. 105G) between the respective side 5002, 5004 and the component 5300. The seventh point 5020G can be substantially in line with the second, third, and sixth points 5020B, 5020C, 5020F. The needle 5200 can be pulled out through the cover 5000 at the seventh point 5020G such that at least a portion of the thread 5100 is passed through the cover 5000. This process can be repeated between the first and second sides 5002, 5004 of the cover 5000 such that the thread 5100 connects the desired amount of the cover 5000.

Figure 105H:
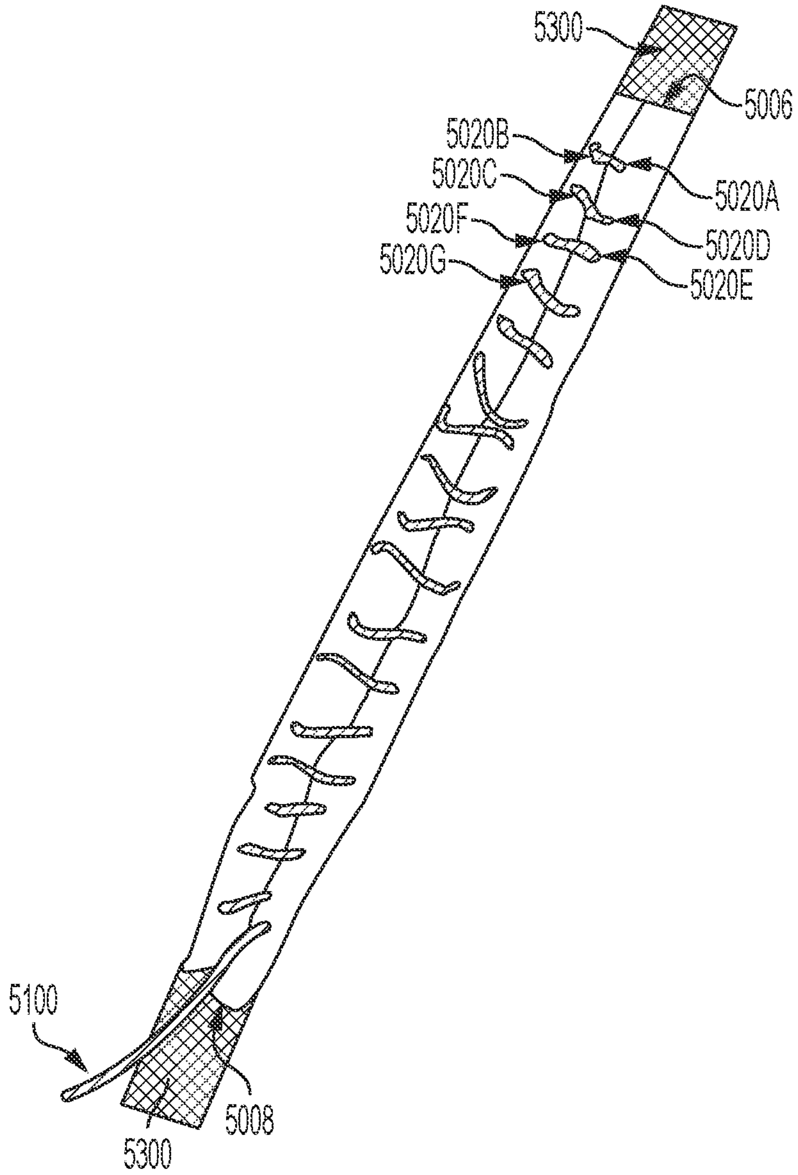

As shown in FIG. 105H, the process can be repeated such that the thread 5100 extends between the first and second sides 5002, 5004 in an alternating in and out arrangement which substantially extends from the first end 5006 of the cover 5000 to the second end 5008 of the cover 5000. In the illustrated embodiment, the thread 5100 is passed through the cover 5000 at thirty-five points using the alternating in-and-out stitch. However, the pattern can have more or fewer than thirty-five points and/or the thread 5100 may not extend substantially between the first and second ends 5006, 5008 of the cover 5000. For example, the thread 5100 can be stitched between the first and second sides 5002, 5004 from the second end 5008 of the cover 5000 to the first end 5006 of the cover 5000 or the first point 5020A can be anywhere between the first and second ends 5006, 5008 and extend toward either the first or second end 5006, 5008.

When the pattern has been repeated a sufficient number of times such that the thread 5100 extends the desired length along the first and second sides 5002, 5004 of the cover 5000, the pattern can be stopped. At the final point where the thread 5100 is passed through the cover 5000, the thread 5100 can be passed from the second surface 5012 to the first surface 5010 such that the first end 5102 of the thread 5100 is disposed outside the cover 5000 beyond the first surface 5010. As shown in FIG. 105H, once the pattern is complete, the thread 5100 can have some slack between one or more of the points 5020 and/or the second end 5104 of the thread 5100 may not be flush with or abut the second surface 5012 of the cover 5000 at the first point 5020A.

After the pattern is complete, the first end 5102 of the thread 5100 can be pulled until the second end 5104 of the thread 5100 is flush with and/or abuts the second surface 5012 of the cover 5000 at the first point 5020A and the portions of the thread 5100 extending between the first and second sides 5002, 5004 are as taught. The first end 5102 of the thread 5100 can be pulled until the first and second sides 5002, 5004 of the cover 5000 are brought toward the strut 5300 and the points 5020 on opposite portions 5014, 5016 are brought substantially into contact with each other.

Once the thread 5100 has been pulled taught through the cover 5000, the portion of the thread 5100 extending between the cover 5000 and the first end 5102 of the thread 5100 can be secured to the other portions of the thread 5100 and/or the cover 5000 by any suitable means. For example, the portion of the thread 5100 extending between the cover 5000 and the first end 5102 can be looped around and/or tied to the thread 5100 at a point prior to the thread 5100 passing through the cover 5000 at the last point 5020. The excess thread 5100 can then be cut and/or tucked between the cover 5000 and component 5300. However, in other embodiments, the portion of the thread 5100 extending between the cover 5000 and the first end 5102 may not be secured to the other portions of the thread 5100 and/or the cover 5000, and the excess portion of the thread 5100 can be cut and/or tucked between the cover 5000 and the component 5300.

Figure 106A:
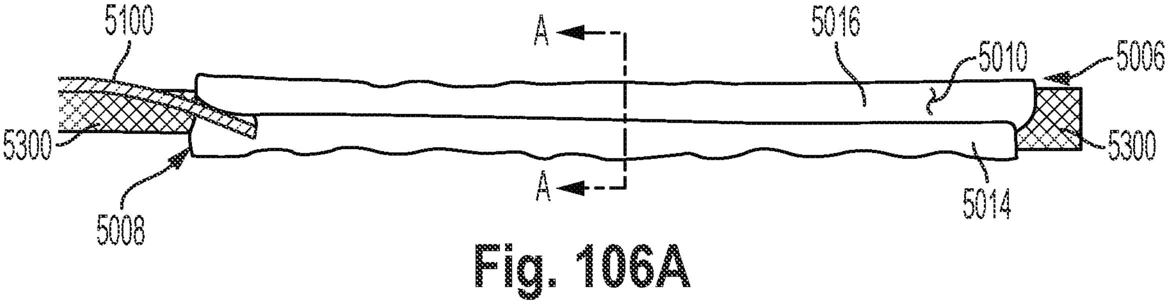
FIG. 106A is a plan view of an example embodiment of a cover disposed and stitched around a portion of an implantable device.
Figure 106B:
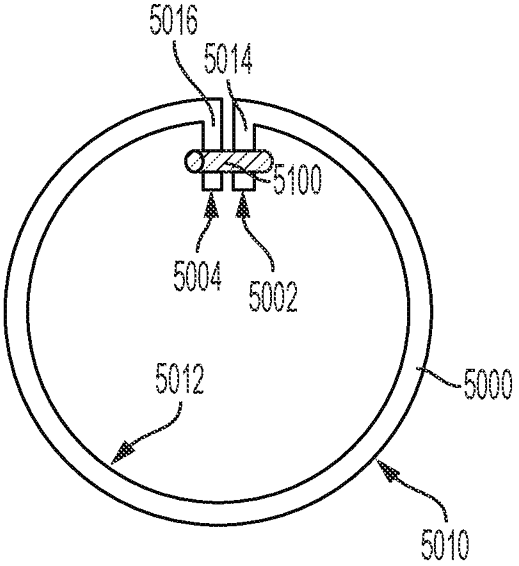
FIG. 106B is a cross-sectional view of the cover of FIG. 106A taken along line A-A.

As shown in FIG. 106B, after the thread 5100 has been pulled tight, the first and second sides 5002, 5004 of the cover 5000 can be pulled inwardly toward the center of the cover 5000 such that the first surface 5010 at the first portion 5014 is directed toward the first surface 5010 at the second portion 5016. The portions of the thread 5100 extending between the first portion 5014 and the second portion 5016 can be disposed between the portions of the cover 5000 which are directed inward. In such an embodiment, the thread 5100 is disposed substantially within the cover 5000 such that substantially no portion of the thread 5100 is exposed. As such, substantially only the first surface 5010 of the cover 5000 is exposed when the cover 5000 is secured by the thread 5100.

Referring now to FIGS. 107 through 111, the alternating in and out stitches described above can be used to secure one or more covers 5000 having one or more cover portions 5600 and/or 5700 (See FIGS. 107 and 110) on a prosthetic device 5500. The device 5500 can include any other features for an implantable prosthetic device discussed in the present application, and the device can be positioned to engage valve tissue as part of any suitable valve repair system (e.g., any valve repair system disclosed in the present application). In one example embodiment, the prosthetic device 5500 with cover illustrated by FIGS. 107 through 111 can have the structural features of the prosthetic device 500 illustrated by FIGS. 28 and 29.

Referring to FIGS. 28-31 and 239, the device 5500 can comprise a plurality of anchors 508. The plurality of anchors can be configured to include outer paddle portions 520, inner paddle portions 522, and clasps 530. The device 5500 can optionally also include one or more of a coaption element or spacer member 510, a first or proximal collar 511 (See FIGS. 28 and 29), and a second collar or cap 514. These components of the prosthetic spacer device 5500 can be configured substantially similar to the corresponding components of any of the devices discussed in the present application.

Still referring to FIGS. 28-31 and 239, the prosthetic device 5500 can also include a plurality of paddle extension members or paddle frames 524. The paddle frames 524 can be configured with a round three-dimensional shape with first connection portions 526 coupled to and extending from the cap 514 and second connection portions 528 disposed opposite the first connection portions 526 (See FIGS. 28 and 29). The paddle frames 524 can be configured to extend circumferentially farther around the coaption member 510 than the outer paddles 520. For example, in some embodiments, each of the paddle frames 524 can extend around approximately half of the circumference of the coaption member 510 (as shown in FIG. 29), and the outer paddles 520 can extend around less than half of the circumference of the coaption member 510 (as shown in FIG. 28). The paddle frames 524 can also be configured to extend laterally (i.e., perpendicular to a longitudinal axis of the coaption member 510) beyond an outer diameter of the coaption member 510. In the illustrated example, the inner paddle portions 522 and the outer paddle portions 520 are formed from a continuous strip of fabric that are connected to the paddle frames 524. For example, the inner paddle portions and the outer paddle portions can be connected to the connection portion of the paddle frame at the flexible connection between the inner paddle portion and the outer paddle portion.

Referring to FIGS. 28 and 29, the paddle frames 524 can further be configured such that connection portions 528 of the paddle frames 524 are connected to or axially adjacent a joint portion 523. The connection portions of the paddle frames 534 can be positioned between outer and inner paddles 520, 522, on the outside of the paddle portion 520, on the inside of the inner paddle portion, or on top of the joint portion 523 when the prosthetic device 5500 is in a folded configuration (e.g., FIGS. 28-30). The connections between the paddle frames 524, the single strip that forms the outer and inner paddles 520, 522, the cap 514, and the coaption element can constrain each of these parts to the movements and positions described herein. For example, the joint portion 523 can be constrained by its connection between the outer and inner paddles 520, 522 and by its connection to the paddle frame. Similarly, the paddle frame 524 is constrained by its attachment to the joint portion 523 (and thus the inner and outer paddles) and to the cap.

Referring now to FIGS. 96, and 107 through 111, portions of example covers are shown which can be attached to or otherwise secured around the device 5500 and/or around any of the other devices (or components thereof) shown or described anywhere in this disclosure or on other known medical devices. While cover 5000 is used as an example here, cover 540A or other covers herein can incorporate similar features and/or techniques.

The portions of the cover 5000 can be cut from flat sheets of material. The illustrated cover 5000 includes the outer cover 5600 and the inner cover 5700. Each of the covers 5600, 5700 include different shaped segments or portions to attach to different portions of the device 5500. In particular, the covers 5600, 5700 are shaped to smooth transitions between portions of the device 5500 to reduce catch points and provide a smoother exterior to the device 5500.

The various segments of the covers 5600, 5700 extend from a middle portion that is shaped to attach to an end of the device 5500. In some embodiments, the portion of the cover 5600, 5700 that attaches to an end of the device 5500 is located at an end of the covers 5600, 5700 or can be located anywhere between the middle and ends of the covers 5600, 5700. Various portions of the covers 5600, 5700 can be shaped to wrap around portions of the device 5500. The cover 5000 can be made of any suitable material, such as a polyethylene cloth of a fine mesh. In some embodiments, the cover 5000 is formed out of a single piece of material. In some embodiments, the cover can be formed of any number of pieces of material that are attached to the device and/or joined together by any suitable means, such as by stitching, adhesives, welding, or the like.

Referring to FIGS. 107 through 109B, the inner cover 5700 can be at least partially attached to or otherwise secured around the device 5500 using the alternating in and out stitch. The inner cover 5700 can include any other features for an inner cover discussed in the present application. In the illustrated embodiment, the inner cover 5700 includes a top piece 5702 and a bottom piece 5704. However, the inner cover 5700 can have another configuration. For example, the inner cover 5700 can be substantially similar to the inner covers described in other locations herein (e.g., FIG. 96).

Figure 107:
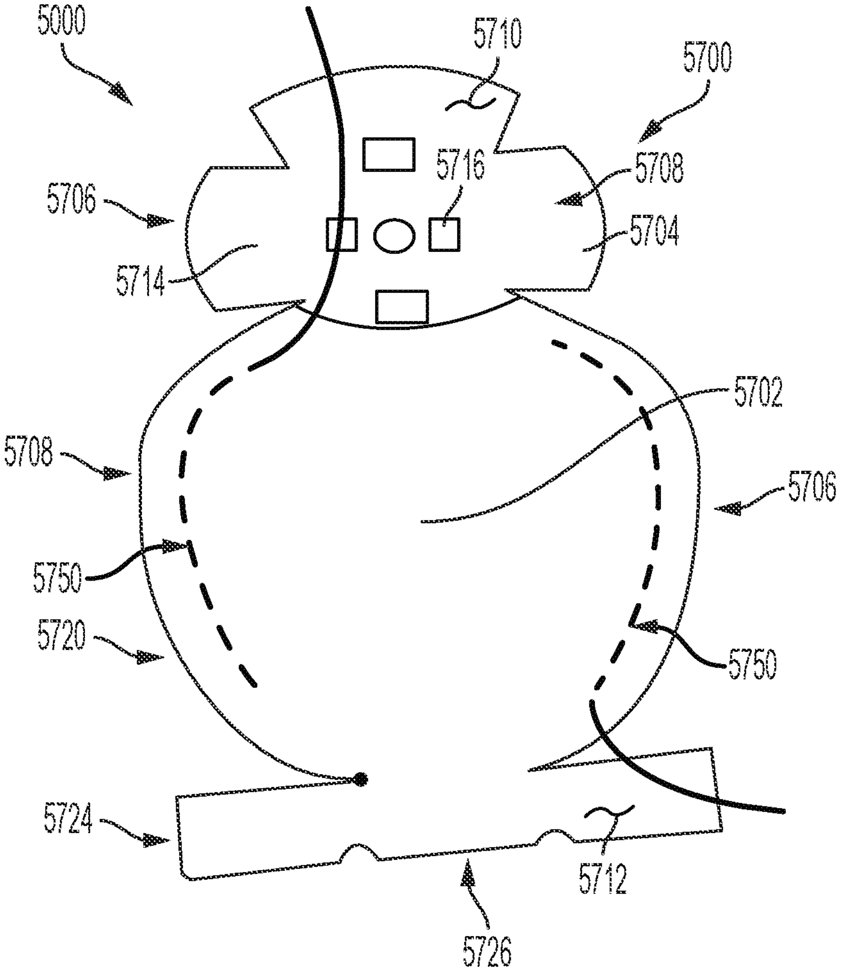
FIG. 107 is a plan view of an example embodiment of a first inner cover folded over and stitched to a second inner cover.

As shown in FIG. 107, the top piece 5702 is disposed on top of the bottom piece 5704 and the two pieces 5702, 5704 can be sewn or otherwise attached together. The top and bottom pieces 5702, 5704 each have a first side 5706, a second side 5708, a first surface 5710, and a second surface 5712 opposite the first surface 5710. The first surfaces 5710 face each other in FIG. 107 and the second surfaces face away from each other in FIG. 107. The top and bottom pieces 5702, 5704 each can also have a coaption portion 5720 which extends outwardly in one direction to a transition portion 5724 and an end portion 5726. The coaption portions 5720 of the top and bottom pieces 5702, 5704 are configured to be joined or attached together, turned inside-out and then disposed around the coaption element 510 (See FIGS. 28 and 29). For example, first stitches 5750 connect the top and bottom pieces 5702, 5704 together, the pieces 5702, 5704 are turned inside out, and placed over the coaption element. The top and bottom pieces 5702, 5704 can each include holes (not pictured) along the edges of the coaption portions 5720 to allow each of the coaption portions 5720 to be joined together, such as, for example, by stitches. However, the coaption portions 5720 may not include holes along the edges and the coaption portions 5720 can still be joined together after being folded around the coaption elements 510 (See FIGS. 28 and 29). For example, a needle and thread can be used to pierce the edges of the coaption portions 5720 to sew or otherwise secure the coaption portions 5720 around the coaption element 510.

The transition portions 5724 of the top and bottom pieces 5702, 5704 are configured to be wrapped around the inner paddle 522 and ends of the clasp 530 of the device 5500. The top and bottom pieces 5702, 5704 can include holes (not pictured) along the edges of the transition portions 5724 to allow each of the transition portions 5724 to be disposed or wrapped around the inner paddle 522 and ends of the clasp 530 and secured to each other by stitches or other suitable securing means. However, the transition portions 5724 may not include holes along the edges and the transition portions 5596 can still be secured around the inner paddle 522 and ends of the clasp 530. For example, a needle and thread can be used to pierce the edges of the transition portions 5724 to sew or otherwise secure the transition portions 5724 around the inner paddle 522 and ends of the clasp 530.

The coaption portion 5720, the transition portion 5724, and the end portions 5726 of the bottom piece 5704 can be substantially mirror images to the coaption portion 5720, the transition portion 5724, and the end portion 5726 of the top piece 5544A. In the illustrated embodiment, the coaption portions 5720 of the top and bottom pieces 5702, 5704 extend directly to the transition portions 5724. However, the top and bottom pieces 5702, 5704 can each have a flexible hinge portion which extends from the coaption portion 5720 to the transition portion 5724. The flexible hinge portions bridge the gaps between the coaption element 510 and the clasp 530 when the device 5500 is opened, as can be seen in FIG. 91. The flexible hinge portion can be substantially similar to the flexible hinge portions previously described, such as the flexible hinge portions 594 described in FIG. 96.

The bottom piece 5704 also has a middle portion 5714 which extends outwardly from the coaption portion 5720 at an end opposite the transition portion 5724. The collar portion 5714 is configured to be attached to the collar 514 of the device 5500. Openings 5716 in the collar portion expose the protrusions from the collar 511 when the collar portion 5714 is attached to the collar 511 so that the protrusions can be engaged by a delivery device.

As shown in FIG. 107, the top and bottom pieces 5702, 5704 can be attached to one another before the inner cover 5700 is disposed on the device 5500. The top piece 5702 can be disposed on top of the bottom piece 5704 with the first surface 5710 of the bottom piece 5704 facing the first surface 5710 of the top piece 5702 such that the coaption portions 5720, the transition portions 5724, and the end portions 5726 of the top and bottom pieces 5702, 5704 are aligned and the middle portion 5714 of the bottom piece 5704 is exposed. The edges of the coaption portions 5720 can then be joined together by the first stitches 5750, connecting the first side 5706 of the top piece 5702 to the second side 5708 of the bottom piece 5704 and the second side 5708 of the top piece 5702 to the first side 5706 of the bottom piece 5704.

The first stitches 5750 can extend along the coaption portions 5720 on the first and second sides 5706, 5708. The first stitches 5750 may not extend the entire length of the first and second sides 5706, 5708 of the coaption portions 5720 to allow the cover to be turned inside out and placed over the coaption element 510 (See FIGS. 28 and 29). The first stitches 5750 can be an in and out stitch (after the cover is turned inside out) or any other suitable stitch. After the coaption portions 5720 are sewn together, the inner cover 5700 can be turned inside out such that the first surfaces 5710 of the top and bottom pieces 5702, 5704 face outward.

Figure 108:
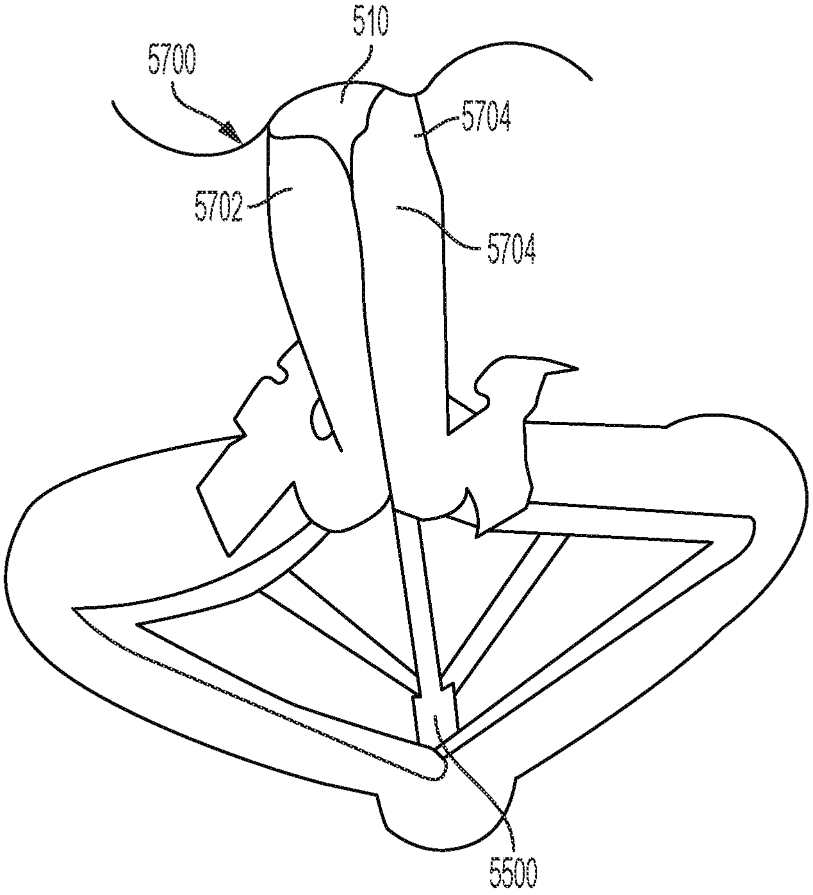
FIG. 108 is a perspective view of an example embodiment of the inner cover of FIGS. 96 and 107 and the outer cover of FIG. 97 disposed around an example prosthetic device.

As shown in FIG. 108, the inner cover 5700 can be disposed on the device 5500 with the coaption portions 5720 disposed around the coaption element 510 of the device 5500 5500 (See FIGS. 28 and 29 for details of the coaption element). The middle portion 5714 of the bottom piece 5704 can be disposed on the collar 511D of the device 5500 with the protrusions exposed through the openings 5716 (See FIG. 28).

Figure 109A:
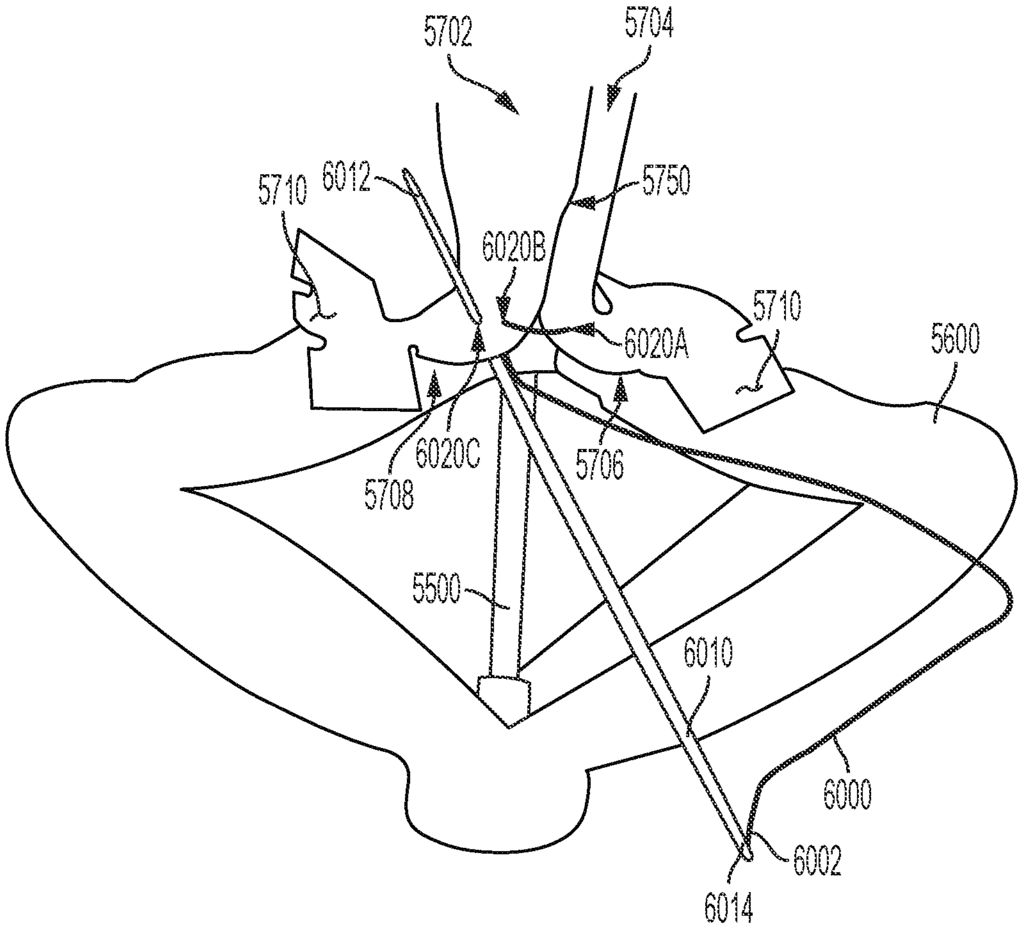
FIGS. 109A and 109B are perspective views of an example method of stitching the cover of FIGS. 96, 107, and 108 around an example prosthetic device.
Figure 109B:
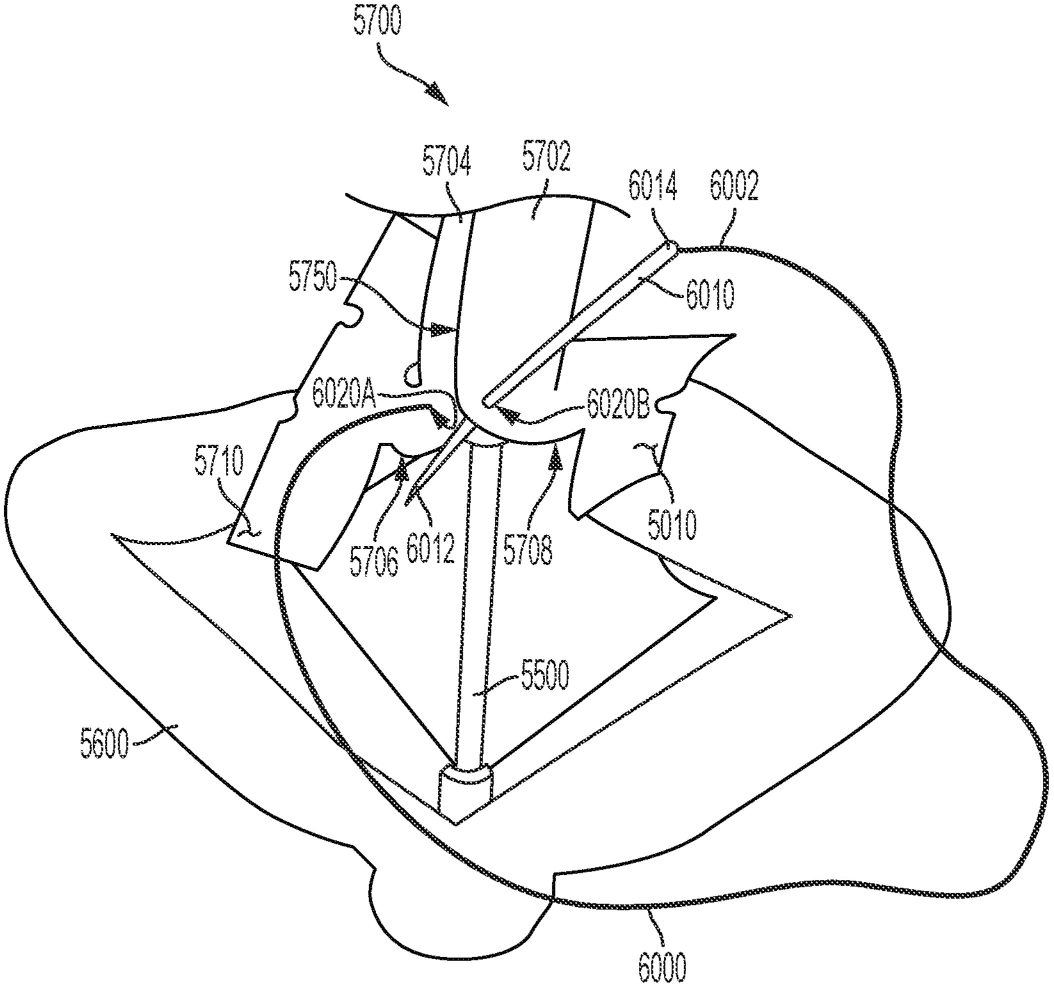
Figure 110:
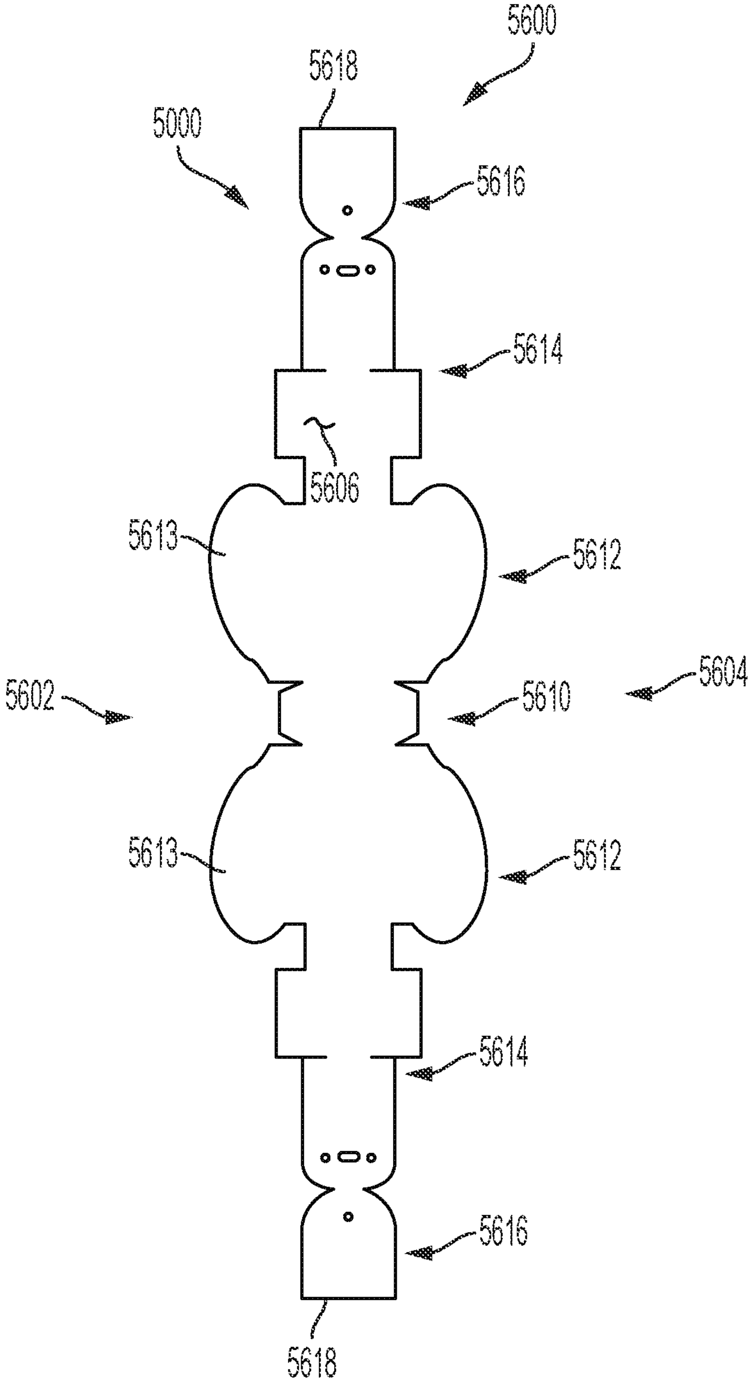
FIG. 110 is a plan view of an example outer cover for an example prosthetic device.

Referring to FIGS. 109A and 109B, the top and bottom pieces 5702, 5704 can be further joined together around the device 5500 using the alternating in and out stitching method discussed above. As shown in FIG. 109A, a thread 6000 having a first end 6002 and a second end 6004 joins the first side 5706 of the top piece 5702 to the second side 5708 of the bottom piece 5704. The first end 6002 of the thread 6004 can be attached to a rear end 6014 of a needle 6010 having a front end 6012 opposite the rear end 6014. The needle 6010 and the thread 6000 can be passed through the bottom piece 5704 from the second surface 5712 to the first surface 5710 at a first point 6020A near the first side 5706 and below the first stitch 5750, through the top piece 5702 from the first surface 5710 to the second surface 5712 at a second point 6020B near the second side 5708, and through the top piece 5702 from the second surface 5712 to the first surface 5710 at a third point 6020C near the second side 5708. The first and second points 6020A, 6020B can be substantially directly across from each other. The alternating in and out stitch can be continued as desired. Once the first side 5706 of the bottom piece 5704 and the second side 5708 of the top piece 5702 are sufficiently joined, the thread 6000 can be pulled tight and secured as described above.

As shown in FIG. 109B, the pattern can be repeated on the other side of the device 5500 such that the thread 6000 joins the second side 5708 of the bottom piece 5704 to the first side 5706 of the top piece 5702. The needle 6010 and the thread 6000 can be passed through the bottom piece 5704 from the second surface 5712 to the first surface 5710 at a first point 6020A near the second side 5708 and below the first stitch 5750, and through the top piece 5702 from the first surface 5710 to the second surface 5712 at a second point 6020B near the first side 5706. The alternating in and out stitch can be continued as desired. Once the second side 5708 of the bottom piece 5704 and the first side 5706 of the top piece 5702 are sufficiently joined, the thread 6000 can be pulled tight and secured as described above. The middle portion 5714 of the bottom piece 5704 can be joined to the top of the coaption portion 5720 of the top piece 5702 using the same alternating in and out stitch.

While the alternating in and out stitch has been described as starting in the bottom piece 5704 below the first stitch 5750, the alternating in and out stitch can be used in other ways to join the top and bottom pieces 5702, 5704. For example, the thread 6000 can be first passed through the top piece 5702 and/or the alternating in and out stitch can be used along the entire length of the top and bottom pieces 5702, 5704 in lieu of the first stitches 5750.

Referring to FIGS. 97 and 108 through 111, the outer cover 5600 can be at least partially attached to or otherwise secured around the device 5500 using the alternating in and out stitch. The outer cover 5600 can include any other features for a cover or outer cover discussed in the present application (e.g., outer cover 541A). The outer cover 5600 has a first side 5602, a second side 5604, a first surface 5606, and a second surface 5608 opposite the first surface 5608. The outer cover 5600 extends outward from a middle portion 5610 to end portions 5618. The middle portion 5610 is shaped to be attached to the cap 514 of the device 5500. Outer paddle portions 5612 extend from the middle portion 5610 to inner paddle and inside clasp portion 5614. The inner paddle and inside clasp portions 5614 extend from the outer paddle portions 5612 to outside moveable clasp portions 5616. The outside moveable clasp portions 5616 extend from the inner paddle portions 5614 to the end portions 5618.

Figure 111:
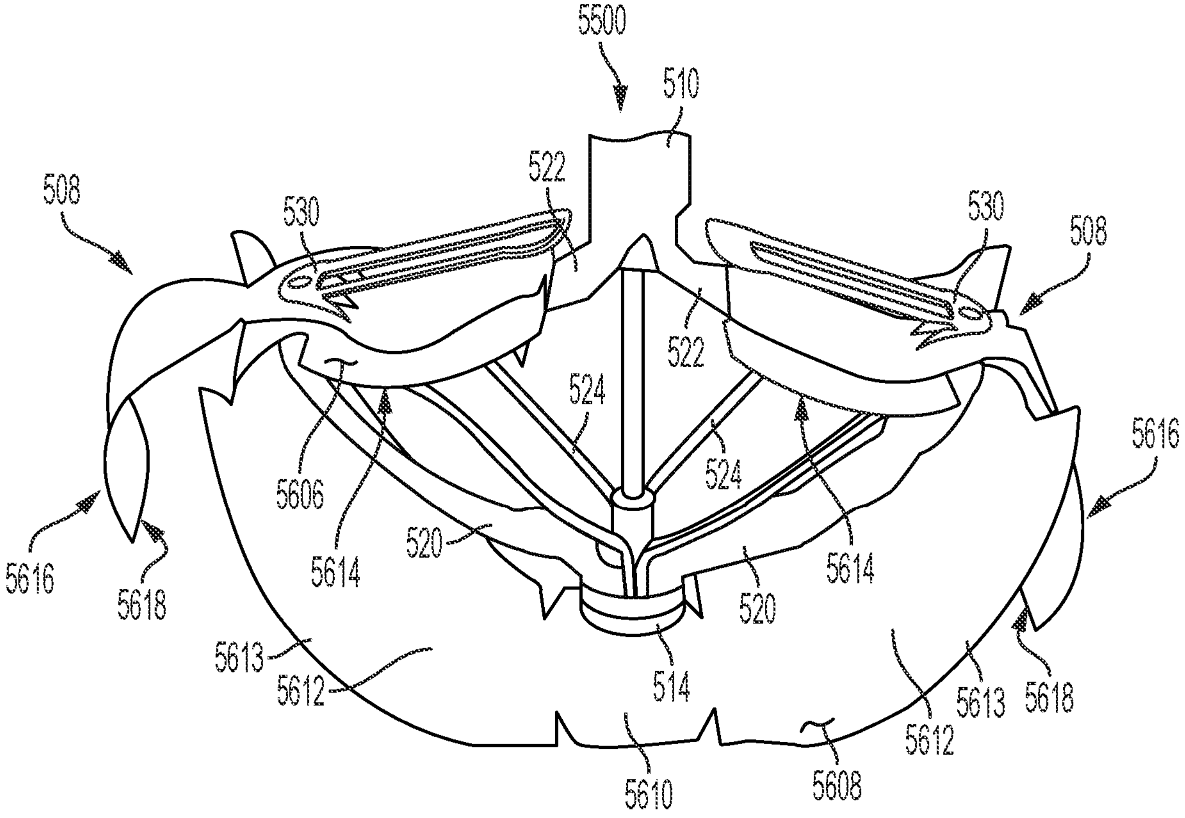
FIG. 111 is a perspective view of an example embodiment of an outer cover disposed around an example prosthetic device.

The outer paddle portions 5612 include wing portions 5613 that extend laterally to a width that is wider than the other portions of the outer cover 5600 so that the outer paddle portions 5612 can attach to the outer paddles 520 and paddle frames 524 of the device 5500. The inner paddle portions 5614 attach to the inner paddles 522, stationary clasp arms 532, and the inside surface (the side with the barbs) of the moveable clasp arms 534 (See FIG. 31 for details of the clasps 530). The outside clasp portions 5616 attach to the outside surface (the side without the barbs) of the moveable arms 534 of the clasps 530 (FIG. 111 shows the outside clasp portions before this attachment). When the outside clasp portions are attached, the ends 5618 of the outer cover 5600 terminate near the joint portion 538 of the clasp 530 on the outside of the clasps 530. The inner paddle and inside clasp portions 5614 can include openings (not pictured) that allow the barbs 536 of the clasps 530 to protrude through the outer cover 5541 to engage tissue of the native heart valve.

As shown in FIGS. 109A, 109B, and 111, the outer cover 5600 can be disposed around the device 5500 such that second surface 5608 of the middle portion 5610 is against the cap 514, the second surface 5608 of the outer paddle portions 5612 is disposed around the outer paddles 520 and paddle frames 524. The wing portions 5613 are both above the outer paddles 520 and paddle frames 524. The second surface 5608 of the inner paddle and inside clasp portions 5614 is disposed above and around the inner paddles 522, the stationary arms 532, and the inside surface (the side with the barbs) of the moveable arm 534. The second surface 5608 of the moveable clasp portions 5616 will be disposed around the outside surface (the side without the barbs) of the moveable arms 534 of the clasps 530. The alternating in and out stitch can then be used to secure the outer cover 5600 around the device 5500. The alternating in and out stitch can optionally first be used to join the wing portions 5613 of the outer paddle portions 5612 together around the outer paddles 520 and paddle frames 524. The alternating in and out stitch can optionally then be used to join the first and second sides 5602, 5604 of the inner paddle and inside clasp portions 5614 around the inner paddles 522, the stationary arms 532, and the inside surface (the side with the barbs) of the moveable arm 534. Finally, the alternating in and out stitch can optionally be used to join the first and second sides 5602, 5604 of the moveable clasp portions 5616 around the outside surface (the side without the barbs) of the moveable arms 534 of the clasps 530. However, the alternating in and out stitch can be used to attach the outer cover 5600 around the device 5500 in any order.

While various inventive aspects, concepts and features of the disclosures may be described and illustrated herein as embodied in combination in the example embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, example or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of example methods or processes are not limited to inclusion of all steps as being required in all cases, nor is the order that the steps are presented to be construed as required or necessary unless expressly so stated. Further, the treatment techniques, methods, operations, steps, etc. described or suggested herein can be performed on a living animal or on a non-living simulation, such as on a cadaver, cadaver heart, simulator (e.g. with the body parts, tissue, etc. being simulated), etc. The words used in the claims have their full ordinary meanings and are not limited in any way by the description of the embodiments in the specification.

What is claimed is:

1. A valve repair device for repairing a native valve of a patient, the valve repair device comprising:

a coaption element;

a cover that at least partially surrounds the coaption element;

wherein at least a portion of the cover is closed around the coaption element by alternating in and out stitches formed by a thread;

wherein the cover has a first surface, a first side and a first portion near the first side and has further a second surface opposite the first surface, a second side opposite the first side and a second portion near the second side; and wherein the thread is pulled tight such that the first and second sides are pulled inwardly toward a center of the cover such that the first surface at the first portion is directed toward the first surface at the second portion, such that the in and out stitches are disposed within the cover, the in and out stitches are unexposed, and the cover is closed around the coaption element.

2. The valve repair device of claim 1, wherein the stitches are substantially unexposed when the cover is closed around the coaption element.

3. The valve repair device of claim 1, wherein the cover comprises a top piece and a bottom piece, the top and bottom pieces each having a first side and a second side.

4. The valve repair device of claim 1, wherein the cover is entirely closed by the alternating in and out stitch.

5. The valve repair device of claim 1, wherein the cover is at least partially closed by a stitch that is not an alternating in and out stitch.

6. A valve repair device for repairing a native valve of a patient, the valve repair device comprising:

a pair of anchors, wherein the pair of anchors are movable between an open position and a closed position; and a cover that at least partially surrounds at least one anchor of the pair of anchors;

wherein the cover has a first surface, a first side and a first portion near the first side and has further a second surface opposite the first surface, a second side opposite the first side and a second portion near the second side;

wherein at least a portion of the cover is closed around the at least one anchor by alternating in and out stitches formed by a thread; and wherein the thread is pulled tight such that the first and second sides are pulled inwardly toward a center of the cover such that the first surface at the first portion is directed toward the first surface at the second portion, such that the in and out stitches are disposed within the cover, the in and out stitches are unexposed, and the cover is closed around the at least one anchor.

7. The valve repair device of claim 6, wherein the cover has a first side and a second side, wherein the alternating in any out stitch extends between the first side and the second side.

8. The valve repair device of claim 6, wherein the at least one anchor comprises a paddle having an inner paddle portion and an outer paddle portion that is extendable away from the inner paddle portion, and wherein the cover includes an outer paddle covering portion that covers the outer paddle portion and an inner paddle covering portion that covers the inner paddle portion.

9. The valve repair device of claim 6, wherein the cover is entirely closed by the alternating in and out stitch.

10. A valve repair system for repairing a native valve of a patient, the valve repair system comprising:

a catheter; and a valve repair device comprising:

a coaption element;

a pair of paddles connected to the coaption element, wherein the paddles are movable between an open position and a closed position; and a cover that at least partially surrounds the coaption element and at least partially surrounds the at least one of the pair of paddles;

wherein the cover has a first surface, a first side and a first portion near the first side and has further a second surface opposite the first surface, a second side opposite the first side and a second portion near the second side;

wherein at least a portion of the cover is closed around one or more of the coaption element and the at least one paddle by alternating in and out stitches formed by a thread; and wherein the thread is pulled tight such that the first and second sides are pulled inwardly toward a center of the cover such that the first surface at the first portion is directed toward the first surface at the second portion, such that the in and out stitches are disposed within the cover, the in and out stitches are unexposed, and the cover is closed around the coaption element.

11. The valve repair system of claim 10, where in the coaption element is formed from a folded strip of material.

12. The valve repair system of claim 10, wherein the coaption element has a rounded shape.

13. The valve repair system of claim 10, wherein the cover is at least partially closed by a stitch that is not an alternating in and out stitch.

14. The valve repair system of claim 10, wherein the each of the paddles comprise a strip of woven material.

15. The valve repair system of claim 10, wherein each of the paddles comprises a metal frame.

16. The valve repair system of claim 10, wherein the at least one paddle comprises an inner paddle portion and an outer paddle portion that is extendable away from the inner paddle portion, and wherein the cover includes an outer paddle covering portion that covers the outer paddle portion and an inner paddle covering portion that covers the inner paddle portion.

* * * * *